US012448636B2

(12) United States Patent
Bachmann et al.

(10) Patent No.: US 12,448,636 B2
(45) **Date of Patent: *Oct. 21, 2025**

(54) HIGH-EFFICIENCY RECONSTITUTION OF RNA MOLECULES

(71) Applicant: Salk Institute for Biological Studies, La Jolla, CA (US)

(72) Inventors: Lukas Christoph Bachmann, San Diego, CA (US); Samuel Lawrence Pfaff, San Diego, CA (US)

(73) Assignee: Salk Institute for Biological Studies, La Jolla, CA (US)

( * ) Notice: Subject to any disclaimer, the term of this patent is extended or adjusted under 35 U.S.C. 154(b) by 900 days.

This patent is subject to a terminal disclaimer.

(21) Appl. No.: 17/486,488

(22) Filed: Sep. 27, 2021

(65) Prior Publication Data

US 2022/0145347 A1 May 12, 2022

Related U.S. Application Data

(63) Continuation of application No. PCT/US2020/025430, filed on Mar. 27, 2020.

(60) Provisional application No. 62/933,714, filed on Nov. 11, 2019, provisional application No. 62/888,855, filed on Aug. 19, 2019, provisional application No. 62/834,305, filed on Apr. 15, 2019, provisional application No. 62/826,854, filed on Mar. 29, 2019.

(51) Int. Cl.

| | |
|---|---|
| ***C12P 19/34*** | (2006.01) |
| ***C12N 15/86*** | (2006.01) |
| ***C12Q 1/6813*** | (2018.01) |

(52) U.S. Cl.

CPC .............. *C12P 19/34* (2013.01); *C12N 15/86* (2013.01); *C12Q 1/6813* (2013.01); *C12N 2750/14111* (2013.01)

(58) Field of Classification Search

None

See application file for complete search history.

(56) References Cited

U.S. PATENT DOCUMENTS

| | | | |
|---|---|---|---|
| 8,236,557 | B2 | 8/2012 | Dongsheng et al. |
| 10,214,572 | B2 | 2/2019 | Boye et al. |
| 2006/0134658 | A1 | 6/2006 | Garcia-Blanco |
| 2006/0246422 | A1 | 11/2006 | Mitchell et al. |
| 2009/0105139 | A1 | 4/2009 | Kole et al. |
| 2016/0348143 | A1 | 12/2016 | Enenkel |
| 2017/0253671 | A1 | 9/2017 | Aebischer-Gumy et al. |
| 2017/0253938 | A1 | 9/2017 | Weng |
| 2018/0044423 | A1 | 2/2018 | Eberbach et al. |
| 2019/0002916 | A1 | 1/2019 | Kalatzis et al. |
| 2019/0032091 | A1 | 1/2019 | Dever et al. |
| 2022/0265855 | A1 | 8/2022 | Bachmann et al. |

FOREIGN PATENT DOCUMENTS

| | | |
|---|---|---|
| JP | 2017-520255 | 7/2017 |
| WO | WO 2013/075008 A1 | 5/2013 |
| WO | WO 2016/004370 | 1/2016 |
| WO | WO 2017/197238 A1 | 11/2017 |
| WO | WO 2018/191032 A1 | 10/2018 |
| WO | WO 2020/127831 A1 | 6/2020 |
| WO | WO 2020/205604 A1 | 10/2020 |
| WO | WO 2020/236982 A1 | 11/2020 |
| WO | WO 2021/096605 A1 | 5/2021 |

OTHER PUBLICATIONS

Liu et al., Human Gene Therapy vol. 16:1116-1123, Nov. 2005.*

Becirovic et al., "A fluorescence-based assay for improvement of dual hybrid AAV vectors in the retina.," ARVO Annual Meeting Abstract (Apr. 28-May 2, 2019) (1 page).

Dyka et al., "Dual Adeno-Associated Virus Vectors Result in Efficient In Vitro and In Vivo Expression of an Oversized Gene, MYO7A," *Human Gene Ther.* 25:166-177, 2014.

International Search Report and Written Opinion mailed on Dec. 16, 2020 for Application No. PCT/US2020/053643 (15 pages).

International Search Report and Written Opinion mailed on Jul. 9, 2020 for Application No. PCT/US2020/025430 (13 pages).

Kiuru et al., "Genetic Control of Wayward Pluripotent Stem Cells and Their Progeny after Transplantation," *Cell Stem Cell* 4:289-300, 2009.

Liu et al., 655. Segmental Trans-Splicing of the C57Bl/6 Murine von Willebrand Factor Pre-mRNA to Facilitate Packaging into Gene Transfer Vectors, Molecular Therapy 15, S251, (1 page), 2007.

Lopes & Williams, "Gene Therapy for the Retinal Degeneration of Usher Syndrome Caused by Mutations in MYO7A," *Cold Spring Harb Perspect Med* 5:a017319, (10 pages), 2015.

Lorain et al., "Exon Exchange Approach to Repair Duchenne Dystrophin Transcripts," *PLoS One* 5:e10894, (15 pages), 2010.

Mansfield et al., "RNA repair using spliceosome-mediated RNA trans-splicing," *Trends Mol Med.* 10:263-268, 2004.

Nakayama et al., "Gene Transfer-Mediated Pre-mRNA Segmental Trans-splicing as a Strategy to Deliver Intracellular Toxins for Cancer Therapy," *Cancer Res* 65:254-263, 2005.

Pergolizzi et al., "In Vivo Trans-splicing of 5' and 3' Segments of Pre-mRNA Directed by Corresponding DNA Sequences Delivered by Gene Transfer," *Mol Ther.* 8:999-1008, 2003.

Pergolizzi et al., "Genetic medicine at the RNA level: modifications of the genetic repertoire for therapeutic purposes by pre-mRNA trans-splicing," *CR Biologies* 327:695-709, 2004.

Pergolizzi et al., "160. Overcoming the Size Limitations of Gene Transfer Vectors: Using Segmental Trans-Splicing to Deliver the Coding Sequence of Von Willebrand Factor," *Mol Ther.* 9:S61 (1 page), 2004.

(Continued)

*Primary Examiner* — Sean McGarry

(74) *Attorney, Agent, or Firm* — Klarquist Sparkman, LLP

(57) ABSTRACT

Provided herein are synthetic RNA molecules for reconstitution of RNA molecules, including compositions and methods of using these molecules. For example, such molecules can be used to deliver a protein coding sequence over two or more viral vectors (such as AAVs), resulting in reconstitution of the full-length protein in a cell. Such methods can be used to deliver a therapeutic protein, for example to treat a genetic disease or cancer.

27 Claims, 61 Drawing Sheets

Specification includes a Sequence Listing.

(56) References Cited

OTHER PUBLICATIONS

Riedmayr et al., "477. Development of Novel and Highly Efficient mRNA Trans-Splicing Dual Vectors," Abstract presented at he ASGCT 22nd Annual Meeting (Apr. 28-May 2, 2019), (1 page).
Ryu et al., "Adenine base editing in mouse embryos and an adult mouse model of Duchenne muscular dystrophy," *Nat Biotechnol.* 36:536-539, 2018.
Song et al., "Functional Cystic Fibrosis Transmembrane Conductance Regulator Expression in Cystic Fibrosis Airway Epithelial Cells by AAV6.2-Mediated Segmental Trans-Splicing," *Human Gene Ther.* 20:267-281, 2009.
Tornabene et al., "Intein-mediated protein trans-splicing expands adeno-associated virus transfer capacity in the retina," *Sci Transl Med.* 11:eaav4523, (14 pages), 2019.
Trapani, "Adeno-Associated Viral Vectors as a Tool for Large Gene Delivery to the Retina," *Genes* 10:287, (12 pages), 2019.
Walsh, "New Paradigms for Gene Transfer: RNA Trans-Splicing and Small Interfering RNA as Therapeutic Strategies," *Semin Hematol.* 41:297-302, 2004.
Wang et al., "In Vivo Gene Transfer Strategies to Achieve Partial Correction of von Willebrand Disease," *Human Gene Ther.* 23:576-588, 2012.
Williams et al., "Gene therapy approaches for prevention of retinal degeneration in Usher syndrome," *Gene Ther.* 24:68-71, 2017.
Yang and Walsh, Splicesome-Mediated RNA Trans-splicing, *Mol Ther.* 12:1006-1012, 2005.
International Search Report and Written Opinion for Application No. PCT/US2022/029459, mailed Sep. 1, 2022 (13 pages).
Truong et al., "Development of an intein-mediated split-Cas9 system for gene therapy," *Nucleic Acids Res.* vol. 43, No. 13, pp. 6450-6458 (2015).
Extended European Search Report for EP 22808481.0, mailed on Mar. 31, 2025, 15 pages.
Hsieh-Feng et al., "Efficient expression of multiple guide RNAs for CRISPR/Cas genome editing", *aBIOTECH,* 1(2): 123-134, Jan. 23, 2020.

* cited by examiner

Mouse tibialis anterior

CMV-N.YFP-5'.Synthetic.Intron-DimerizationDomain(Loop2)-pA

CMV-N.YFP-5'.Synthetic.Intron-DimerizationDomain(Loop2)-pA

```
                      >>>
                      SD

              1310      1320      1330      1340      1350      1360      1370      1380      1390      1400
            *    *    *    *    *    *    *    *    *    *    *    *    *    *    *    *    *    *    *    *
1301 GGttatGGGACCTGAAAAGCGgccctgaaaaagggcCGCGATGAAAACGAAGCGAGCTAAAGCCTCCTCTCTTCTTCAGAACTCCTCTCTTTTCTCTC 1400
                                 >>>>>>>>      >>>>>>>>>>>>>>>>>>>>>>>>>>>>>>>>>>>>>>>>>>>>>>>>>>>>>>>>>>
                                 boxBr         LoopDim2R
     >>>>>>>>>>>>>>>>
     ISE (Human molecular genetics 7.9 (1998): 1491-1496)
     >>>>>>>>>>>>         >>>>>>>
     GGGttatGGGACC        boxBr

              1410      1420      1430      1440      1450      1460      1470      1480      1490      1500
            *    *    *    *    *    *    *    *    *    *    *    *    *    *    *    *    *    *    *    *
1401 CTCCAGGAGTTCTTCCTCTCTCCCTTCTTCTCAAATGCTTTCTCCCTCTCTCCTGCATTTGAGCTCCTTCTTTCCTCTCTCGACAATCCCCTTTTCTCCC 1500
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     LoopDim2R

              1510      1520      1530      1540      1550      1560      1570      1580      1590      1600
            *    *    *    *    *    *    *    *    *    *    *    *    *    *    *    *    *    *    *    *
1501 TCTTGATTGTCGACTAGCTCGCAATCATCGCGGTATCaaaaaGCGGTCaggcaGctaAACCAAAAGGTTtagCAATtgcctCTGATGAGTCGCTGAAATG 1600
                                                                                 <<<<<                      >
                                                                                 StemI                      StemII
                                          >>>>>                               >>>                   >>>>>>
                                          3'HHrz (leaving 6xT-GCGGTC)         B1                    L2
                                                     >>>>>>>>>>>>>         <<<<                >>>>>
                                                     StemI                 StemI               StemII
                                                    >
                                                    Cleavage site (-1)
                                               >>>>>>>>>>>>>>>>>>>>>>>>>>>>>>>>>>>>>>>>>>>>>>>>>>>>>>>>>>
                                               3'HHrz (leaving 6xA-GCGGTC)
                                          >>>>>
                                          StemIII
                                               >>>>>
                                               StemIII
     >>>>>>>>>>>>>>>>>>>>>>>>>>>>>>>>>>
     LoopDim2R

              1610      1620      1630      1640      1650      1660      1670      1680      1690      1700
            *    *    *    *    *    *    *    *    *    *    *    *    *    *    *    *    *    *    *    *
1601 CGACGAAAACCGCtttttGGTACCAATAAAATATCTTTATTTTCATTACATCTGTGTGTTGGTTTTTTGTGTGACTAGTCCACTCCCTCTCTGCGCGCTC 1700
                  >>>>>                                                               >>>>>>>>>>>>>>>>>>>>>
                  SaCas9 sgRNA scaffold                                               ITR
                  >>>>>
                  3'HHrz (leaving 6xT-GCGGTC)
                       >>>>>>
                       KpnI
                             >>>>>>>>>>>>>>>>>>>>>>>>>>>>>>>>>>>>>>>>>>>>>>>>>
                             polyA (pGL4.26)
             >>
             StemIII
     >>>>         >>>>>
     StemII       StemIII
             >>>>>
             StemIII
     >>>>>>>>>>>>>
     3'HHrz (leaving 6xA-GCGGTC)
```

FIG. 10B

FIG. 10C

CMV-DimerizationDomain(Loop2)-3'.Synthetic.Intron-C.YFP-pA

```
             1110      1120      1130      1140      1150      1160      1170      1180      1190      1200
         *    *    *    *    *    *    *    *    *    *    *    *    *    *    *    *    *    *    *    *
1101 CCTAGGcgttacataacttacggtaaatggcccgcctggctgaccgcccaacgacccccgcccattgacgtcaataatgacgtatgttcccatagtaacg 1200
           >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
           CMV enhancer

             1210      1220      1230      1240      1250      1260      1270      1280      1290      1300
         *    *    *    *    *    *    *    *    *    *    *    *    *    *    *    *    *    *    *    *
1201 ccaatagggactttccattgacgtcaatgggtggagtatttacggtaaactgcccacttggcagtacatcaagtgtatcatatgccaagtacgcccccta 1300
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     CMV enhancer

             1310      1320      1330      1340      1350      1360      1370      1380      1390      1400
         *    *    *    *    *    *    *    *    *    *    *    *    *    *    *    *    *    *    *    *
1301 ttgacgtcaatgacggtaaatggcccgcctggcattatgcccagtacatgaccttatgggactttcctacttggcagtacatctacgtattagtcatcgc 1400
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     CMV enhancer

             1410      1420      1430      1440      1450      1460      1470      1480      1490      1500
         *    *    *    *    *    *    *    *    *    *    *    *    *    *    *    *    *    *    *    *
1401 tattaccatggtgatgcggttttggcagtacatcaatgggcgtggatagcggtttgactcacggggatttccaagtctccaccccattgacgtcaatggg 1500
     >>>>>>>>>>
     CMV enhancer
               >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
               CMV promoter

             1510      1520      1530      1540      1550      1560      1570      1580      1590      1600
         *    *    *    *    *    *    *    *    *    *    *    *    *    *    *    *    *    *    *    *
1501 agtttgttttggcaccaaaatcaacgggactttccaaaatgtcgtaacaactccgccccattgacgcaaatgggcggtaggcgtgtacggtgggaggtct 1600
                                                                                                        >
                                                                                                        TATA
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     CMV promoter

             1610      1620      1630      1640      1650      1660      1670      1680      1690      1700
         *    *    *    *    *    *    *    *    *    *    *    *    *    *    *    *    *    *    *    *
1601 atataagcagagctTGGATGTTGCCTTTACTTCTAGGCGCGCCGCGGAAAACCGCGGGATACCGCGATGATTGCGAGCTAGTCGACAATCACACCAACAC 1700
     >>>>>>        >>>>>>>>>>>>>>>>>>>>>>                                      <<<<<<<<<<<<<<<<<<<<<<<<<<<<<<<<<<<<<<<<
     TATA          SV40int spacer                                              LoopDim1R
     >>>>>>>>>>>>>>              >
     CMV promoter                putative transcription start site

             1710      1720      1730      1740      1750      1760      1770      1780      1790      1800
         *    *    *    *    *    *    *    *    *    *    *    *    *    *    *    *    *    *    *    *
1701 CAAAACGATTGTCGACACAAAACACACCCAACCTCAAATGCACAAAACAACCACCACGCATTTGAGCCCACAAAACACAACAAGAACTCCTCCCAAAAAC 1800
     <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
     LoopDim1R

             1810      1820      1830      1840      1850      1860      1870      1880      1890      1900
         *    *    *    *    *    *    *    *    *    *    *    *    *    *    *    *    *    *    *    *
1801 ACCAACAAGGAGTTCTACCAAAACAAACCCACGCTTTAGCTCGCTTCGTTTTCATCATTATTGCGgccctgaaaaagggcCGCTTATAACGTTGCTCGAA 1900
                                                                      >>>>>>>>>>>>>>>
                                                                             boxBr

     <<<<<<<<<<<<<<<<<<<<<<<<<<<<<<<<<<<<<<<<<<<<<<<<<<<<<
     LoopDim1R
```

FIG. 10D

CMV-DimerizationDomain(Loop2)-3'.Synthetic.Intron-C.YFP-pA

```
              1910      1920      1930      1940      1950      1960      1970      1980      1990      2000
          *    *    *    *    *    *    *    *    *    *    *    *    *    *    *    *    *    *    *    *
1901 TTCGGGttatGGGACCAGTGAAGGCTGAGGGAAGGACTGTCCTGGGACTGGACAGGCGGGttatGGGACCTGAAAATACTAACAATCGATTTTTTTTCCC 2000
                                                                          >>>>>>>>
                                                                          Branchpoint
                                                                                        >>>>>>>>>>
                                                                                        PPT
                                                           >>>>>>>>>>>>>>>>>>>>>>>
                                                           ISE (Human molecular genetics 7.9 (1998): 1491-1496)
     >>>>>>>>>>>>>>>>>>>                                          >>>>>>>>>>>>>
     ISE (Human molecular genetics 7.9 (1998): 1491-1496)         GGGttatGGGACC
        >>>>>>>>>>>>>      >>>>>>>>>>>>>>>>>>>>>>>>
        GGGttatGGGACC      cTNT (chicken cardiac troponin T ISE)

              2010      2020      2030      2040      2050      2060      2070      2080      2090      2100
          *    *    *    *    *    *    *    *    *    *    *    *    *    *    *    *    *    *    *    *
2001 TTTTTTTCCAGgtgaacttcaagatccgccacaacatcgaggacggcagcgtgcagctcgccgaccactaccagcagaacacccccatcggcgacggccc 2100
                >>
                SA
                >>>>>>>>>>>>>>>>>>>>>>>>>>>>>>>>>>>>>>>>>>>>>>>>>>>>>>>>>>>>>>>>>>>>>>>>>>>>>>>>>>>>>>
                citrine
              >>
              SA
     >>>>>>>>>
     PPT

              2110      2120      2130      2140      2150      2160      2170      2180      2190      2200
          *    *    *    *    *    *    *    *    *    *    *    *    *    *    *    *    *    *    *    *
2101 cgtgctgctgcccgacaaccactacctgagctaccagtccgccctgagcaaagaccccaacgagaagcgcgatcacatggtcctgctggagttcgtgacc 2200
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     citrine

              2210      2220      2230      2240      2250      2260      2270      2280      2290      2300
          *    *    *    *    *    *    *    *    *    *    *    *    *    *    *    *    *    *    *    *
2201 gccgccgggatcactctcggcatggacgagctgtacaaggacctttgaGAATTCCTCACCTGCGATCTCGATGCTTTATTTGTGAAATTTGTGATGCTAT 2300
                                                    >>>                       >>>>>>>>>>>>>>>>>>>>>>>>>>>>>
                                                    STOP                      SV40 polyA
     >>>>>>>>>>>>>>>>>>>>>>>>>>>>>>>>>>>>>>>>
     citrine

              2310      2320      2330      2340      2350      2360      2370      2380      2390      2400
          *    *    *    *    *    *    *    *    *    *    *    *    *    *    *    *    *    *    *    *
2301 TGCTTTATTTGTAACCATTATAAGCTGCAATAAACAAGTTAACAACAACAATTGCATTCATTTTATGTTTCAGGTTCAGGGGGAGGTGTGGGAGGTTTTT 2400
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     SV40 polyA
                                 >>>>>>
                                 AATAAA

              2410      2420      2430      2440      2450      2460      2470      2480      2490      2500
          *    *    *    *    *    *    *    *    *    *    *    *    *    *    *    *    *    *    *    *
2401 TAAACTAGTCCACTCCCTCTCTGCGCGCTCGCTCGCTCACTGAGGCCGGGCGACCAAAGGTCGCCCGACGCCCGGGCTTTGCCCGGGCGGCCTCAGTGAG 2500

     >>>>
     SV40 polyA
```

FIG. 10E

5'.Synthetic.Intron-DimerizationDomain(Lin)

```
              2210      2220      2230      2240      2250      2260      2270      2280      2290      2300
         *    *    *    *    *    *    *    *    *    *    *    *    *    *    *    *    *    *    *    *
2201 tatcatggccgacaagcagaagaacggcatcaagGTAAGTATTagctctttctttccatgggttggcctcgccgcgtgGGCTGAGGGAAGGACTGTCCTG 2300
     >>>>>>>>>>>>>>>>>>>>>>>>>>>>>>>>>>              >>>>>>>>>>>>>>>>>>>>>>>>
     citrine                                         ratFgfr2 DISE                    cTNT (chicken cardiac troponin T ISE)
                                        >>>>>>>>>
                                        SD consesus
                                     >>>
                                     SD

              2310      2320      2330      2340      2350      2360      2370      2380      2390      2400
         *    *    *    *    *    *    *    *    *    *    *    *    *    *    *    *    *    *    *    *
2301 GGACTGGACAGGCGGGttatGGGACCTGAAAAGCGgccctgaaaaagggcCGCGATGAAAACGAAGCGAGCTAAAGCCTTTCTCCCTTCCCTTCTTTTTT 2400
            >>>>>>>>>>>>>>>>>>>>>>>
            ISE (Human molecular genetics 7.9 (1998): 1491-1496)
     >>                                             >>>>>>>>       >>>>>>>>>>>>>>>>>>>>>>>>>>>>>>>>>>>>>>>>>>>>
     cTNT (chicken cardiac troponin T ISE)          boxBr          LinDim1
                  >>>>>>>>>>>>>           >>>>>>>
                  GGGttatGGGACC           boxbr

              2410      2420      2430      2440      2450      2460      2470      2480      2490      2500
         *    *    *    *    *    *    *    *    *    *    *    *    *    *    *    *    *    *    *    *
2401 TCTCCTTTCTCCTCCTCCTCCCCTCTTTTCCTCTTCTTTCTTTCTTCCCTTCCTCCCTTCTCTCCTTTCCCTCCCCTCTCTCCCCTCTTTCCTCCTCCTC 2500
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     LinDim1

              2510      2520      2530      2540      2550      2560      2570      2580      2590      2600
         *    *    *    *    *    *    *    *    *    *    *    *    *    *    *    *    *    *    *    *
2501 TTTCTCTTTTCTTTCCCCTCTCTCTCCCTAGCTCGCAATCATCGCGGTATCaaaaaGCGGTCaggcaGctaAACCAAAAGGTTtagCAATtgcctCTGAT 2600
                                                                                                   <<<<<
                                                                                                   StemI
                                                                                                >>>
                                                                                                B1
                                                                    >>>>>>>>>>>>>          <<<<
                                                                    StemI                  StemI
                                                                   >
                                                                   Cleavage site (-1)
                                                              >>>>>>>>>>>>>>>>>>>>>>>>>>>>>>>>>>>>>>>>>>>>
                                                              3'HHrz (leaving 6xA-GCGGTC)
                                                         >>>>>
                                                         3'HHrz (leaving 6xT-GCGGTC)
                                                         >>>>>
                                                         StemIII
                                                              >>>>>
                                                              StemIII
     >>>>>>>>>>>>>>>>>>>>>>>>>>>>>>>>>>>>>>>>>>>>>>>>
     LinDim1

              2610      2620      2630      2640      2650      2660      2670      2680      2690      2700
         *    *    *    *    *    *    *    *    *    *    *    *    *    *    *    *    *    *    *    *
2601 GAGTCGCTGAAATGCGACGAAAACCGCttttGGTACCAATAAAATATCTTTATTTTCATTACATCTGTGTGTTGGTTTTTTGTGTGACTAGTCCACTCC 2700

                           >>                                                                           >>>>>>>
                           StemIII                                                                      ITR
                  >>>>>
                  StemII
            >>>>>>         >>>>>            >>>>>>>>>>>>>>>>>>>>>>>>>>>>>>>>>>>>>>>>>>>>>>>>
            L2             StemIII          polyA (pGL4.26)
     >>>>>>>>>>>>>>>>>>>>>>>>>>>
     3'HHrz (leaving 6xA-GCGGTC)

                                >>>>>
                                3'HHrz (leaving 6xT-GCGGTC)
                                >>>>>
                                StemIII
       >>>>>
       StemII
```

LCB290 - simpleSD-gfphybrid

```
           10        20        30        40        50        60        70        80        90       100
      *     *    *    *    *    *    *    *    *    *    *    *    *    *    *    *    *    *    *    *
  1 GTAAGTGTCCCGCGGAACATTATTATAACGTTGCTCGAAGATATCagatggtgcgctcctggacgtagccttcgggcatggcggacttgaagaagtcgtg 100
              >>>>>>>>>>>>>>>>>>>>>>>>>>>>>>>>>>>>
              spacer
                                                  S  P  A  S  R  S  T  A  K  P  C  P  P  S  S  S  T  T  S
                                                  83
                                                  <<<<<<<<<<<<<<<<<<<<<<<<<<<<<<<<<<<<<<<<<<<<<<<<<<<<<<<
                                                  eGFP homology
    >>>>>>>>>                                >>>>>>
    SD (consensus)                           EcoRV
              >>>>>>
              SacII

           110       120       130       140       150       160       170       180       190       200
      *     *    *    *    *    *    *    *    *    *    *    *    *    *    *    *    *    *    *    *
101 ctgcttcatgtggtcggggtagcggctgaagcactgcacgccgtaggtcagggtggtcacgagggtgggccagggcacgggcagcttgccggtggtgcag 200
     S  *  T  T  P  T  A  A  S  A  S  C  A  T  P  *  P  P  *  S  P  P  G  P  C  P  C  S  A  P  P  A  S
    64
    <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
    eGFP homology

           210       220       230       240       250       260       270       280       290       300
      *     *    *    *    *    *    *    *    *    *    *    *    *    *    *    *    *    *    *    *
201 atgaacttcagggtcagcttgccgtaggtggcatcgccctcgccctcgccggacacgctgaacttgtggccgtttacgtcgccgtccagctcgacTCTAG 300
                                                                                                <<<<<
                                                                                                XbaI
     S  S  *  P  *  S  A  T  P  P  M  A  R  A  R  A  P  C  A  S  S  T  A  T  *  T  A  T  W  S  S
    31
    <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
    eGFP homology

           310       320       330
      *     *    *    *    *    *
301 ataacttcgtataATGTATGCtatacgaacggta 334
    <<<<<<<<<<<<<<<<<<<<<<<<<<<<<<<<<<
    Lox71
    <
    XbaI
```

FIG. 10F

LCB291 - simpleSA-gfphybrid

```
            10        20        30        40        50        60        70        80        90       100
        *    *    *    *    *    *    *    *    *    *    *    *    *    *    *    *    *    *    *    *
  1 ATGCATataacttcgtataGCATACATtatagcaatttatAGCTAGCgtcgagctggacggcgacgtaaacggccacaagttcagcgtgtccggcgaggg 100
                                             <<<<<<
                                             NheI
                                                   V  E  L  D  G  D  V  N  G  H  K  F  S  V  S  G  E  G
                                                   1
          <<<<<<<<<<<<<<<<<<<<<<<<<<<<<<<<<<       >>>>>>>>>>>>>>>>>>>>>>>>>>>>>>>>>>>>>>>>>>>>>>>>>>>>>
          LoxJTZ17                                 eGFP homology
    <<<<<<
    NsiI

           110       120       130       140       150       160       170       180       190       200
        *    *    *    *    *    *    *    *    *    *    *    *    *    *    *    *    *    *    *    *
101 cgagggcgatgccacctacggcaagctgaccctgaagttcatctgcaccaccggcaagctgcccgtgccctggcccaccctcgtgaccaccctgacctac 200
     E  G  D  A  T  Y  G  K  L  T  L  K  F  I  C  T  T  G  K  L  P  V  P  W  P  T  L  V  T  T  L  T  Y
    19
    >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
    eGFP homology

           210       220       230       240       250       260       270       280       290       300
        *    *    *    *    *    *    *    *    *    *    *    *    *    *    *    *    *    *    *    *
201 ggcgtgcagtgcttcagccgctaccccgaccacatgaagcagcacgacttcttcaagtccgccatgcccgaaggctacgtccaggagcgcaccatctCCG 300
                                                                                                     >>>
                                                                                                     SacII
    G  V  Q  C  F  S  R  Y  P  D  H  M  K  Q  H  D  F  F  K  S  A  M  P  E  G  Y  V  Q  E  R  T  I
    52
    >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
    eGFP homology
                                                                                                     >>>
                                                                                                     spacer

           310       320       330       340       350       360
        *    *    *    *    *    *    *    *    *    *    *    *    *
301 CGGAACATTATTATAACGTTGCTCGAATACTAACTGGTACCTCTTCTTTTTTTTTTGATATCTGCAG 367
    >>>                                                             >>>
    SacII                                                           3'SpliceSite
                                                                  >>
                                                                  PPT
                                      >>>>>>>>>>            <<<<<<
                                      intronic              EcoRV
                               >>>>>>>
                               Branchpoint (BP)
    >>>>>>>>>>>>>>>>>>>>>>>>>>>                 >>>>>>>>>>>>
    spacer                                      PPT
```

FIG. 10G

LCB300 - boxBloops with ISE

```
          10        20        30        40        50        60        70        80        90        100
     *    *    *    *    *    *    *    *    *    *    *    *    *    *    *    *    *    *    *    *
1 ACTTCTGGCGCGCCaaaaGGCGTGCCAGAAGTACCGGGCTAATAATGTTTCGCGGTCCTCTTaaaTCTgCCTaaaTACgTATaaaTTTgATCgccctgaa 100
                                          <<<<<< <<<<<<<<<                                        >>>>>>>>
                                          spacer                                                  boxBr
                                        <
                                        spacer
>>>>>>                        <<<<<<
SV40int spacer                SV40int spacer
      >                      <          <
      SV40intron             SV40intron 4\boxBr
      >>>>>>>>                        <<
      StuI AGG^CCT                    ISE (Human molecular genetics 7.9 (1998): 1491-1496)
                                      <<<
                                      Kozak
>                                       <
putative transcription start site       insert
                                 <
                                 putative transcription start site
        >>>>>>
        AscI

           110       120       130       140       150       160       170       180       190       200
     *    *    *    *    *    *    *    *    *    *    *    *    *    *    *    *    *    *    *    *
101 aaagggcGATGATcAAAgccctgaaaaagggcATAcGTAgccctgaaaaagggcAGGcAGAgccctgaaaaagggcAAGAGGACCGCGGAACATTATTAG 200
                                                                                  >>>>>>>>>>>>>>>
                                                                                  spacer
                                                                                                 >
                                                                                                 spacer
                                                                                                 >
                                                                                                 Kozak
                                                                                                >
                                                                                                4\boxBr
                                                                                                >
                                                                                                insert
                                             >>>>>>>>       >>>>>>>>>>>>>>>
                                             boxBr          boxBr
                 >>>>>>>>>>>>>>>       >>>>>>>
                 boxBr                 boxBr
>>>>>>>
boxBr

           210       220       230       240       250       260       270
     *    *    *    *    *    *    *    *    *    *    *    *    *    *
201 CCGCCACCATGGACAGGCGGGttatGGGACCTGAAAATACTAACAATCGATTTTTTTTCCCTTTTTTTCCAG 272
                                    >>                >>>>>>>>>>>>>>>>>>>
                                    spacer            PPT
>>>>>>>>>>>>>>>>>>>>>>>>>>>>>>>>>>>>                                     >>
ISE (Human molecular genetics 7.9 (1998): 1491-1496)                     SA
                  >>>>>>>>>>>>>     >>>>>>>>
                  GGGttatGGGACC     Branchpoint
                                       >>>
                                       STOP
                                 >>>           >>>>>>
                                 STOP          ClaI
>>>>>>>>>>>>>>
Kozak
        >>>
        Start(out-of-frame-decoy)
```

FIG. 10H

LCB414 - 3′intron 3xISE without hybridization domain

```
            10        20        30        40        50        60        70        80        90       100
        *    *    *    *    *    *    *    *    *    *    *    *    *    *    *    *    *    *    *    *
  1 ACTTCTAGGCGCGCCGCGGAAAACCGCGGATATCATTATTGCGgccctgaaaaagggcCGCTTATAACGTTGCTCGAATTCGGGttatGGGACCAGTGA 100
    >>>>>>                                                                         >>>>>>>>>>>>>>>>>>>
    SV40int spacer                                                                 ISE (Human molecular genetics 7.9 (1998): 1491-1496)
    >                                                                                 >>>>>>>>>>>>>
    putative transcription start site                                                 GGGttatGGGACC
             >>>>          <<<<<<                                 >>>>>>>>>>>>>>>>>                   >>
             AscI          spacer                                 spacer                              spacer
                 >>>>>>>>>>                            >>>>>>>>
                 spacer                                boxBr
          >>                                    >>>>>>>
          SV40int spacer                        boxBr
                 >>>>>>    <<<<<<       >>>>>
                 SacII     SacII        spacer
          >>>>>>>                >>>>>>
          StuI AGG^CCT           EcoRV

           110       120       130       140       150       160       170       180       190
        *    *    *    *    *    *    *    *    *    *    *    *    *    *    *    *    *    *
101 AGGCTGAGGGAAGGACTGTCCTGGGACTGGACAGGCGGGttatGGGACCTGAAAATACTAACAATCGATTTTTTTTCCCTTTTTTTCCAG 190
                                                         >>              >>>>>>>>>>>>>>>>>>>
                                                         spacer          PPT
                                  >>>>>>>>>>>>>>>>>>>>>>>                                   >>
                                  ISE (Human molecular genetics 7.9 (1998): 1491-1496)      SA
                                        >>>>>>>>>>>>>      >>>>>>>>
                                        GGGttatGGGACC      Branchpoint
                                                                   >>>>>>
                                                                   ClaI

     >>>>>>>>>>>>>>>>>>>>>>>>
     cTNT (chicken cardiac troponin T ISE)
    >
    spacer
```

FIG. 10I

LCB470

```
             10         20         30         40         50         60         70         80         90        100
       *      *    *     *    *     *    *     *    *     *    *     *    *     *    *     *    *     *    *     *
    1 GTAAGTATTagctctttctttccatgggttggcctcgccgcgtgGGCTGAGGGAAGGACTGTCCTGGGACTGGACAGGCGGGttatGGGACCTGAAAAGC 100
                 >>>>>>>>>>>>>>>>>>>>>>>>                                                        >>
                 ratFgfr2 DISE                                                                   spacer
      >>>>>>>>>                                                              >>>>>>>>>>>>>>>>>>>>>>>>
      SD consesus                                                            ISE (Human molecular genetics 7.9 (1998): 1491-1496)
                                                      >>>>>>>>>>>>>>>>>>>>>>>>
                                                      cTNT (chicken cardiac troponin T ISE)
                                                                                   >>>>>> >>>>>>
                                                                                   GGGttatGGGACC

             110        120        130        140        150        160        170        180        190        200
       *      *    *     *    *     *    *     *    *     *    *     *    *     *    *     *    *     *    *     *
  101 GgccctgaaaaagggcCGCGATGAAAACGAAGCGAGCTAAAGCCTCCTCTCTCTTCTTCAGAACTCCTCTCTTTTCTCTCCTCCAGGAGTTCTTCCTCTC 200
              >>>>>>>>        >>>>>>>>>>>>>>>>>>>>>>>>>>>>>>>>>>>>>>>>>>>>>>>>>>>>>>>>>>>>>>>>>>>>>
              boxBr           LoopDim2R
       >>>>>>>               >>>
       boxBr                 EcoRV

             210        220        230        240        250        260        270        280        290        300
       *      *    *     *    *     *    *     *    *     *    *     *    *     *    *     *    *     *    *     *
  201 TCCCTTCTTCTCAAATGCTTTCTCCCTCTCTCCTGCATTTGAGCTCCTTCTTTCCTCTCTCGACAATCCCCTTTTCTCCCTCTTGATTGTCGACTAGCTC 300
      >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
      LoopDim2R

             310        320        330        340        350        360        370        380        390        400
       *      *    *     *    *     *    *     *    *     *    *     *    *     *    *     *    *     *    *     *
  301 GCAATCATCGCGGTATCaaaaaGCGGTCaggcaGctaAACCAAAAGGTTtagCAATtgcctCTGATGAGTCGCTGAAATGCGACGAAAACCGCttttttGG 400
                                                         <<<<<                                   >>
                                                         StemI                                   StemIII
                                                      >>>                              >>>>>        >>>>>
                                                      B1                               StemII       gBlock-SA-sg-HDV
                                  >>>>>>>>>>       <<<<                            >>>>>>        >>>>>
                                  XPD DR36         XPD DR36                        L2            StemIII
                               >>>>>>>>>>>>>                                                        >>>>>
                               StemI                                                                SaCas9 sgRNA scaffold
                               >                                                                    >>>>>
                               Cleavage site (-1)                                                   3'HHrz (leaving 6xT-GCGGTC)
                                           >>>>                                                        >>
                                           L1                                                          KpnI
                          >>>>>>>>>>>>>>>>>>>>>>>>>>>>>>>>>>>>>>>>>>>>>>>>>>>>>>>>>>>>>>>>>>>>>>>       >>
                          3'HHrz (leaving 6xA-GCGGTC)                                                  SapI.gBlock.splitter.LCB
                     >>>>>                                                                          >>>>>
                     3'HHrz (leaving 6xT-GCGGTC)                                                    StemIII
                                                   <<<<            >>>>>
                                                   StemI           StemII
                     >>>>>
                     StemIII
                          >>>>>
                          StemIII
                  >>>
                  EcoRV
      >>>>>>>>>>>>>>
      LoopDim2R

  401 TACC 404
      >>>>
      KpnI
      >>>>
      SapI.gBlock.splitter.LCB
```

FIG. 10J

LCB469

```
          10        20        30        40        50        60        70        80        90       100
     *    *    *    *    *    *    *    *    *    *    *    *    *    *    *    *    *    *    *    *
  1 ACTTCTAGGCGCGCCGCGGAAAACCGCGGGATACCGCGATGATTGCGAGCTAGTCGACAATCAAGAGGGAGAAAAGGGGATTGTCGAGAGAGGAAAGAAG 100
         >>>>>>           <<<<<<
         AscI             spacer
    >>>>>>>>              <<<<<<
    SV40int spacer        SacII
       >>>>>>>>>>               >>>
       StuI AGG^CCT             EcoRV
    >
    putative transcription start site
                   >>>>>>>>          <<<<<<<<<<<<<<<<<<<<<<<<<<<<<<<<<<<<<<<<<<<<<<<<<<<<<<<<<<<<<<<<<<<<<<<<<
                   spacer            LoopDim2R
                   >>>>
                   SacII
    >>>>>>>>>>>>>>>
    5452_1stCreF
    >>>>>>>>>>>>>>>>
    5480_SV40f
    >>>>>>>>>>>>>>>>
    5731_347P1F

         110       120       130       140       150       160       170       180       190       200
     *    *    *    *    *    *    *    *    *    *    *    *    *    *    *    *    *    *    *    *
101 GAGCTCAAATGCAGGAGAGAGGGAGAAAGCATTTGAGAAGAAGGGAGAGAGGAAGAACTCCTGGAGGAGAGAAAAGAGAGGAGTTCTGAAGAAGAGAGAG 200
    <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
    LoopDim2R

         210       220       230       240       250       260       270       280       290       300
     *    *    *    *    *    *    *    *    *    *    *    *    *    *    *    *    *    *    *    *
201 GAGGCTTTAGCTCGCTTCGTTTTCATCATTATTGCGgccctgaaaaagggcCGCTTATAACGTTGCTCGAATTCGGGttatGGGACCAGTGAAGGCTGAG 300
                                                                           >>>>>>>>>>>>>>>>>>>
                                                                           ISE (Human molecular genetics 7.9 (1998): 1491-1496)
                                                                              >>>>>>>>>>>>>      >>>>>>>
                                                                              GGGttatGGGACC      cTNT (chicken cardiac troponin T ISE)
                                                          >>>>>>>>>>>>>>>>>                   >>>
                                                          spacer                              spacer
                            >>>>>          >>>>>>>>
                            spacer         boxbr
                                   >>>>>>>
                                   boxBr
                         >>>
                         EcoRV
    <<<<<<<<<<<<<<<<<<<<<<<<
    LoopDim2R

         310       320       330       340       350       360       370       380
     *    *    *    *    *    *    *    *    *    *    *    *    *    *    *    *
301 GGAAGGACTGTCCTGGGACTGGACAGGCGGGttatGGGACCTGAAAATACTAACAATCGATTTTTTTTCCCTTTTTTTCCAG 382
                                             >>                                >>
                                             spacer                            SA
                          >>>>>>>>>>>>>>>>>>>>>>>
                          ISE (Human molecular genetics 7.9 (1998): 1491-1496)
                                               >>>>>>>>
                                               Branchpoint
                                                       >>>>>>
                                                       ClaI
    >>>>>>>>>>>>>>>>>                                       >>>>>>>>>>>>>>>>>>>
    cTNT (chicken cardiac troponin T ISE)                   PPT
                            >>>>>>>>>>>>>
                            GGGttatGGGACC
```

FIG. 10K

LCB570

```
                10        20        30        40        50        60        70        80        90       100
        *       *    *    *    *    *    *    *    *    *    *    *    *    *    *    *    *    *    *    *
  1 GTAAGTATTAAGCGgccctgaaaaagggcCGGATGAAAACGAAGCGAGCTAAAGCCTCCTCTCTCTTCTTCAGAACTCCTCTCTTTTCTCTCCTCCAGG 100
    >>> >>>>>>           >>>>>>> >>      >>>>>>>>>>>>>>>>>>>>>>>>>>>>>>>>>>>>>>>>>>>>>>>>>>>>>>>>>>>>>>>>>
    SD conseesus         boxBr           LoopDim2R
             >>                     >>>
             spacer                 EcoRV
                  >>>>>>>
                  boxBr

                110       120       130       140       150       160       170       180       190       200
        *       *    *    *    *    *    *    *    *    *    *    *    *    *    *    *    *    *    *    *
101 AGTTCTTCCTCTCTCCCTTCTTCTCAAATGCTTTCTCCCTCTCTCCTGCATTTGAGCTCCTTCTTTCCTCTCTCGACAATCCCCTTTTCTCCCTCTTGAT 200
    >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
    LoopDim2R

                210       220       230       240       250       260       270       280       290       300
        *       *    *    *    *    *    *    *    *    *    *    *    *    *    *    *    *    *    *    *
201 TGTCGACTAGCTCGCAATCATCGCGGTATCaaaaaGCGGTCaggcaGctaAACCAAAAGGTTtagCAATtgcctCTGATGAGTCGCTGAAATGCGACGAA 300
                                                                       <<<<<                  >>>>>
                                                                       StemI                  StemII
                                                                    >>>                 >>>>>>
                                                                    B1                  L2
                                                 >>>>>>>>>>     <<<<                 >>>>>
                                                 XPD DR36       XPD DR36             StemII
                                              >>>>>> >>>>>>>     <<<<
                                              StemI             StemI
                                             >
                                             Cleavage site (-1)
                                                           >>>>
                                                           L1
                                        >>>>>>>>>>>>>>>>>>>>>>>>>>>>>>>>>>>>>>>>>>>>>>>>>>>>>>>>>>>>>>>>
                                        3'HHrz (leaving 6xA-GCGGTC)
                                   >>>>>
                                   3'HHrz (leaving 6xT-GCGGTC)
                                   >>>>>
                                   StemIII
                                        >>>>>
                                        StemIII
                                >>>
                                EcoRV
    >>>>>>>>>>>>>>>>>>>>>>>>>>>
    LoopDim2R

                310
        *       *    *
301 AACCGCtttttGGTACC 317
     >>
     StemIII
     >>>>>
     StemIII
    >>>>>>
    3'HHrz (leaving 6xA-GCGGTC)
          >>>>>
          gBlock-SA-sg-HDV
          >>>>>
          SaCas9 sgRNA scaffold
          >>>>>
          3'HHrz (leaving 6xT-GCGGTC)
               >>>>>>
               KpnI
          >>>>>
          StemIII
               >>>>>>
               SapI.gBlock.splitter.LCB
```

FIG. 10L

LCB571

```
            10        20        30        40        50        60        70        80        90       100
        *    *    *    *    *    *    *    *    *    *    *    *    *    *    *    *    *    *    *    *
  1 GTAAGTATTagctctttctttccatgggttggcctcgccgcgtgAAGCGgccctgaaaaagggcCGCGATGAAAACGAAGCGAGCTAAAGCCTCCTCTCT 100
               >>>>>>>>>>>>>>>>>>>>>>>>         >>          >>>>>>>>      >>>>>>>>>>>>>>>>>>>>>>>>>>>>>>
               ratFgfr2 DISE                    spacer      boxBr         LoopDim2R
    >>>>>>>>>                                        >>>>>>>           >>>
    SD conseus                                       boxBr             EcoRV

           110       120       130       140       150       160       170       180       190       200
        *    *    *    *    *    *    *    *    *    *    *    *    *    *    *    *    *    *    *    *
101 CTTCTTCAGAACTCCTCTCTTTTCTCTCCTCCAGGAGTTCTTCCTCTCTCCCTTCTTCTCAAATGCTTTCTCCCTCTCTCCTGCATTTGAGCTCCTTCTT 200
    >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
    LoopDim2R

           210       220       230       240       250       260       270       280       290       300
        *    *    *    *    *    *    *    *    *    *    *    *    *    *    *    *    *    *    *    *
201 TCCTCTCTCGACAATCCCCTTTTCTCCCTCTTGATTGTCGACTAGCTCGCAATCATCGCGGTATCaaaaaGCGGTCaggcaGctaAACCAAAAGGTTtag 300
                                                                                   >>>>>>>>>>        <<<
                                                                                   XPD DR36          XPD DR36
                                                                                >>>>>>>>>>>>>        <<<
                                                                                StemI                StemI
                                                                               >
                                                                               Cleavage site (-1)
                                                                                             >>>>
                                                                                             L1
                                                                          >>>>>>>>>>>>>>>>>>>>>>>>>>>>>>
                                                                          3'HHrz (leaving 6xA-GCGGTC)
                                                                     >>>>>
                                                                     3'HHrz (leaving 6xT-GCGGTC)
                                                                     >>>>>
                                                                     StemIII
                                                                          >>>>>
                                                                          StemIII
                                                                  >>>
                                                                  EcoRV
    >>>>>>>>>>>>>>>>>>>>>>>>>>>>>>>>>>>>>>>>>>>>>>>>>>>>>>>>>>>>>>
    LoopDim2R

           310       320       330       340       350
        *    *    *    *    *    *    *    *    *    *
301 CAATtgcctCTGATGAGTCGCTGAAAATGCGACGAAAACCGCtttttGGTACC 352
        <<<<<                           >>
        StemI                           StemIII
     >>>                       >>>>>         >>>>>
     B1                        StemII        gBlock-SA-sg-HDV
    <                    >>>>>>         >>>>>
    XPD DR36             L2             StemIII
    >>>>>>>>>>>>>>>>>>>>>>>>>>>>>>>>>>>>>>>>>     >>>>>>
    3'HHrz (leaving 6xA-GCGGTC)                   KpnI
                                             >>>>>
                                             SaCas9 sgRNA scaffold
                                             >>>>>
                                             3'HHrz (leaving 6xT-GCGGTC)
                                             >>>>>
                                             StemIII
    <               >>>>>                         >>>>>>
    StemI           StemII                        SapI.gBlock.splitter.LCB
```

FIG. 10M

LCB572

```
              10        20        30        40        50        60        70        80        90       100
         *     *    *    *    *    *    *    *    *    *    *    *    *    *    *    *    *    *    *    *
  1 GTAAGTATTagctctttctttccatgggttggcctcgccgcgtgGGCTGAGGGAAGGACTGTCCTGGGACTGGACAGGCGGGttatGGGACCTGAAAAGC 100
               >>>>>>>>>>>>>>>>>>>>>>>>                                                            >>
               ratFgfr2 DISE                                                                       spacer
    >>>>>>>>>                                                            >>>>>>>>>>>>>>>>>>>>>>>
    SD consesus                                                          ISE (Human molecular genetics 7.9 (1998): 1491-1496)
                                            >>>>>>>>>>>>>>>>>>>>>>>
                                            cTNT (chicken cardiac troponin T ISE)
                                                                               >>>>>>>>>>>>>
                                                                               GGGttatGGGACC

              110       120       130       140       150       160       170       180       190       200
         *     *    *    *    *    *    *    *    *    *    *    *    *    *    *    *    *    *    *    *
101 GgccctgaaaaagggcCGCGATGAAAACGAAGCGAGCTAAAGCCTCCTCTCTCTTCTTCAGAACTCCTCTCTTTTCTCTCCTCCAGGAGTTCTTCCTCTC 200
            >>>>>>>       >>>>>>>>>>>>>>>>>>>>>>>>>>>>>>>>>>>>>>>>>>>>>>>>>>>>>>>>>>>>>>>>>>>>>>>>
            boxBr         LoopDim2R
     >>>>>>>           >>>
     boxBr             EcoRV

              210       220       230       240       250       260       270       280       290       300
         *     *    *    *    *    *    *    *    *    *    *    *    *    *    *    *    *    *    *    *
201 TCCCTTCTTCTCAAATGCTTTCTCCCTCTCTCCTGCATTTGAGCTCCTTCTTTCCTCTCTCGACAATCCCCTTTTCTCCCTCTTGATTGTCGACTAGCTC 300
    >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
    LoopDim2R

              310       320
         *     *    *    *
301 GCAATCATCGCGGTATCGGTACC 323
                     >>>>>>
                     KpnI
                     >>>>>>
                     SapI.gBlock.splitter.LCB
                  >>>
                  EcoRV
    >>>>>>>>>>>>>>
    LoopDim2R
```

FIG. 10N

LCB573

```
            10        20        30        40        50        60        70        80        90       100
        *    *    *    *    *    *    *    *    *    *    *    *    *    *    *    *    *    *    *    *
  1 TTCTAGGCGCGCCGCGGAAAACCGCGGGATACCGCGATGATTGCGAGCTAGTCGACAATCAAGAGGGAGAAAAGGGGATTGTCGAGAGAGGAAAGAAGGA 100
           >>>>>>        <<<<<<
           AscI          spacer
    >>>>>>               <<<<<<
    SV40int spacer   SacII
        >>>>>>>>>              >>>
        StuI AGG^CCT           EcoRV
                 >>>>>>>>         <<<<<<<<<<<<<<<<<<<<<<<<<<<<<<<<<<<<<<<<<<<<<<<<<<<<<<<<<<<<<<<<<<<<<<
                 spacer           LoopDim2R
                 >>>>
                 SacII

    >>>>>>>>>>>>
    5452_1stCreF
    >>>>>>>>>>>>>
    5480_SV40f
    >>>>>>>>>>>>>
    5731_347P1F

           110       120       130       140       150       160       170       180       190       200
        *    *    *    *    *    *    *    *    *    *    *    *    *    *    *    *    *    *    *    *
101 GCTCAAATGCAGGAGAGAGGGAGAAAGCATTTGAGAAGAAGGGAGAGAGGAAGAACTCCTGGAGGAGAGAAAAGAGAGGAGTTCTGAAGAAGAGAGAGGA 200
    <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
    LoopDim2R

           210       220       230       240       250       260       270       280       290       300
        *    *    *    *    *    *    *    *    *    *    *    *    *    *    *    *    *    *    *    *
201 GGCTTTAGCTCGCTTCGTTTTCATCATTATTGCGgccctgaaaaagggcCGCTTATAACGTTGCTCGAATTCTACTAACAATCGATTTTTTTTCCCTTTT 300
    <<<<<<<<<<<<<<<<<<<<<<            >>>>>>>                                             >>>>>>>>>>>>>>
    LoopDim2R                         boxBr                                               PPT
                          >>>                >>>>>>>>                               >>>>>>
                          EcoRV              boxBr                                  ClaI
                              >>>>>                     >>>>>>>>>>>>>>>>>
                              spacer                    spacer
                                                                            >>>>>>>>
                                                                            Branchpoint
                                                                         >>>
                                                                         ISE (Human molecular genetics 7.9 (1998): 1491-1496)

        *
301 TTTCCAG 307
    >>>>>
    PPT
        >>
        SA
```

FIG. 10O

LCB605

```
          10        20        30        40        50        60        70        80        90       100
     *    *    *    *    *    *    *    *    *    *    *    *    *    *    *    *    *    *    *    *
  1 atatccttTTagggcagagtgaagagttaggaggaaggtggttgggagagggatttccaggccttaggacatcatgacaGATGAAAACGAAGCGAGCTAA 100
    >>>>>>>>>>>>>>>>>>>>>>>>>>>>>>>>>>>>>>>>>>>>>>>>>>>>>>>>>>>>>>>>>>>>>>>>>>>>>>>>
    hNOP216
    >>>>>>>>>>>                                                         >>                          >>>
    U12atac-consensus                                                   deconserverd split point    EcoRV
                                                                                                       >>>>>>>>>>>>>>>>>>>
                                                                                                       LoopDim2R
             >>>>>>>>>>>>>>>>
             overhang

          110       120       130       140       150       160       170       180       190       200
     *    *    *    *    *    *    *    *    *    *    *    *    *    *    *    *    *    *    *    *
101 AGCCTCCTCTCTCTTCTTCAGAACTCCTCTCTTTTCTCTCCTCCAGGAGTTCTTCCTCTCTCCTTCTTCTCAAATGCTTTCTCCCTCTCTCCTGCATTT 200
    >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
    LoopDim2R

          210       220       230       240       250       260       270       280       290       300
     *    *    *    *    *    *    *    *    *    *    *    *    *    *    *    *    *    *    *    *
201 GAGCTCCTTCTTTCCTCTCTCGACAATCCCCTTTTCTCCCTCTTGATTGTCGACTAGCTCGCAATCATCGCGGTATCaaaaaGCGGTCaggcaGctaAAC 300
                                                                                >>>>>
                                                                                3'HHrz (leaving 6xT-GCGGTC)
                                                                                              >>>>>>>>>
                                                                                              XPD DR36
                                                                                           >>>>>>>>>>>>
                                                                                           StemI
                                                                                          >
                                                                                          Cleavage site (-1)
                                                                                     >>>>>>>>>>>>>>>>>>
                                                                                     3'HHrz (leaving 6xA-GCGGTC)
                                                                                >>>>>
                                                                                StemIII
                                                                                     >>>>>
                                                                                     StemIII
                                                                             >>>
                                                                             EcoRV
    >>>>>>>>>>>>>>>>>>>>>>>>>>>>>>>>>>>>>>>>>>>>>>>>>>>>>>>>>>>>>>>>>>>>>>>>>>>
    LoopDim2R

          310       320       330       340       350       360
     *    *    *    *    *    *    *    *    *    *    *    *
301 CAAAAGGTTtagCAATtgcctCTGATGAGTCGCTGAAATGCGACGAAAACCGCtttttGGTACC 364
                                                         >>>>>
                                                         gBlock-SA-sg-HDV
                                                         >>>>>
                                                         SaCas9 sgRNA scaffold
                  <<<<<                                  >>>>>
                  StemI                                  3'HHrz (leaving 6xT-GCGGTC)
             <<<<                                             >>>>>>
             XPD DR36                                         KpnI
                 >>>                                ~>>
                 B1                                 StemIII
    >                                      >>>>>         >>>>>
    XPD DR36                               StemII        StemIII
    >                                >>>>>>         >>>>>
    StemI                            L2             StemIII
     >>>>    <<<<                >>>>>                        >>>>>>
     L1      StemI               StemII                       SapI.gBlock.splitter.LCB
    >>>>>>>>>>>>>>>>>>>>>>>>>>>>>>>>>>>>>>>>>>>>>>>>>>>>>
    3'HHrz (leaving 6xA-GCGGTC)
```

FIG. 10P

LCB606

```
          10        20        30        40        50        60        70        80        90       100
     *    *    *    *    *    *    *    *    *    *    *    *    *    *    *    *    *    *    *    *
  1 TTTACTTCTAGGCGCGCCGCGGAAAACCGCGGGATACCGCGATGATTGCGAGCTAGTCGACAATCAAGAGGGAGAAAAGGGGATTGTCGAGAGAGGAAAG 100
                                       <<<<<<<<<<<<<<<<<<<<<<<<<<<<<<<<<<<<<<<<<<<<<<<<<<<<<<<<<<<<<<<<<
                                       LoopDim2.1
                >>>>>>         <<<<<<
                AscI           spacer
    >>>>>>>>>>>       >>>>>>>>      >>>
    SV40int spacer    spacer        EcoRV
             >>>>>>>>>     <<<<<<
             StuI AGG^CCT  SacII
     >
     putative transcription start site
                          >>>>
                          SacII
    >>>>>>>>>>>>>>>>>
    5452_1stCreF
    >>>>>>>>>>>>>>>>>>
    5480_SV40f
    >>>>>>>>>>>>>>>>>>
    5731_347P1F

          110       120       130       140       150       160       170       180       190       200
     *    *    *    *    *    *    *    *    *    *    *    *    *    *    *    *    *    *    *    *
101 AAGGAGCTCAAATGCAGGAGAGAGGGAGAAAGCATTTGAGAAGAAGGGAGAGAGGAAcAACTCgTGGAGGAGAGAAAAGAGAcGAGTTgTGAAGAAGAGA 200
    <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
    LoopDim2.1

          210       220       230       240       250       260       270
     *    *    *    *    *    *    *    *    *    *    *    *    *    *    *
201 GAGGAGGCTTTAGCTCGCTTCGTTTTCATCatttccaggccttaggacatcatgacaTTTttccttaacTTTgcTcac 278
                              >>>>>>>>>>>>>>>>>>>>>>>>>>>>>>>>>>>>>>>>>>>>>>>>
                              hNOP2i6
                                                                      >>>>>>>>
                                                                      U12atac-acceptor(consensus)
                                                         >>>>>>>>>>>>>
                                                         U12-branchpoint(consensus)
                                                                   >
                                                                   Branchsite
                              >
                              deconserverd split point
    <<<<<<<<<<<<<<<<<<<<<<<<<<<                     >>>>>>>>>>>>>>>>
    LoopDim2.1                                      overhang
                           >>>
                           EcoRV
```

FIG. 10Q

LCB610 N.Abca4

```
             10        20        30        40        50        60        70        80        90       100
       *     *    *    *    *    *    *    *    *    *    *    *    *    *    *    *    *    *    *    *
   1 ACTTCTAGGCGCGCCgccaccATGGGATTCGTGCGGCAGATTCAGCTGCTGCTGTGGAAGAACTGGACCCTGCGGAAGCGGCAGAAAATCAGATTCGTGG 100
     >>>>>>>>              >>>>>>>>>>>>>>>>>>>>>>>>>>>>>>>>>>>>>>>>>>>>>>>>>>>>>>>>>>>>>>>>>>>>>>>>>>>>>
     SV40int spacer        Abca4 (co,sd)
              >>>>>>
              AscI
     >
     putative transcription start site
                     >>>>>>
                     New Feature

            110       120       130       140       150       160       170       180       190       200
       *     *    *    *    *    *    *    *    *    *    *    *    *    *    *    *    *    *    *    *
 101 TGGAACTCGTGTGGCCCCTGAGCCTGTTTCTGGTGCTGATCTGGCTGCGGAACGCCAATCCTCTGTACAGCCACCACGAGTGTCACTTCCCCAACAAGGC 200
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

            210       220       230       240       250       260       270       280       290       300
       *     *    *    *    *    *    *    *    *    *    *    *    *    *    *    *    *    *    *    *
 201 CATGCCTTCTGCCGGAATGCTGCCTTGGCTGCAGGGCATCTTCTGCAACGTGAACAACCCCTGCTTTCAAAGCCCCACACCTGGCGAAAGCCCTGGCATC 300
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

            310       320       330       340       350       360       370       380       390       400
       *     *    *    *    *    *    *    *    *    *    *    *    *    *    *    *    *    *    *    *
 301 GTGTCCAACTACAACAACAGCATCCTGGCCAGAGTGTACCGGGACTTCCAAGAGCTGCTGATGAACGCCCCTGAGTCTCAGCACCTGGGCAGAATCTGGA 400
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

            410       420       430       440       450       460       470       480       490       500
       *     *    *    *    *    *    *    *    *    *    *    *    *    *    *    *    *    *    *    *
 401 CCGAGCTGCACATCCTGAGCCAGTTCATGGACACCCTGAGAACACACCCCGAGAGAATCGCCGGCAGGGGCATCAGAATCCGGGACATCCTGAAGGACGA 500
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

            510       520       530       540       550       560       570       580       590       600
       *     *    *    *    *    *    *    *    *    *    *    *    *    *    *    *    *    *    *    *
 501 GGAAACCCTGACACTGTTCCTCATCAAGAACATCGGCCTGAGCGACAGCGTGGTGTACCTGCTGATCAACAGCCAAGTGCGGCCCGAGCAGTTTGCTCAT 600
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

            610       620       630       640       650       660       670       680       690       700
       *     *    *    *    *    *    *    *    *    *    *    *    *    *    *    *    *    *    *    *
 601 GGCGTGCCAGATCTCGCCCTGAAGGATATCGCCTGTTCTGAGGCCCTGCTGGAACGGTTCATCATCTTCAGCCAGCGGAGAGGCGCCAAGACCGTCAGAT 700
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

            710       720       730       740       750       760       770       780       790       800
       *     *    *    *    *    *    *    *    *    *    *    *    *    *    *    *    *    *    *    *
 701 ATGCCCTGTGCAGTCTGAGCCAGGGAACCCTGCAGTGGATCGAGGATACCCTGTACGCCAACGTGGACTTCTTCAAGCTGTTCCGGGTGCTGCCCACACT 800
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

            810       820       830       840       850       860       870       880       890       900
       *     *    *    *    *    *    *    *    *    *    *    *    *    *    *    *    *    *    *    *
 801 GCTGGATTCTcggTCCcaaGGCATCAACCTGAGAAGCTGGGGCGGCATCCTGTCCGACATGAGCCCAAGAATCCAAGAGTTCATCCACCGGCCTAGCATG 900
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

            910       920       930       940       950       960       970       980       990      1000
       *     *    *    *    *    *    *    *    *    *    *    *    *    *    *    *    *    *    *    *
 901 CAGGACCTGCTGTGGGTTACCAGACCTCTGATGCAGAACGGCGGACCCGAGACATTCACCAAGCTGATGGGCATTCTGAGCGATCTGCTGTGCGGCTACC 1000
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

           1010      1020      1030      1040      1050      1060      1070      1080      1090      1100
       *     *    *    *    *    *    *    *    *    *    *    *    *    *    *    *    *    *    *    *
1001 CTGAAGGCGGAGGATCTAGAGTGCTGAGCTTCAATTGGTACGAGGACAACAACTACAAGGCCTTCCTGGGCATCGACTCCACCAGAAAGGACCCCATCTA 1100
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)
```

FIG. 10R

LCB610 N.Abca4

```
                                          >>
                                          cryptic SD
           1110      1120      1130      1140      1150      1160      1170      1180      1190      1200
1101 CAGCTACGACCGGCGGACAACCAGCTTCTGCAATGCCCTGATCCAGAGCCTGGAAAGCAACCCTCTGACCAAGATCGCTTGGAGGGCCGCCAAACCTCTG 1200
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

           1210      1220      1230      1240      1250      1260      1270      1280      1290      1300
1201 CTGATGGGAAAGATCCTGTACACCCCTGACAGCCCTGCCGCCAGAAGAATCCTGAAGAACGCCAACAGCACCTTCGAGGAACTGGAACACGTGCGCAAGC 1300
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

           1310      1320      1330      1340      1350      1360      1370      1380      1390      1400
1301 TGGTCAAGGCCTGGGAAGAAGTGGGACCTCAGATCTGGTACTTCTTCGACAATAGCACCCAGATGAACATGATCAGAGACACCCTGGGCAACCCTACCGT 1400
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

           1410      1420      1430      1440      1450      1460      1470      1480      1490      1500
1401 GAAGGACTTCCTGAACAGACAGCTGGGCGAAGAGGGCATTACCGCCGAGGCCATCCTGAACTTTCTGTACAAGGGCCCCAGAGAGTCCCAGGCCGACGAC 1500
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

           1510      1520      1530      1540      1550      1560      1570      1580      1590      1600
1501 ATGGCCAACTTCGATTGGCGGGACATCTTCAACATCACCGACAGAACCCTGCGGCTGGTCAACCAGTACCTGGAATGCCTGGTGCTGGACAAGTTCGAGA 1600
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

           1610      1620      1630      1640      1650      1660      1670      1680      1690      1700
1601 GCTACAACGACGAGACACAGCTGACCCAGAGAGCCCTGTCTCTGCTGGAAGAGAATATGTTCTGGGCTGGCGTGGTGTTCCCCGACATGTACCCTTGGAC 1700
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

           1710      1720      1730      1740      1750      1760      1770      1780      1790      1800
1701 AAGCAGCCTGCCTCCTCACGTGAAGTACAAGATCCGGATGGACATCGACGTGGTCGAAAAGACCAACAAGATCAAGGACCGGTACTGGGACAGCGGCCCT 1800
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

           1810      1820      1830      1840      1850      1860      1870      1880      1890      1900
1801 AGAGCTGATCCCGTGGAAGATTTTCGcTACATCTGGGGCGGATTCGCATACCTGCAGGACATGGTGGAACAGGGAATCACACGGTCCCAGGTGCAGGCTG 1900
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

           1910      1920      1930      1940      1950      1960      1970      1980      1990      2000
1901 AAGCTCCTGTGGGAATCTACCTGCAGCAGATGCCTTATCCTTGCTTCGTGGACGACAGCTTCATGATCATCCTGAATCGGTGCTTCCCCATCTTCATGGT 2000
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)
                                                                          >>>>>>>>>>>>>>>>>>>>
                                                                          overhang
           2010      2020      2030      2040      2050      2060      2070      2080      2090      2100
2001 GCTGGCCTGGATCTACTCCGTGTCTATGACCGTGAAGTCCATCGTGCTGGAAAAAGAGCTGCGGCTGAAAGAGACACTGAAGAACCAGGGCGTGTCCAAT 2100
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

           2110      2120      2130      2140      2150      2160      2170      2180      2190      2200
2101 GCCGTGATCTGGTGCACCTGGTTTCTGGACAGCTTCTCCATTATGAGCATGAGCATCTTTCTGCTGACGATCTTCATCATGCACGGCCGGATCCTGCACT 2200
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

           2210      2220      2230      2240      2250      2260      2270      2280      2290      2300
2201 ACAGCGACCCCTTTATCCTCTTCCTGTTCCTGCTGGCCTTCtccACCGCTACAATCATGCTGTGTTTTCTGCTGTCCACCTTCTTCtccaaaGCCTCTCT 2300
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)
                                                                                               >>
                                                                                               Cryptic SA
```

FIG. 10S

FIG. 10T

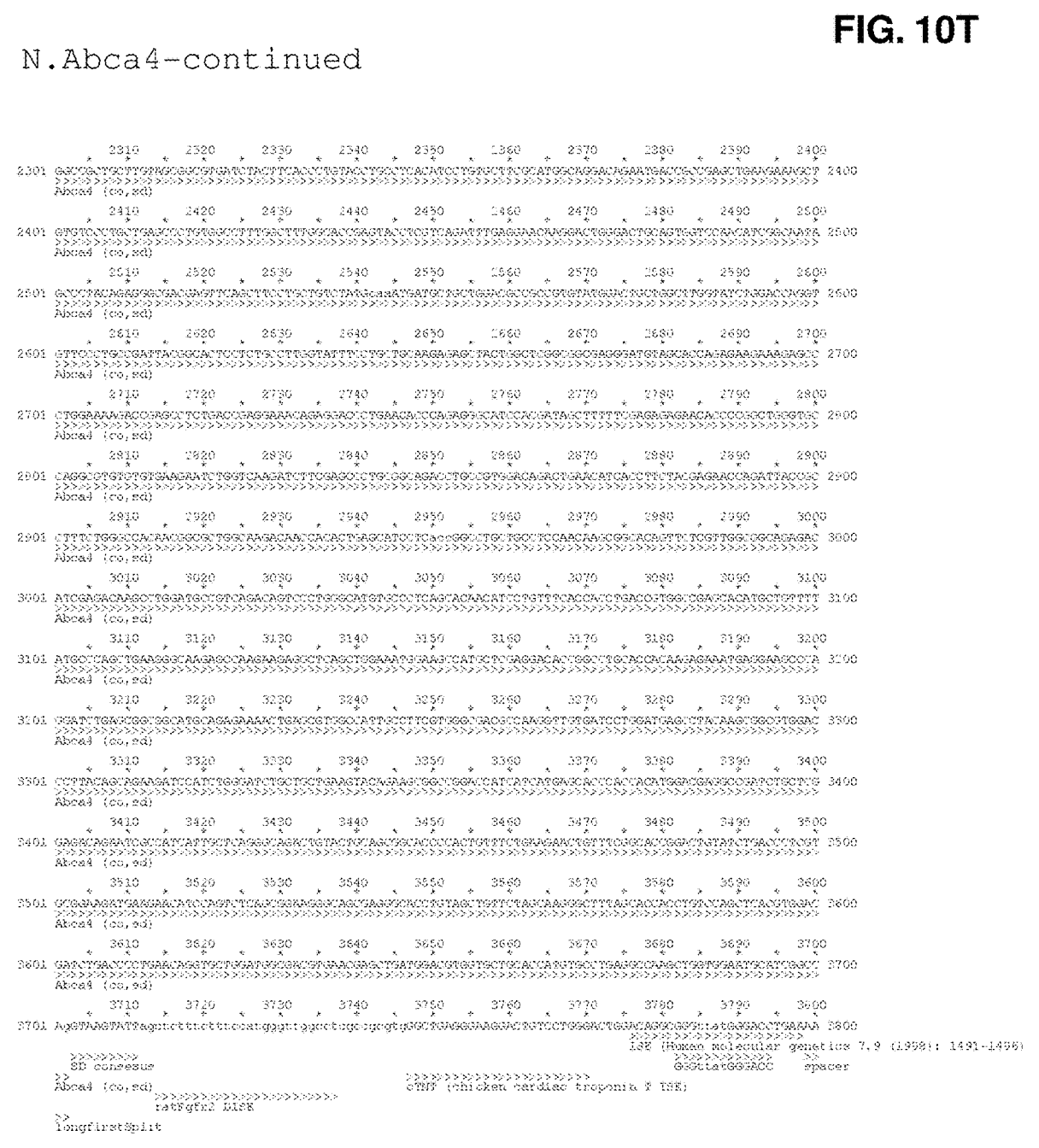

N.Abca4-continued

```
2301 GGCCGCTGCTTGTAGCGGCGTGATCTACTTCACCCTGTACCTGCCTCACATCCTGTGCTTCGCATGGCAGGACAGAATGACCGCCGAGCTGAAGAAGCT 2400
     Abca4 (co,sd)
2401 GTGTCCCTGCTGAGCCCTGTGGCCTTTGGCTTTGGCACCGAGTACCTCGTCAGATTTGAGGAACAAGGACTGGGACTGCAGTGGTCCAACATCGGCAATA 2500
     Abca4 (co,sd)
2501 GCCCTACAGAGGGCGACGAGTTCAGCTTCCTGCTGTCTATGcaaATGATGCTGCTGGACGCCGCCGTGTATGGACTGCTGGCTTGGTATCTGGACCAGGT 2600
     Abca4 (co,sd)
2601 GTTCCCTGCCGATTACGGCACTCCTCTGCCTTGGTATTTCCTGCTGCAAGAGAGCTACTGGCTCGGCGGCGAGGGATGTAGCACCAGAGAAGAAAGAGCC 2700
     Abca4 (co,sd)
2701 CTGGAAAAGACCGAGCCTCTGACCGAGGAAACAGAGGACCCTGAACACCCAGAGGGCATCCACGATAGCTTTTTCGAGAGAGAACACCCCGGCTGGGTGC 2800
     Abca4 (co,sd)
2801 CAGGCGTGTGTGTGAAGAATCTGGTCAAGATCTTCGAGCCCTGCGGCAGACCTGCCGTGGACAGACTGAACATCACCTTCTACGAGAACCAGATTACCGC 2900
     Abca4 (co,sd)
2901 CTTTCTGGGCCACAACGGCGCTGGCAAGACAACCACACTGAGCATCCTCaccGGCCTGCTGCCTCCAACAAGCGGCACAGTTCTCGTTGGCGGCAGAGAC 3000
     Abca4 (co,sd)
3001 ATCGAGACAAGCCTGGATGCCGTCAGACAGTCCCTGGGCATGTGCCCTCAGTACAACATCCTGTTTCACCACCTGACCGTGGCCGAGCACATGCTGTTTT 3100
     Abca4 (co,sd)
3101 ATGCTCAGCTGAAGGGCAAGAGCCAAGAAGAGGCTCAGCTGGAAATGGAAGTCATGCTCGAGGACACTGGCCTGCACCACAAGAGAAATGAGGAAGCCTA 3200
     Abca4 (co,sd)
3201 GGATCTGAGCGGTGGCATGCAGAGAAAACTGAGCGTGGCCATTGCCTTCGTGGGCGACGCCAAGGTTGTGATCCTGGATGAGCCTACAAGCGGCGTGGAC 3300
     Abca4 (co,sd)
3301 CCTTACAGTAGAAGATCCATCTGGGATCTGCTGCTGAAGTACAGAAGTGGCTGGACCATCATCATGAGCACCCACCACATGGACGAGGCCGATCTGCTCG 3400
     Abca4 (co,sd)
3401 GAGACAGAATCGCCATCATTGCTCAGGGCAGACTGTACTGCAGCGGCACCCCACTGTTTCTGAAGAACTGTTTCGGCACCGGACTGTATCTGACCCTCGT 3500
     Abca4 (co,sd)
3501 GCGGAAGATGAAGAACATCCAGTCTCAGCGGAAGGGCAGCGAGGGCACCTGTAGCTGTTCTAGCAAGGGCTTTAGCACCACCTGTCCAGCTCACGTGGAC 3600
     Abca4 (co,sd)
3601 GATCTGACCCCTGAACAGGTGCTGGATGGCGACGTGAACGAGCTGATGGACGTGGTGCTGCACCATGTGCCTGAGGCCAAGCTGGTGGAATGCATCGGCC 3700
     Abca4 (co,sd)
3701 AgGTAAGTATTagcttctttcttccatgggttggcctgcgcgcgtgGGCTGAGGGAAGGACTGTCCTGGGACTGGACAGGCGGGttatGGGACCTGAAAA 3800
                                                                                         ISE (Human molecular genetics 7,9 (1998): 1491-1496)
      SD consesus                                                                          GGGttatGGGACC    spacer
     Abca4 (co,sd)                                         cTNT (chicken cardiac troponin T ISE)
                ratFgfr2 DISE
     longfirstSplit
```

N.Abca4-continued

```
          3810      3820      3830      3840      3850      3860      3870      3880      3890      3900
     *    *    *    *    *    *    *    *    *    *    *    *    *    *    *    *    *    *    *    *
3801 GCGgccctgaaaaagggcCGCGATGAAAACGAAGCGAGCTAAAGCCTCCTCTCTCTTCTTCAGAACTCCTCTCTTTTCTCTCCTCCAGGAGTTCTTCCTC 3900
                         >>>
                         EcoRV
              >>>>>>>>     >>>>>>>>>>>>>>>>>>>>>>>>>>>>>>>>>>>>>>>>>>>>>>>>>>>>>>>>>>>>>>>>>>
              boxBr        LoopDim2R
       >>>>>>>
       boxBr

          3910      3920      3930      3940      3950      3960      3970      3980      3990      4000
     *    *    *    *    *    *    *    *    *    *    *    *    *    *    *    *    *    *    *    *
3901 TCTCCCTTCTTCTCAAATGCTTTCTCCCTCTCTCCTGCATTTGAGCTCCTTCTTTCCTCTCTCGACAATCCCCTTTTCTCCCTCTTGATTGTCGACTAGC 4000
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     LoopDim2R

          4010      4020      4030      4040      4050      4060      4070      4080      4090      4100
     *    *    *    *    *    *    *    *    *    *    *    *    *    *    *    *    *    *    *    *
4001 TCGCAATCATCGCGGTATCaaaaaGCGGTCaggcaGctaAACCAAAAGGTTtagCAATtgcctCTGATGAGTCGCTGAAATGCGACGAAAACCGCttttt 4100
                                                                                               >>>>>
                                                                                               gBlock-SA-sg-HDV
                   >>>>>                                                                       >>>>>
                   3'HHrz (leaving 6xT-GCGGTC)                                                 3'HHrz (leaving 6xT-GCGGTC)
                                                                                               >>>>>
                                                                                               SaCas9 sgRNA scaffold
                                 >>>>>>>>>>                                               >>
                                 XPD DR36                                                 StemIII
                                                                                 >>>>>         >>>>>
                                                                                 StemII        StemIII
                                                                           >>>>>>         >>>>>
                                                                           L2             StemIII
                             >                          >>>             >>>>>
                             Cleavage site (-1)         B1              StemII
                              >>>>>>>>>>>>>                 <<<<<
                              StemI                         StemI
                                          >>>>     <<<<
                                          L1       StemI
                        >>>>>>>>>>>>>>>>>>>>>>>>>>>>>>>>>>>>>>>>>>>>>>>>>>>>>>>>>>>>>>>>>>>>>>
                        3'HHrz (leaving 6xA-GCGGTC)
                   >>>>>                           <<<<
                   StemIII                         XPD DR36
                        >>>>>
                        StemIII
                 >>>
                 EcoRV
     >>>>>>>>>>>>>>>>
     LoopDim2R

          *
4101 GGTACC 4106
     >>>>>>
     KpnI
     >>>>>>
     SapI.gBlock.splitter.LCB
```

FIG. 10U

C.Abca4

```
            10        20        30        40        50        60        70        80        90       100
     *       *    *    *    *    *    *    *    *    *    *    *    *    *    *    *    *    *    *    *
  1 TTGCCTTTACTTCTAGGCGCGCCGCGGAAAACCGCGGGATACCGCGATGATTGCGAGCTAGTCGACAATCAAGAGGGAGAAAAGGGGATTGTCGAGAGAG 100
                           >>>>          >>>
                           SacII         EcoRV
                     >>>>>>                 <<<<<<<<<<<<<<<<<<<<<<<<<<<<<<<<<<<<<<<<<<<<<<<<<<<<<<<<<<<<
                     AscI                   LoopDimCR
    >>>>>>>>>>>>>>>>       >>>>>>>>
    SV40int spacer         spacer
                  >>>>>>>>>       <<<<<<
                  StuI AGG^CCT    spacer
            >
            putative transcription start site
     >>>>>>>>>>>>>>>>>>>>>>       <<<<<<
     5452_1stCreF                 SacII
        >>>>>>>>>>>>>>>>>>>
        5480_SV40f
    >>>>>>>>>>>>>>>>>>>>>>>
    5731_347P1F

            110       120       130       140       150       160       170       180       190       200
     *       *    *    *    *    *    *    *    *    *    *    *    *    *    *    *    *    *    *    *
101 GAAAGAAGGAGCTCAAATGCAGGAGAGAGGGAGAAAGCATTTGAGAAGAAGGGAGAGAGGAAGAACTCCTGGAGGAGAGAAAAGAGAGGAGTTCTGAAGA 200
    <<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<<
    LoopDim2R

            210       220       230       240       250       260       270       280       290       300
     *       *    *    *    *    *    *    *    *    *    *    *    *    *    *    *    *    *    *    *
201 AGAGAGAGGAGGCTTTAGCTCGCTTCGTTTTCATCATTATTGCGgccctgaaaaagggcCGCTTATAACGTTGCTCGAATTCGGGttatGGGACCAGTGA 300
                                                                                                   >>
                                                                                                   spacer
                                                                              >>>>>>>>>>>>>>>>>>>
                                                                              ISE (Human molecular genetics 7.9 (1998): 1491-1496)
                                                   >>>>>>>>                      >>>>>>>>>>>>>
                                                   boxBr                         GGGttatGGGACC
                                            >>>>>>>          >>>>>>>>>>>>>>>>>
                                            boxBr            spacer
    <<<<<<<<<<<<<<<<<<<<<<<<<<<<<<<<   >>>>>
    LoopDim2R                          spacer
                                   >>>
                                   EcoRV

            310       320       330       340       350       360       370       380       390       400
     *       *    *    *    *    *    *    *    *    *    *    *    *    *    *    *    *    *    *    *
301 AGGCTGAGGGAAGGACTGTCCTGGGACTGGACAGGCGGGttatGGGACCTGAAAATACTAACAATCGATTTTTTTTCCCTTTTTTTCCAGGAACTGATTT 400
                                                                                           >>>>>>>>>>
                                                                                           Abca4 (co,sd)
                                >>>>>>>>>>>>>>>>>>>>>>>                                    >>
                                ISE (Human molecular genetics 7.9 (1998): 1491-1496)       longfirstSplit
                                      >>>>>>>>>>>>>      >>             >>>>>>>>>>>>>>>>>>>
                                      GGGttatGGGACC      spacer         PPT
    >                                                      >>>>>>>>                       >>
    spacer                                                 Branchpoint                    SA
                                                                   >>>>>>
                                                                   ClaI
     >>>>>>>>>>>>>>>>>>>>>>>>                     >>>>>>>>>>>>>>>>>>>>
     cTNT (chicken cardiac troponin T ISE)        overhang
```

FIG. 10V

FIG. 10W

C.Abca4

```
          410        420        430        440        450        460        470        480        490        500
 401 TTCTGCTCCCGAACAAGAACTTCAAGCACCGGGCCTACGCCAGCCTGTTCAGAGAGCTGGAAGAAACCCTGGCCGACCTGGGCCTGTCTAGCTTTGGCAT 500
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

          510        520        530        540        550        560        570        580        590        600
 501 CAGCGACACCCCTCTCGAAGAGATCTTCCTGAAAGTGACAGAGGACAGCGATAGCGGCCCTCTGTTTGCTGGCGGAGCACAGCAAAAGCGCGAGAACGTG 600
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

          610        620        630        640        650        660        670        680        690        700
 601 AACCCTAGACACCCCTGTCTGGGCCCAAGAGAGAAAGCCGGACAGACCCCTCAGGACAGCAATGTGTGCTCTCCTGGTGCTCCTGCCGCTCATCCTGAGG 700
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

          710        720        730        740        750        760        770        780        790        800
 701 GACAACCTCCACCTGAACCTGAGTGTCCTGGACCTCAGCTGAACACCGGAACACAGCTGGTTCTGCAGCACGTGCAGGCTCTGCTCGTGAAGAGATTCCA 800
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

          810        820        830        840        850        860        870        880        890        900
 801 GCACACCATCAGAAGCCACAAGGACTTTCTGGCCCAGATCGTGCTGCCGGCCACCTTTGTTTTTCTGGCTCTGATGCTGAGCATCGTGATCCCTCCATTC 900
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

          910        920        930        940        950        960        970        980        990       1000
 901 GGCGAGTACCCCGCTCTGACACTGCACCCTTGGATCTACGGCCAGCAGTACACCTTTTTCTCCATGGACGAACCCGGCAGCGAGCAGTTCACAGTGCTGG 1000
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

         1010       1020       1030       1040       1050       1060       1070       1080       1090       1100
1001 CTGATGTCCTGCTGAACAAGCCCGGCTTCGGCAACCGGTGTCTGAAAGAAGGATGGCTGCCTGAGTACCCTTGCGGCAACAGCACACCTTGGAAAACCCC 1100
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

         1110       1120       1130       1140       1150       1160       1170       1180       1190       1200
1101 TAGCGTGTCCCCTAACATCACCCAGCTGTTCCAAAAGCAGAAATGGACCCAAGTGAACCCCTCTCCATCCTGCCGGTGCTCCACAAGGGAAAGCTGACC 1200
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

         1210       1220       1230       1240       1250       1260       1270       1280       1290       1300
1201 ATGCTGCCCGAGTGTCCAGAAGGCGCTGGCGGACTTCCTCCACCTCAGAGAACACAGAGATCCACCGAGATTCTCCAGGACCTGACCGACCGGAATATCA 1300
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

         1310       1320       1330       1340       1350       1360       1370       1380       1390       1400
1301 GCGACTTCCTGGTTAAGACATACCCCGCACTGATCCGGTCCAGCCTGAAGTCCAAGTTCTGGGTCAACGAACAGAGATACGGCGGCATCAGCATCGGCGG 1400
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

         1410       1420       1430       1440       1450       1460       1470       1480       1490       1500
1401 AAAACTGCCTGTGGTGCCTATCACAGGCGAGGCCCTTGTGGGCTTTCTGTCCGATCTGGGGAGAATCATGAACGTGTCCGGCGGACCTATCACCAGGGAA 1500
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

         1510       1520       1530       1540       1550       1560       1570       1580       1590       1600
1501 GCCAGCAAAGAGATCCCCGATTTCCTGAAGCACCTGGAAACCGAGGACAATATCAAAGTGTGGTTCAACAACAAAGGATGGCACGCCCTCGTGTCTTTTC 1600
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

         1610       1620       1630       1640       1650       1660       1670       1680       1690       1700
1601 TGAACGTGGCCCACAATGCCATCCTGCGGGCTAGCCTGCCTAAGGACAGAAGCCCTGAGGAATACGGCATCACCGTGATCTCCCAGCCTCTGAATCTGAC 1700
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

         1710       1720       1730       1740       1750       1760       1770       1780       1790       1800
1701 CAAAGAGCAGCTGAGCGAGATCACCGTGCTGACCACCTCTGTGGATGCTGTGGTGGCCATCTGCGTGATCTTCAGCATGAGCTTCGTGCCCGCCTCCTTC 1800
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)
```

C.Abca4 continued

```
            1810       1820       1830       1840       1850       1860       1870       1880       1890       1900
        *     *    *     *    *     *    *     *    *     *    *     *    *     *    *     *    *     *    *     *
1801 GTGCTGTACCTGATTCAAGAGAGAGTGAACAAGAGCAAGCACCTCCAGTTCATCTCCGGGGTGTCCCAACCACCTACTGGGTCACCAATTTTCTGTGGG 1900
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

            1910       1920       1930       1940       1950       1960       1970       1980       1990       2000
        *     *    *     *    *     *    *     *    *     *    *     *    *     *    *     *    *     *    *     *
1901 ACATCATGAACTACAGCGTGTCAGCCGGCCTGGTCGTGGGCATCTTTATCGGCTTTcaaAAGAAGGCCTACACGAGCCCCGAGAACCTGCCTGCTTTGGT 2000
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

            2010       2020       2030       2040       2050       2060       2070       2080       2090       2100
        *     *    *     *    *     *    *     *    *     *    *     *    *     *    *     *    *     *    *     *
2001 TGCTCTGCTGCTCCTGTATGGCTGGGCCGTGATTCCCATGATGTACCCCGCCAGCTTTCTGTTTGACGTGCCCAGCACAGCCTACGTGGCCCTGTCTTGC 2100
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

            2110       2120       2130       2140       2150       2160       2170       2180       2190       2200
        *     *    *     *    *     *    *     *    *     *    *     *    *     *    *     *    *     *    *     *
2101 GCCAATCTGTTCATCGGCATCAACAGCAGCGCCATCACATTCATCCTGGAACTGTTCGAGAACAACAGGACCCTGCTGCGGTTCAACGCCGTGCTGCGGA 2200
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

            2210       2220       2230       2240       2250       2260       2270       2280       2290       2300
        *     *    *     *    *     *    *     *    *     *    *     *    *     *    *     *    *     *    *     *
2201 AACTGCTGATCGTGTTCCCTCACTTCTGTCTCGGCcggGGCCTGATCGACCTGGCTCTGTCTcaaGCCGTGACCGATGTGTACGCCAGATTTGGCGAGGA 2300
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

            2310       2320       2330       2340       2350       2360       2370       2380       2390       2400
        *     *    *     *    *     *    *     *    *     *    *     *    *     *    *     *    *     *    *     *
2301 ACACTCCGCCAATCCATTCCACTGGGACCTGATCGGCAAGAACCTGTTCGCCATGGTGGTGGAAGGCGTCGTGTACTTCCTGCTCACTCTGCTGGTGCAG 2400
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)
                                >>>>>>>>>>>>>>>>>>>>
                                overhang
```

FIG. 10X

C.Abca4 continued

```
             2410      2420      2430      2440      2450      2460      2470      2480      2490      2500
         *    *    *    *    *    *    *    *    *    *    *    *    *    *    *    *    *    *    *    *
2401 AGACACTTTTTTCTGTCCCAATGGATCGCCGAGCCTACCAAAGAACCCATTGTGGACGAGGACGACGATGTGGCCGAGGAAAGACAGAGAATCATCACCG 2500
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

             2510      2520      2530      2540      2550      2560      2570      2580      2590      2600
         *    *    *    *    *    *    *    *    *    *    *    *    *    *    *    *    *    *    *    *
2501 GCGGCAACAAGACCGATATCCTGAGACTGCACGAGCTGACAAAGATCTACCCCGGCACAAGCTCCCCAGCCGTGGATAGGCTTTGTGTGGGAGTTAGACC 2600
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

             2610      2620      2630      2640      2650      2660      2670      2680      2690      2700
         *    *    *    *    *    *    *    *    *    *    *    *    *    *    *    *    *    *    *    *
2601 CGGCGAGTGCTTTGGCCTGCTGGGAGTTAATGGCGCCGGAAAGACCACCACCTTCAAGATGCTGACCGGCGACACCACAGTGACAAGCGGAGATGCTACA 2700
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

             2710      2720      2730      2740      2750      2760      2770      2780      2790      2800
         *    *    *    *    *    *    *    *    *    *    *    *    *    *    *    *    *    *    *    *
2701 GTGGCCGGCAAGAGCATCCTGACCAACATCAGCGAAGTGCATCAGAACATGGGCTACTGCCCTCAGTTCGACGCCATCGACGAACTGCTGACAGGCCGCG 2800
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

             2810      2820      2830      2840      2850      2860      2870      2880      2890      2900
         *    *    *    *    *    *    *    *    *    *    *    *    *    *    *    *    *    *    *    *
2801 AACACCTGTATCTGTATGCCAGACTGAGAGGCGTGCCCGCTGAAGAGATCGAGAAGGTGGCCAACTGGTCCATCAAGTCTCTGGGCCTGACAGTGTACGC 2900
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

             2910      2920      2930      2940      2950      2960      2970      2980      2990      3000
         *    *    *    *    *    *    *    *    *    *    *    *    *    *    *    *    *    *    *    *
2901 CGACTGTCTGGCCGGAACATACAGCGGAGGAAACAAGCGGAAGCTGAGCACCGCCATTGCTCTGATCGGATGCCCACCTCTGGTCCTGCTGGATGAACCC 3000
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

             3010      3020      3030      3040      3050      3060      3070      3080      3090      3100
         *    *    *    *    *    *    *    *    *    *    *    *    *    *    *    *    *    *    *    *
3001 ACCACCGGAATGGATCCCCAGGCTAGAAGAATGCTCTGGAACGTGATCGTGTCTATCATCCGCGAGGGCAGAGCTGTGGTGCTGACCTCTCACtccATGG 3100
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

             3110      3120      3130      3140      3150      3160      3170      3180      3190      3200
         *    *    *    *    *    *    *    *    *    *    *    *    *    *    *    *    *    *    *    *
3101 AAGAGTGCGAGGCTCTGTGTACCCGGCTGGCCATTATGGTCAAGGGCGCCTTCAGATGCATGGGCACCATTCAGCATCTGAAAAGCAAGTTCGGCGACGG 3200
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

             3210      3220      3230      3240      3250      3260      3270      3280      3290      3300
         *    *    *    *    *    *    *    *    *    *    *    *    *    *    *    *    *    *    *    *
3201 CTACATCGTGACAATGAAGATCAAGAGCCCCAAGGACGACCTCCTGCCTGATCTGAACCCCGTGGAACAGTTTTTTCAGGGCAACTTCCCCGGCTCCGTG 3300
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

             3310      3320      3330      3340      3350      3360      3370      3380      3390      3400
         *    *    *    *    *    *    *    *    *    *    *    *    *    *    *    *    *    *    *    *
3301 CAGCGGGAAAGACACTATAACATGCTGCAGTTTCAGGTGTCCTCCTCCAGCCTGGCTCGGATCTTTCAACTGCTGCTCTCTCACAAGGACAGCCTGCTGA 3400
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)
```

FIG. 10Y

C.Abca4 continued

```
              3410      3420      3430      3440      3450      3460      3470      3480      3490      3500
          *    *    *    *    *    *    *    *    *    *    *    *    *    *    *    *    *    *    *    *
3401 TTGAAGAGTACAGCGTGACACAGACCACACTCGACCAGGTTTTCGTGAACTTCGCCAAGCAGCAGACCGAGAGCCACGACCTGCCTCTGCATCCTcggGC 3500
     >>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>>
     Abca4 (co,sd)

              3510      3520      3530      3540      3550      3560      3570      3580      3590      3600
          *    *    *    *    *    *    *    *    *    *    *    *    *    *    *    *    *    *    *    *
3501 CGCTGGTGCCTCTAGACAAGCTCAGGACGGCGCTCGGGCTGACTACAAAGACCATGACGGTGATTATAAAGATCATGACATCGACTATAAGGATGACGAT 3600
                                 >>>>>>
                                 GA
     >>>>>>>>>>>>>>>>>>>>>>>>>>>>      >>>>>>>>>>>>>>>>>>>>>>>>>>>>>>>>>>>>>>>>>>>>>>>>>>>>>>>>>>>>>>>>>>
     Abca4 (co,sd)                      3xFlag(v.M2)

              3610      3620      3630      3640      3650      3660      3670      3680      3690      3700
          *    *    *    *    *    *    *    *    *    *    *    *    *    *    *    *    *    *    *    *
3601 GACAAATGAGGTACCAATTCCTCACCTGCGATCTCGAGCTTTATTTGTGAAATTTGTGATGCTATTGCTTTATTTGTAACCATTATAAGCTGCAATAAAC 3700
     >>>>>>>>>                               >>>>>>>>>>>>>>>>>>>>>>>>>>>>>>>>>>>>>>>>>>>>>>>>>>>>>>>>>>>>>>>>
     3xFlag(v.M2)                            SV40 polyA
                    >>>>>                                                                             >>>>>>
                    EcoRI:G^AATTC                                                                     AATAAA
                    >>>>>
                    destroyed StuI AGG^CCT
                    <<<<<
                    5412_InfCreRRzR
                    <<<<<
                    5461_gBlockR
                    <<<<<
                    5467_SpAcc-CreR
                   >>>>>>>>>>>>>>>>>>>>
                   overhang
                         >>
                         destroyed StuI AGG^CCT
                         <<<<<<<<<<<<
                         5412_InfCreRRzR
                    <<<<<
                    5406_infR
              >>>>>>
              New Feature

              3710      3720      3730      3740      3750      3760      3770
          *    *    *    *    *    *    *    *    *    *    *    *    *    *
3701 AAGTTAACAACAACAATTGCATTCATTTTATGTTTCAGGTTCAGGGGGAGGTGTGGGAGGTTTTTTAAACTAGT 3774
     >>>>>>>>>>>>>>>>>>>>>>>>>>>>>>>>>>>>>>>>>>>>>>>>>>>>>>>>>>>>>>>>>>>>>>
     SV40 polyA
                                                          <<<<<<<<<<<<<<<<<<<<<
                                                          5353r
                                                          <<<<<<<<<<<<<<<<<<<<<
                                                          5353_scSeqPaR
                            >>>>>>>>>>>>>>>>>>>>>>>>
                            5667_Seq-SV40pA-F
                                                  >>>>>>>>>>>>>>>>>>>>>>>>>
                                                  5690_SV40pA-F
```

FIG. 10Z

FIG. 13D
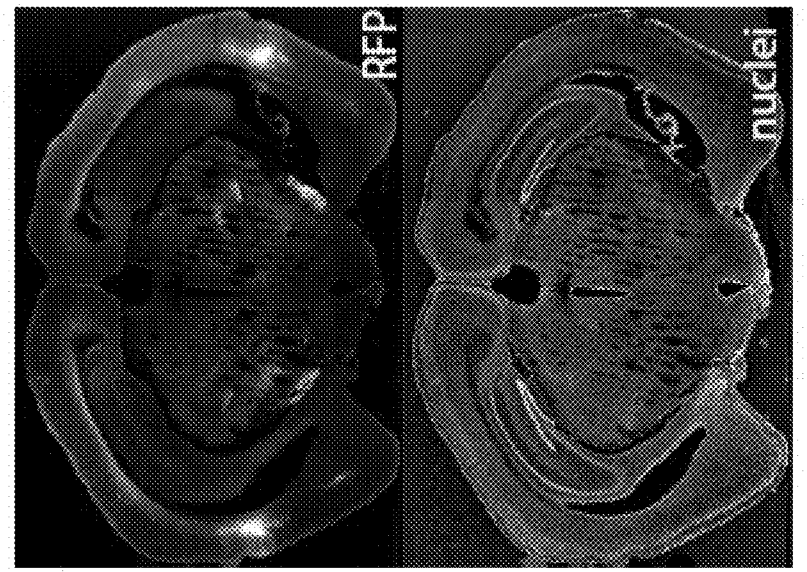
FIG. 13C
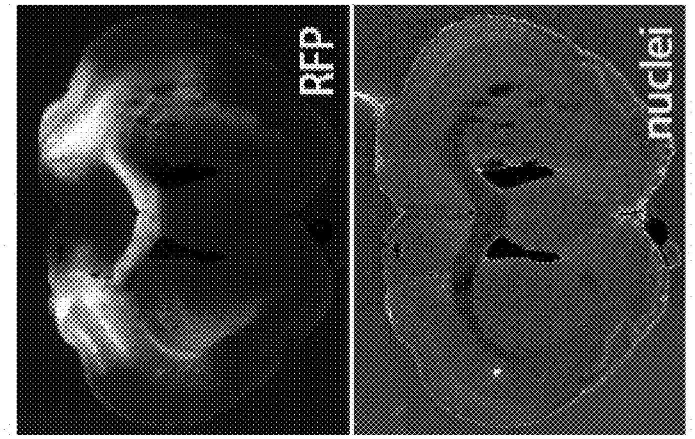
FIG. 13A
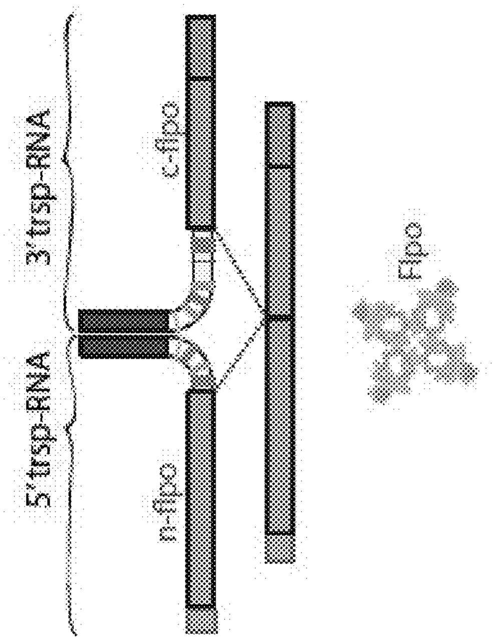
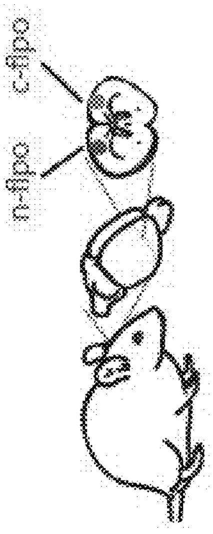
FIG. 13B

YFP (+ DRAQ5 for context)

FIG. 17A

HIV-1 based kissing loop dimerization domain

```
5'-[...]aggcuucggagcAAggaggcAgcuccgaagccu[...]-3' (N-fragment)
5'-[...]((((((((((((.........))))))))))))[...]-3'
           \\\\\\\\\\\\ |||||| \\\\\\\\\\\\
 3'-[...]((((((((((((.........))))))))))))[...]-5'
 3'-[...]uccgaagccucgaccuccgaacgaggcuucgga[...]-5' (C-fragment)
```

FIG. 17B

HIV-2 based kissing loop dimerization domain

```
 5'-[...]GUCGAGGCCGAgcgggcAAAGGCCUCGAC[...]-3' (N-fragment)
 5'-[...](((((((((...........)))))))))[...]-3'
          /////////  ||||||  /////////
3'-[...](((((((((...........)))))))))[...]-5'
3'-[...]CAGCUCCGGAAAcgcccgAGCCGGAGCUG[...]-5' (C-fragment)
```

HIGH-EFFICIENCY RECONSTITUTION OF RNA MOLECULES

CROSS-REFERENCE TO RELATED APPLICATIONS

This application is a continuation of PCT Application No. PCT/US2020/025430, filed Mar. 27 2020, which claims priority to U.S. Provisional Application No. 62/826,854 filed Mar. 29, 2019, U.S. Provisional Application No. 62/834,305 filed Apr. 15, 2019, U.S. Provisional Application No. 62/888,855 filed Aug. 19, 2019, and U.S. Provisional Application No. 62/933,714 filed Nov. 11, 2019, all herein incorporated by reference.

REFERENCE TO AN ELECTRONIC SEQUENCE LISTING

The present application is filed along with a sequence listing in electronic format. The sequence listing is provided as a file entitled Sequence-Listing.txt, created on Sep. 24, 2021, which is approximately 80,948 bytes in size. The information in the electronic format of the sequence listing is incorporated herein by reference in its entirety.

FIELD

The present disclosure provides systems, kits, compositions, and methods that allow for reconstitution of two or more RNA molecules, allowing expression of a full-length protein.

BACKGROUND

Several hereditary diseases are caused by recessive loss of function mutations in a single gene. In such cases, gene replacement therapy (or gene therapy) is a promising treatment strategy. Adeno-associated virus (AAV) is a preferred vector for gene replacement therapy, but treatment of several diseases has remained challenging due to the incompatibility of large size of disease-linked genes with the limited packaging capacity of AAV (or other gene therapy vectors). For example, the genome-packaging capacity of AAV is about 5000 nucleotides. Even if the replacement gene is within the cargo capacity of the gene therapy vector, lack of space for adequate regulatory sequences can prevent efficient expression in a desired tissue.

Strategies to overcome the packaging constraints of gene therapy vectors have been explored in the past, but efficiencies of such attempts have remained low which highlights the need for further clinical methods.

SUMMARY

Provided herein are systems for expressing a target protein. In one example, the system includes (1) a first synthetic nucleic acid molecule, comprising from 5' to 3', a first promoter; an RNA molecule encoding an N-terminal portion of the target protein operably linked to the first promoter, which includes a first splice junction at a 3'-end of the RNA molecule encoding the N-terminal portion of the target protein; a splice donor; and a first dimerization domain; and (2) a second synthetic nucleic acid molecule; comprising from 5' to 3', a second promoter; a second dimerization domain operably linked to the second promoter, and having reverse complementarity to the first dimerization domain; a branch point sequence; a polypyrimidine tract; a splice acceptor; and an RNA molecule encoding a C-terminal portion of a target protein, which includes a splice junction at a 5'-end of the RNA molecule encoding the C-terminal portion of a target protein.

In one example, the system includes (1) a first synthetic nucleic acid molecule, comprising from 5' to 3', a first promoter, an RNA molecule encoding an N-terminal portion of the target protein operably linked to the first promoter, which includes a splice junction at a 3'-end of the RNA molecule encoding the N-terminal portion of the target protein; a first splice donor; and a first dimerization domain; (2) a second synthetic nucleic acid molecule, comprising from 5' to 3', a second promoter; a second dimerization domain operably linked to the second promoter, and having reverse complementarity to the first dimerization domain; a first branch point sequence; a first polypyrimidine tract; a first splice acceptor; an RNA molecule encoding a middle portion of a target protein, which includes a splice junction at a 5'-end of the RNA molecule encoding the middle portion of a target protein and a splice junction at a 3'-end of the RNA molecule encoding the middle portion of the target protein; a second splice donor; and a third dimerization domain; and (3) a third synthetic nucleic acid molecule; comprising from 5' to 3', a third promoter, a fourth dimerization domain operably linked to the third promoter, and having reverse complementarity to the third dimerization domain; a second branch point sequence, a second polypyrimidine tract, a second splice acceptor; and an RNA molecule encoding a C-terminal portion of a target protein, which includes a splice junction at a 5'-end of the RNA molecule encoding the C-terminal portion of a target protein.

In some examples, the synthetic nucleic acid molecules include one or more splicing enhancers.

In some examples, the synthetic nucleic acid molecules are part of a vector, such as a viral vector, such as AAV or a lentiviral vector.

Also provided are compositions and kits that include the disclosed systems.

Also provided are methods of using the disclosed systems to express a protein in a cell. Such a method can include introducing the system into a cell, and expressing the synthetic first and second, first, second, and third, or first, second, third and fourth nucleic acid molecules in the same cell. In some examples, the cell is a subject, and the method treats a disease in the subject, such as a genetic disease caused by a mutation in a gene encoding the target protein, or treats cancer in the subject (wherein the target protein is a toxin or thymidine kinase). In some examples, administration is via injection, such as iv.

The foregoing and other objects and features of the disclosure will become more apparent from the following detailed description, which proceeds with reference to the accompanying figures.

BRIEF DESCRIPTION OF THE DRAWINGS

FIGS. 10A-10Z are exemplary synthetic nucleic acid molecules that can be used with the systems and methods. In some examples, a synthetic nucleic acid molecule as at least 80%, at least 85%, at least 90%, at least 95%, at least 98%, at last 99% or 100% sequence identity to the sequence of any one of SEQ ID NOS: 1 (FIGS. 10A-10B), 2 (FIGS. 10C-10E), 7 (FIG. 10E), 8 (FIG. 10F), 9 (FIG. 10G), 10 (FIG. 10H), 11 (FIG. 10I), 12 (FIG. 10J), 13 (FIG. 10K), 14 (FIG. 10L), 15 (FIG. 10M), 16 (FIG. 10N), 17 (FIG. 10O), 18 (FIG. 10P), 19 (FIG. 10Q), 20 (FIGS. 10R-10U), and 21 (FIGS. 10V-10Z), but with a different target protein coding sequence. Thus an intronic region using with any of the systems or methods provided herein can have at least 80%, at least 85%, at least 90%, at least 95%, at least 98%, at last 99% or 100% sequence identity to any intronic sequence of SEQ ID NOS: 1, 2, 3, 4, 7, 8, 9, 10, 11, 12, 13, 14, 15, 16, 17, 18, 19, 20, or 21. For example, FIGS. 10A-D show exemplary (A,B) first (SEQ ID NO: 1) and (C,D) second (SEQ ID NO: 2) synthetic molecules that can be used to express full-length YFP, while SEQ ID NO: 3 and 4 provide the corresponding synthetic intron portion without the YFP coding portion. In some examples, a synthetic intron sequence has at least 80%, at least 85%, at least 90%, at least 95%, at least 98%, at last 99% or 100% sequence identity to SEQ ID NO: 3 or 4. Thus, the coding sequence portion of any synthetic molecule provided herein (e.g., nt 544 to 1032 of SEQ ID NO: 1 and nt 905 to 1141 of SEQ ID NO: 2), can be replaced with another coding sequence portion.

FIG. 12A is a schematic drawing of the 5'-N and 3'-C-terminal constructs used (SEQ ID NO: 1 and 2). FIG. 12B is a bar graph showing the resulting YFP fluorescence following transfection of SEQ ID NO: 1 and 2 into cells, or various truncations thereof. n=3 samples per condition.

FIGS. 13A-13D shows dual projection tracing by reconstitution of full-length flp recombinase (Flpo) from two fragments (SEQ ID NOS: 147 and 148). (A) Schematic representation of the 5'- and 3'-sequences used to reconstitute flpo. (B) Schematic representation of a mouse injected with the 5'- and 3'-sequences in different regions of the brain. (C and D) show cells with dual projections to both primary motor cortices in red. Hoechst staining (nuclei) is shown for context.

FIGS. 17A and 17B provide (A) HIV-1 based kissing loop dimerization domain (N-fragment, SEQ ID NO: 139, C-fragment SEQ ID NO: 140); and (B) HIV-2 based kissing loop dimerization domain (N-fragment, SEQ ID NO: 141, C-fragment SEQ ID NO: 142).

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NOS: 1 and 2 are N- and C-terminal sequences, respectively, used to express full-length YFP. SEQ ID NO: 1, CMV promoter nt 1 to 543, YFP coding sequence nt 544 to 1032, synthetic intron nt 1033 to 1436, and untranslated poly A region nt 1437 to 1491. SEQ ID NO: 2, CMV promoter nt 1 to 522, synthetic intron nt 523 to 904, YFP coding sequence nt 905 to 1141, and nt 1142 to 1302 is the untranslated poly A region.

SEQ ID NOS: 3 and 4 are 5'- and 3'-intronic sequences, respectively, that can be used to express a desired full-length protein, wherein a N-terminal portion of the full-length protein can be added at nt 1 of SEQ ID NO: 3, and C-terminal portion of the full-length protein can be added at nt 382 of SEQ ID NO: 4.

SEQ ID NOS: 5 and 6 are N- and C-terminal coding sequences, respectively, used to express full-length YFP.

Figure 10A:
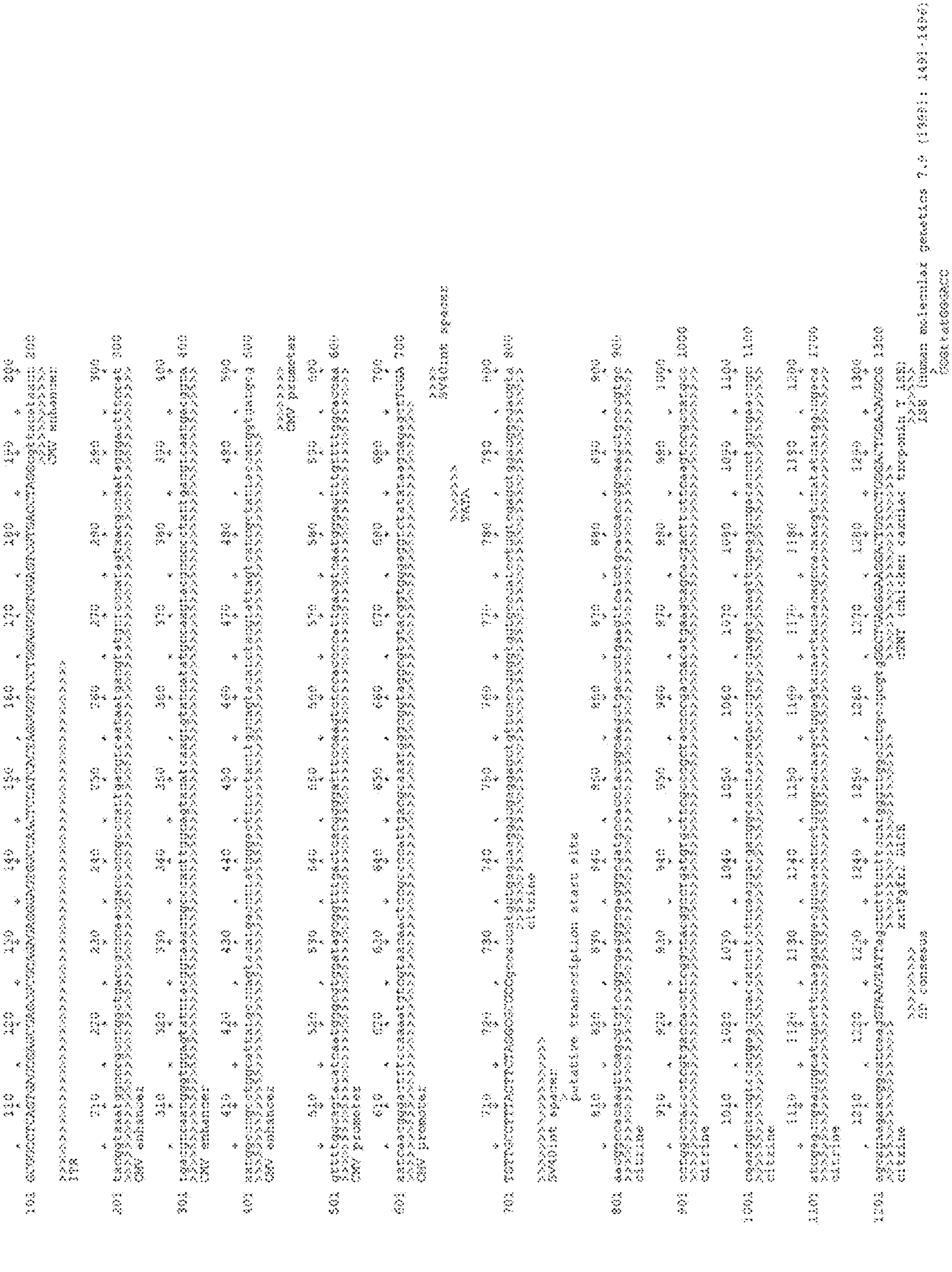

SEQ ID NO: 7 is an exemplary synthetic intron dimerization domain (FIG. 10E).

SEQ ID NO: 8 is an exemplary synthetic intron without intronic splicing enhancers (FIG. 10F).

SEQ ID NO: 9 is an exemplary synthetic intron without intronic splicing enhancers (FIG. 10G).

SEQ ID NO: 10 is an exemplary synthetic intron without intronic splicing enhancers (FIG. 10H).

SEQ ID NO: 11 is an exemplary synthetic intron without binding domain (FIG. 10I).

SEQ ID NO: 12 is an exemplary synthetic intron with dimerization domain (FIG. 10J). SEQ ID NO: 13 is an exemplary synthetic intron with dimerization domain (FIG. 10K).

SEQ ID NO: 14 is an exemplary synthetic intron without intronic splicing enhancers (FIG. 10L).

SEQ ID NO: 15 is an exemplary synthetic intron with DISE only (FIG. 10M).

SEQ ID NO: 16 is an exemplary synthetic intron without HHrz (FIG. 10N).

SEQ ID NO: 17 is an exemplary synthetic intron without intronic splicing enhancers (FIG. 10O).

SEQ ID NO: 18 is an exemplary U12 dependent intron with binding domain (FIG. 10P).

SEQ ID NO: 19 is an exemplary U12 dependent intron with binding domain (FIG. 10Q).

SEQ ID NOS: 20 and 21 are the N- and C-terminal sequences, respectively, used to express full-length Abca4. In SEQ ID NO: 20, N-terminal Abca4 coding region nt 22 to 3702 and nt 3703 to 3975 is the synthetic intron. In SEQ ID NO: 21, nt 1 to 228 is the synthetic intron, nt 229 to 3366 C-terminal Abca4 coding region, and nt 3367 to 3611 is the untranslated poly A region.

SEQ ID NOS: 22 and 23 are the N- and C-terminal sequences, respectively, used to express a long full-length YFP, wherein each includes splice enhancers. In SEQ ID NO: 22, N-terminal YFP coding region nt 22 to 3702 and nt 3703 to 3975 is the synthetic intron. In SEQ ID NO: 23, nt 1 to 225 is the synthetic intron, nt 226 to 3747 C-terminal YFP coding region, nt 3748 to 3912 is the untranslated poly A region.

SEQ ID NOS: 24 and 25 are the N- and C-terminal sequences, respectively, used to express full-length human Factor VIII. In SEQ ID NO: 24, N-terminal FVIII coding region nt 22 to 3559 and nt 3560 to 3828 is the synthetic intron. In SEQ ID NO: 25, nt 1 to 225 is the synthetic intron, nt 226 to 3636 C-terminal FVIII coding region, and nt 3637 to 3802 is the untranslated poly A region.

Figure 6A:
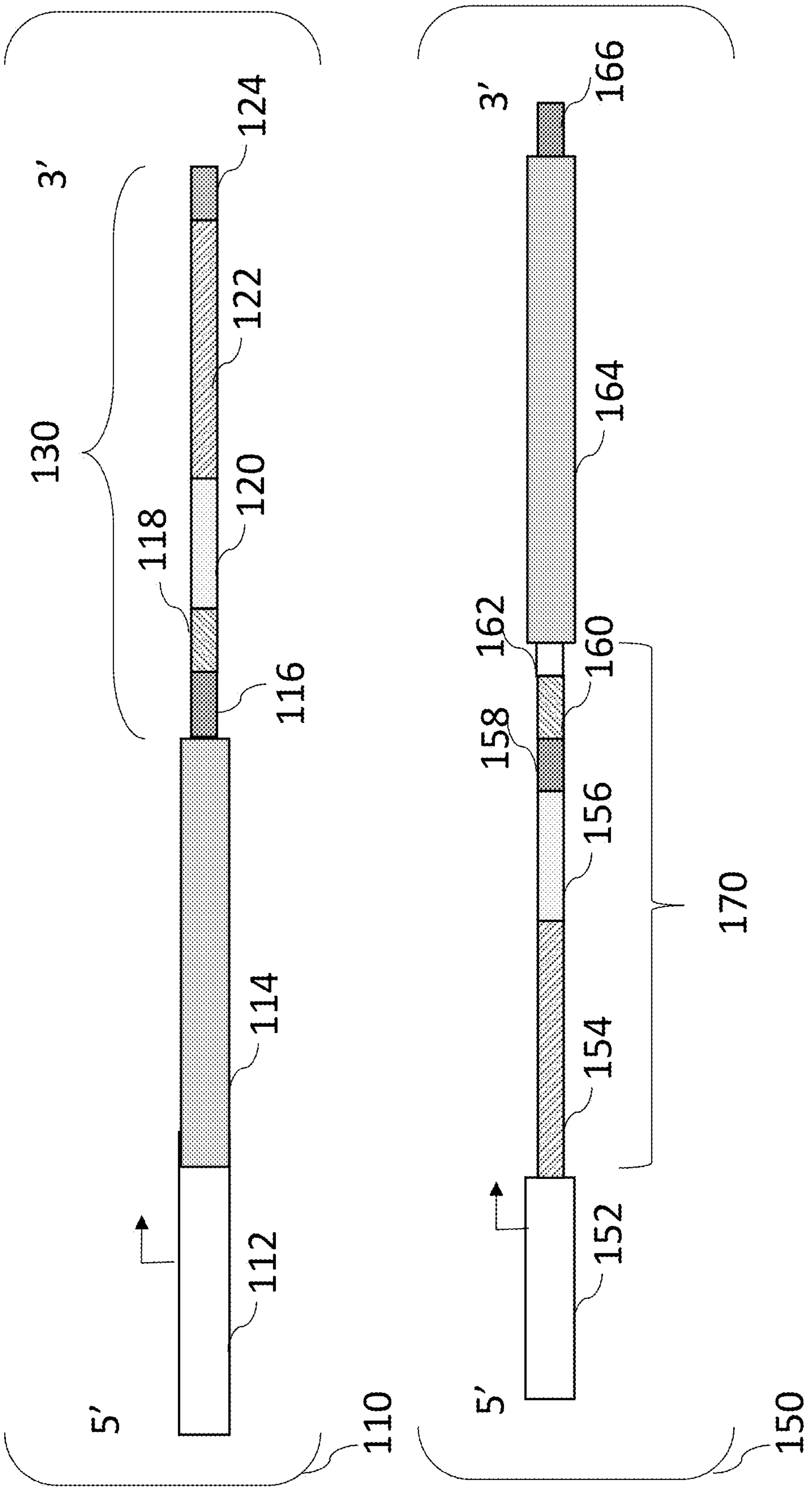
FIG. 6A is a schematic drawing providing an exemplary system for the disclosed RNA recombination methods, using two nucleic acid molecules 110, 150, wherein the target protein is divided into two portions and each portion is encoded by a different nucleic acid molecule. Drawing not to scale.

SEQ ID NOS: 26-136 are exemplary splicing enhancers that can be used with the systems provided herein (e.g., 118, 120, 156 of FIG. 6A).

SEQ ID NOS: 137 and 138 are exemplary splice donor sequences.

SEQ ID NOS: 139 and 140 are the N- and C-fragment respectively, of an HIV-1 based kissing loop dimerization domain.

SEQ ID NOS: 141 and 142 are the N- and C-fragment, respectively, of an HIV-2 based kissing loop dimerization domain.

SEQ ID NO: 143 is an exemplary cryptic splice acceptor sequence.

SEQ ID NO: 144 is an exemplary branch point consensus sequence.

SEQ ID NOS: 145 and 146 are the N- and middle sequences, respectively, used to express a long full-length YFP, along with SEQ ID NO: 2 (C-terminal fragment). In SEQ ID NO: 145, nt 1 to 543 is the CMV promoter sequence, nt 544 to 849 N-terminal YFP coding region, and nt 850 to 1305 is the synthetic intron. In SEQ ID NO: 146, nt 1 to 522 is the CMV promoter sequence, nt 523 to 901 is the synthetic intron, nt 902 to 1084 is the middle YFP coding region, and nt 1085 to 1543 is the untranslated poly A region.

SEQ ID NOS: 147 and 148 are the 5' and 3'-synthetic sequences, respectively, used to express a long full-length Flpo. In SEQ ID NO: 147, nt 1 to 540 is the CMV promoter sequence, nt 541 to 1112 N-terminal Flpo coding region, and nt 1113 to 1571 is the synthetic intron. In SEQ ID NO: 148, nt 1 to 522 is the CMV promoter sequence, nt 523 to 904 is the synthetic intron, nt 905 to 1604 is the C-terminal Flpo coding region, nt 1605 to 1765 is the untranslated poly A region.

SEQ ID NOS: 149 and 150 are exemplary hypodiverse sequences.

SEQ ID NOS: 151 and 152 are exemplary splice donor consensus sequences.

SEQ ID NO: 153 is an exemplary kissing loop based on the HIV-2 kissing loop dimerization domain (SEQ ID NOS: 141 and 142, FIG. 17B).

SEQ ID NO: 154 is an exemplary Kozak enhanced start codon.

DETAILED DESCRIPTION

Unless otherwise noted, technical terms are used according to conventional usage. Definitions of common terms in molecular biology can be found in Benjamin Lewin, Genes VII, published by Oxford University Press, 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. As used herein, the term "comprises" means "includes." Thus, "comprising a nucleic acid molecule" means "including a nucleic acid molecule" without excluding other elements. It is further to be understood that any and all base sizes given for nucleic acids are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. All references, including patent applications and patents, are herein incorporated by reference in their entireties.

In order to facilitate review of the various embodiments of the disclosure, the following explanations of specific terms are provided:

Administration: To provide or give a subject an agent, such as a therapeutic nucleic acid molecule provided herein, or other therapeutic agent, by any effective route. Exemplary routes of administration include, but are not limited to, injection (such as subcutaneous, intramuscular, intradermal, intraperitoneal, intrathecal, intratumoral, intraosseous, and intravenous), transdermal, intranasal, and inhalation routes. Administration can be systemic or local.

Aptamer: Nucleic acid molecules (such as DNA or RNA) that bind a specific target agent with high affinity and specificity. Aptamers can be used in the disclosed nucleic acid molecules as a dimerization domain, for example to allow RNA recombination only in the presence of one or more targets recognized by the aptamer. Aptamers have been obtained through a combinatorial selection process called systematic evolution of ligands by exponential enrichment (SELEX) (see for example Ellington et al., *Nature* 1990, 346, 818-822; Tuerk and Gold *Science* 1990, 249, 505-510; Liu et al., *Chem. Rev.* 2009, 109, 1948-1998; Shamah et al., *Acc. Chem. Res.* 2008, 41, 130-138; Famulok, et al., *Chem. Rev.* 2007, 107, 3715-3743; Manimala et al., *Recent Dev. Nucleic Acids Res.* 2004, 1, 207-231; Famulok et al., *Acc. Chem. Res.* 2000, 33, 591-599; Hesselberth, et al., *Rev. Mol. Biotech.* 2000, 74, 15-25; Wilson et al., *Annu. Rev. Biochem.* 1999, 68, 611-647; Morris et al., *Proc. Natl. Acad. Sci. U.S.A.* 1998, 95, 2902-2907). In such a process, DNA or RNA molecules that are capable of binding a target molecule of interest are selected from a nucleic acid library consisting of $10^{14}$-$10^{15}$ different sequences through iterative steps of selection, amplification and mutation. The affinity of the aptamers towards their targets can rival that of antibodies, with dissociation constants in as low as the picomolar range (Morris et al., *Proc. Natl. Acad. Sci. U.S.A.* 1998, 95, 2902-2907; Green et al., *Biochemistry* 1996, 35, 14413-14424).

Aptamers that are specific to a wide range of targets from small organic molecules such as adenosine, to proteins such as thrombin, and even viruses and cells have been identified (Liu et al., *Chem. Rev.* 2009, 109, 1948-1998; Lee et al., *Nucleic Acids Res.* 2004, 32, D95-D100; Navani and Li, *Curr. Opin. Chem. Biol.* 2006, 10, 272-281; Song et al., TrAC, *Trends Anal. Chem.* 2008, 27, 108-117). For example, aptamers are available that recognize metal ions such as Zn(II) (Ciesiolka et al., *RNA* 1: 538-550, 1995) and Ni(II) (Hofmann et al., *RNA,* 3:1289-1300, 1997); nucleotides such as adenosine triphosphate (ATP) (Huizenga and Szostak, *Biochemistry,* 34:656-665, 1995); and guanine (Kiga et al., *Nucleic Acids Res.,* 26:1755-60, 1998); co-factors such as NAD (Kiga et al., *Nucleic Acids Res.,* 26:1755-60, 1998) and flavin (Lauhon and Szostak, *J. Am. Chem. Soc.,* 117: 1246-57, 1995); antibiotics such as viomycin (Wallis et al., *Chem. Biol.* 4: 357-366, 1997) and streptomycin (Wallace and Schroeder, *RNA* 4:112-123, 1998); proteins such as HIV reverse transcriptase (Chaloin et al., *Nucleic Acids Res.,* 30:4001-8, 2002) and hepatitis C virus RNA-dependent RNA polymerase (Biroccio et al., *J. Virol.* 76:3688-96, 2002); toxins such as cholera whole toxin and staphylococcal enterotoxin B (Bruno and Kiel, *BioTechniques,* 32: pp. 178-180 and 182-183, 2002); and bacterial spores such as the anthrax (Bruno and Kiel, *Biosensors & Bioelectronics,* 14:457-464, 1999).

Binding: An association between two substances or molecules, such as the hybridization of one nucleic acid molecule to another (or itself), such as between two dimerization domains, or the binding of an aptamer to its target. An oligonucleotide molecule binds or stably binds to another nucleic acid molecule if there are a sufficient number of complementary base pairs between the oligonucleotide molecule and the target nucleic acid to permit detection of that binding.

C-terminal portion: A region of a protein sequence that includes a contiguous stretch of amino acids that begins at or near the C-terminal residue of the protein. A C-terminal portion of the protein can be defined by a contiguous stretch of amino acids (e.g., a number of amino acid residues).

Cancer: A malignant tumor characterized by abnormal or uncontrolled cell growth. Other features often associated with cancer include metastasis, interference with the normal functioning of neighboring cells, release of cytokines or other secretory products at abnormal levels and suppression or aggravation of inflammatory or immunological response, invasion of surrounding or distant tissues or organs, such as lymph nodes, etc. "Metastatic disease" refers to cancer cells that have left the original tumor site and migrate to other parts of the body for example via the bloodstream or lymph system.

Complementarity: The ability of a nucleic acid to form hydrogen bond(s) with another nucleic acid sequence by either traditional Watson-Crick base pairing or other nontraditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions. Thus, in some examples, a first dimerization domain and a second dimerization domain have perfect complementary to one another (e.g., 100%). In other examples, a first dimerization domain and a second dimerization domain are substantially complementary to one another (e.g., at least 80%).

Contact: Placement in direct physical association, including a solid or a liquid form. Contacting can occur in vitro or ex vivo, for example, by adding a reagent to a sample (such as one containing cells), or in vivo by administering to a subject.

Downregulated or knocked down: When used in reference to the expression of a molecule, such as a target nucleic acid or protein, refers to any process which results in a decrease in production of the target RNA or protein, but in some examples not complete elimination of the target RNA product or target RNA function. In one example, downregulation or knock down does not result in complete elimination of detectable target nucleic acid/protein expression or activity. In some examples, downregulation or knock down of a target nucleic acid includes processes that decrease translation of the target RNA and thus can decrease the presence of corresponding proteins. The disclosed system can be used to downregulate any target nucleic acid/protein of interest.

Downregulation or knock down includes any detectable decrease in the target nucleic acid/protein. In certain examples, detectable target nucleic acid/protein in a cell or cell free system decreases by at least 10%, at least 20%, at least 30%, at least 40%, at least 50%, at least 60%, at least 70%, at least 75%, at least 80%, at least 90%, at least 95%, at least 96%, at least 97%, at least 98%, or at least 99% (such as a decrease of 40% to 90%, 40% to 80% or 50% to 95%) as compared to a control (such an amount of target nucleic acid/protein detected in a corresponding untreated cell or sample). In one example, a control is a relative amount of expression in a normal cell (e.g., a non-recombinant cell that does not include a nucleic acid molecule for RNA recombination provided herein).

Effective amount: The amount of an agent (such as a system providing multiple vectors, each encoding a different portion of a therapeutic protein, such as dystrophin) that is sufficient to effect beneficial or desired results. An effective amount also can refer to an amount of correctly joined RNA or therapeutic protein produced that is sufficient to effect beneficial or desired results.

An effective amount (also referred to as a therapeutically effective amount) may vary depending upon one or more of: the subject and disease condition being treated, the weight and age of the subject, the severity of the disease condition, the manner of administration and the like, which can be determined by one of ordinary skill in the art. The beneficial therapeutic effect can include enablement of diagnostic determinations; amelioration of a disease, symptom, disorder, or pathological condition; reducing or preventing the onset of a disease, symptom, disorder or condition; and generally counteracting a disease, symptom, disorder or pathological condition.

In one embodiment, an "effective amount" of two or more synthetic nucleic acid molecules provided herein, sufficient to treat a disease, such as a genetic disease or cancer. In one embodiment, an "effective amount" of two or more synthetic nucleic acid molecules provided herein is amount sufficient to increase the survival time of a treated patient, for example by at least 10%, at least 20%, at least 25%, at least 50%, at least 70%, at least 75%, at least 80%, at least 90%, at least 95%, at least 99%, at least 100%, at least 200%, at least 300%, at least 400%, at least 500%, or at least 600% (as compared to no administration of the two or more synthetic nucleic acid molecules provided herein). In one embodiment, an "effective amount" of two or more synthetic nucleic acid molecules provided herein is an amount sufficient to increase the survival time of a treated patient, for example by at least 6 months, at least 9 months, at least 1 year, at least 1.5 years, at least 2 years, at least 2.5 years, at least 3 years, at least 4 years, at least 5 years, at least 10 years, at least 12 years, at least 15 years, or at least 20 years (as compared to no administration of the two or more synthetic nucleic acid molecules provided herein). In one embodiment, an "effective amount" of two or more synthetic nucleic acid molecules provided herein is an amount sufficient to increase mobility of a treated patient (such as a DMD patient), for example by at least 10%, at least 20%, at least 25%, at least 50%, at least 70%, at least 75%, at least 80%, at least 90%, at least 95%, at least 99%, at least 100%, at least 200%, at least 300%, at least 400%, at least 500%, or at least 600% (as compared to no administration of the two or more synthetic nucleic acid molecules provided herein). In one embodiment, an "effective amount" of two or more synthetic nucleic acid molecules provided herein is an amount sufficient to increase mobility of a treated patient (such as a DMD patient), for example by at least 10%, at least 20%, at least 25%, at least 50%, at least 70%, at least 75%, at least 80%, at least 90%, at least 95%, at least 99%, at least 100%, at least 200%, at least 300%, at least 400%, at least 500%, or at least 600% (as compared to no administration of the two or more synthetic nucleic acid molecules provided herein). In one embodiment, an "effective amount" of two or more synthetic nucleic acid molecules provided herein is an amount sufficient to increase cognitive ability of a treated patient (such as a DMD patient), for example by at least 10%, at least 20%, at least 25%, at least 50%, at least 70%, at least 75%, at least 80%, at least 90%, at least 95%, at least 99%, at least 100%, at least 200%, at least 300%, at least 400%, at least 500%, or at least 600% (as compared to no administration of the two or more synthetic nucleic acid molecules provided herein). In one embodiment, an "effective amount" of two or more synthetic nucleic acid molecules provided herein is an amount sufficient to increase respiratory function of a treated patient (such as a DMD patient), for example by at least 10%, at least 20%, at least 25%, at least 50%, at least 70%, at least 75%, at least 80%, at least 90%, at least 95%, at least 99%, at least 100%, at least 200%, at least 300%, at least 400%, at least 500%, or at least 600% (as compared to no administration of the two or more synthetic nucleic acid molecules provided herein). In one embodiment, an "effective amount" of two or more synthetic nucleic acid molecules provided herein is an amount sufficient to increase blood clotting of a treated patient (such as a hemophilia patient), for example by at least 10%, at least 20%, at least 25%, at least 50%, at least 70%, at least 75%, at least 80%, at least 90%, at least 95%, at least 99%, at least 100%, at least 200%, at least 300%, at least 400%, at least 500%, or at least 600% (as compared to no administration of the two or more synthetic nucleic acid molecules provided herein). In one embodiment, an "effective amount" of two or more synthetic nucleic acid molecules provided herein is an amount sufficient to increase vision of a treated patient (such as a Usher or Stargardt patient), for example by at least 10%, at least 20%, at least 25%, at least 50%, at least 70%, at least 75%, at least 80%, at least 90%, at least 95%, at least 99%, at least 100%, at least 200%, at least 300%, at least 400%, at least 500%, or at least 600% (as compared to no administration of the two or more synthetic nucleic acid molecules provided herein). In one embodiment, an "effective amount" of two or more synthetic nucleic acid molecules provided herein is an amount sufficient to increase hearing of a treated patient (such as a Usher patient), for example by at least 10%, at least 20%, at least 25%, at least 50%, at least 70%, at least 75%, at least 80%, at least 90%, at least 95%, at least 99%, at least 100%, at least 200%, at least 300%, at least 400%, at least 500%, or at least 600% (as compared to no administration of the two or more synthetic nucleic acid molecules provided herein).

In one embodiment, an "effective amount" of two or more synthetic nucleic acid molecules provided herein is an amount sufficient to reduce calf muscle size of a treated DMD patient, for example by at least 10%, at least 20%, at least 25%, at least 50%, at least 70%, at least 75%, at least 80%, at least 90%, or at least 95% (as compared to no administration of the two or more synthetic nucleic acid molecules provided herein). In one embodiment, an "effective amount" of two or more synthetic nucleic acid molecules provided herein is an amount sufficient to reduce cardiomyopathy muscle size of a treated DMD patient, for example by at least 10%, at least 20%, at least 25%, at least 50%, at least 70%, at least 75%, at least 80%, at least 90%, or at least 95% (as compared to no administration of the two or more synthetic nucleic acid molecules provided herein). In some examples, combinations of these effects are achieved.

Increase or Decrease: A statistically significant positive or negative change, respectively, in quantity from a control value (such as a value representing no therapeutic agent, such as no administration of the two or more synthetic nucleic acid molecules provided herein). An increase is a positive change, such as an increase at least 50%, at least 100%, at least 200%, at least 300%, at least 400% or at least 500% as compared to the control value. A decrease is a negative change, such as a decrease of at least 20%, at least 25%, at least 50%, at least 75%, at least 80%, at least 90%, at least 95%, at least 98%, at least 99%, or at least 100% decrease as compared to a control value. In some examples the decrease is less than 100%, such as a decrease of no more than 90%, no more than 95%, or no more than 99%.

Hybridization: Hybridization of a nucleic acid occurs when two nucleic acid molecules undergo an amount of hydrogen bonding to each other. The stringency of hybridization can vary according to the environmental conditions surrounding the nucleic acids, the nature of the hybridization method, and the composition and length of the nucleic acids used. Calculations regarding hybridization conditions required for attaining particular degrees of stringency are discussed in Sambrook et al., *Molecular Cloning: A Laboratory Manual* (Cold Spring Harbor Laboratory Press, Cold Spring Harbor, N.Y., 2001); and Tijssen, *Laboratory Techniques in Biochemistry and Molecular Biology—Hybridization with Nucleic Acid Probes* Part I, Chapter 2 (Elsevier, New York, 1993). The $T_m$ is the temperature at which 50% of a given strand of nucleic acid is hybridized to its complementary strand.

Isolated: An "isolated" biological component (such as a nucleic acid molecule or a protein) has been substantially separated, produced apart from, or purified away from other biological components in the cell or tissue of an organism in which the component occurs, such as other cells (e.g., RBCs), chromosomal and extrachromosomal DNA and RNA, and proteins. Nucleic acids and proteins that have been "isolated" include nucleic acids and proteins purified by standard purification methods. The term also embraces nucleic acids and proteins prepared by recombinant expression in a host cell as well as chemically synthesized nucleic acids and proteins.

Kissing loop/kissing stem loop: An RNA structure that forms when bases between two hairpin loops form pair interactions. These intermolecular "kissing interactions" occur when the unpaired nucleotides in one hairpin loop, base pair with the unpaired nucleotides in another hairpin loop to form a stable interaction complex. See FIG. 9A for an example.

N-terminal portion: A region of a protein sequence that includes a contiguous stretch of amino acids that begins at the N-terminal residue of the protein. An N-terminal portion of the protein can be defined by a contiguous stretch of amino acids (e.g., a number of amino acid residues).

Non-naturally occurring, synthetic, or engineered: Terms used herein as interchangeably and indicate the involvement of the hand of man. The terms, when referring to nucleic acid molecules or polypeptides indicate that the nucleic acid molecule or the polypeptide is at least substantially free from at least one other component with which they are naturally associated in nature and as found in nature. In addition, the terms can indicate that the nucleic acid molecules or polypeptides have a sequence not found in nature.

Nucleic acid molecule: A deoxyribonucleotide (DNA) or ribonucleotide (RNA) polymer, which can include natural nucleotides/ribonucleotides and/or analogues of natural nucleotides/ribonucleotides that hybridize to nucleic acid molecules in a manner similar to naturally occurring nucleotides. A nucleic acid molecule can be a single stranded (ss) DNA or RNA molecule or a double stranded (ds) nucleic acid molecule.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence (such as a portion of a DMD, factor 8, factor 9, or ABCA4 coding sequence). Generally, operably linked DNA sequences are contiguous and, where necessary to join two protein coding regions, in the same reading frame.

Pharmaceutically acceptable carriers: The pharmaceutically acceptable carriers useful in this invention are conventional. *Remington's Pharmaceutical Sciences*, by E. W. Martin, Mack Publishing Co., Easton, PA, 15th Edition (1975), describes compositions and formulations suitable for pharmaceutical delivery of a therapeutic agent, such as a nucleic acid molecule disclosed herein.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide, peptide and protein: Refer to polymers of amino acids of any length. The polymer may be linear or branched, it may include modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics. In one example, a protein is one associated with disease, such as a genetic disease (e.g., see Table 1). In one example, a protein is a therapeutic protein, such as one used in the treatment of a disease, such as cancer. In one example a protein is at least 50 aa in length, at least 100 aa in length, at least 500 aa in length, at least 1000 aa in length, at least 1500 aa in length, such as at least 2000 aa, at least 2500 aa, at least 3000 aa, or at least 5000 aa.

Polypyrimidine tract: A region of pre-messenger RNA (mRNA) that promotes the assembly of the spliceosome, the protein complex specialized for carrying out RNA splicing during the process of post-transcriptional modification. This tract can be primarily pyrimidine nucleotides, such as uracil, and in some examples is 15-20 base pairs long, located about 5-40 base pairs before the 3' end of the intron to be spliced.

Promoter/Enhancer: An array of nucleic acid control sequences which direct transcription of a nucleic acid. A promoter includes necessary nucleic acid sequences near the start site of transcription, such as, in the case of a polymerase II type promoter, a TATA element. A promoter also optionally includes distal enhancer or repressor elements which can be located as much as several thousand base pairs from the start site of transcription. In some examples a promoter sequence+its corresponding coding sequence is larger than the capacity for an AAV. In some examples a promoter sequence of a target protein is at least 3500 nt, at least 4000 nt, at least 5000 nt, or even at least 6000 nt.

A "constitutive promoter" is a promoter that is continuously active and is not subject to regulation by external signals or molecules. In contrast, the activity of an "inducible promoter" is regulated by an external signal or molecule (for example, a transcription factor). Both constitutive and inducible promoters can be used in the methods and systems provided herein (see e.g., Bitter et al., *Methods in Enzymology* 153:516-544, 1987). A tissue-specific promoter can be used in the methods and systems provided herein, for example to direct expression primarily in a desired tissue or cell of interest, such as muscle, neuron, bone, skin, blood, specific organs (e.g., liver, pancreas), or particular cell types (e.g., lymphocytes). In some examples, a promoter used herein is endogenous to the target protein expressed. In some examples, a promoter used herein is exogenous to the target protein expressed.

Also included are promoter elements which are sufficient to render promoter-dependent gene expression controllable for cell-type specific, tissue-specific, or inducible by external signals or agents; such elements may be located in the 5' or 3' regions of the gene. Promoters produced by recombinant DNA or synthetic techniques can also be used to provide for transcription of the nucleic acid sequences.

Exemplary promoters that can be used with the methods and systems provided herein include, but are not limited to an SV40 promoter, cytomegalovirus (CMV) promoter (optionally with the CMV enhancer), a pol III promoter (e.g., U6 and H1 promoters), a pol II promoter (e.g., the retroviral Rous sarcoma virus (RSV) LTR promoter (optionally with the RSV enhancer), the dihydrofolate reductase promoter, the β-actin promoter, the phosphoglycerol kinase (PGK) promoter, and the EF1α promoter).

Recombinant: A recombinant nucleic acid molecule or protein sequence is one that has a sequence that is not naturally occurring or has a sequence that is made by an artificial combination of two otherwise separated segments of sequence (e.g., a viral vector that includes a portion of a dystrophin coding sequence, such as about a third, half, or two-thirds of a coding sequence). This artificial combination can be accomplished by, for example, chemical synthesis or the artificial manipulation of isolated segments of nucleic acids, such as by genetic engineering techniques. Similarly, a recombinant or transgenic cell is one that contains a recombinant nucleic acid molecule.

Sequence identity: The similarity between amino acid (or nucleotide) sequences is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are known. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, MD) and on the internet, for use in connection with the sequence analysis programs blastp, blastn, blastx, tblastn and tblastx. A description of how to determine sequence identity using this program is available on the NCBI website on the internet.

Variants of a native protein or coding sequence (such as a DMD, factor 8, factor 9, or ABCA4 sequence) are typically characterized by possession of at least about 80%, at least 90%, at least 95%, at least 96%, at least 97%, at least 98% or at least 99% sequence identity counted over the full length alignment with the amino acid sequence using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or at least 95% depending on their similarity to the reference sequence. Methods for determining sequence identity over such short windows are available at the NCBI website on the internet. These sequence identity ranges are provided for guidance only; it is possible that strongly significant homologs could be obtained that fall outside of the ranges provided.

Variants of the disclosed nucleic acid sequences (such as synthetic intron sequences and coding sequences) are typically characterized by possession of at least about 80%, at least 90%, at least 95%, at least 96%, at least 97%, at least 98% or at least 99% sequence identity counted over the full length alignment with the nucleic acid sequence using the NCBI Blast 2.0, gapped blastn set to default parameters. One of skill in the art will appreciate that these sequence identity ranges are provided for guidance only; it is possible that functional sequences could be obtained that fall outside of the ranges provided.

Subject: A mammal, for example a human. Mammals include, but are not limited to, murines, simians, humans, farm animals, sport animals, and pets. In one embodiment, the subject is a non-human mammalian subject, such as a monkey or other non-human primate, mouse, rat, rabbit, pig, goat, sheep, dolphin, dog, cat, horse, or cow. In some examples, the subject is a laboratory animal/organism, such as a mouse, rabbit, or rat. In some examples, the subject treated using the methods disclosed herein is a human.

In some examples, the subject has genetic disease, such as one listed in Table 1, that can be treated using the methods disclosed herein. In some examples, the subject treated using the methods disclosed herein is a human subject having a genetic disease. In some examples, the subject treated using the methods disclosed herein is a human subject having cancer Therapeutic agent: Refers to one or more molecules or compounds that confer some beneficial effect upon administration to a subject. The disclosed synthetic nucleic acid molecules and systems provided herein are therapeutic agents. The beneficial therapeutic effect can include enablement of diagnostic determinations; amelioration of a disease, symptom, disorder, or pathological condition; reducing or preventing the onset of a disease, symptom, disorder or condition; and generally counteracting a disease, symptom, disorder or pathological condition.

Transduced, Transformed and Transfected: A virus or vector "transduces" a cell when it transfers nucleic acid molecules into a cell. A cell is "transformed" or "transfected" by a nucleic acid transduced into the cell when the nucleic acid becomes stably replicated by the cell, either by incorporation of the nucleic acid into the cellular genome, or by episomal replication.

These terms encompasses all techniques by which a nucleic acid molecule can be introduced into such a cell, including transfection with viral vectors, transformation with plasmid vectors, and introduction of naked DNA by electroporation, lipofection, particle gun acceleration and other methods in the art. In some example the method is a chemical method (e.g., calcium-phosphate transfection), physical method (e.g., electroporation, microinjection, particle bombardment), fusion (e.g., liposomes), receptor-mediated endocytosis (e.g., DNA-protein complexes, viral envelope/capsid-DNA complexes) and biological infection by viruses such as recombinant viruses (Wolff, J. A., ed, *Gene Therapeutics*, Birkhauser, Boston, USA, 1994). Methods for the introduction of nucleic acid molecules into cells are known (e.g., see U.S. Pat. No. 6,110,743). These methods can be used to transduce a cell with the disclosed nucleic acid molecules.

Transgene: An exogenous gene, for example supplied by a vector, such as AAV. In one example, a transgene encodes a portion of a target protein, such as about a third, half, or two-thirds of a target protein, for example operably linked to a promoter sequence. In one example, a transgene includes a portion of a dystrophin coding sequence, such as about a third, half, or two-thirds of a dystrophin coding sequence (or other therapeutic coding sequence, such as one encoding a protein listed in Table 1), for example operably linked to a promoter sequence.

Treating, Treatment, and Therapy: Any success or indicia of success in the attenuation or amelioration of an injury, pathology or condition, including any objective or subjective parameter such as abatement, remission, diminishing of symptoms or making the condition more tolerable to the patient, slowing in the rate of degeneration or decline, making the final point of degeneration less debilitating, improving a subject's physical or mental well-being, or prolonging the length of survival. The treatment may be assessed by objective or subjective parameters; including the results of a physical examination, blood and other clinical tests, and the like. In some examples, treatment with the disclosed methods results in a decrease in the number or severity of symptoms associated with a genetic disease, such as increasing the survival time of a treated patient with the genetic disease.

In some examples, treatment with the disclosed methods results in a decrease in the number or severity of symptoms associated with DMD or other genetic disease, such as increasing survival, increasing the mobility (e.g., walking, climbing), improving cognitive ability, reducing calf muscle size, reduce cardiomyopathy, improving vision, improving hearing, improving blood clotting, or improve respiratory function. In some examples, combinations of these effects are achieved.

Tumor, neoplasia, malignancy or cancer: A neoplasm is an abnormal growth of tissue or cells which results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." A "non-cancerous tissue" is a tissue from the same organ wherein the malignant neoplasm formed, but does not have the characteristic pathology of the neoplasm. Generally, noncancerous tissue appears histologically normal. A "normal tissue" is tissue from an organ, wherein the organ is not affected by cancer or another disease or disorder of that organ. A "cancer-free" subject has not been diagnosed with a cancer of that organ and does not have detectable cancer.

Exemplary tumors, such as cancers, that can be treated with the disclosed methods and systems include solid tumors, such as breast carcinomas (e.g. lobular and duct carcinomas), sarcomas, carcinomas of the lung (e.g., non-small cell carcinoma, large cell carcinoma, squamous carcinoma, and adenocarcinoma), mesothelioma of the lung, colorectal adenocarcinoma, stomach carcinoma, prostatic adenocarcinoma, ovarian carcinoma (such as serous cystadenocarcinoma and mucinous cystadenocarcinoma), ovarian germ cell tumors, testicular carcinomas and germ cell tumors, pancreatic adenocarcinoma, biliary adenocarcinoma, hepatocellular carcinoma, bladder carcinoma (including, for instance, transitional cell carcinoma, adenocarcinoma, and squamous carcinoma), renal cell adenocarcinoma, endometrial carcinomas (including, e.g., adenocarcinomas and mixed Mullerian tumors (carcinosarcomas)), carcinomas of the endocervix, ectocervix, and vagina (such as adenocarcinoma and squamous carcinoma of each of same), tumors of the skin (e.g., squamous cell carcinoma, basal cell carcinoma, malignant melanoma, skin appendage tumors, Kaposi sarcoma, cutaneous lymphoma, skin adnexal tumors and various types of sarcomas and Merkel cell carcinoma), esophageal carcinoma, carcinomas of the nasopharynx and oropharynx (including squamous carcinoma and adenocarcinomas of same), salivary gland carcinomas, brain and central nervous system tumors (including, for example, tumors of glial, neuronal, and meningeal origin), tumors of peripheral nerve, soft tissue sarcomas and sarcomas of bone and cartilage, and lymphatic tumors (including B-cell and T-cell malignant lymphoma). In one example, the tumor is an adenocarcinoma.

The methods and systems can also be used to treat liquid tumors, such as a lymphatic, white blood cell, or other type of leukemia. In a specific example, the tumor treated is a tumor of the blood, such as a leukemia (for example acute lymphoblastic leukemia (ALL), chronic lymphocytic leukemia (CLL), acute myelogenous leukemia (AML), chronic myelogenous leukemia (CML), hairy cell leukemia (HCL), T-cell prolymphocytic leukemia (T-PLL), large granular lymphocytic leukemia, and adult T-cell leukemia), lymphomas (such as Hodgkin's lymphoma and non-Hodgkin's lymphoma), and myelomas).

Upregulated: When used in reference to the expression of a molecule, such as a target nucleic acid/protein, refers to any process which results in an increase in production of the target nucleic acid/protein. In some examples, upregulation or activation of a target RNA includes processes that increase translation of the target RNA and thus can increase the presence of corresponding proteins.

Upregulation includes any detectable increase in target nucleic acid/protein. In certain examples, detectable target nucleic acid/protein expression in a cell or cell free system increases by at least 20%, at least 30%, at least 40%, at least 50%, at least 60%, at least 70%, at least 75%, at least 80%, at least 90%, at least 95%, at least 100%, at least 200%, at least 400%, or at least 500% as compared to a control (such an amount of target nucleic acid/protein detected in a corresponding sample not treated with a nucleic acid molecule provided herein). In one example, a control is a relative amount of expression in a normal cell (e.g., a non-recombinant cell that does not include a system provided herein).

Under conditions sufficient for: A phrase that is used to describe any environment that permits a desired activity. In one example the desired activity is increased expression or activity of a protein needed to treat a disease. In one example the desired activity is treatment of or slowing the progression of a genetic disease such as DMD (or other genetic disease listed in Table 1) in vivo, for example using the disclosed methods and systems.

Vector: A nucleic acid molecule into which a foreign nucleic acid molecule can be introduced without disrupting the ability of the vector to replicate and/or integrate in a host cell. Vectors include, but are not limited to, nucleic acid molecules that are single-stranded, double-stranded, or partially double-stranded; nucleic acid molecules that comprise one or more free ends, no free ends (e.g., circular); nucleic acid molecules that comprise DNA, RNA, or both; and other varieties of polynucleotides.

A vector can include nucleic acid sequences that permit it to replicate in a host cell, such as an origin of replication. A vector can also include one or more selectable marker genes and other genetic elements. An integrating vector is capable of integrating itself into a host nucleic acid. An expression vector is a vector that contains the necessary regulatory sequences to allow transcription and translation of inserted gene or genes.

One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses). Viral vectors also include polynucleotides carried by a virus for transfection into a host cell. In some embodiments, the vector is a lentivirus (such as an integration-deficient lentiviral vector) or adeno-associated viral (AAV) vector.

In some embodiments, the vector is an AAV, such as AAV serotypes AAV9 or AAVrh.10. In some embodiments, the vector is one that can penetrate the blood-brain barrier, for example following intravenous administration. The adeno-associated virus serotype rh.10 (AAV.rh10) vector partially penetrates the blood-brain barrier, providing high levels and spread of transgene expression.

II. Overview of Several Embodiments

One approach to curing patients who suffer from genetic diseases is gene replacement therapy (generally referred to as gene therapy). In such an approach, the defective gene is replaced by an intact version of it, delivered through e.g., a viral vector, which achieves sustained expression from months to years. Although adeno associated viruses (AAVs) have been used for clinical gene replacement therapy, they have a limited packaging capacity (e.g., about less than 5 kb). Thus, strategies to overcome this packaging limitation are needed to achieve gene replacement of genes that exceed the about 5 kb size limit. For example some promoters alone, coding sequences alone, or the combined promoter+coding sequence, exceed the about 5 kb size limit of an AAV. Thus, such proteins encoded by such promoters and coding sequences can be expressed using the disclosed systems.

Prior methods to overcome the cargo limitations of AAV do not appear to achieve the efficiency required to produce adequate levels of target protein in sufficient numbers of cells to treat disease. For example as dystrophin is about 11 kb, it needs to be delivered in a minimum of three fragments to be compatible with AAV packaging limitations.

Splicing mediated recombination of two RNA molecules using naturally occurring intron sequences for one or both of the RNA fragments is inefficient. First, these natural intron sequences are sequences from naturally occurring introns and are comprised of a mix of all four RNA nucleotides. Such sequences tend to fold up into structures that can obstruct trans-interaction by forming strong intramolecular base pairs rather than being available for intermolecular interactions. Second, these naturally occurring intron sequences have not evolved to strongly attract the spliceosome components, since exon rather than introns drive the exon definition in higher eukaryotes. These two limitations of previous strategies are addressed herein by designing synthetic intronic sequences that are not found in nature. These synthetic sequences contain elements that strongly attract and stimulate spliceosome recruitment on the one hand while minimizing the secondary structure (and in some examples other structure, such as tertiary structure) that obstructs bringing the two RNA fragments together.

The inventors developed a novel RNA based element that can be used to efficiently reconstitute the coding sequence of large genes from multiple serial fragments. The disclosed methods and systems differ from prior methods. The disclosed highly efficient synthetic introns utilize an optimal arrangement of RNA elements that efficiently drive the RNA splicing reaction between non-covalently linked RNAs. The method/system is a significant advancement over previous attempts to harness trans-splicing because it generates high levels of functional protein that more closely approximate the therapeutic levels of a protein to treat genetic diseases. The innovation is based on selecting non-natural RNA domains that inherently are incapable of forming strong cis-binding interactions that interfere with trans-interactions with a second RNA having a complementary strand (also having inherently low cis-binding capacity). These optimized dimerization domains are non-natural sequences (e.g., sequences are not found in human cells) used in combination with optimized motifs that facilitate RNA splicing (including splice donor, splice acceptor, splice enhancer, and splice branch point sequences). By optimizing the trans-dimerization of the RNA strands in the context of the appropriate RNA motifs that mediate efficient splicing, it is demonstrated herein for the first time that two or three different RNAs can be precisely and efficiently covalently linked in the same cell producing high levels of functional proteins in vivo and in vitro. Unlike the "hybrid" approach that provides an inefficient combination at the DNA level via DNA recombination that is ultimately followed by RNA splicing in cis to excise the DNA recombination site from the mature transcript, the disclosed method/system promotes a more efficient reaction in which two protein coding RNA fragments are joined together on the pre-mRNA level with less risk of producing recombination products that encode non-functional and/or deleterious products.

The data demonstrate that by using efficient synthetic RNA-dimerization and recombination domains (sRdR domains, also referred to as RNA end-joining (REJ) domains), a gene of interest can efficiently reconstitute from two or three separate gene fragments expressed in the same cell. These results show the ability of the disclosed methods and systems to reconstitute large genes like dystrophin or the blood clotting Factor VIII, or the ATP binding cassette subfamily A member 4 (Abca4) using AAVs, in order to treat Duchenne Muscular Dystrophy and Hemophilia A, or Stargardt's Disease respectively. Based on these observations, other genetic diseases can be similarly treated, such as ones benefiting from expression of a large protein (e.g., see disorders listed in Table 1). Other applications include research and biotechnology applications.

To address some of the limitations with existing strategies for reconstitution of fragmented genes from multiple AAVs, provided herein is a system that serially aligns and recombines two or more individual synthetic RNA molecules in the target cell. Each individual synthetic RNA molecule includes a synthetic intron sequence, containing a dimerization domain and elements needed for RNA splicing, which upon binding of dimerization domains to one another in the correct order, mediates efficient RNA recombination of individual fragments. In one example, reconstitution of a coding sequence from two fragments is achieved by appending a first synthetic intron (A) to the 3' end of the N-terminal coding fragment and a complimentary second synthetic domain (A') to the 5' end of the C-terminal coding fragment. The two RNAs are recombined by a cell's intrinsic RNA splicing machinery (i.e., the spliceosome machinery). The synthetic intron domains contain two functional elements: (1) a dimerization domain to mediate base pairing between the two halves that are to be recombined and (2) a domain optimized to efficiently recruit the splicing machinery to mediate efficient reconstitution of the two RNA molecules. In some examples, a synthetic intron includes a sequence having at least 50% at least 60%, at least 70%, at least 75%, 80%, at least 85%, at least 90%, at least 95%, at least 98%, at least 99%, or 100% sequence identity to any synthetic intron provided in SEQ ID NOS: 1, 2, 3, 4, 5, 6, 7, 8, 9, 10, 11, 12, 13, 14, 15, 16, 17, 18, 19, 20, 21, 22, 23, 24, 25, 145, 146, 17, and 148 (e.g., see FIGS. 10A-10Z). One skilled in the art will appreciate that any of the molecules provided in SEQ ID NOS: 1, 2, 20, 21, 22, 23, 24, 25, 145, 146, 17, and 148 can be modified to replace the protein coding portions (e.g., 114 and 164 of FIG. 6A) with another protein coding sequence of interest (e.g., YFP coding sequence of SEQ ID NO: 1, 2, 22 or 23 can be replaced with a therapeutic protein coding sequence). Thus, also provided herein are synthetic intron molecules having at least 80%, at least 85%, at least 90%, at least 95%, at least 98%, at least 99%, or 100% sequence identity to any synthetic intron portion provided in SEQ ID NO: 1, 2, 20, 21, 22, 23, 24, 25, 145, 146, 17, and 148 (e.g., nt 3703-3975 of SEQ ID NO: 22 and nt 1-225 of SEQ ID NO: 23).

Exemplary dimerization domains were bioinformatically selected to minimize/optimize their internal secondary/tertiary structure. The dimerization domains tested contained long stretches of low diversity nucleotide sequences to avoid intramolecular annealing. By avoiding intramolecular annealing, these dimerization domains are present in an open configuration and therefore are available for pairing with the corresponding complementary dimerization domain sequence. The synthetic intron domains contain intronic splice enhancing elements which lead to efficient recruitment of the splicing machinery.

The disclosed synthetic RNA molecules are designed to have at least an open and available single-stranded region that is available to bind to the complementary dimerization domain to allow efficient splicing and recombination of the RNAs. In some examples, this is achieved by utilizing only purines or only pyrimidines for the binding domains. Due to the inability of purines to pair with themselves (and pyrimidines likewise) these stretches of RNA have an open predicted structure.

RNA molecules are present as a single strand in the cells. Being single stranded they are inherently prone to hybridize to themselves and thereby form strong secondary and tertiary structures. The most stable base pairs will be G with C, A with U, and the G with U wobble pair. Thermodynamically, the pairing of two bases is favored over an open configuration. To design efficient synthetic nucleic acid molecules, the two dimerization domains having reverse complementary to one another are present in an open configuration such that the dimerization domains are available for inter-molecular base pairing. To avoid intra-molecular base pairing in between other parts of the synthetic nucleic acid molecules, a long stretch of non-diverse sequences containing incompatible bases can be included. For example, a long stretch of pyrimidines (i.e., C and T) or purines (i.e., A and G) can be present in the synthetic nucleic acid molecules. Pyrimidines cannot form canonical base pairs with other pyrimidines, purines cannot form canonical base pairs with other purines. Such a stretch of purines or pyrimidines can range from a couple bases to a couple hundreds of bases. Since these stretches cannot intra-molecularly bind, they are available for inter-molecular base pairing with a complementary fragment. For example, the synthetic nucleic acid molecules A and A' may be configured with A containing a pyrimidine stretch (e.g., 5'-CCUU( . . . )CCUU-3') and A' containing the complementary purine sequence (e.g., 5'-AAGG( . . . )AAGG-3').

The disclosed synthetic RNA molecules are designed to minimize any off-target binding to incorrect sites in the genome. Off target binding can be reduced by altering the sequence of the nucleic acid molecule.

The same design principle, that is the use of hypodiverse stretches of RNA bases to achieve open synthetic nucleic acid configurations, can be extended to using stretches of single bases e.g. using a series of Gs that would base pair with a series of Cs and a series of As that would base pair with a series of Us, in the dimerization domains.

To increase recombination of two or more synthetic nucleic acid molecules, the following methods can be used. RNA splicing depends on the recruitment of spliceosome components to the 5' end of the intron (the splice donor site) and the 3' end of the intron (the splice acceptor site, with its associated branch point sequence and the polypyrimidine tract). Different ribonucleoproteins are recruited to the intron through base pairing of protein associated small nuclear RNA (snRNA) with intronic sequences. By placing perfect match consensus sequences into the RNA dimerization and recombination domains, the recruitment of spliceosome components can be facilitated which in turn enhances the efficiency of spliceosome mediated recombination. Previously characterized intronic splice enhancer sequences can recruit additional splicing promoting factors that are referred to as intronic splice enhancers.

In some examples, instead of using naturally occurring RNA sequences for the RNA splicing sequences, consensus sequences are used. For example, consensus sequences can be used for any of the sequences that are involved in splicing, including splice donor, splice acceptor, splice enhancer and splice branch point sequences. With these synthetic nucleic acid molecules, two (or more) RNA molecules can be serially joined together in a cell ex vivo, in vitro, or in vivo. Outside of the synthetic intronic domains, synthetic nucleic acid molecules can include any promoter and coding sequence. For example, two synthetic nucleic acid molecules could carry two halves of a single gene. This was tested in vitro and in vivo by reconstituting two halves of a yellow fluorescent protein (YFP), and was shown to be efficient (see FIGS. 3A-3D).

The modular nature of the synthetic nucleic acid molecules allowed for the testing the efficiency of achieving serial recombination (i.e., >2) of multiple RNA fragments using a combinatorial set of optimized complimentary dimerization domains (FIGS. 4A-4D). A three-way split yellow fluorescent protein was efficiently reconstituted and expressed at high levels in >80% of transfected cells.

These results demonstrate that a single RNA molecule can be reconstituted from at least three different synthetic nucleic acid molecules, such as when expression of a disease causing gene (or therapeutic protein) that has a promoter and/or a coding sequence that is too long to fit into a single gene therapy vector such as AAV.

The disclosed system allows for the efficient RNA recombination between individual fragments. In some examples, reconstitution (i.e., splicing or recombination) efficiency achieved using the compositions, systems or methods of the disclosure is determined using any suitable method known to one of skill in the art. In some examples, reconstitution efficiency is represented by a measure of correctly joined RNA relative to a control RNA, or a measure of full-length protein or protein activity relative to that of a control protein. In some examples the control RNA is the unjoined RNA, wherein reconstitution efficiency is represented by a measure of joined RNA relative to unjoined RNA. This measurement can be made by detecting and comparing junction RNA and the unjoined 3' RNA species 3' (e.g., junction RNA: 3' RNA). In some examples wherein more than two RNAs are joined, joining at either or all junctions are evaluated. In some examples, reconstitution efficiency is represented by a measure of full-length or active protein relative to a protein fragment or inactive protein.

In some examples, the reconstitution, recombination or splicing efficiency (a measure of the correct joining of the two or more different coding sequences present on different RNA molecules, and/or the production of the desired full-length protein) is about 10% to about 100%. In some examples, the reconstitution efficiency is about 10% to about 15%, about 10% to about 20%, about 10% to about 25%, about 10% to about 30%, about 10% to about 40%, about 10% to about 50%, about 10% to about 60%, about 10% to about 70%, about 10% to about 80%, about 10% to about 90%, about 10% to about 100%, about 15% to about 20%, about 15% to about 25%, about 15% to about 30%, about 15% to about 40%, about 15% to about 50%, about 15% to about 60%, about 15% to about 70%, about 15% to about 80%, about 15% to about 90%, about 15% to about 100%, about 20% to about 25%, about 20% to about 30%, about 20% to about 40%, about 20% to about 50%, about 20% to about 60%, about 20% to about 70%, about 20% to about 80%, about 20% to about 90%, about 20% to about 100%, about 25% to about 30%, about 25% to about 40%, about 25% to about 50%, about 25% to about 60%, about 25% to about 70%, about 25% to about 80%, about 25% to about 90%, about 25% to about 100%, about 30% to about 40%, about 30% to about 50%, about 30% to about 60%, about 30% to about 70%, about 30% to about 80%, about 30% to about 90%, about 30% to about 100%, about 40% to about 50%, about 40% to about 60%, about 40% to about 70%, about 40% to about 80%, about 40% to about 90%, about 40% to about 100%, about 50% to about 60%, about 50% to about 70%, about 50% to about 80%, about 50% to about 90%, about 50% to about 100%, about 60% to about 70%, about 60% to about 80%, about 60% to about 90%, about 60% to about 100%, about 70% to about 80%, about 70% to about 90%, about 70% to about 100%, about 80% to about 90%, about 80% to about 100%, or about 90% to about 100%. In some examples, the reconstitution efficiency is about 10%, about 15%, about 20%, about 25%, about 30%, about 40%, about 50%, about 60%, about 70%, about 80%, about 90%, or about 100%. In some examples, the reconstitution efficiency is at least about 10%, about 15%, about 20%, about 25%, about 30%, about 40%, about 50%, about 60%, about 70%, about 80%, or about 90%. In some examples, the reconstitution efficiency is at most about 15%, about 20%, about 25%, about 30%, about 40%, about 50%, about 60%, about 70%, about 80%, about 90%, or about 100%.

In some examples, the compositions, systems or methods of the disclosure are evaluated by determining an RNA or protein production level using any suitable method known to one of skill in the art. In some examples, the RNA production level is represented by a measure of correctly joined RNA relative to a control RNA, or a measure of full-length protein relative to a control. In some examples the control RNA is a corresponding mutant RNA or an endogenous RNA. For example, the ratio of the amount of joined RNA to the amount of mutant or endogenous RNA produced in the transfected cell is compared with same ratio in nontransfected cells, to determine the production level of the correctly joined RNA. In some examples, the ratio of the amount of the correctly joined RNA, full-length protein, or the protein activity, to the amount of the control RNA, or the amount or activity of the control protein, are compared.

In some examples, the RNA production level achieved is 5% to 100%. In some examples, the RNA production level achieved is about 5% to about 100%. In some examples, the RNA production level achieved is about 5% to about 10%, about 5% to about 20%, about 5% to about 25%, about 5% to about 30%, about 5% to about 40%, about 5% to about 50%, about 5% to about 60%, about 5% to about 70%, about 5% to about 80%, about 5% to about 90%, about 5% to about 100%, about 10% to about 20%, about 10% to about 25%, about 10% to about 30%, about 10% to about 40%, about 10% to about 50%, about 10% to about 60%, about 10% to about 70%, about 10% to about 80%, about 10% to about 90%, about 10% to about 100%, about 20% to about 25%, about 20% to about 30%, about 20% to about 40%, about 20% to about 50%, about 20% to about 60%, about 20% to about 70%, about 20% to about 80%, about 20% to about 90%, about 20% to about 100%, about 25% to about 30%, about 25% to about 40%, about 25% to about 50%, about 25% to about 60%, about 25% to about 70%, about 25% to about 80%, about 25% to about 90%, about 25% to about 100%, about 30% to about 40%, about 30% to about 50%, about 30% to about 60%, about 30% to about 70%, about 30% to about 80%, about 30% to about 90%, about 30% to about 100%, about 40% to about 50%, about 40% to about 60%, about 40% to about 70%, about 40% to about 80%, about 40% to about 90%, about 40% to about 100%, about 50% to about 60%, about 50% to about 70%, about 50% to about 80%, about 50% to about 90%, about 50% to about 100%, about 60% to about 70%, about 60% to about 80%, about 60% to about 90%, about 60% to about 100%, about 70% to about 80%, about 70% to about 90%, about 70% to about 100%, about 80% to about 90%, about 80% to about 100%, or about 90% to about 100%. In some examples, the RNA production level achieved is about 5%, about 10%, about 20%, about 25%, about 30%, about 40%, about 50%, about 60%, about 70%, about 80%, about 90%, or about 100%. In some examples, the RNA production level achieved is at least about 5%, about 10%, about 20%, about 25%, about 30%, about 40%, about 50%, about 60%, about 70%, about 80%, or about 90%. In some examples, the RNA production level achieved is at most about 10%, about 20%, about 25%, about 30%, about 40%, about 50%, about 60%, about 70%, about 80%, about 90%, or about 100%.

In some examples, the protein production level is represented by a measure of the amount of full-length protein or protein activity relative to that of a control protein. In some examples the control protein is a corresponding mutant protein or an endogenous protein. For example, the ratio of the amount of full-length protein or protein activity to the amount of mutant or endogenous protein produced in the transfected cell is compared with same ratio in nontransfected cells. In some examples, the control protein is the full-length protein produced in, e.g., a cell that is engineered to express a control full-length protein (wherein the cell is not transfected with the inventive constructs) or a nontransfected cell from a normal subject that expresses a control full-length protein, and the protein production level is determined by measuring the amount or activity of the protein in the transfected cell and comparing it to that of the control protein. In some examples, the control protein is a mutant form of the protein, produced in a cell that is transfected or nontransfected with the construct, and the amount of full-length protein or protein activity is compared with that of the control protein to determine the protein production level. In some examples, the amount of full-length protein or protein activity is compared with that of an endogenous, or housekeeping, protein to determine the protein production level.

In some examples, the protein production level achieved is about 1% to about 100%. In some examples, the protein production level achieved is about 10% to about 100%. In some examples, the protein production level achieved is about 10% to about 20%, about 10% to about 30%, about 10% to about 40%, about 10% to about 50%, about 10% to about 60%, about 10% to about 70%, about 10% to about 75%, about 10% to about 80%, about 10% to about 85%, about 10% to about 90%, about 10% to about 100%, about 20% to about 30%, about 20% to about 40%, about 20% to about 50%, about 20% to about 60%, about 20% to about 70%, about 20% to about 75%, about 20% to about 80%, about 20% to about 85%, about 20% to about 90%, about 20% to about 100%, about 30% to about 40%, about 30% to about 50%, about 30% to about 60%, about 30% to about 70%, about 30% to about 75%, about 30% to about 80%, about 30% to about 85%, about 30% to about 90%, about 30% to about 100%, about 40% to about 50%, about 40% to about 60%, about 40% to about 70%, about 40% to about 75%, about 40% to about 80%, about 40% to about 85%, about 40% to about 90%, about 40% to about 100%, about 50% to about 60%, about 50% to about 70%, about 50% to about 75%, about 50% to about 80%, about 50% to about 85%, about 50% to about 90%, about 50% to about 100%, about 60% to about 70%, about 60% to about 75%, about 60% to about 80%, about 60% to about 85%, about 60% to about 90%, about 60% to about 100%, about 70% to about 75%, about 70% to about 80%, about 70% to about 85%, about 70% to about 90%, about 70% to about 100%, about 75% to about 80%, about 75% to about 85%, about 75% to about 90%, about 75% to about 100%, about 80% to about 85%, about 80% to about 90%, about 80% to about 100%, about 85% to about 90%, about 85% to about 100%, or about 90% to about 100%. In some examples, the protein production level achieved is about 10%, about 20%, about 30%, about 40%, about 50%, about 60%, about 70%, about 75%, about 80%, about 85%, about 90%, or about 100%. In some examples, the protein production level achieved is at least about 10%, about 20%, about 30%, about 40%, about 50%, about 60%, about 70%, about 75%, about 80%, about 85%, or about 90%. In some examples, the protein production level achieved is at most about 20%, about 30%, about 40%, about 50%, about 60%, about 70%, about 75%, about 80%, about 85%, about 90%, or about 100%.

In some examples, the protein activity level achieved is about 50% to about 100%. In some examples, the protein activity level achieved is about 50% to about 100%. In some examples, the protein activity level achieved is about 50% to about 55%, about 50% to about 60%, about 50% to about 65%, about 50% to about 70%, about 50% to about 75%, about 50% to about 80%, about 50% to about 85%, about 50% to about 90%, about 50% to about 95%, about 50% to about 100%, about 55% to about 60%, about 55% to about 65%, about 55% to about 70%, about 55% to about 75%, about 55% to about 80%, about 55% to about 85%, about 55% to about 90%, about 55% to about 95%, about 55% to about 100%, about 60% to about 65%, about 60% to about 70%, about 60% to about 75%, about 60% to about 80%, about 60% to about 85%, about 60% to about 90%, about 60% to about 95%, about 60% to about 100%, about 65% to about 70%, about 65% to about 75%, about 65% to about 80%, about 65% to about 85%, about 65% to about 90%, about 65% to about 95%, about 65% to about 100%, about 70% to about 75%, about 70% to about 80%, about 70% to about 85%, about 70% to about 90%, about 70% to about 95%, about 70% to about 100%, about 75% to about 80%, about 75% to about 85%, about 75% to about 90%, about 75% to about 95%, about 75% to about 100%, about 80% to about 85%, about 80% to about 90%, about 80% to about 95%, about 80% to about 100%, about 85% to about 90%, about 85% to about 95%, about 85% to about 100%, about 90% to about 95%, about 90% to about 100%, or about 95% to about 100%. In some examples, the protein activity level achieved is about 50%, about 55%, about 60%, about 65%, about 70%, about 75%, about 80%, about 85%, about 90%, about 95%, or about 100%. In some examples, the protein activity level achieved is at least about 50%, about 55%, about 60%, about 65%, about 70%, about 75%, about 80%, about 85%, about 90%, or about 95%. In some examples, the protein activity level achieved is at most about 55%, about 60%, about 65%, about 70%, about 75%, about 80%, about 85%, about 90%, about 95%, or about 100%.

In some examples, the amount of correctly joined RNA or full-length protein produced in a cell is sufficient to ameliorate or cure a condition or disease in a subject, as understood by one of skill in the art for the particular condition or disease. In some examples, the amount of correctly joined RNA or full-length protein produced in a cell is an effective amount. In some examples, this amount is equivalent to about 50% to 100% the amount of the RNA or protein produced in a normal cell. In some examples, this amount is equivalent to about 40% to about 100% the amount of the RNA or protein produced in a normal cell. In some examples, this amount is equivalent to about 40% to about 45%, about 40% to about 50%, about 40% to about 55%, about 40% to about 60%, about 40% to about 65%, about 40% to about 70%, about 40% to about 75%, about 40% to about 80%, about 40% to about 85%, about 40% to about 90%, about 40% to about 100%, about 45% to about 50%, about 45% to about 55%, about 45% to about 60%, about 45% to about 65%, about 45% to about 70%, about 45% to about 75%, about 45% to about 80%, about 45% to about 85%, about 45% to about 90%, about 45% to about 100%, about 50% to about 55%, about 50% to about 60%, about 50% to about 65%, about 50% to about 70%, about 50% to about 75%, about 50% to about 80%, about 50% to about 85%, about 50% to about 90%, about 50% to about 100%, about 55% to about 60%, about 55% to about 65%, about 55% to about 70%, about 55% to about 75%, about 55% to about 80%, about 55% to about 85%, about 55% to about 90%, about 55% to about 100%, about 60% to about 65%, about 60% to about 70%, about 60% to about 75%, about 60% to about 80%, about 60% to about 85%, about 60% to about 90%, about 60% to about 100%, about 65% to about 70%, about 65% to about 75%, about 65% to about 80%, about 65% to about 85%, about 65% to about 90%, about 65% to about 100%, about 70% to about 75%, about 70% to about 80%, about 70% to about 85%, about 70% to about 90%, about 70% to about 100%, about 75% to about 80%, about 75% to about 85%, about 75% to about 90%, about 75% to about 100%, about 80% to about 85%, about 80% to about 90%, about 80% to about 100%, about 85% to about 90%, about 85% to about 100%, or about 90% to about 100% the amount of the RNA or protein produced in a normal cell. In some examples, this amount is equivalent to about 40%, about 45%, about 50%, about 55%, about 60%, about 65%, about 70%, about 75%, about 80%, about 85%, about 90%, or about 100% the amount of the RNA or protein produced in a normal cell. In some examples, this amount is equivalent to about at least about 40%, about 45%, about 50%, about 55%, about 60%, about 65%, about 70%, about 75%, about 80%, about 85%, or about 90% the amount of the RNA or protein produced in a normal cell. In some examples, this amount is equivalent to about at most about 45%, about 50%, about 55%, about 60%, about 65%, about 70%, about 75%, about 80%, about 85%, about 90%, or about 100% the amount of the RNA or protein produced in a normal cell.

The measurements of RNA or protein used to determine recombination efficiency or production level can be made by any suitable method known to those of skill in the art. In some examples, recombination efficiency or production level is determined by measuring an amount of functional protein expressed, for example by Western blotting. In some examples, recombination efficiency or production level is determined by measuring the RNA transcript, for example using two probe based quantitative real-time PCR. For example, the first assay spans a sequence fully contained in the 3' exonic coding sequence (labelled 3' probe). The second assay spans the junction between the 5' and the 3' exonic coding sequence (labelled junction probe). Reconstitution efficiency can be calculated as the ratio of (junction probe count)/(3' probe count). "Reconstitution efficiency," "recombination efficiency," and "splicing efficiency" are used interchangeably herein.

In some examples, a dimerization domain is about 20 to about 1000 nt, or about 50 to about 160 nt, or about 50 to about 500 nt, or about 50 to 1000 nt, wherein reconstitution efficiency results in production of an effective amount of correctly joined RNA or full-length protein. In some examples, a dimerization domain is about 50 to about 160 nt, wherein reconstitution efficiency results in production of an effective amount of correctly joined RNA or full-length protein.

Achieving efficient recombination between multiple RNA molecules allows for packaging and delivery of transgenes into AAVs, which exceed the packaging limit of a single AAV. AAV packaging limits represent a major hurdle for gene therapy approaches for diseases caused by the absence/defect of large genes. One application of this system is expression of large disease-causing genes using viral vectors with restricted packaging capacity. Disease and genes include but are not limited to (Disease (gene, OMIM gene identifier)): 1) Duchenne muscular dystrophy and Becker muscular dystrophy (dystrophin, OMIM:300377); 2) Dysferlinopathies (Dysferlin, OMIM:603009); 3) Cystic fibrosis (CFTR, OMIM:602421); 4) Usher's Syndrome 1B (Myosin VIIA, OMIM:276903); 5) Stargardt disease 1 (ABCA4, OMIM:601691); 6) Hemophilia A (Coagulation Factor VIII, OMIM:300841); 7) Von Willebrand disease (von Willebrand Factor, OMIM:613160); 8) Marfan Syndrome (Fibrillin 1, OMIM:134797); and 9) Von Recklinghausen disease (neurofibromatosis-1, OMIM:162200). Others are provided in Table 1. Delivery of a transgene can be achieved by splitting it into multiple fragments using the approach provided herein.

Additional applications of the disclosed methods and systems include intersectional gene delivery for targeted gene expression. One can make use of differential infection/expression patterns of two viruses encoding a fragmented gene. The reconstituted protein will get expressed in an overlapping population of cells that represents the intersection of what either virus would express in on its own. Examples for such an application may include: (1) delivery of two halves (or three thirds, or other portions) of a protein using retrogradely transported viral vectors from two (or more) projection targets to label bifurcating dual projection neurons, (2) delivery of one fragment under the control of a promoter that is active in population A and the second fragment from a promoter active in population B to specifically tag/manipulate the A∪B population, (3) delivery of the first half of a protein with a viral vector that has a tropism for population A and the second half with a viral vector that has a tropism for population B to specifically tag/manipulate the A∪B population. Or, combinations of these approaches.

In one example the dimerization domains are aptamer sequences, for example to facilitate dimerization in the presence of a (a) small molecular trigger recognized by the aptamers, a (b) protein that is present in the cell binding to the two halves and therefore stimulating dimerization, or (c) an antisense oligonucleotide sequence with homology to the two halves (RNA triggered dimerization). In such an example, an antisense oligonucleotide having a complementariy sequence to both halves bridges the two molecules together, thus facilitating spliceosome mediated recombination of the two molecules.

These molecule, protein, or RNA mediated interactions allow for controllable/fine tuned gene expression levels: Through titrating in molecules that interact with the binding domains (e.g., antisense oligonucleotides), dimerization efficiency between the two halves can be modulated to regulate expression levels independent of promoter activity. Such an installment can be used if a narrow range of protein expression levels are needed.

III. Systems

Provided herein is a system that can be used to recombine two or more RNA molecules, such as at least two, at least three, at least four, or at least five different RNA molecules (such as 2, 3, 4, 5, 6, 7, 8, 9 or 10 different RNA molecules) using synthetic introns containing dimerization sequences. Unlike fragmentation and reconstitution of two fragments at the protein level, the disclosed approach does not require extensive protein engineering to find a suitable split point. Reconstitution on an RNA level allows for seamless joining of two fragments of a protein. The disclosed methods and systems allow for large genes (and corresponding proteins), such as those greater than about 4.5 kb, at least 5 kb, at least 5.5 kb, at least 6 kb, at least kb, at least 8 kb, at least 8 kb, or at least 10 kb to be divided into two or more fragments or portions, which can each be introduced into a cell or subject via separate vectors, such as multiple AAV. This helps to overcome the limited space available in vectors. In some examples, an endogenous promoter length limits the capability of its corresponding gene to be expressed in an AAV. In some examples, a coding sequence length limits its capability to be expressed in an AAV. In some examples, an endogenous promoter length and is coding sequence length limits their capability to be expressed together in an AAV. The disclosed systems can be used to express such long sequences that have been previously difficult to express in AAV.

In some examples, the target protein to be reconstituted is a protein associated with disease, such as a monogenic disease, recessive genetic disease, a disease caused by a mutation in a large gene (e.g., greater than about 4500 nt, such as those of at least 5 kb, at least 5.5 kb, at least 6 kb, at least kb, at least 8 kb, at least 8 kb, or at least 10 kb), and/or disease caused by a gene (such as a promoter+coding sequence) that exceed AAV's capacity (e.g., greater than 5000 nt). Examples of such diseases include, but are not limited to, hemophilia A (caused by mutations in the F8 gene, 7 kb coding region), hemophilia B (caused by mutations in the F9 gene), Duchenne muscular dystrophy (caused by mutations in the dystrophin gene, 11 kb coding region), sickle cell anima (caused by mutation in beta globin domain of hemoglobin, which has a promoter of about 3.5 kb), Stargardt disease (caused by mutations in the ABCA4 gene, 6.9 kb coding region), Usher syndrome (caused by a mutation in MYO7A, 7 kb coding region, resulting in hearing loss and visual impairment).

In one example, the target protein to be reconstituted is one that can treat a disease, such as a cancer, such as a cancer of the breast, lung, prostate, liver, kidney, brain, bone, ovary, uterus, skin, or colon. In one example, the therapeutic target protein to be reconstituted is a toxin, such as an AB toxin, such as diphtheria toxin A or *pseudomonas* exotoxin A, or a form that lacks receptor binding activity (e.g., diphtheria toxin DAB389, DAB486, DT388, DT390, or *pseudomonas* exotoxin A PE38 or PE40).

In some examples, an RNA sequence encoding the target protein and used in the disclosed methods and systems are codon optimized for expression in a target organism or cell, such as codon optimized for expression in a human, canine, pig, feline, mouse, or rat cell. Thus, in some examples, the RNA coding sequence includes preferred codons (e.g., does not include rare codons with low utilization). Codon optimization can be performed by identifying abundant tRNA levels in the target organism or cells. In some examples, an RNA sequence encoding the protein is de-enriched for cryptic splice donor and acceptor sites to maximize an RNA recombination reaction.

In some examples, a protein is divided into two portions, such as about two equal halves (or other proportions, such as portion A expressing about ⅓ and portion B expressing about ⅔, or portion A expressing about ¼ and portion B expressing about ¾, etc.). However, it is not required that each portion be the same number of nucleotides (or encode the same number of amino acids). In such an example, the method can use two synthetic RNA molecules, one which includes a coding sequence for an N-terminal portion of the protein, and another which includes a coding sequence for a C-terminal portion of the protein. Based on this foundation, one skilled in the art will appreciate that in addition to dividing a protein into two fragments or portions, proteins of interest can be divided or split into more than two fragments, such as three fragments. The design principle of the intronic sequences of three RNA molecules is similar to that of the two, but instead a different pair of dimerization domains for one of the two junctions is utilized. Thus, for example, an N-terminal protein coding sequence is followed by an intronic sequence with a specific binding domain (e.g., first dimerization sequence), the middle coding sequence includes an intronic sequence with a complementary sequence to the first dimerization sequence (second dimerization sequence). The middle coding fragment is followed by another intronic fragment with another dimerization sequence (third dimerization sequence, different from the second dimerization sequence). The third fragment includes the C-terminal coding sequence of the protein, and includes an intronic region with a dimerization sequence (fourth dimerization sequence) complementary to the third dimerization sequence.

In one example, a desired protein is divided into an N-terminal portion and a C-terminal portion (e.g., divided in roughly half, or unequal apportionment, such as ⅓ and ⅔ or ¼ and ¾), which can be reconstituted using the disclosed systems and methods. Referring to FIG. 6A, in such an example, the system includes at least two synthetic nucleic acid molecules 110, 150. Each nucleic acid molecule 110, 150 can be composed of RNA. In some examples, each of 110, 150 is about at least 100 nucleotides/ribonucleotides (nt) in length, such as at least 200, at least 300, at least 500, at least 1000, at least 2000, at least 3000, at least 4000, at least 5000, at least 6000, at least 7000, at least 8000 nt, at least 10,000 nt, such as 200 to 10,000 nt, 200 to 8000 nt, 500 to 5000 nt, or 200 to 1000 nt. The molecules 110, 150 can include natural and/or non-natural nucleotides or ribonucleotides.

Molecule 110 is the 5'-located molecule of the system, as it includes a splice donor 116. Molecule 110 includes from 5' to 3', a promoter 112 operably linked to a 5'-fragment of RNA 114 encoding an N-terminal portion of a target protein (which includes a splice junction at its 3'-end). Any promoter 112 (or enhancer) can be used, such as one that utilizes RNA polymerase II, such as a constitutive or inducible promoter. In some examples, promoter 112 is a tissue-specific promoter, such as one constitutively active in muscle tissue (such as skeletal or cardiac), optical tissue (such as retinal tissue), inner ear tissue, liver tissue, pancreatic tissue, lung tissue, skin tissue, bone, or kidney tissue. In some examples, promoter 112 is a cell-specific promoter, such as one constitutively active in a cancer cell, or a normal cell. In some examples, promoter 112 is an endogenous promoter of the target protein expressed, and in some example is long (e.g., at least 2500 nt, at least 3000 nt, at least 4000 nt, at least 5000 nt, or at least 7500 nt). In some examples, promoter 112 is at least about 50 nucleotides/ribonucleotides (nt) in length, such as at least 100, at least 200, at least 300, at least 500, at least 1000, at least 2000, at least 3000, at least 4000, at least 5000, at least 6000, at least 7000, at least 8000 nt, at least 9000 nt, or at least 10,000 nt, such as 50 to 10,000 nt, 100 to 5000 nt, 500 to 5000 nt, or 50 to 1000 nt in length. The splice junction at the 3' end of the N-terminal coding sequence 114 is an exonic sequence, which can match the consensus sequence found in the target cell or organism into which molecules 110, 150 are introduced. In humans the splice junction sequence is AG (adenine-guanine) or UG (uracil-guanine) at positon −1 and −2 of the 5' splice site for U2-dependent introns or AG, UG, CU (cytosine-uracil), or UU for U12-dependent introns. Thus, in some examples, the splice junction is 2 nt in length, and the 3' end of the N-terminal coding portion 114 is AG, UG, CU or UU. In some examples an RNA molecule encoding a portion of a target protein comprises multiple splice junctions, e.g., at the 3' end of the RNA molecule encoding the N-terminal portion of the target protein, and at the 5' end of the RNA molecule encoding the C-terminal portion of the target protein. In some examples, these splice junctions may be referred to as a first and second splice junction. In some examples wherein the system comprises more than two RNA molecules, it is understood that the molecules can comprise third, fourth, etc. splice junctions.

The remaining 3'-terminal portion of molecule 110 is intronic, 130. In some examples, intronic sequence 130 is about at least 10 nt, such as at least 20 nt, at least 50 nt, at least 100 nt, at least 250 nt, at least 250 nt, at least 300 nt, at least 400 nt, or at least 500 nt in length, such as 20 to 500, 20 to 250, 20 to 100, 50 to 100, or 50 to 200 nt in length Immediately following N-terminal coding sequence 114 is a splice donor (SD) 116 (such as a SD consensus sequence, such as a SD human consensus sequence). Thus SD 116 of intronic sequence 130 is 3' to N-terminal coding sequence 114. SD 116 forms a recognition sequence for the spliceosome components to bind to the RNA molecule. The sequence of SD 116 can be a SD consensus sequence found in the target cell or organism into which molecules 110, 150 are introduced. In some examples, SD 116 is at least 2 nt, such as at least 5 nt, or at least 10 nt in length, such as 2 to 10, 2 to 8, 2 to 5 or 5 to 10 nt. The SD 116 can be used to recruit U2 or U12 dependent splicing machinery. In one example, U2 dependent splicing is used in human cells, and the SD 116 sequence includes or is GUAAGUAUU. In one example, U12 dependent splicing is used in human cells, and the SD 116 sequence includes or is AUAUCCUUUUUA (SEQ ID NO: 137) or GUAUCCUUUUUA (SEQ ID NO: 138).

Intronic sequence 130 optionally includes one or both of a set of splicing enhancer sequences referred to as downstream intronic splice enhancer (DISE) 118 and intronic splice enhancer (ISE) 120, which stimulate action (e.g., increase activity) of the spliceosome. In some examples, intronic sequence 130 includes at least two splicing enhancer sequences, such as at least 3, at least 4, or at least 5 splicing enhancer sequences. Exemplary splicing enhancer sequences include DISE 118 and ISE 120. In some examples, inclusion of one or more splicing enhancer sequences 118, 120 in intronic sequence 130 increases splicing efficiency by at least 20%, at least 30%, at least 40%, at least 50%, at least 75%, at least 80%, at least 90% or at least 95%. Exemplary splicing enhancer sequences that can be used are provided in SEQ ID NOS: 26-136, 151, and 152, as well as GGGTTT, GGTGGT, TTTGGG, GAGGGG, GGTATT, GTAACG, GGGGGTAGG, GGAGGGTTT, GGGTGGTGT TTCAT, CCATTT, TTTTAAA, TGCAT, TGCATG, TGTGTT, CTAAC, TCTCT, TCTGT, TCTTT, TGCATG, CTAAC, CTGCT, TAACC, AGCTT, TTCATTA, GTTAG, TTTTGC, ACTAAT, ATGTTT, CTCTG, GGG, GGG(N)2-4GGG, TGGG, YCAY, UGCAUG, or $3\times(G_{3-6}N_{1-7})$. In some examples, if DISE 118 is present, can be at least 3 nt, at least 4 nt, at least 5 nt, at least 10 nt, at least 25 nt, at least 50 nt, at least 75 nt, or at least 100 nt in length, such as 3 to 10, 3 to 11, 4 to 11, 5 to 11, 10 to 50, 5 to 100, 10 to 25, 10 to 20, or 20 to 75 nt, the sequence of DISE 118 is or comprises CUCUUUCUUUTCCAUGG-GUUGGCU (SEQ ID NO: 134), TGCATG, CTAAC, CTGCT, TAACC, AGCTT, TTCATTA, GTTAG, TTTTGC, ACTAAT, ATGTTT or CTCTG. In some examples, if ISE 120 is present, it can be about at least 3 nt, at least 4 nt, at least 5 nt, at least 10 nt, such as at least 20 nt, at least 25 nt, at least 30 nt, at least 40 nt, or at least 50 nt in length, such as 3 to 10, 3 to 11, 4 to 11, 5 to 11, 10 to 50, 20 to 25, 10 to 25, 10 to 20, or 20 to 40 nt in length. In one example, the sequence of ISE 120 is or comprises GGCUGAGG-GAAGGACUGUCCUGGG (SEQ ID NO: 135), GGGUUAUGGGACC (SEQ ID NO: 136), TTCAT, CCATTT, TTTTAAA, TGCAT, TGCATG, TGTGTT, CTAAC, TCTCT, TCTGT, or TCTTT. In some examples, intronic sequence 130 includes at least two, at least 3, or at least 4 ISEs 120.

The SD 116 (and if present also enhancer sequences 118, 120) is followed 3' by a dimerization domain 122 used to bring the N-terminal coding sequence 114, and C-terminal coding sequence 154 to be combined, together. Intronic sequence 130 portion of molecule 110 can optionally include at the 3'-end a polyadenylation site 124, which terminates transcription of that fragment. In some examples, polyadenylation sequence 124 is a polyA sequence of at least 15 As, such as 15 to 30 or 15 to 20 As.

In some examples, first dimerization domain 122 (and second dimerization domain 154 of molecule 150) includes a plurality of unpaired nucleotides (that is, unpaired within the structure of the molecule 110 itself). Having unpaired nucleotides in the dimerization domain allows the 5' (or first) dimerization domain 122 and the 3' (or second) dimerization domain 154 to interact through base pairing. Through this interaction, molecules 110 and 150 are kept in proximity which prompts the spliceosome to recombine the two molecules by joining the N-terminal coding region 114 and the C terminal coding region 164.

Figure 6B:
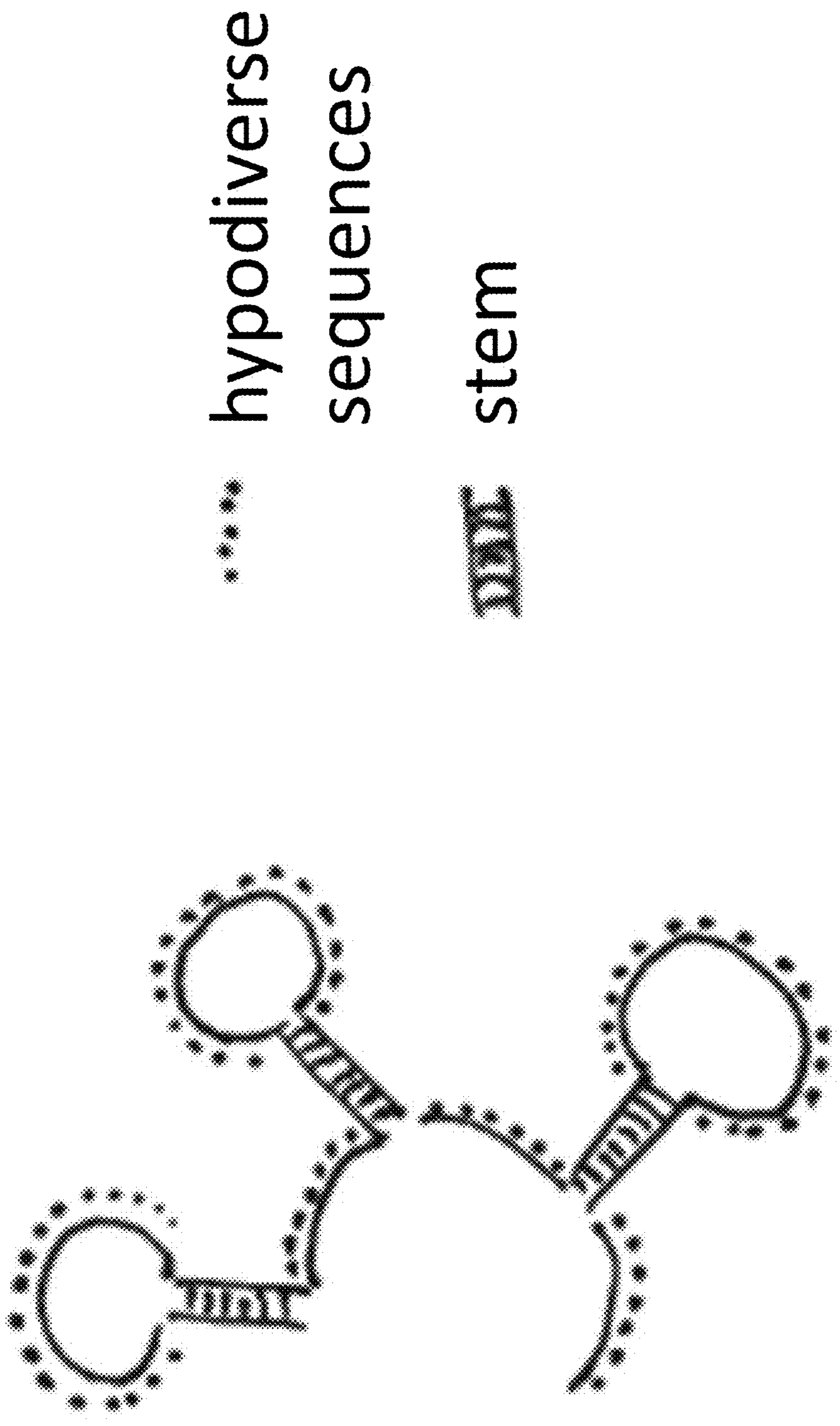
FIG. 6B is a schematic drawing providing an exemplary dimerization domain (e.g., 122, 154 of FIG. 6A) that includes hypodiverse sequences interspersed with sequences that can form a stem, which results in local RNA loops that are open and available for basepairing in the absence of pseudoknot formation. Drawing not to scale.

In one example, dimerization domain 122 (and 154) includes "hypodiverse sequences," which contain a limited diversity of nucleotides and are thus unlikely to form stem loops with themselves in the secondary structure of each molecule 110, 150. Such a hypodiverse dimerization domain 122 (and 154) can be a relatively open configuration, independent of the sequences of the RNA encoding the N- and C-terminus of the protein 114, 164. This allows the nucleotides of the first dimerization domain 122 to be available to form base pairs with the corresponding second dimerization domain 154 of molecule 150, allowing subsequent joining of the N-terminal coding sequence 114 and C-terminal coding sequence 164. In some examples, first and second dimerization domain 122, 154 includes hypodiverse sequences interspersed with sequences that can form a stem, which results in local RNA loops that are open and available for base-pairing in the absence of pseudoknot formation (FIG. 6B). Exemplary hypodiverse sequences include a repeated series of Us (such as 30 to 500 Us), a repeated series of As (such as 30 to 500 As), a repeated series of Gs (such as 30 to 500 Gs), a repeated series of Cs (such as 30 to 500 Cs), a mixture containing only As and Gs (such as 30 to 500 As and Gs, e.g., AAAGAAGGAA( . . . ) (SEQ ID NO: 149) which can be repeated), a mixture containing only Cs and Us (such as 30 to 500 Cs and Us, e.g., CUUUCUUUUCUU( . . . ) (SEQ ID NO: 150) which can be repeated). Other exemplary hypodiverse sequences include complementary sequences that form helices flanked by hypodiverse sequences.

In some examples, first and second dimerization domain 122, 154 only include purines or only include pyrimidines. In one example, the first dimerization domain 122 only includes purines, while the second dimerization domain 154 only includes pyrimidines. In another example, the first dimerization domain 122 only includes pyrimidines, while the second dimerization domain 154 only includes purines. Due to the inability of purines to pair with themselves (and pyrimidines likewise) these stretches of RNA have an open predicted structure.

In some examples, first and second dimerization domain 122, 154 do not include cryptic splice acceptors that could compete with RNA recombination, such as sequences similar to the splice donor consensus sequence NNNAGGUNNNN (SEQ ID NO: 151) or NNNUGGUNNNN (SEQ ID NO: 152) (wherein N refers to any nucleotide). In some examples, first dimerization domain 122 is no more than 1000 nt, such as no more than 750 nt, or more than 500 nt, such as 6 to 1000 nt, 10 to 1000 nt, 20 to 1000 nt, 30 to 1000 nt, 30 to 750 nt, 30 to 500 nt, 50 to 500 nt, 50 to 100 nt, or 100 to 250 nt. In some examples, first dimerization domain 122 is greater than 50 nt, such as at least 51 nt, at least 100 nt, at least 150 nt, at least 161 nt, or at least 170 nt, such as 51 to 159 nt, 51 to 150 nt, 51 to 120 nt, 51 to 100 nt, or 51 to 70 nt. In some examples, first dimerization domain 122 is greater than 160 nt, such as at least 161 nt, at least 170 nt, at least 180 nt, at least 200 nt, at least 300 nt, at least 400 nt, at least 500 nt, at least 600 nt, at least 700 nt, at least 800 nt, at least 900 nt, or at least 1000 nt, such as 161 to 100 nt, 161 to 500 nt, 161 to 300 nt, 161 to 200 nt, or 161 to 170 nt. In some examples, first dimerization domain 122 is less than 50 nt, such 6 to 49 nt, 6 to 45 nt, 6 to 40 nt, 6 to 30 nt, 6 to 20 nt, or 6 to 10 nt.

In some examples, a dimerization domain is 20 to 160 nt, 50-500 nt, or 500-1000 nt. In some examples, a dimerization domain is about 20 nt to about 160 nt. In some examples, a dimerization domain is about 20 nt to about 40 nt, about 20 nt to about 50 nt, about 20 nt to about 70 nt, about 20 nt to about 90 nt, about 20 nt to about 100 nt, about 20 nt to about 110 nt, about 20 nt to about 120 nt, about 20 nt to about 130 nt, about 20 nt to about 140 nt, about 20 nt to about 150 nt, about 20 nt to about 160 nt, about 40 nt to about 50 nt, about 40 nt to about 70 nt, about 40 nt to about 90 nt, about 40 nt to about 100 nt, about 40 nt to about 110 nt, about 40 nt to about 120 nt, about 40 nt to about 130 nt, about 40 nt to about 140 nt, about 40 nt to about 150 nt, about 40 nt to about 160 nt, about 50 nt to about 70 nt, about 50 nt to about 90 nt, about 50 nt to about 100 nt, about 50 nt to about 110 nt, about 50 nt to about 120 nt, about 50 nt to about 130 nt, about 50 nt to about 140 nt, about 50 nt to about 150 nt, about 50 nt to about 160 nt, about 70 nt to about 90 nt, about 70 nt to about 100 nt, about 70 nt to about 110 nt, about 70 nt to about 120 nt, about 70 nt to about 130 nt, about 70 nt to about 140 nt, about 70 nt to about 150 nt, about 70 nt to about 160 nt, about 90 nt to about 100 nt, about 90 nt to about 110 nt, about 90 nt to about 120 nt, about 90 nt to about 130 nt, about 90 nt to about 140 nt, about 90 nt to about 150 nt, about 90 nt to about 160 nt, about 100 nt to about 110 nt, about 100 nt to about 120 nt, about 100 nt to about 130 nt, about 100 nt to about 140 nt, about 100 nt to about 150 nt, about 100 nt to about 160 nt, about 110 nt to about 120 nt, about 110 nt to about 130 nt, about 110 nt to about 140 nt, about 110 nt to about 150 nt, about 110 nt to about 160 nt, about 120 nt to about 130 nt, about 120 nt to about 140 nt, about 120 nt to about 150 nt, about 120 nt to about 160 nt, about 130 nt to about 140 nt, about 130 nt to about 150 nt, about 130 nt to about 160 nt, about 140 nt to about 150 nt, about 140 nt to about 160 nt, or about 150 nt to about 160 nt. In some examples, a dimerization domain is about 20 nt, about 40 nt, about 50 nt, about 70 nt, about 90 nt, about 100 nt, about 110 nt, about 120 nt, about 130 nt, about 140 nt, about 150 nt, or about 160 nt. In some examples, a dimerization domain is at least about 20 nt, about 40 nt, about 50 nt, about 70 nt, about 90 nt, about 100 nt, about 110 nt, about 120 nt, about 130 nt, about 140 nt, or about 150 nt. In some examples, a dimerization domain is at most about 40 nt, about 50 nt, about 70 nt, about 90 nt, about 100 nt, about 110 nt, about 120 nt, about 130 nt, about 140 nt, about 150 nt, or about 160 nt.

In some examples, a dimerization domain is about 50 nt to about 500 nt. In some examples, a dimerization domain is about 50 nt to about 100 nt, about 50 nt to about 150 nt, about 50 nt to about 200 nt, about 50 nt to about 250 nt, about 50 nt to about 300 nt, about 50 nt to about 350 nt, about 50 nt to about 400 nt, about 50 nt to about 500 nt, about 100 nt to about 150 nt, about 100 nt to about 200 nt, about 100 nt to about 250 nt, about 100 nt to about 300 nt, about 100 nt to about 350 nt, about 100 nt to about 400 nt, about 100 nt to about 500 nt, about 150 nt to about 200 nt, about 150 nt to about 250 nt, about 150 nt to about 300 nt, about 150 nt to about 350 nt, about 150 nt to about 400 nt, about 150 nt to about 500 nt, about 200 nt to about 250 nt, about 200 nt to about 300 nt, about 200 nt to about 350 nt, about 200 nt to about 400 nt, about 200 nt to about 500 nt, about 250 nt to about 300 nt, about 250 nt to about 350 nt, about 250 nt to about 400 nt, about 250 nt to about 500 nt, about 300 nt to about 350 nt, about 300 nt to about 400 nt, about 300 nt to about 500 nt, about 350 nt to about 400 nt, about 350 nt to about 500 nt, or about 400 nt to about 500 nt. In some examples, a dimerization domain is about 50 nt, about 100 nt, about 150 nt, about 200 nt, about 250 nt, about 300 nt, about 350 nt, about 400 nt, or about 500 nt. In some examples, a dimerization domain is at least about 50 nt, about 100 nt, about 150 nt, about 200 nt, about 250 nt, about 300 nt, about 350 nt, or about 400 nt. In some examples, a dimerization domain is at most about 100 nt, about 150 nt, about 200 nt, about 250 nt, about 300 nt, about 350 nt, about 400 nt, or about 500 nt.

In some examples, the sequence of first and second dimerization domains 122 and 154 are determined by in silico structure prediction screening (e.g., RNA folding structure prediction is used to screen a library of possible dimerization domain sequences; sequences with a large proportion of unpaired nucleotides in both the dimerization domain and the corresponding anti-dimerization domain are selected), hypodiverse nucleotide design (e.g., dimerization domain designed to include a stretch of hypodiverse sequence, such as a repeat sequence of only U, only A, only C, only G, only R (G and A), or only Y (U and C), the sequence cannot fold onto itself), or empirical screening (e.g., a library of dimerization domains and corresponding anti-dimerization domains are synthesized and screened for maximal recombination efficiency).

In some examples, the sequence of first and second dimerization domains 122, 154 are designed to contain complementary RNA hairpin structures (also called stem loops) that can form strong kissing loop interactions with their counter parts. In some examples, kissing loops are used when three or more dimerization domains are used to join three or more portions of a coding sequence, such as four or more or five or more dimerization domains, such as 3, 4, 5, 6, 7, 8, 9 or 10 dimerization domains (e.g., FIG. 6E). Each hairpin loop (or stem loop) of a kissing loop is composed of at least two complementary sequences (e.g., form a stem) separated by a region of non-complementary sequence (e.g., form a loop). In some examples, a dimerization domain can be composed of 1 or more (such as at least 2, at least 3, at least 4, or at least 5, such as 2, 3, 4, 5, 6, 7, 8, 9, 10, 11, 12, 13, 14, 15, 16, 17, 18, 19, or 20) loops. In some examples with multiple loops, all or some of the loops can be repeated. In some examples with multiple loops, all or some loops can be different In some examples, each complementary sequence is about 4 to 100 nt, which are separated by a loop of about 3 to 20 nt. Base-pairing between the two complementary sequences results in a helix (or stem), for example of at least 4 bp, at least 5 bp, at least 10 bp, at least 20 bp, at least 30 bp, at least 40 bp, at least 50 bp, at least 75 bp, at least 90 bp, or at least 100 bp, such as 4 to 100 bp, 5 to 75 bp, or 10 to 50 bp. In some examples, the loop portion is at least 3 nt, at least 5 nt, at least 10 nt, at least 15 nt, or at least 20 nt, such as 3 to 20 nt, 5 to 15 nt or 5 to 10 nt, wherein the loop is not base paired. Complementary sequences between two hairpin loops result in base pairing, and generation of a kissing loop/kissing stem loop interaction. In some examples, the complementary sequences between the two hairpin loops occurs between at least 3 nucleotides of one loop with at least 3 nucleotides of a second loop, such as at least 4, at least 5, at least 6, at least 7, at least 8, at least 9, at least 10, at least 11, at least 12, at least 13, at least 14, at least 15, at least 16, at least 17, at least 19, or at least 20 nt (such as 3, 4, 5, 6, 7, 8, 9, 10, 11, 12, 13, 14, 15, 16, 17, 18, 19 or 20) of the first loop, with at least 4, at least 5, at least 6, at least 7, at least 8, at least 9, at least 10, at least 11, at least 12, at least 13, at least 14, at least 15, at least 16, at least 17, at least 19, or at least 20 nt (such as 3, 4, 5, 6, 7, 8, 9, 10, 11, 12, 13, 14, 15, 16, 17, 18, 19 or 20) of the second loop. In some examples, the complementary sequences between the two hairpin loops occurs between at least 15%, at least 20%, at least 30%, at least 40%, at least 50%, at least 60%, at least 70%, at least 80%, at least 90%, at least 95%, or 100% of the total loop sequence.

In some instances, the stems of the kissing loops are chosen to base pair in trans between the two RNA molecules. In such an example, after forming a kissing loop interaction of one hairpin loop on one molecule with another hairpin loop on a second molecule, the respective stem (or helix) regions of the initial hairpin loops can base pair in trans between the two RNA molecules through strand replacement/invasion and extended duplex formation. In some examples, within the initial loop sequence, up to about 85% of nucleotides can remain unpaired after extended duplex formation (e.g., about 15% of the nt are paired between the two loops). In some examples, the kissing loop is based on the HIV-1 DIS loop (SEQ ID NOS: 139 and 140, FIG. 17A), and includes two A nucleotides on the 5' side of 6 nucleotides of complementary sequence, followed by one A nucleotide on the 3' side (e.g., AANNNNNNA where N can be any of A, U, G, or C). In some examples, the kissing loop is based on the HIV-2 kissing loop dimerization domain (SEQ ID NOS: 141 and 142, FIG. 17B), and includes a G and an A nucleotide on the 5' side of six nucleotides of complementary sequence followed by three A nucleotides on the 3' side (e.g., GANNNNNNAAA (SEQ ID NO: 153) where N can be A, U, G, or C).

In one configuration, extended duplex formation is favored by inclusion of mismatches in the initial stems that result in higher percentage of matching in the extended duplex. Thus, in some examples, the helix or stem region of a hairpin loop can contain up to 30% of base pairs that are not paired initially (e.g., no more than 30%, no more than 20%, no more than 15%, no more than 10%, no more than 5%, or no more than 1%, such as 1 to 30%, 5 to 30%, 10 to 30%, or 25 to 30% of base pairs are not paired initially). These regions of non-pairing can form bulges, mismatches, or internal loops.

In addition to an interaction of two hairpin loops (kissing loop interaction), other forms of loop interactions can be utilized for the first and second dimerization domains 122, 154. In one example the loops are bulges, where one strand of a base paired helix contains one or more nucleotides that bulge out from the stem structure. Exemplary bulges are at least 1 nt, at least 2 nt, at least 3 nt, at least 4 nt, at least 5 nt, at least 10 nt or at least 20 nt, such as 1 to 20 nt, 1 to 15 nt, 1 to 10 nt, or 5 to 10 nt, or 1, 2, 3, 4, 5, 6, 7, 8, 9, 10, 11, 12, 13, 14, 15, 16, 17, 18, 19 or 20 nt. In one example the loops are internal loops, for example, where 1 or more nucleotides in a helix are mismatched, resulting in a helix interrupted by an internal loop at the positions of mismatch. In some examples the helix is at least 4 nt on each of the strands (e.g., at least 5 nt, at least 10 nt, at least 20 nt, at least 30 nt, at least 40 nt, at least 50 nt, at least 75 nt, at least 90 nt, or at least 100 nt, such as 4 to 100 nt, 5 to 75 nt, or 10 to 50 nt. such as 4 to 100 nt), on either side of the internal loop that is at least 1 nt (e.g., at least 2 nt, at least 3 nt, at least 4 nt, at least 5 nt, at least 10 nt or at least 20 nt, such as 1 to 20 nt, 1 to 15 nt, 1 to 10 nt, or 5 to 10 nt, or 1, 2, 3, 4, 5, 6, 7, 8, 9, 10, 11, 12, 13, 14, 15, 16, 17, 18, 19 or 20 nt on each of the strands). In one example the loops are multi-branched loops, wherein three helices or stems from a triangle with one or more unpaired nucleotides connecting the three helices. In some examples, each of the helices is at least 4 bp (e.g., at least 5 bp, at least 10 bp, at least 20 bp, at least 30 bp, at least 40 bp, at least 50 bp, at least 75 bp, at least 90 bp, or at least 100 bp, such as 4 to 100 bp, 5 to 75 bp, or 10 to 50 bp), and the unpaired nucleotides that form the triangle are at least 3 nt (e.g., at least 4 nt, at least 5 nt, at least 10 nt, at least 20, at least 15, at least 30, at least 40, at least 50, or at least 60 nt, such as 3 to 60 nt, 3 to 30 nt, 3 to 25 nt, or 5 to 20 nt, such as 1, 2, 3, 4, 5, 6, 7, 8, 9, 10, 11, 12, 13, 14, 15, 16, 17, 18, 19, 2, 25, 30, 35, 40, 45, 50, 55 or 60 nucleotides). A kissing interaction can occur between any two of these types of loops (e.g., between two or more binding domains that each include one or more helices). In some examples, helices within one dimerization domain (e.g., first dimerization domain 122) have a direct counterpart in the other binding domain (e.g., second dimerization domain 154) to allow for extended duplex formation after initial loop kissing interaction. In some examples, dimerization domains containing helices to generate loops, form a single kissing stem loop upon interaction between the two or more dimerization domains (e.g., 122, 154 of FIG. 6A). In some examples, dimerization domains containing helices form multiple loops for kissing loop interactions upon interaction between the two or more dimerization domains (e.g., 122, 154 of FIG. 6A). In some examples, one or more dimerization domains (e.g., 122 of FIG. 6A) contain helices destabilized by the inclusion of bulges, single base bulges, mismatches or internal loops, or G-U wobble pairs, but match to the other binding domain (e.g., 154 of FIG. 6A), to favor extended duplex formation after initial kissing/pairing. In some examples, one or more dimerization domains (e.g., 122 of FIG. 6A) contain destabilized helices, which when stabilized (e.g., theophylline switch kissing loop) expose a loop that can interact with a second dimerization domain (e.g., 122 of FIG. 6A) via loop-loop interactions (e.g., kissing/pairing).

In some examples these stem loops contain at least 10 nt, such as at least 20 nt, at least 25 nt, at least 50 nt, at least 75 nt, or at least 100 nt in length, such as 10 to 50, 20 to 25, 10 to 100, 10 to 20, or 20 to 40 nt in length. Each dimerization domain can contain at least 1 individual stem loop, such as at least 2, at least 5, at least 10, at least 15, or at least 20, such as 1 to 20, 2 to 5 or 1 to 10 individual stem loops.

In some examples, 3 to 10 portions of a coding sequence are joined by 2 to 9 kissing loops, e.g., 3 portions are joined by 2 kissing loops, 4 portions are joined by 3 kissing loops, etc., wherein each of the 2 to 9 kissing loops are different. In some examples, a kissing loop comprises multiple stem loops, e.g., 2 to 20 stem loops. In some examples, each of the multiple stem loops in the kissing loop are the same. In some examples, each of the multiple stem loops in the kissing loop are different. In some examples, a dimerization domain comprises 1 to 20 stem loops. In some examples, a dimerization domain comprises 1 stem loop to 20 stem loops. In some examples, a dimerization domain comprises 1 stem loop to 2 stem loops, 1 stem loop to 3 stem loops, 1 stem loop to 4 stem loops, 1 stem loop to 5 stem loops, 1 stem loop to 6 stem loops, 1 stem loop to 7 stem loops, 1 stem loop to 8 stem loops, 1 stem loop to 9 stem loops, 1 stem loop to 10 stem loops, 1 stem loop to 15 stem loops, 1 stem loop to 20 stem loops, 2 stem loops to 3 stem loops, 2 stem loops to 4 stem loops, 2 stem loops to 5 stem loops, 2 stem loops to 6 stem loops, 2 stem loops to 7 stem loops, 2 stem loops to 8 stem loops, 2 stem loops to 9 stem loops, 2 stem loops to 10 stem loops, 2 stem loops to 15 stem loops, 2 stem loops to 20 stem loops, 3 stem loops to 4 stem loops, 3 stem loops to 5 stem loops, 3 stem loops to 6 stem loops, 3 stem loops to 7 stem loops, 3 stem loops to 8 stem loops, 3 stem loops to 9 stem loops, 3 stem loops to 10 stem loops, 3 stem loops to 15 stem loops, 3 stem loops to 20 stem loops, 4 stem loops to 5 stem loops, 4 stem loops to 6 stem loops, 4 stem loops to 7 stem loops, 4 stem loops to 8 stem loops, 4 stem loops to 9 stem loops, 4 stem loops to 10 stem loops, 4 stem loops to 15 stem loops, 4 stem loops to 20 stem loops, 5 stem loops to 6 stem loops, 5 stem loops to 7 stem loops, 5 stem loops to 8 stem loops, 5 stem loops to 9 stem loops, 5 stem loops to 10 stem loops, 5 stem loops to 15 stem loops, 5 stem loops to 20 stem loops, 6 stem loops to 7 stem loops, 6 stem loops to 8 stem loops, 6 stem loops to 9 stem loops, 6 stem loops to 10 stem loops, 6 stem loops to 15 stem loops, 6 stem loops to 20 stem loops, 7 stem loops to 8 stem loops, 7 stem loops to 9 stem loops, 7 stem loops to 10 stem loops, 7 stem loops to 15 stem loops, 7 stem loops to 20 stem loops, 8 stem loops to 9 stem loops, 8 stem loops to 10 stem loops, 8 stem loops to 15 stem loops, 8 stem loops to 20 stem loops, 9 stem loops to 10 stem loops, 9 stem loops to 15 stem loops, 9 stem loops to 20 stem loops, 10 stem loops to 15 stem loops, 10 stem loops to 20 stem loops, or 15 stem loops to 20 stem loops. In some examples, a dimerization domain comprises 1 stem loop, 2 stem loops, 3 stem loops, 4 stem loops, 5 stem loops, 6 stem loops, 7 stem loops, 8 stem loops, 9 stem loops, 10 stem loops, 15 stem loops, or 20 stem loops. In some examples, a dimerization domain comprises at least 1 stem loop, 2 stem loops, 3 stem loops, 4 stem loops, 5 stem loops, 6 stem loops, 7 stem loops, 8 stem loops, 9 stem loops, 10 stem loops, or 15 stem loops. In some examples, a dimerization domain comprises at most 2 stem loops, 3 stem loops, 4 stem loops, 5 stem loops, 6 stem loops, 7 stem loops, 8 stem loops, 9 stem loops, 10 stem loops, 15 stem loops, or 20 stem loops.

Other mechanisms can be used to allow the two or more dimerization domains (e.g., 122, 154 of FIG. 6A) to bind or interact with one another sufficient for recombination of the coding sequences to occur. In some examples, the two or more dimerization domains (e.g., 122, 154 of FIG. 6A) are nucleic acid aptamers (such as RNA aptamers) that can interact with one another, for example through a non-base pairing interaction, or can bind to a common molecule (e.g., protein, ATP, metal ion, co-factor, or synthetic ligand). In some examples, two or more dimerization domains (e.g. 122, 154 of FIG. 6A) do not hybridize to one another, but can both (or all) hybridize to the same bridge nucleic acid molecule. In some examples, such a bridge nucleic acid molecule can be exogenously provided to the cells, tissues, or organism. In some examples, such a bridge nucleic acid molecule can be a DNA or RNA sequence inside the cell, such as a transcript or genomic locus. In some examples, the two or more dimerization domains (e.g., 122, 154 of FIG. 6A) are sequences that can interact with one another, for example through a non-base pairing interaction.

Molecule 150 is the 3'-located molecule, and includes a splice acceptor (SA) 162 and a second dimerization domain 154. Molecule 150 includes from 5' to 3', a promoter 152 followed by intronic sequence 170. Promoter 152 can be is operably linked to intronic sequence 170. Any promoter 152 can be used, such as a constitutive or inducible promoter. In some examples, promoter 152 is a tissue-specific promoter, such as one constitutively active in muscle tissue (such as skeletal or cardiac), optical tissue (such as retinal tissue), inner ear tissue, liver tissue, pancreatic tissue, lung tissue, skin tissue, bone, or kidney tissue. In some examples, promoter 112 is a cell-specific promoter, such as one constitutively active in a cancer cell, or a normal cell. In some examples, promoter 112 is an endogenous promoter of to target protein expressed, and in some example is long (e.g., at least 2500 nt, at least 3000 nt, at least 4000 nt, at least 5000 nt, or at least 7500 nt). In some examples, promoter 112 is at least about 50 nucleotides/ribonucleotides (nt) in length, such as at least 100, at least 200, at least 300, at least 500, at least 1000, at least 2000, at least 3000, at least 4000, at least 5000, at least 6000, at least 7000, at least 8000 nt, at least 9000 nt, or at least 10,000 nt, such as 50 to 10,000 nt, 100 to 5000 nt, 500 to 5000 nt, or 50 to 1000 nt in length. In some examples promoter 112 and promoter 152 are the same promoter. In other examples, promoter 112 and promoter 152 are the different promoters.

The intronic sequence 170 includes a second dimerization domain 154, optional ISE 156, branching point 158, polypyrimidine tract 160, followed by a splice acceptor sequence 162. In some examples, intronic sequence 130 is about at least 10 nt, such as at least 20 nt, at least 30 nt, at least 50 nt, at least 100 nt, at least 250 nt, at least 250 nt, at least 300 nt, at least 400 nt, or at least 500 nt in length, such as 20 to 500, 20 to 250, 20 to 100, 50 to 100, 30 to 500, or 50 to 200 nt in length.

Second dimerization domain 154 has a sequence that is the reverse complement of first dimerization domain 122 sequence of molecule 110. Thus, same design features and considerations of first dimerization domain 122 discussed above also apply to second dimerization domain 154. For example, in some examples the second dimerization domain 154 contains a stem loop that can form a kissing loop interaction the first dimerization domain 122. In some examples, second dimerization domain 154 does not include cryptic splice acceptors (e.g., NNNAGGUNNN; SEQ ID NO: 143) that could compete with RNA recombination. In some example, second dimerization domain 154 has a hypodiverse sequence. In some examples, second dimerization domain 154 is no more than 1000 nt, such as no more than 750 nt, or more than 500 nt, such as 30 to 1000 nt, 30 to 750 nt, 30 to 500 nt, 50 to 500 nt, 50 to 100 nt, or 100 to 250 nt. In some examples, second dimerization domain 154 is greater than 50 nt, such as at least 51 nt, at least 100 nt, at least 150 nt, at least 161 nt, or at least 170 nt, such as 51 to 159 nt, 51 to 150 nt, 51 to 120 nt, 51 to 100 nt, or 51 to 70 nt. In some examples, second dimerization domain 154 is greater than 160 nt, such as at least 161 nt, at least 170 nt, at least 180 nt, at least 200 nt, at least 300 nt, at least 400 nt, at least 500 nt, at least 600 nt, at least 700 nt, at least 800 nt, at least 900 nt, or at least 1000 nt, such as 161 to 100 nt, 161 to 500 nt, 161 to 300 nt, 161 to 200 nt, or 161 to 170 nt. In some examples, second dimerization domain 154 is less than 50 nt, such 6 to 49 nt, 6 to 45 nt, 6 to 40 nt, 6 to 30 nt, 6 to 20 nt, or 6 to 10 nt.

3'- to second dimerization domain 154 is an optional ISE 156, branch point sequence 158 (such as a branch point consensus sequence), polypyrimidine tract 160, followed by a splice acceptor sequence 162. ISE 156, like ISE 120 and DISE 118 of molecule 110, stimulates the spliceosome to catalyze the recombination reaction. In some examples, intronic sequence 150 includes at least two ISE 156, such as at least 3, at least 4, or at least 5 ISEs 156. Exemplary splicing enhancer sequences include ISE 156. In some examples, inclusion of one or more splicing enhancer sequences 156 in intronic sequence 150 increases recombination or splicing efficiency by at least 10%, at least 20%, at least 30%, at least 40%, or at least 50%. Exemplary splicing enhancer sequences that can be used are provided in SEQ ID NOS: 26-136, 151, and 152, as well as GGGTTT, GGTGGT, TTTGGG, GAGGGG, GGTATT, GTAACG, GGGGGTAGG, GGAGGGTTT, GGGTGGTGT TTCAT, CCATTT, TTTTAAA, TGCAT, TGCATG, TGTGTT, CTAAC, TCTCT, TCTGT, TCTTT, TGCATG, CTAAC, CTGCT, TAACC, AGCTT, TTCATTA, GTTAG, TTTTGC, ACTAAT, ATGTTT, CTCTG, GGG, GGG(N)2-4GGG, TGGG, YCAY, UGCAUG, or $3\times(G_{3-6}N_{1-7})$. In some examples, if ISE 156 is present, it can be about least 3 nt, at least 4 nt, at least 5 nt, at least 10 nt, such as at least 20 nt, at least 25 nt, at least 30 nt, at least 40 nt, or at least 50 nt in length, such as 3 to 10, 3 to 11, 4 to 11, 5 to 11, 10 to 50, 20 to 25, 10 to 25, 10 to 20, or 20 to 40 nt in length. In one example, the sequence of ISE 156 is or comprises GGCUGAGGGAAGGACUGUCCUGGG (SEQ ID NO: 135), GGGUUAUGGGACC (SEQ ID NO: 136), TTCAT, CCATTT, TTTTAAA, TGCAT, TGCATG, TGTGTT, CTAAC, TCTCT, TCTGT, or TCTTT. In some examples ISE 120 and ISE 156 are the same sequence. In other examples, ISE 120 and ISE 156 are the different sequences.

3'- to second dimerization domain 154 (and ISE 156 if present) is branch point sequence 158 (such as a branch point consensus sequence), a polypyrimidine tract 160, followed by a splice acceptor sequence 162 (such as a splice acceptor consensus sequence). The sequence of branch point 158 is based on the consensus sequence of the species of the target cell or organism. For example, for human splicing, the consensus sequence can include or be YUNAY. Thus, a sequence that it uses can be CUAAC for U2-dependent introns, or for U12-dependent introns UUUUCCUUAACU (SEQ ID NO: 144).

Polypyrimidine tract 160 includes C, U, or both C and U nucleotides, such as CnUy, wherein n+y is greater than or equal to 10 nucleotides, and can include nucleotides −3 to −22 relative to the 3'-splice junction. In some examples, polypyrimidine tract 160 includes at least 80% Y nucleotides (i.e., U, C, or both U and C). In some examples, polypyrimidine tract 160 is a polyC or polyU sequence. In some examples, polypyrimidine tract 160 is a polyU sequence of at least 15 Us, such as 15 to 30 or 15 to 20 Us. Branch point 158 and polypyrimidine tract 160 are essential splicing components. The sequence of SA 162 can be based on the consensus sequence of the species of the target cell or organism. For example, in humans, the SA sequence can be AG in positions −1 and −2 relative to the 3'-splice site for U2-dependent introns and AC or AG for U12-dependnet introns. Thus, in some examples, SA 162 can be 2 nt in length, such as AG or AC.

Immediately following SA 162 is an exonic sequence which includes RNA sequence encoding a C-terminal portion of a target protein 164 having a splice junction at its 5'end. The splice junction at the 5'end of RNA sequence encoding a C-terminal portion of a target protein 164, that can match the consensus sequence found in the target cell or organism into which molecules 110, 150 are introduced. In some example splice junction can be GA or GU at positon +1 and +2 of the 3' splice site for U2-dependent introns or GU or AU for U12-dependent introns. Thus, in some examples, the splice junction is 2 nt in length, and the 5' end of the C-terminal coding portion 164 is GA, GU, or AU.

The exonic sequence following intronic portion 170 of molecule 150 includes a second coding portion (e.g., half) of the target protein, e.g., the C terminal fragment 164, and optional polyadenylation sequence 166. Thus, molecule 150 includes RNA sequence 164 encoding a C-terminal portion of a target protein. The 3'-end of molecule 150 optionally includes a polyadenylation sequence 166, which promotes the assembly of the spliceosome. In some examples, polyadenylation sequence 166 is a polyA sequence of at least 15 As, such as 15 to 30 or 15 to 20 As. In some examples polyadenylation sequence 166 and polyadenylation sequence 124 are the same sequence. In other examples, polyadenylation sequence 166 and polyadenylation sequence 124 are the different sequences.

In some examples, the N-terminal coding region 114 and/or the C terminal coding region 164 is a native coding sequence. For example, the coding sequence is one that is found in the cell or organism into which the disclosed system is introduced. (e.g., a human coding sequence when introduced into a human cell or subject). In some examples, the N-terminal coding region 114 and/or the C terminal coding region 164 is codon optimized relative to a native coding sequence, for example to maximize tRNA availability, or to de-enrich for cryptic splice sites (e.g., to reduce or avoid incorrect splicing and promote the correct junction formation). In some examples, a portion of the N-terminal coding region 114 and/or the C terminal coding region 164 is codon optimized relative to a native coding sequence, for example the about 200 nt adjacent to each junction (e.g., the 3'-end of 114, and the 5'end of 164) can be codon optimized or altered to contain exonic splice enhancer sites (ESE) (which would bind SR proteins). For example, the coding sequence can be one not found in the cell or organism into which the disclosed system is introduced. (e.g., a human coding sequence when introduced into a mouse cell or subject).

In some examples, the N-terminal coding region 114 and/or the C terminal coding region 164 include an intron that is either natural or synthetic in nature and contains both a splice donor and acceptor site. For example, an intron embedded inside the to the coding sequence to be expressed can be included upstream (e.g., about 200 nt upstream) of sequence 116, inside the N-terminal coding region 114, an intron embedded inside the coding sequence to be expressed can be included downstream (e.g., about 200 nt downstream) of the sequence 162 and inside the C-terminal coding region 164, or both. Inclusion of such introns can be used to stimulate splicing machinery attachment to the trans-splicing intron donor and acceptor. In some examples, such (stimulatory-)introns could be derived from the host in which 110 and 150 are expressed. In some examples, such (stimulatory-) introns could be derived from other organisms, or viral in origin, or synthetic in origin.

In some examples, inclusion of a sequence to stabilize the RNA (e.g., placed between 164 and 166 in the 3' untranslated region of 150 in FIG. 6A) can increase expression efficiency of the recombined product by at least 25%, at least 30%, at least 40%, at least 50%, at least 60%, or at least 75%, such as 25 to 95%, 25 to 75%, 25 to 60%, 25 to 50%, 40 to 95%, 40 to 60%, or 50 to 60%. In some examples, woodchuck post-transcriptional regulatory element (WPRE) or truncations thereof (e.g. WPRE3) are included in the 3'-UTR as a stabilizing element to enhance recombined product expression efficiency. In some example a WPRE sequence has at least 80%, at least 85%, at least 90%, at least 95%, or 100% sequence identity to nt 1093 to 1684 of GenBank accession no. J04514 or to the 247 bp sequence of WPRE3.

Figure 6C:
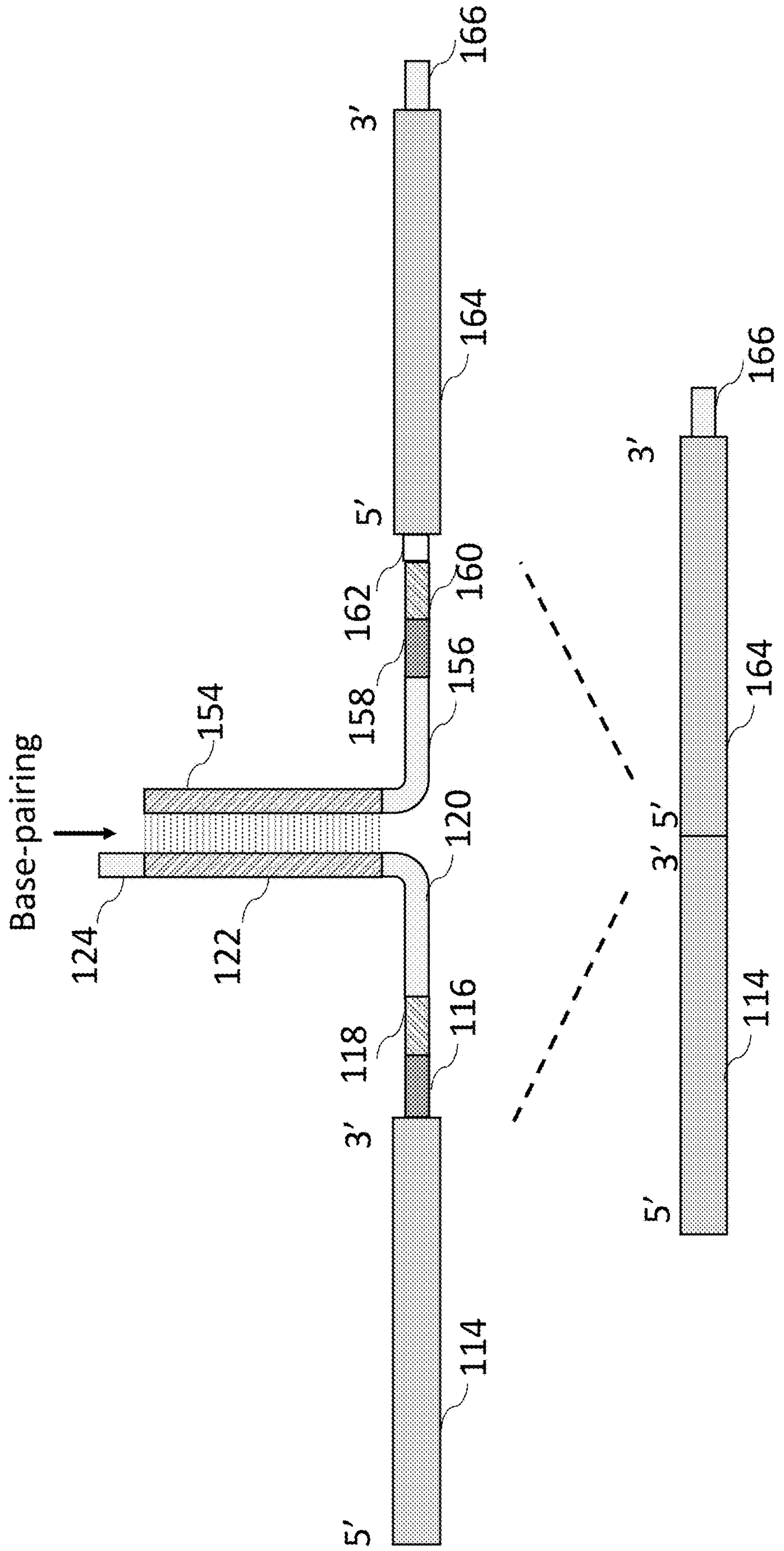
FIG. 6C is a schematic drawing showing the interaction and hybridization (base pairing) between dimerization domain 122 of molecule 110 (FIG. 6A) and dimerization domain 154 of molecule 150 (FIG. 6A), allows the spliceosome components to recombine N-terminal coding sequence 114 and C-terminal coding sequence 164. The results in the 3' end of the N terminal protein coding sequence 114 fusing to the 5' end of the C terminal protein sequence 164, and a seamless junction between the N- and C-terminal portions.

As shown in FIG. 6C, interaction and hybridization (base pairing) between first dimerization domain 122 of molecule 110 and second dimerization domain 154 of molecule 150, allows the spliceosome components to recombine N-terminal coding sequence 114 and C-terminal coding sequence 164. Specifically the 3' end of the N terminal protein coding sequence 114 is fused to the 5' end of the C terminal protein sequence 164 as a seamless junction between the two portions.

Figure 6D:
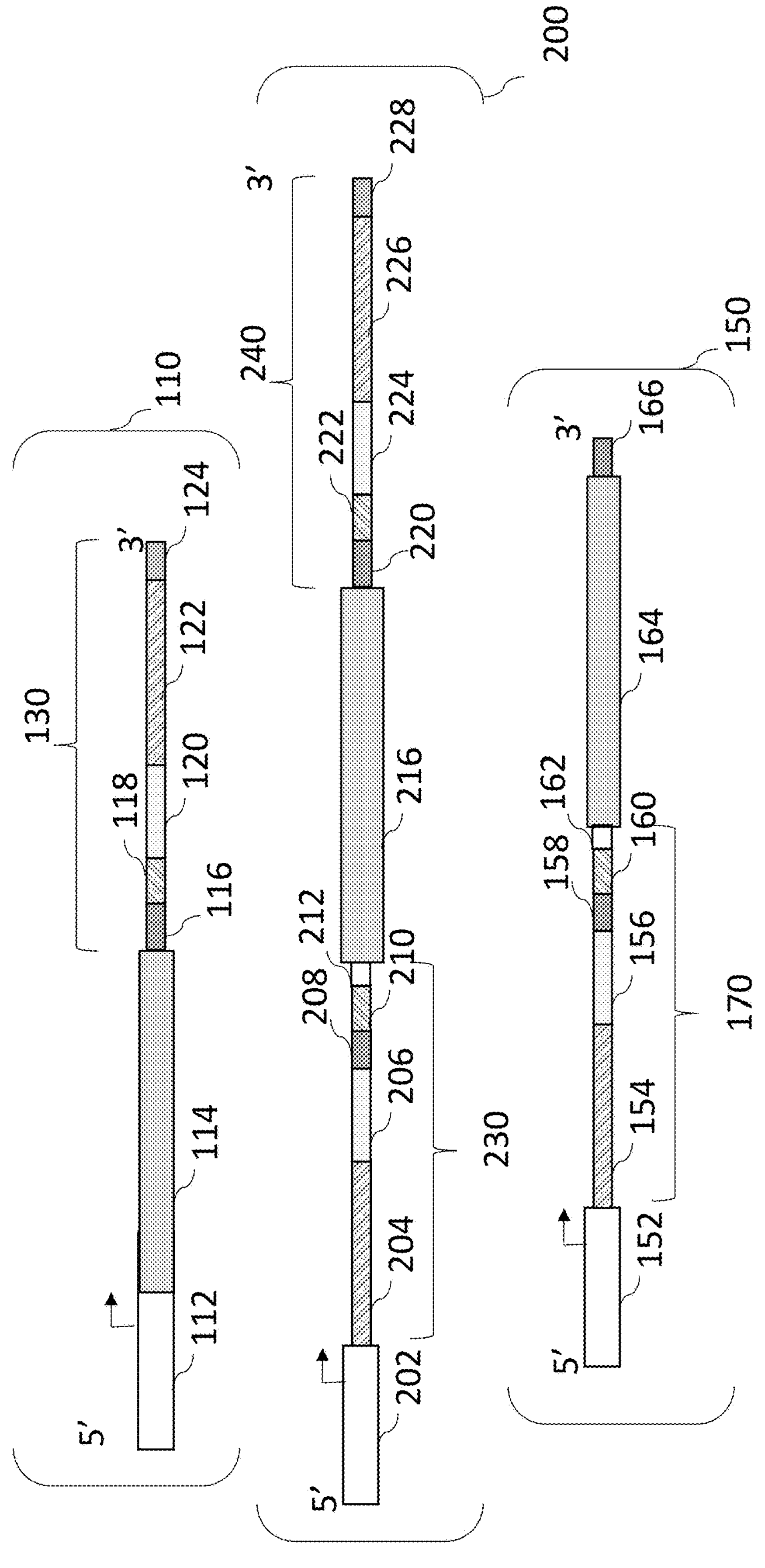
FIG. 6D is a schematic drawing providing an exemplary system for the disclosed RNA recombination methods, using three nucleic acid molecules 110, 200, 150, wherein the target protein is divided into three portions (N-terminal, middle, C-terminal) and each portion is encoded by a different nucleic acid molecule. Drawing not to scale.

FIG. 6D shows a schematic of a system wherein a target protein is divided into three portions, an N-terminal, middle, and C-terminal portion (wherein each portion can be similar or different in size). One skilled in the art will appreciate that a protein can thus be divided into any number of desired segments or portions, and an appropriate number of molecules designed using the information provided herein. In such an example, the system includes at least three synthetic nucleic acid molecules 110, 200, and 150, wherein molecule 110 includes RNA molecule 114 which encodes the N-terminal portion of the protein, molecule 200 includes RNA molecule 216 which encodes the middle portion of the protein, and molecule 150 includes RNA molecule 164 which encodes the C-terminal portion of the protein. Each nucleic acid molecule 110, 200, 150 can be composed of RNA. In some examples, each of 110, 200, 150 is at least about 100 nucleotides/ribonucleotides (nt) in length, such as at least 200, at least 300, at least 500, at least 1000, at least 2000, at least 3000, at least 4000, at least 5000, at least 6000, at least 7000, or at least 8000 nt, such as 200 to 10,000 nt, 200 to 8000 nt, 500 to 5000 nt, or 200 to 1000 nt. The molecules 110, 150, 200 can include natural and/or non-natural nucleotides or ribonucleotides. In addition to using two (or more) orthogonal dimerization domains, one of the two introns can be a U2-type intron and the second intron can be a U12-type intron. Splice donor and acceptors of U2 and U12 dependent introns show minimal cross reactivity since the consensus recognition sequences between the two types of introns are different. Both strategies (i.e., the orthogonal dimerization domains, and the U2 vs U12 type introns) promote recombination of the three fragments in the correct order (e.g., to avoid the first fragment to directly join up to the last fragment and to avoid the middle fragment circularizing onto itself).

Figure 1A:
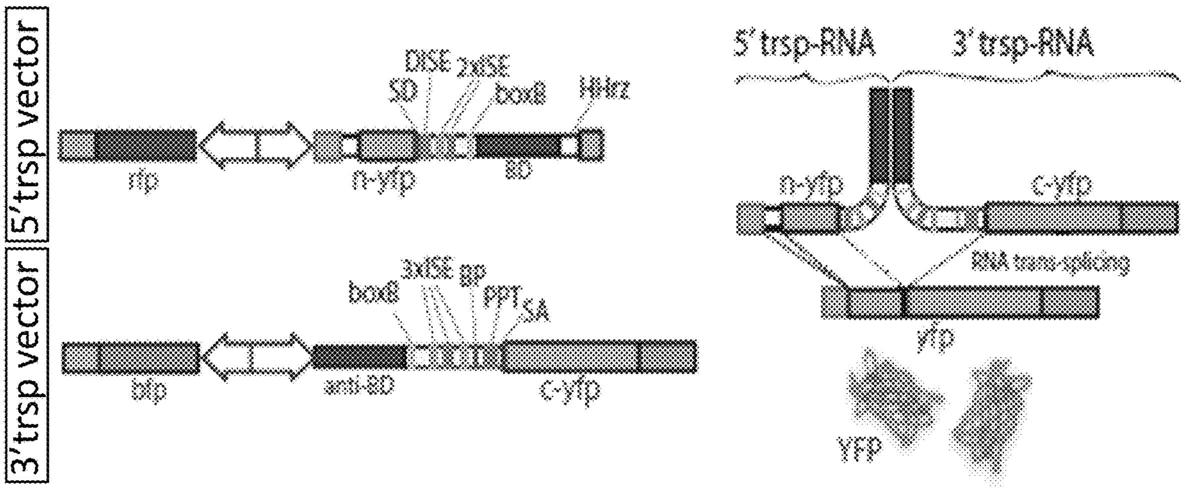
FIG. 1A depicts a schematic of vector designs.

Molecule 110 of FIG. 6D includes the same features disclosed above for FIG. 1A, namely from 5' to 3', promoter 112, RNA encoding an N-terminal portion of a target protein 114 with a splice junction at its 3'-end, SD 116, optional DISE 118, optional ISE 120, dimerization domain 122, and optional polyadenylation sequence 124, but wherein first dimerization domain 122 has reverse complementary to third dimerization domain 204 of molecule 200.

Molecule 150 of FIG. 6D includes the same features disclosed above for FIG. 1A, namely from 5' to 3', promoter 152, second dimerization domain 154, optional ISE 156, branch point 158, polypyrimidine tract 160, SA 162, RNA encoding a C-terminal portion of a target protein 164 with a splice junction at its 5'-end, and optionally polyadenylation sequence 166, but wherein second dimerization domain 154 has reverse complementary to fourth dimerization domain 226 of molecule 200.

Molecule 200 allows for the joining of the N- and C-terminal coding RNAs 114, 164, by providing dimerization domains having reverse complementarity to dimerization domains 122, 154 of molecule 110 and molecule 150, respectively. Molecule 200 includes features from both molecule 110 and molecule 150, including two intronic sequences 230, 240. Specifically, molecule 220 includes from 5' to 3', promoter 210 (which can be the same or different than promoter 112 and/or 152), third dimerization domain 204 (which is the reverse complement to first dimerization domain 122 of molecule 110 in FIG. 6D), optional ISE 206, branch point 208, polypyrimidine tract 210, SA 212, RNA encoding a middle portion of a target protein 216 with a splice junction at both its 5'-end and 3'-end, SD 220, optional DISE 222, optional ISE 224, fourth dimerization domain 226 (which is the reverse complement to fourth dimerization domain 154 of molecule 150 in FIG. 6D), and optional polyadenylation sequence 228.

Figure 6E:
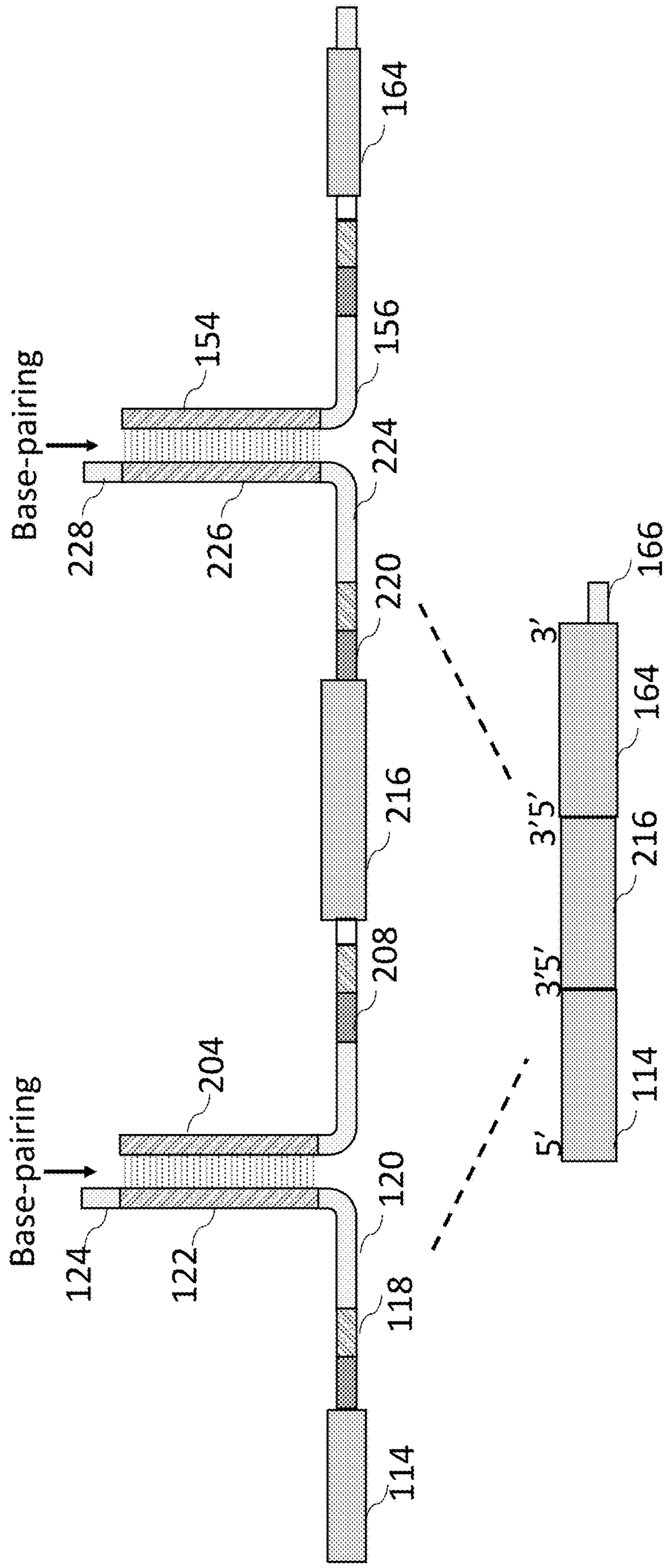
FIG. 6E is a schematic drawing showing the interaction and hybridization (base pairing) between dimerization domain 122 of molecule 110 (FIG. 6D) and dimerization domain 204 of molecule 200 (FIG. 6D), and between dimerization domain 226 of molecule 200 (FIG. 6D) and dimerization domain 154 of molecule 150 (FIG. 6D), allows the spliceosome components to recombine N-terminal coding sequence 114, middle coding sequence 216, and C-terminal coding sequence 164. The results in the 3' end of the N terminal coding sequence 114 fusing to the 5' end of the middle protein sequence 216, and the 3' end of the middle coding sequence 216 fusing to the 5' end of the C-terminal sequence 216, and a seamless junction between the N-, middle, and C-terminal portions.

As shown in FIG. 6E, interaction and hybridization (base pairing) between first dimerization domain 122 of molecule 110 and third dimerization domain 204 of molecule 200, and interaction and hybridization (base pairing) between fourth dimerization domain 226 of molecule 200 and second dimerization domain 154 of molecule 150, allows the spliceosome components to recombine N-terminal coding sequence 114, middle coding sequence 216, and C-terminal coding sequence 164. Specifically the 3' end of the N terminal protein coding sequence 114 is fused to the 5' end of the middle protein sequence 216, and the 3' end of middle protein sequence 216, is fused to the 5' end of the C-terminal protein sequence 164 as a seamless junction between the three portions.

Figure 7A:
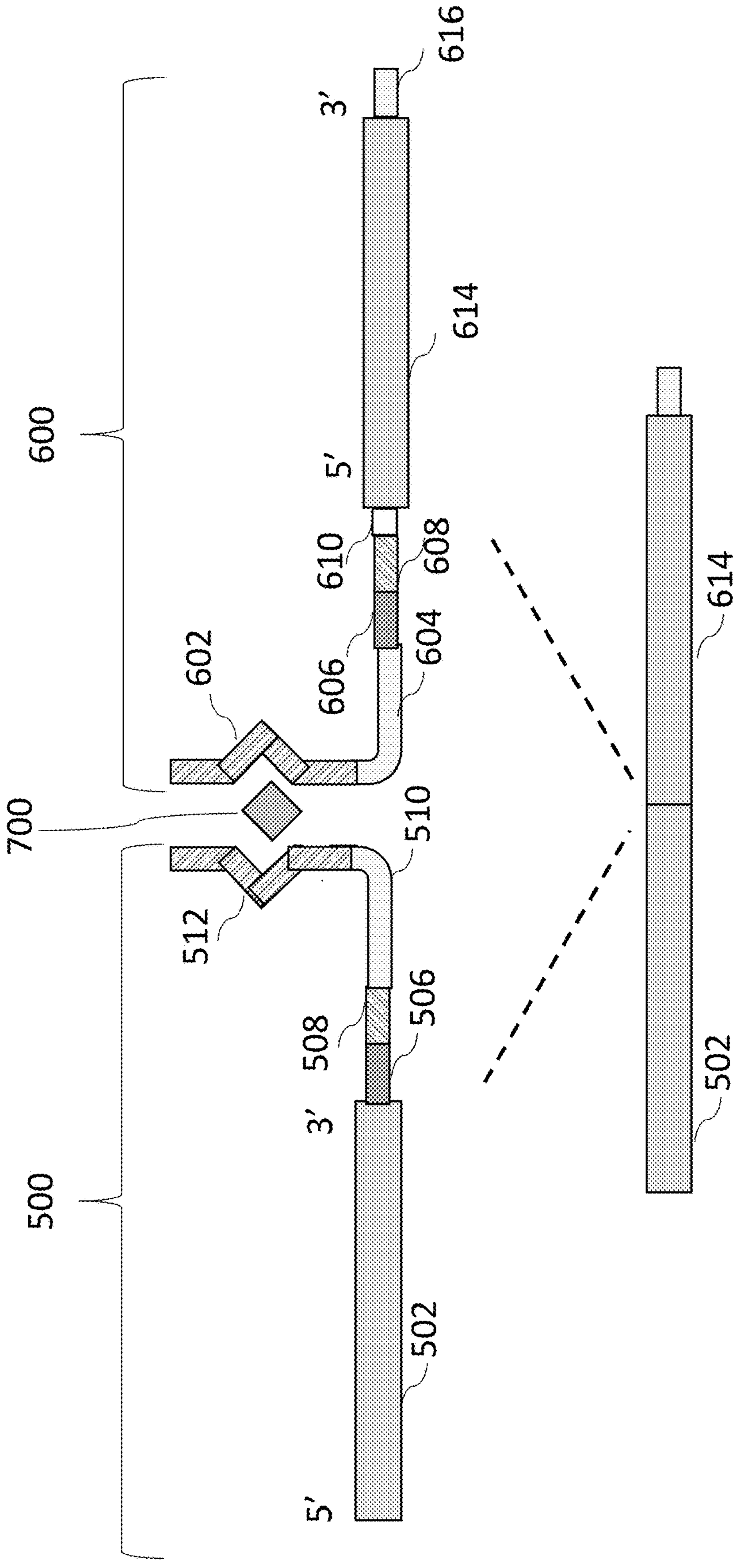
FIG. 7A is a schematic drawing providing an exemplary system for the disclosed RNA recombination methods, that like FIG. 6A uses two nucleic acid molecules 500, 600, but the dimerization domains are aptamers 512, 602, that recognize the same target molecule 700. Drawing not to scale.
Figure 7B:
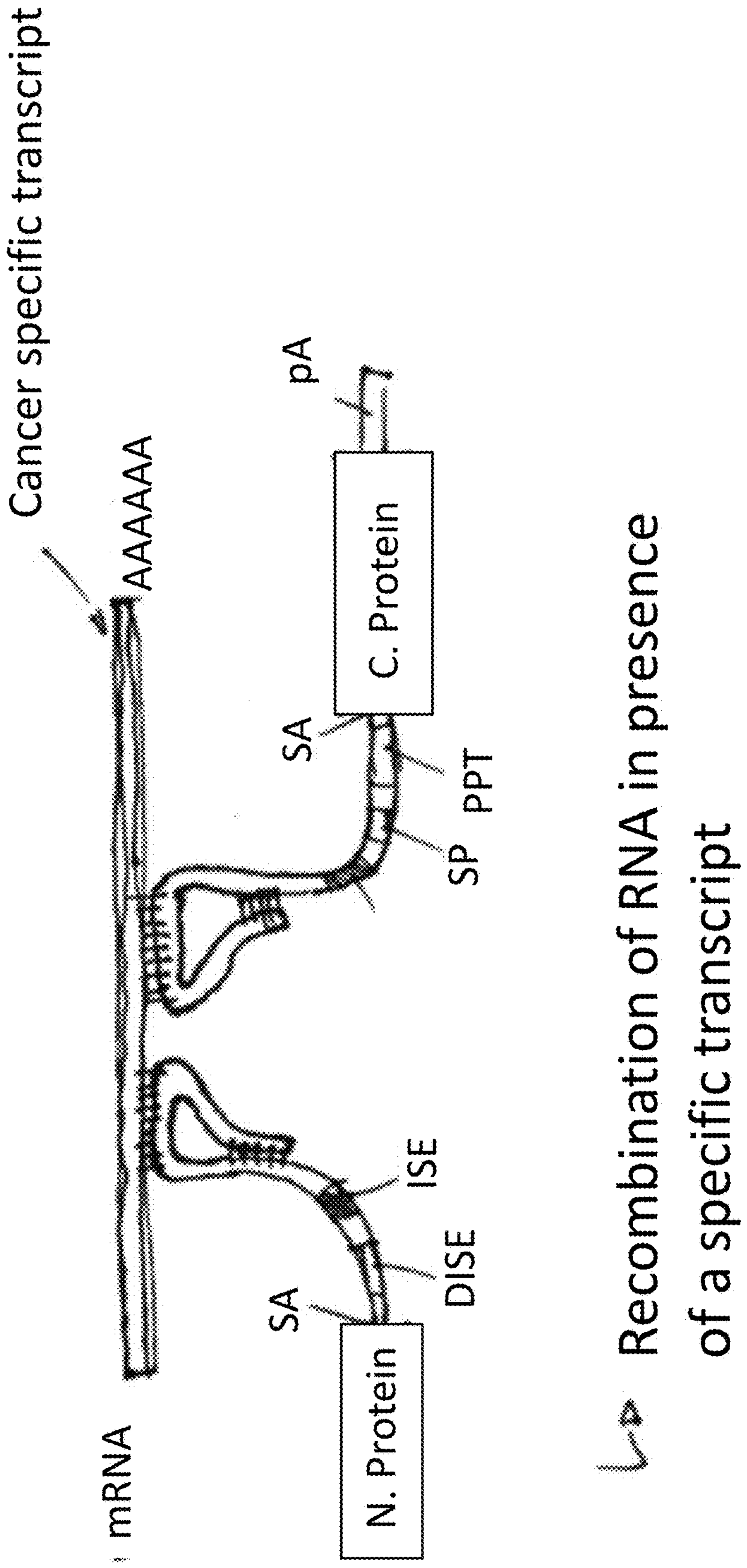
FIG. 7B is a schematic drawing providing an exemplary system for the disclosed RNA recombination methods, that, related to FIG. 7A, uses dimerization domains that recognize the same target molecule. Here, the target recognized by the dimerization domain is a specific RNA molecule (instead of molecule 700 in FIG. 7A, e.g., protein or small molecule). Each domain recognizes a different portion of an mRNA molecule only expressed in target cells (i.e., cells where target protein expression is desired), such as a cancer-specific transcript. Drawing not to scale.
Figure 9A:
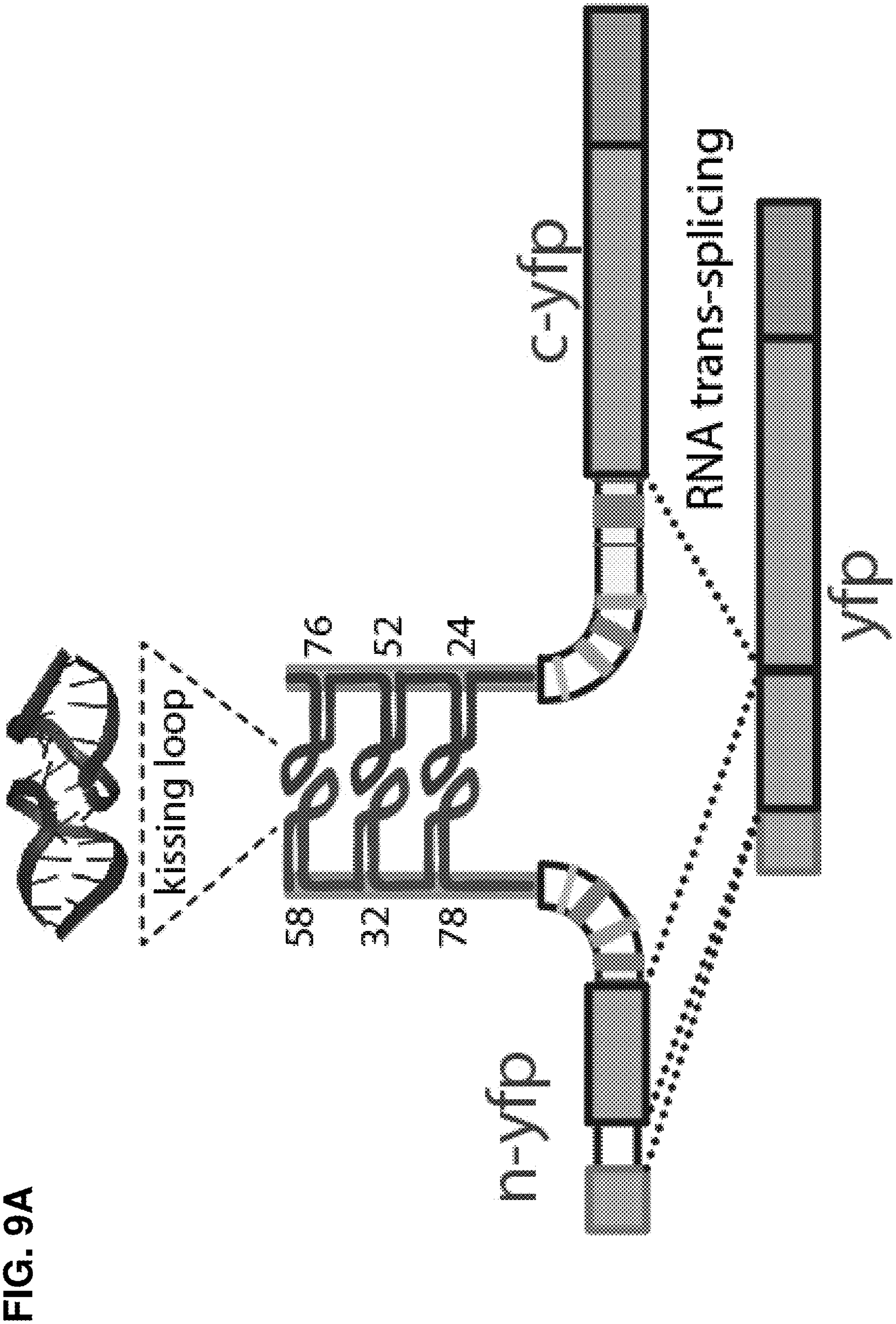
FIG. 9A is a schematic drawing providing an example for the use of dimerization domain (e.g., 122, 154 of FIG. 6A) that includes kissing loop interaction for high affinity dimerization. Using the teachings provided herein, one will appreciate that any of the disclosed coding portions (e.g., YFP) can be replaced with other target protein coding sequences.
Figure 9B:
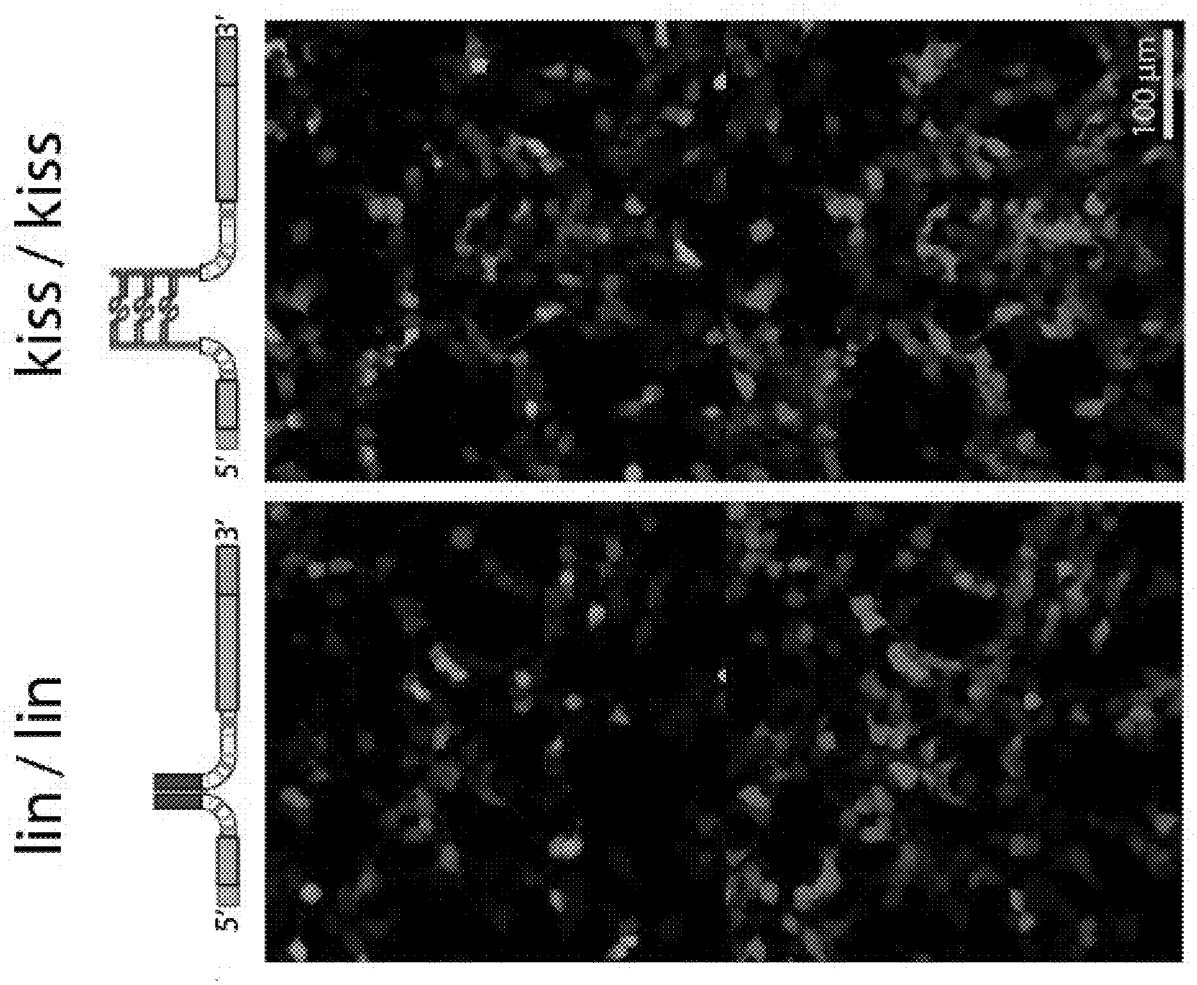
FIG. 9B depicts RFP, BFP, and YFP signal in HEK293T cells transfected with both halves of the split YFP. Equipped with either a linear dimerization adhering to the hypodiverse design principle or a structured dimerization domain designed for kissing loop-loop interactions. Strong yellow fluorescent signal indicates efficient reconstitution.

Alternative dimerization domains are shown in FIGS. 7A-7B and 9A. That is, as an alternative to using dimerization domains that hybridize to one another (e.g., 112 to 204, 226 to 154, FIGS. 6D, 6E), in one example aptamer sequences are used. As shown in FIG. 7A, in both synthetic nucleic acid molecules 500, 600, aptamer sequences 512, 602 are used instead of the dimerization domains, and the aptamers come together via their interaction with a target (such as adenosine, dopamine, or caffeine). In such an example, the aptamer sequence 512, 602 of each molecule 500, 600 can be the same, or even be different sequences. Molecule 500 of FIG. 7A includes the same features disclosed above for molecule 110 of FIG. 6A, namely from 5' to 3', promoter, RNA encoding an N-terminal portion of a target protein 502 with a splice junction at its 3'-end, SD 506, optional DISE 508, optional ISE 510, a first aptamer 512 instead of a first dimerization domain, and optional polyadenylation sequence. Similarly, molecule 600 of FIG. 7A includes the same features disclosed above for molecule 150 of FIG. 6A, namely from 5' to 3', promoter, aptamer 602 instead of second dimerization domain 154, optional ISE 604, branch point 606, polypyrimidine tract 608, SA 610, RNA encoding a C-terminal portion of a target protein 614 with a splice junction at its 5'-end, and optional polyadenylation sequence 616. Interaction of the two aptamers 512, 602, with each other or molecule 700 allows the spliceosome components to recombine N-terminal coding sequence 502 and C-terminal coding sequence 614. Specifically the 3' end of the N terminal protein coding sequence 502 is fused to the 5' end of the C terminal protein sequence 614 as a seamless junction between the two portions.

In some examples, aptamer sequences 512, 602 recognize (e.g., specifically bind) the same target 700 (FIG. 7A), or can even recognize different targets (wherein a synthetic molecule is also administered with the system provided herein, which includes each molecule specifically recognized by each aptamer, or the part of the molecule recognized by the aptamer, such as a caffeine/dopamine hybrid molecule). Exemplary targets recognized by aptamers include cellular proteins, small molecules, exogenous proteins, or an RNA molecule.

FIG. 7B shows an example similar to FIG. 7A. The dimerization domains (512, 602 FIG. 7A) recognize an RNA molecule. In the example shown in FIG. 7B, each domain recognizes a different portion of an mRNA molecule only expressed in target cells (cells where target protein expression is desired), such as a cancer-specific transcript. In such an example, the RNA coding sequences (502, 614 of FIG. 7A) only recombine in the presence of the specific RNA molecule recognized by the dimerization domains. Here, the target protein would only be expressed in cancer cells, not normal cells. Such a system allows for control of the target protein expression (e.g., a therapeutic protein for cancer, such as a toxin or a cytotoxic enzyme such as thymidine kinase with ganciclovir; thus in some examples the target protein is a toxin or thymidine kinase) in cancer cells, reducing undesirable side effects of expression the target protein in normal, non-cancer cells.

Figure 7C:
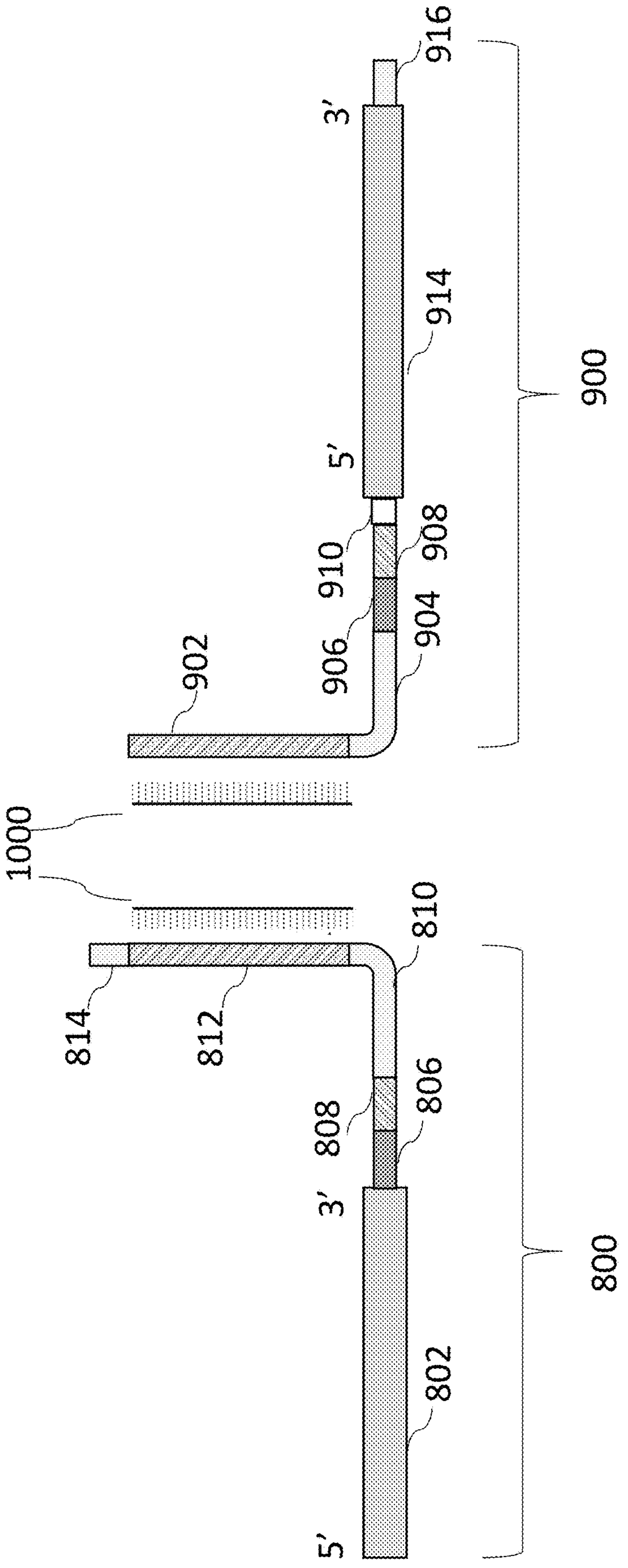
FIG. 7C is a schematic drawing providing an exemplary system for the disclosed RNA recombination methods, that like FIGS. 6A and 7A, uses two nucleic acid molecules 800, 900, and shows the dimerization domains 812, 902 hybridizing to an oligonucleotide 1000 that prevents the dimerization domains from interacting with one another, and therefore prevents or reduces recombination of the N-terminal coding sequence 802 and C-terminal coding sequence 914. Drawing not to scale.

FIG. 7C provides an exemplary "off-switch" example. Here, the hybridization/binding of dimerization domains 812, 902 (which are reverse complements of one another) of synthetic nucleic acid molecules 800, 900 can be reduced by providing an anti-binding domain oligonucleotide (e.g, RNA or DNA) 1000 (which can be two different anti-binding domain oligonucleotides 1000, one that is the reverse complement of 812, and one that is the reverse complement of 912) that competes for the binding/hybridization. Anti-binding domain oligonucleotide 1000 can thus act as an "off-switch" for reconstitution of the protein encoded by N- and C-terminal coding portions 802 and 914, respectively. Molecule 800 of FIG. 7C includes the same features disclosed above for molecule 110 of FIG. 6A, namely from 5' to 3', promoter, RNA encoding an N-terminal portion of a target protein 802, splice junction 804, SD 806, optional DISE 808, optional ISE 810, dimerization domain 812, and optional polyadenylation sequence 814. Similarly, molecule 900 of FIG. 7B includes the same features disclosed above for molecule 150 of FIG. 6A, namely from 5' to 3', promoter, anti-dimerization domain 902, optional ISE 904, branch point 906, polypyrimidine tract 908, SA 910, RNA encoding a C-terminal portion of a target protein 914, and optional polyadenylation sequence 916. The two dimerization domains 812, 902 cannot interact/hybridize to each other in the presence of the anti-binding domain oligonucleotides 1000, and therefore prevents or reduces recombination of the N-terminal coding sequence 802 and C-terminal coding sequence 914. Such an application can be used to reduce or eliminate expression of the protein encoded by the system.

FIG. 9A provides an exemplary dimerization domain that uses kissing loop interactions instead of reverse complementary sequence hybridization for dimerization. Kissing loop interactions are formed when the bases in the loops of two RNA hairpins form interacting pairs between two RNA molecules.

Although FIGS. 6A-7C and 9A show embodiments where a system uses two synthetic nucleic acid molecules are used (i.e., the target protein coding sequence is split between two synthetic nucleic acid molecules), one skilled in the art will appreciate that such embodiments can be used similarly with more than two synthetic nucleic acid molecules, such as three, four, five, six, seven, eight, nine, or 10 synthetic nucleic acid molecules using the teachings herein.

In some examples, the system includes a nucleic acid molecule that suppresses expression of un-assembled/un-recombined fragments. In such an example, if the two or more portions of a full-length coding sequence (e.g., 114 of 110, 164 of 150 of FIG. 6A, respectively), did not recombine, the nucleic acid molecule would suppress expression of each portion of a full-length coding sequence that was not recombined into a full-length protein. For example, such a suppressive nucleic acid molecule can destabilize the RNA once outside the nucleus, prevent translation, stimulate translation from a shifted start codon, contain microRNA target sites, or contain protein degron or destabilization domains that when translated suppress the protein activity or flag it for degradation.

In one example, destabilization of the un-recombined RNA molecule is achieved by including a self-cleaving RNA sequence (e.g., Hammerhead ribozyme or HDV ribozyme) into the synthetic intron, for example at any position within intronic sequence 130 of FIG. 6A. In one example, cleaving the RNA molecule leads to a loss of the RNA stabilizing poly A tail, which can suppress expression of an un-recombined protein from open reading frame 114 of FIG. 6A. In one example, a self-cleaving RNA sequence is included at any position within s intronic sequence 170 of FIG. 6A to cleave off the 5' terminal CAP which in one example can lead to reduced expression of an open reading frame that includes parts or the whole of coding sequence 164 of FIG. 6A. In one example self-cleaving RNA sequences are substituted with an RNA cleaving enzyme target site, such as a Csy4 target site.

In some examples, a suppressive nucleic acid molecule includes a start codon (ATG) or a Kozak enhanced start codon (GCCGCCACCATG (SEQ ID NO: 154) or GCCACCATG or ACCATG) at any position within intronic sequence 170 of FIG. 6A that directs translation of an open reading frame that is shifted −1, −2, +1, or +2 nucleotides relative to the open reading frame sequence 164 of FIG. 6A. In one example, un-assembled fragment expression is reduced or suppressed by using this decoy start codon strategy to direct translation away from the to be suppressed open reading frame of sequence 164 of FIG. 6A.

In some examples, a suppressive nucleic acid molecule includes one or more micro RNA target sites at any position within intronic sequence 130 of FIG. 6A, and/or at any position within intronic sequence 170 of FIG. 6A. If a particular RNA molecule (e.g., 110 or 150 in FIG. 6A) is exported from the nucleus, it becomes subject to micro RNA/small hairpin RNA dependent degradation which can suppress unintended un-joined fragment expression by degrading/suppressing un-joined RNA that was exported from the nucleus. In one example, such a micro RNA target sequence can be complementary to a micro RNA known to be expressed in the cell, or tissue, or animal into which the molecules 110 and 150 of FIG. 6A are introduced. In one example, this micro RNA target sequence is complementary to a sequence that is introduced into the cell, or tissue, or animal. In one example, such a microRNA can be expressed from an RNA-polymerase III dependent promoter in the form of a small hairpin RNA. In one example, such a microRNA can be expressed from an RNA polymerase II dependent promoter and embedded in a micro RNA processing loop (e.g., mir30 scaffold).

In some examples, destabilization of the un-recombined protein product from an open reading frame (e.g., 114 in FIG. 6) can be achieved by depleting stop codon occurrence in intronic sequence 130 of FIG. 6A and an additional inclusion of an RNA sequence coding for an in frame protein signal that can flag a protein for degradation (e.g., a degron sequence) that is placed at any position within intronic sequence 130 of FIG. 6A and which is in frame with the open reading frame that is extended out from sequence 114 of FIG. 6A. In one example a degron sequence can be that of a PEST sequence, or that of the CL1 degron sequence. Degron sequences used can employ proteasome-dependent, proteasome-independent, ubiquitin-dependent, or ubiquitin-independent pathways. In one example, un-recombined protein destabilization is enhanced by inclusion of several of the same or different degron sequences.

In some examples, destabilization of the un-recombined protein product from open reading frame sequence 164 in FIG. 6A is achieved by introduction of a start codon (ATG) followed by a degron sequence at any position within intronic sequence 170 in FIG. 6A which is in frame with an open reading frame within sequence 164 in FIG. 6. In this example, the degron sequence will be N-terminally joined to the un-recombined protein fragment that will be suppressed by being flagged for degradation.

IV. Compositions and Kits

Compositions and kits are provided that include two or more of the synthetic nucleic acid molecules provided herein, wherein the synthetic nucleic acid molecule encode a full-length protein when recombined. In one example, the composition or kit includes two of the synthetic nucleic acid molecules provided herein, wherein each of the two synthetic nucleic acid molecules encodes a different portion of a target protein (i.e., N-terminal and C-terminal, wherein the whole coding sequence is generated when recombination between the two molecules occurs), such as one listed in Table 1 (or a therapeutic protein, such as a toxin or thymidine kinase). In one example, the composition or kit includes three of the synthetic nucleic acid molecules provided herein, wherein each of the three synthetic nucleic acid molecules encodes a different portion of a target protein (i.e., N-terminal, middle, and C-terminal, wherein the whole coding sequence is generated when recombination between the three molecules occurs), such as one listed in Table 1 (or a therapeutic protein, such as a toxin or thymidine kinase). In one example, the composition or kit includes four or more of the synthetic nucleic acid molecules provided herein, wherein each of the four of more synthetic nucleic acid molecules encodes a different portion of a target protein (i.e., N-terminal, first middle, second middle (and optionally additional middle), and C-terminal, wherein the whole coding sequence is generated when recombination between the four or more synthetic nucleic acid molecules occurs), such as one listed in Table 1 (or a therapeutic protein, such as a toxin or thymidine kinase). In one example, the composition or kit includes two or more sets of two or more of the synthetic nucleic acid molecules provided herein, wherein each set of synthetic nucleic acid molecules encodes a different target protein, such as two or more listed in Table 1 (and/or a therapeutic protein, such as a toxin or thymidine kinase).

In one example, each synthetic nucleic acid molecule in the composition or kit is part of a vector, such as AAV or other gene therapy vector. In one example, the composition or kit includes a cell, such as a bacterial cell or eukaryotic cell, that includes two or more disclosed synthetic nucleic acid molecule, wherein the synthetic nucleic acid molecules encode a full-length target protein when recombined.

Such compositions can include a pharmaceutically acceptable carrier (e.g., saline, water, glycerol, DMSO, or PBS). In some examples, the composition is a liquid, lyophilized powder, or cryopreserved.

In some examples, the kit includes a delivery system (e.g., liposome, a particle, an exosome, or a microvesicle) to direct cell type specific uptake/enhance endosomal escape/enable blood-brain barrier crossing etc. In some examples, the kits further include cell culture or growth media, such as media appropriate for growing bacterial, plant, insect, or mammalian cells. In some examples, such parts of a kit are in separate containers. Exemplary containers include plastic or glass vials or tubes.

In some examples, each of two or more the synthetic nucleic acid molecules provided herein are in separate containers. In some examples, each of two or more sets of two or more of the synthetic nucleic acid molecules provided herein are in separate containers.

V. Methods of Treatment

The disclosed methods and systems can be used to express any protein of interest, for example when a protein is too large to be expressed by a therapeutic virus (e.g., AAV) or when a complete gene sequence (e.g., endogenous promoter+coding sequence) is too large to be expressed by a therapeutic virus (e.g., AAV). In such cases, the coding sequence of the target protein may be divided into two or more portions and recombined in the correct order, allowing for the protein to be expressed when and where desired.

The subject to be treated can be any mammal, such as one with a monogenetic disorder, such as one listed in Table 1. In one example, the subject has cancer. Thus, humans, cats, pigs, rats, mice, cows, goats, and dogs, can be treated with the disclosed methods. In some examples, the subject is a human infant less than 6 months of age. In some examples, the subject is a human infant less than 1 year of age. In some examples, the subject is a human juvenile. In some examples, the subject is a human adult at least 18 years of age. In some examples, the subject is female. In some examples, the subject is male.

The two or more synthetic nucleic acid molecules provided herein used to treat a subject can be matched to the subject treated. Thus, for example, if the subject to be treated is a dog, a dog coding sequence for the target protein can be used and the intronic sequence can be optimized for expression in dog cells, and if the subject to be treated is a human, a human coding sequence for the target protein can be used and the intronic sequence can be optimized for expression in human cells.

The two or more synthetic nucleic acid molecules provided herein can be administered as part of a vector, such as an adeno-associated vector (AAV), for example AAV serotype rh.10. In some examples, vectors (e.g., AAV) including one of the two or more synthetic nucleic acid molecules provided herein are administered systemically, such as intravenously. Thus, if a coding sequence is divided between two synthetic nucleic acid molecules provided herein, two AAV's are administered, each AAV including one of the two synthetic nucleic acid molecules provided herein.

A therapeutically effective amount of two or more synthetic nucleic acid molecules provided herein is administered, for example in AAVs. In some examples, the two or more synthetic nucleic acid molecules provided herein when part of a viral vector (e.g., AAV) is administered at a dose of at least $1\times10^{11}$ genome copies (gc), at least $1\times10^{12}$ gc, at least $2\times10^{12}$ gc, at least $1\times10^{13}$ gc, at least $2\times10^{13}$ gc per subject, or at least $1\times10^{14}$ gc per subject, such as $2\times10^{11}$ gc per subject, $2\times10^{12}$ gc per subject, $2\times10^{13}$ gc per subject, or $2\times10^{14}$ gc per subject. In some examples, the two or more synthetic nucleic acid molecules provided herein when part of a viral vector (e.g., AAV) is administered at a dose of at least $1\times10^{11}$ gc/kg, at least $5\times10^{11}$ gc/kg, at least $1\times10^{12}$ gc/kg, at least $5\times10^{12}$ gc/kg, at least $1\times10^{13}$ gc/kg, or at least $4\times10^{13}$ gc/kg, such as $4\times10^{11}$ gc/kg, $4\times10^{12}$ gc/kg, or $4\times10^{13}$ gc/kg.

If adverse symptoms develop, such as AAV-capsid specific T cells in the blood, corticosteroids can be administered (e.g., see Nathwani et al., *N Engl J Med.* 365(25):2357-65, 2011).

Diseases that can be treated with the disclosed methods include any genetic disease of the blood (e.g. sickle cell disease, primary immunodeficiency diseases), HIV (such as HIV-1), and hematologic malignancies or cancers. Examples of primary immunodeficiency diseases and their corresponding mutations include those listed in Al-Herz et al. (*Frontiers in Immunology*, volume 5, article 162, Apr. 22, 2014, herein incorporated by reference in its entirety). Hematologic malignancies or cancers are those tumors that affect blood, bone marrow, and lymph nodes. Examples include leukemia (e.g., acute lymphoblastic leukemia, acute myelogenous leukemia, chronic lymphocytic leukemia, chronic myelogenous leukemia, acute monocytic leukemia), lymphoma (e.g., Hodgkin's lymphoma and non-Hodgkin's lymphoma), and myeloma. In some examples, the disease is a monogenetic disease. Table 1 provides a list of exemplary disorders and genes that can be targeted by the disclosed systems and methods. Additional examples are provided here rarediseases.info.nih.gov/diseases/diseases-by-category/5/congenital-and-genetic-diseases (list herein incorporated by reference). Any genetic disease caused by a lack of protein (e.g., recessive mutation) or an insufficiency of protein can benefit from the disclosed systems and methods. In cases where the coding region of the gene is relatively small, the disclosed systems and methods are useful to add regulatory sequences, such as tissue specific promoters or specific non-coding RNA segments, to direct gene expression to the appropriate cell types at the appropriate levels.

TABLE 1

Exemplary disorders and corresponding mutations

| Disease | Gene | Mutation |
|---|---|---|
| Blood cell disorder | | |
| sickle cell anemia | β-globin chain of hemoglobin | SNP (A to T) that gives rise to point mutation (Glu->Val at 6$^{th}$ aa) |
| hemophilia | any of clotting factors I through XIII | |
| hemophilia A | clotting factor VIII | large deletions, insertions, inversions, and point mutations |
| hemophilia B | clotting factor IX | |
| Alpha-Thalassemia | HBA1 or HBA2 | Mutation or a deletion in chromosome 16 p |
| Beta-Thalassemia | HBB | Mutations in chromosome 11 |
| Delta-Thalassemia | HBD | mutation |
| von Willebrand Disease | von Willebrand factor | mutations or deletion |
| pernicious anemia | MTHFR | |

TABLE 1-continued

| Exemplary disorders and corresponding mutations | | |
|---|---|---|
| Disease | Gene | Mutation |
| Fanconi anemia | FANCA, FANCC, FANCD2, FANCG, FANCJ | FANCA: c.3788_3790del (p.Phe1263del); c.1115_1118delTTGG (p.Val372fs); Exon 12-17del; Exon 12-31del; c.295C > T (p.Gln99X)<br>FANCC: c.711 + 4A > T (originally reported as IVS4 + 4A > T); c.67delG (originally reported as 322delG)<br>FANCD2: c.1948 − 16T > G<br>FANCG; c.313G > T (p.Glu105X); c.1077 − 2A > G; c.1480 + 1G > C; c.307 + 1G > C; c.1794_1803del (p.Trp599fs); c.637_643del (p.Tyr213fs)<br>FANCJ: c.2392C > T (p.Arg798X) |
| Thrombocytopenic purpura | ADAMTS13 | Missense and nonsense mutations |
| thrombophilia | Factor V Leiden<br>Prothrombin | Mutation in the F5 gene at position 1691<br>Prothrombin G20210A |
| Primary Immunodeficiency Diseases | | |
| T-B+ SCID | IL-2RG, JAK3, defect in gamma chain of receptors for IL-2, -4, -7, -9, -15 and -21 | |
| T-B− SCID | RAG1, RAG2 | |
| WHIM syndrome | CXCR4 | heterozygous mutations (e.g., in the carboxy-terminus); carboxy-terminus truncation (e.g., 10-19 residues) |
| Other Primary immune deficiency (PID) syndromes | | |
| IL-7 receptor severe combined immune deficiency (SCID) | IL7 receptor | |
| Adenosine deaminase deficiency (ADA) SCID | ADA | |
| Purine nucleoside phosphorylase (PNP) deficiency | PNP | |
| Wiskott-Aldrich syndrome (WAS) | WAS | More than 300 mutations identified |
| Chronic granulomatous disease (CGD) | CYBA, CYBB, NCF1, NCF2, or NCF4 | |
| Leukocyte adhesion deficiency (LAD) | Beta-2 integrin | |
| HIV | C-C chemokine receptor type 5 (CCR5),<br>MSRB1<br>HIV long terminal repeats<br>CSCR4<br>P17<br>PSIP1 | Deletion of 32 bp in CCR5 |
| Duchenne muscular dystrophy | CCR5<br>DMD | |
| Glycogen storage disease type IA | G6Pase | |
| Retinal Dystrophy | CEP290<br>ABCA4 | C2991 + 1655A > G<br>5196 + 1216C > A; 5196 + 1056A > G; 5196 + 1159G > A; 5196 + 1137G > A; 938 − 619A > G; 4539 + 2064C > T |
| X-linked immunodeficiency with magnesium defect, Epstein-Barr virus infection, and neoplasia (XMEN) | MAGT1 | |

TABLE 1-continued

| Exemplary disorders and corresponding mutations | | |
|---|---|---|
| Disease | Gene | Mutation |
| MonoGenetic Disorders | | |
| Metachromatic leukodystrophy (MLD) | arylsulfatase A (ARSA) | |
| Adrenoleukodystrophy (ALD) | ABCD1 | |
| Mucopolysaccaridoses (MPS) disorders | IDS<br>IDUA | |
| Hunter syndrome | IDUA | |
| Hurler syndrome | SGSH, NAGLU, | |
| Scheie syndrome | HGSNAT, GNS | |
| Sanfilippo syndrome A, B, C, and D | GALNS<br>GLB1 | |
| Morquio syndrome A | ARSB | |
| Morquio syndrome B | GUSB | |
| Maroteaux-Lamy syndrome | HYAL1 | |
| Sly syndrome | | |
| Natowicz syndrome | | |
| Alpha manosidosis | MAN2B1 | |
| Nieman Pick disease types A, B, and C | SMPD1, NPC1, NPC2 | |
| Cystic fibrosis | cystic fibrosis transmembrane conductance regulator (CFTR) | ΔF508 |
| Polycystic kidney disease | PKD-1, PDK-2, PDK-3 | |
| Tay Sachs Disease | HEXA | 1278insTATC |
| Gaucher disease | GBA | |
| Huntington's disease | HTT | CAG repeat |
| Neurofibromatosis types 1 and 2 | NF-1 and NF2 | CGA->UGA->Arg1306Term in NF1 |
| Familial hypercholesterolemia | APOB, LDLR, LDLRAP1, and PCSK9 | |
| Cancers | | |
| Chronic myeloid leukemia (CML) | BCR-ABL<br>ASXL1 | fusion |
| Acute myeloid leukemia (AML) | Chromosome 11q23 or t(9; 11) | translocation |
| Osteosarcoma | RUNX2 | |
| Colorectal cancer | EPHA1 | |
| Gastric cancer, melanoma | PD-1 | |
| Prostate cancer | Androgen receptor | |
| Cervical cancer | E6, E7 | |
| Glioblastoma | CD | |
| Neurological disorders | | |
| Alzheimer's disease | NGF | |
| Metahchromatic leukodystrophy | ARSA | |
| Multiple sclerosis | MBP | |
| Wiskott-Aldrich syndrome | WASP | |
| X-linked adrenoleukodystrophy | ABCD1 | |
| AACD deficiency | AADC | |
| Batten disease | CLN2 | |
| Canavan disease | ASPA | |
| Giant axonal neuropathy | GAN | |
| Leber's hereditary optic neuropathy | MT-ND4 | |
| MPS IIIA | SGSH, SUMF1 | |
| Parkinson's disease | GAD, NTRN, TH, AADC, CH1, GDNF, AADC | |
| Pompe disease | GAA | |
| Spinal muscular atrophy type 1 | SMN | |

Using the disclosed methods and systems can be used to treat any of the disorders listed in Table 1, or other known genetic disorder. The disclosed methods can also be used to treat other disorders, such as a cancer that can benefit from expression of a therapeutic protein in a cancer cell, such as a toxin or thymidine kinase. If the subject is administered two or more synthetic RNA molecules provided herein that express a full-length thymidine kinase, the subject is also administered ganciclovir. Treatment does not require 100% removal of all characteristics of the disorder, but can be a reduction in such. Although specific examples are provided below, based on this teaching one will understand that symptoms of other disorders can be similarly affected. For example, the disclosed methods can be used to increase expression of a protein that is not expressed or has reduced expression by the subject, or decrease expression of a protein that is undesirably expressed or has reduced expression by the subject. For example, the disclosed methods can be used to treat or reduce the undesirable effects of a genetic disease.

For example, the disclosed methods and systems can treat or reduce the undesirable effects of sickle cell disease by expressing a full-length wild-type β-globin chain of hemoglobin. In one example the disclosed methods reduce the symptoms of sickle-cell disease in the recipient subject (such as one or more of, presence of sickle cells in the blood, pain, ischemia, necrosis, anemia, vaso-occlusive crisis, aplastic crisis, splenic sequestration crisis, and haemolytic crisis) for example a reduction of at least 10%, at least 20%, at least 50%, at least 70%, or at least 90% (as compared to no administration of the therapeutic nucleic acid molecule). In one example the disclosed methods decrease the number of sickle cells in the recipient subject, for example a decrease of at least 10%, at least 20%, at least 50%, at least 70%, at least 90%, or at least 95% (as compared to no administration of the therapeutic nucleic acid molecule).

For example, the disclosed methods and systems can treat or reduce the undesirable effects of thrombophilia by expressing a full-length wild-type factor V Leiden or prothrombin gene. In one example the disclosed methods reduce the symptoms of thrombophilia in the recipie7nt subject (such as one or more of, thrombosis, such as deep vein thrombosis, pulmonary embolism, venous thromboembolism, swelling, chest pain, palpitations) for example a reduction of at least 10%, at least 20%, at least 50%, at least 70%, or at least 90% (as compared to no administration of the therapeutic nucleic acid molecule). In one example the disclosed methods decrease the activity of coagulation factors in the recipient subject, for example a decrease of at least 10%, at least 20%, at least 50%, at least 70%, at least 90%, or at least 95% (as compared to no administration of the therapeutic nucleic acid molecule).

For example, the disclosed methods and systems can treat or reduce the undesirable effects of CD40 ligand deficiency by expressing a full-length wild-type CD40 ligand gene. In one example the disclosed methods reduce the symptoms of CD40 ligand deficiency in the recipient subject (such as one or more of, elevate serum IgM, low serum levels of other immunoglobulins, opportunistic infections, autoimmunity and malignancies) for example a reduction of at least 10%, at least 20%, at least 50%, at least 70%, or at least 90% (as compared to no administration of the therapeutic nucleic acid molecule s). In one example the disclosed methods increase the amount or activity of CD40 ligand deficiency in the recipient subject, for example an increase of at least 10%, at least 20%, at least 50%, at least 70%, at least 90%, at least 100%, at least 200% or at least 500% (as compared to no administration of the therapeutic nucleic acid molecule).

For example, the disclosed methods can be used to treat or reduce the undesirable effects of a primary immunodeficiency disease resulting from a genetic defect. For example, the disclosed methods and systems (which can use two or more synthetic RNA nucleic acid molecules to express a functional protein missing or defective in the subject, for example using AAV) can treat or reduce the undesirable effects of a primary immunodeficiency disease. In one example the disclosed methods reduce the symptoms of a primary immunodeficiency disease in the recipient subject (such as one or more of, a bacterial infection, fungal infection, viral infection, parasitic infection, lymph gland swelling, spleen enlargement, wounds, and weight loss) for example a reduction of at least 10%, at least 20%, at least 50%, at least 70%, or at least 90% (as compared to no administration of the therapeutic nucleic acid molecule). In one example the disclosed methods increase the number of immune cells (such as T cells, such as CD8 cells) in the recipient subject with a primary immune deficiency disorder, for example an increase of at least 10%, at least 20%, at least 50%, at least 70%, at least 90%, at least 95%, at least 100%, at least 200%, at least 300%, at least 400%, or at least 500% (as compared to no administration of the therapeutic nucleic acid molecule). In one example the disclosed methods reduce the number of infections ((such as bacterial, viral, fungal, or combinations thereof) in the recipient subject over a set period of time (such as over 1 year) with a primary immune deficiency disorder, for example a decrease of at least 10%, at least 20%, at least 50%, at least 70%, at least 90%, or at least 95%, (as compared to no administration of the therapeutic nucleic acid molecule).

For example, the disclosed methods can be used to treat or reduce the undesirable effects of a monogenetic disorder. For example, the disclosed methods (which can use two or more synthetic RNA nucleic acid molecules to express a functional protein missing or defective in the subject, for example using AAV) can treat or reduce the undesirable effects of a monogenetic disorder. In one example the disclosed methods reduce the symptoms of a monogenetic disorder in the recipient subject, for example a reduction of at least 10%, at least 20%, at least 50%, at least 70%, or at least 90% (as compared to no administration of the therapeutic nucleic acid molecule). In one example the disclosed methods increase the amount of normal protein not normally expressed by the recipient subject with a monogenetic disorder, for example an increase of at least 10%, at least 20%, at least 50%, at least 70%, at least 90%, at least 95%, at least 100%, at least 200%, at least 300%, at least 400%, or at least 500% (as compared to no administration of the therapeutic nucleic acid molecule).

For example, the disclosed methods can be used to treat or reduce the undesirable effects of a hematological malignancy in the recipient subject. In one example the disclosed methods reduce the number of abnormal white blood cells (such as B cells) in the recipient subject (such as a subject with leukemia), for example a reduction of at least 10%, at least 20%, at least 50%, at least 70%, or at least 90% (as compared to no administration of the disclosed therapies). In one example, administration of the disclosed therapies can be used to treat or reduce the undesirable effects of a lymphoma, such as reduce the size of the lymphoma, volume of the lymphoma, rate of growth of the lymphoma, metastasis of the lymphoma, for example a reduction of at least 10%, at least 20%, at least 50%, at least 70%, or at least 90% (as compared to no administration of the disclosed therapies). In one example, administration of disclosed therapies can be used to treat or reduce the undesirable effects of multiple myeloma, such as reduce the number of abnormal plasma cells in the recipient subject, for example a reduction of at least 10%, at least 20%, at least 50%, at least 70%, or at least 90% (as compared to no administration of the disclosed therapies).

For example, the disclosed methods can be used to treat or reduce the undesirable effects of a malignancy, such as one that results from a genetic defect in the recipient subject. In one example the disclosed methods reduce the number of cancer cells, the size of a tumor, the volume of a tumor, or the number of metastases, in the recipient subject (such as a subject with a cancer listed herein), for example a reduction of at least 10%, at least 20%, at least 50%, at least 70%, or at least 90% (as compared to no administration of the disclosed therapies). In one example, administration of the disclosed therapies can be used to treat or reduce the undesirable effects of a lymphoma, such as reduce the size of the tumor, volume of the tumor, rate of growth of the cancer, metastasis of the cancer, for example a reduction of at least 10%, at least 20%, at least 50%, at least 70%, or at least 90% (as compared to no administration of the disclosed therapies).

For example, the disclosed methods can be used to treat or reduce the undesirable effects of a neurological disease that results from a genetic defect in the recipient subject. In one example the disclosed methods increase neurological function in the recipient subject (such as a subject with a neurological disease listed above), for example an increase of at least 10%, at least 20%, at least 50%, at least 70%, at least 90%, at least 100%, at least 200%, at least 300%, at least 400%, or at least 500% (as compared to no administration of the disclosed therapies).

Treatment of Duchenne Muscular Dystrophy (DMD)

Duchenne muscular dystrophy (DMD, MIM:310200) is a lethal hereditary disease characterized by progressive muscle weakness and degeneration. As the disease progresses, degenerating muscle fibres are replaced by fat and fibrotic tissue. DMD is rooted in deficiency of the gene dystrophin (MIM:300377). The dystrophin gene spans a region of 22 kbp, and is prone to mutations. Thus, DMD can in some cases sporadically manifest even in patients without a familial history of the disease-causing mutation. DMD is one of four conditions known as dystrophinopathies. The other three diseases that belong to this group are Becker Muscular dystrophy (BMD, a mild form of DMD); an intermediate clinical presentation between DMD and BMD; and DMD-associated dilated. cardiomyopathy (heart-disease) with little or no clinical skeletal, or voluntary, muscle disease. Thus, in some examples a patient with DMD, BMD, an intermediate clinical presentation between DMD and BMD; or DMD-associated dilated cardiomyopathy (heart-disease) with little or no clinical skeletal, or voluntary, muscle disease, is treated with the disclosed systems and methods.

The disclosed methods and systems can be used to treat the monogenic cause of DMD, that is expression of dystrophin. Dystrophin has a long coding region, such as dystrophin. Current methods of expressing dystrophin from a single AAV utilize shortened/truncated versions of dystrophin (micro-dystrophin and mini-dystrophin). Several of these truncated dystrophin delivery therapies are being tested in Phase I/II clinical trials (NCT03362502, NCT00428935, NCT03368742, NCT03375164). Although these truncated versions of dystrophin may ameliorate the worst consequences of dystrophin deficiency in DMD, they are not expected to have full functionality when compared to full-length dystrophin as the truncated versions are missing key domains in the rod and hinge region of the full-length protein. The disclosed methods and systems alleviate the size restriction of the transgenic payload of AAV by using "multiplexed" AAV combinations, because multiple AAV viruses can efficiently infect the same cell when introduced at high multiplicity of infection (MOI, i.e., high titer).

Thus, in some examples, a composition that includes two or more AAVs, each containing one of a set of disclosed synthetic RNA molecules, is administered (e.g., i.v.) to a DMD subject in a therapeutically effective amount, such as a set that includes two, three, four or five different synthetic RNA molecules (each in a different AAV), which when recombined, result in a full-length dystrophin coding sequence.

Example 1

Synthetic RNA Dimerization and Recombination Domains

FIG. 1A depicts a schematic of exemplary vector designs. The protein coding sequence of a yellow fluorescent protein (YFP) is split into an N-terminal and a C-terminal fragment. The N-terminal fragment is appended with a synthetic intronic sequence that contains a consensus splice donor sequence (SD), a downstream intronic splice enhancer sequence (DISE), two intronic splice enhancer sequences (ISE), and a stable stem loop BoxB element (boxB). This splicing optimized intronic sequence is followed by a binding domain as described in panels FIGS. 1E-1N. The C-terminal fragment of YFP is preceded by the complementary binding domain sequence, a stable stem loop BoxB element (boxB), three intronic splice enhancer sequences (ISE), a consensus branch point sequence (BP), a polypyrimidine tract (PPT) and a splice acceptor consensus sequence (SA). For transfection control, the N-terminal fragment is coexpressed with a red fluorescent protein from a bidirectional promoter and the C-terminal fragment is coexpressed with a blue fluorescent protein. Once expressed the two RNA molecules, termed 5' trspRNA and 3'trspRNA will dimerize and get recombined through a process called RNA recombination.

Figure 1B:
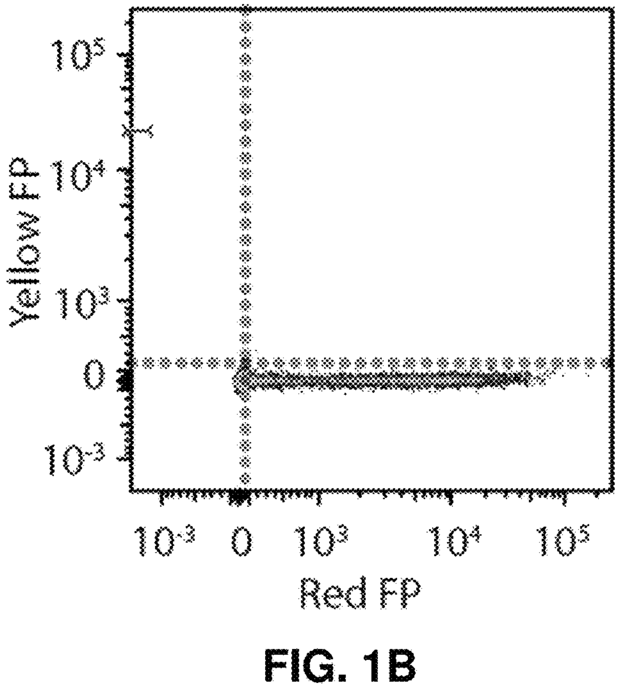
FIG. 1B depicts transfection of only the N-terminal expression plasmid does not lead to YFP fluorescence.

FIG. 1B depicts transfection of only the N-terminal expression plasmid does not lead to YFP fluorescence. Flow cytometry displaying 20 k RFP+ cells.

Figure 1D:
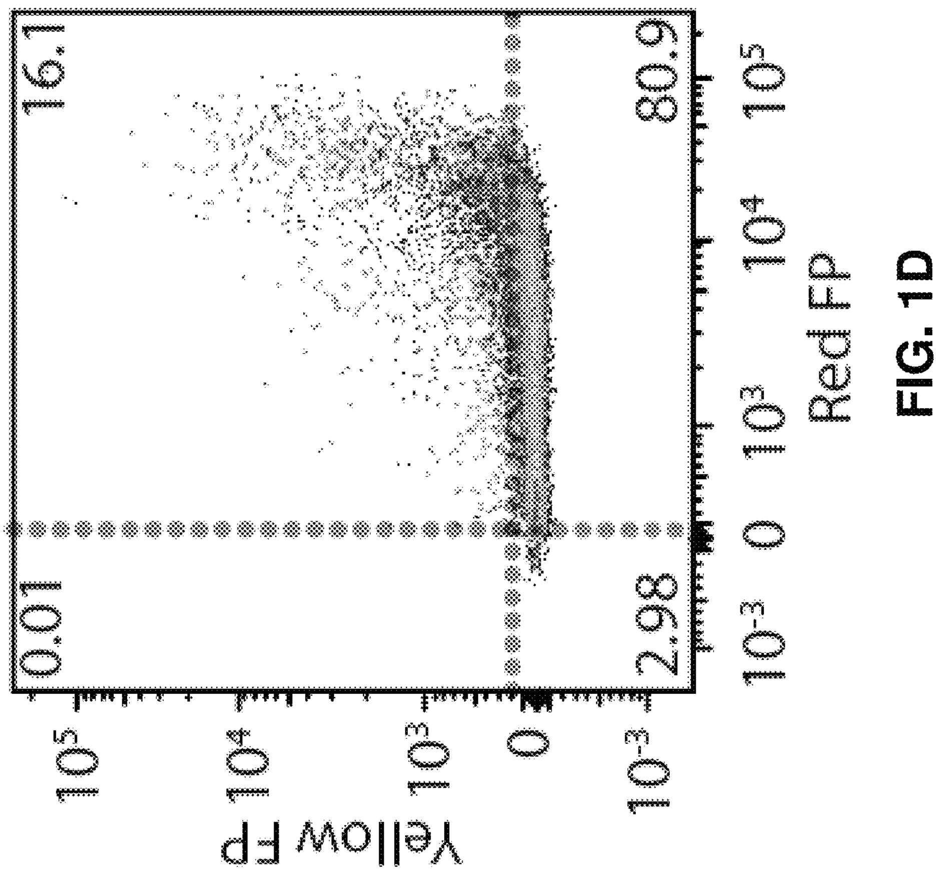
FIG. 1D depicts expression of N-terminal and C-terminal fragments without binding domains shows low levels of YFP induction.
Figure 1C:
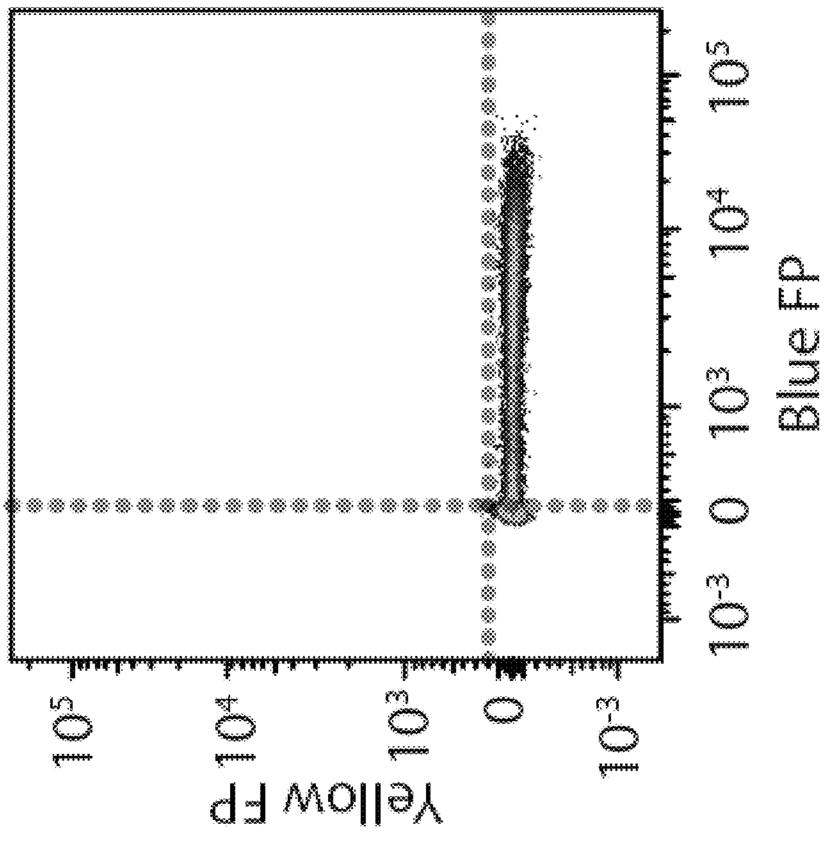
FIG. 1C depicts transfection of only the C-terminal expression plasmid does not lead to YFP fluorescence.

FIG. 1C depicts transfection of only the C-terminal expression plasmid does not lead to YFP fluorescence. Flow cytometry displaying 20 k BFP+ cells.

FIG. 1D depicts expression of N-terminal and C-terminal fragments without binding domains shows low levels of YFP induction. Flow cytometry displaying red and green fluorescence values for 20 k BFP+ cells.

Figure 1E:
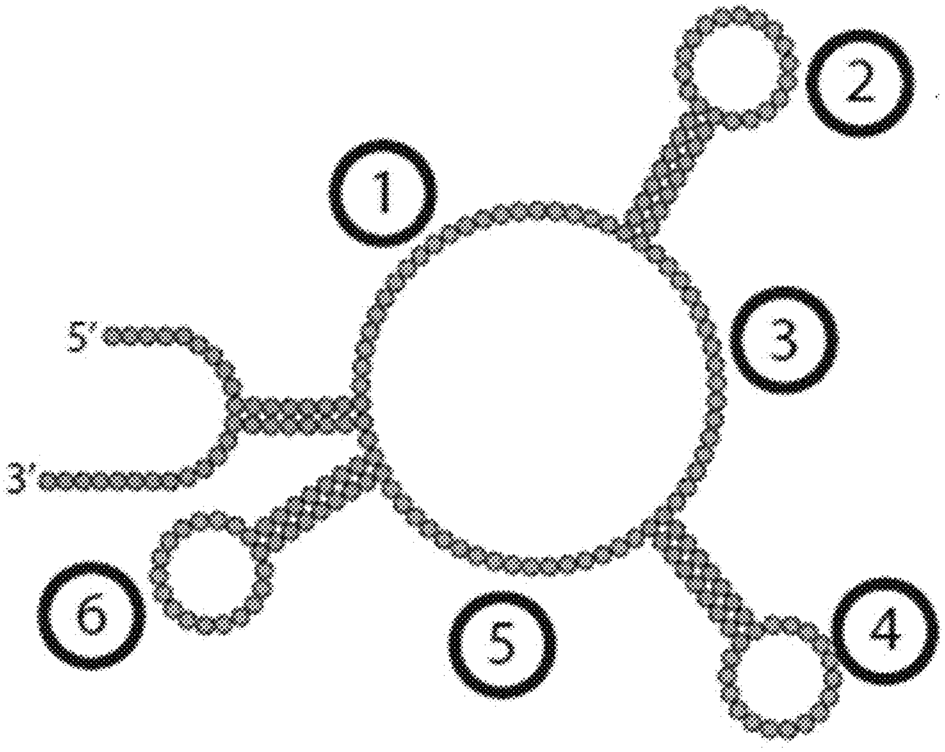
FIG. 1E depicts rationally designed dimerization/binding domain in a looped configuration.

FIG. 1E depicts rationally designed dimerization/binding domain in a looped configuration. Segments of hypodiverse exclusively pyrimidine or exclusively purine containing sequences are interspaced with stable stem sequences. RNA folding predictions shows 6 stretches of open sequence available for base pairing between the binding domain and its complementary sequence.

Figure 1F:
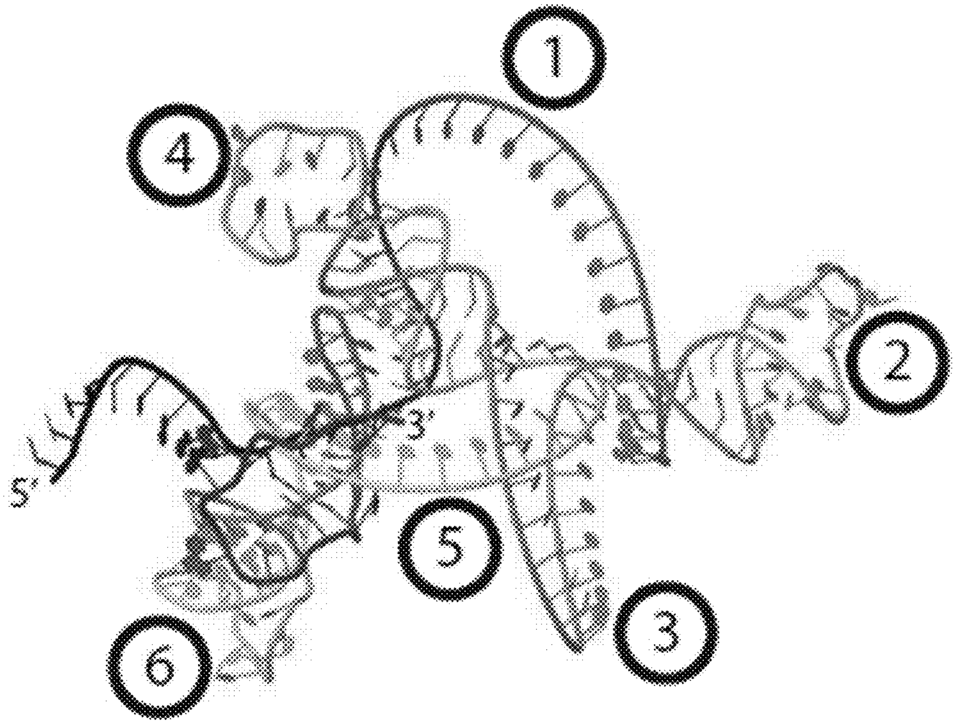
FIG. 1F depicts 3D rendering of the "looped" dimerization domain configuration.

FIG. 1F depicts 3D rendering of the "looped" dimerization domain configuration.

Figure 1G:
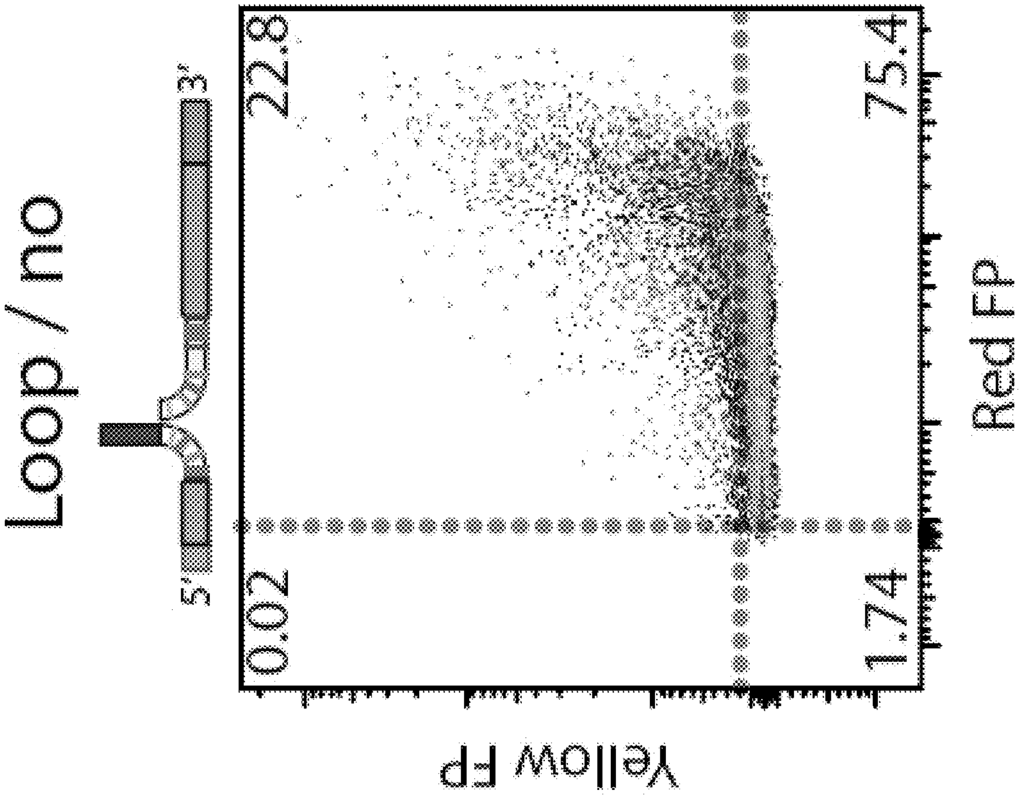
FIG. 1G depicts negative control with no binding domain on the C-terminal half.

FIG. 1G depicts negative control with no binding domain on the C-terminal half. Flow cytometry displaying red and green fluorescence values for 20 k BFP+ cells.

Figure 1H:
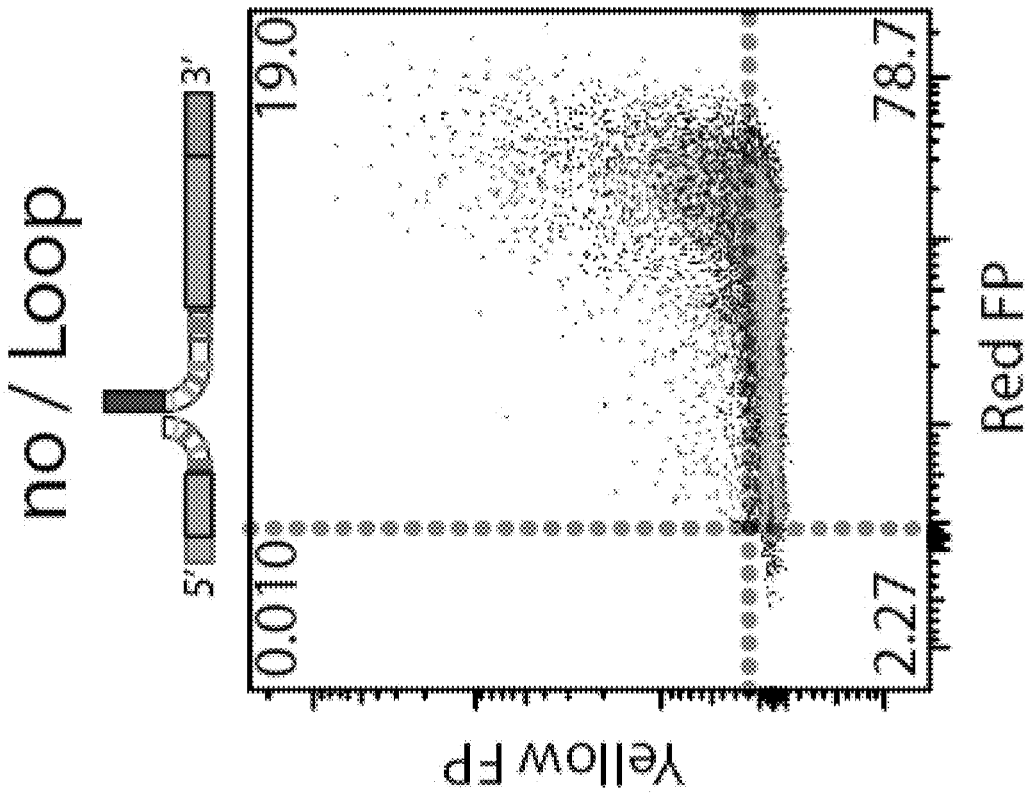
FIG. 1H depicts negative control with no binding domain on the N-terminal half.

FIG. 1H depicts negative control with no binding domain on the N-terminal half. Flow cytometry displaying red and green fluorescence values for 20 k BFP+ cells.

Figure 1I:
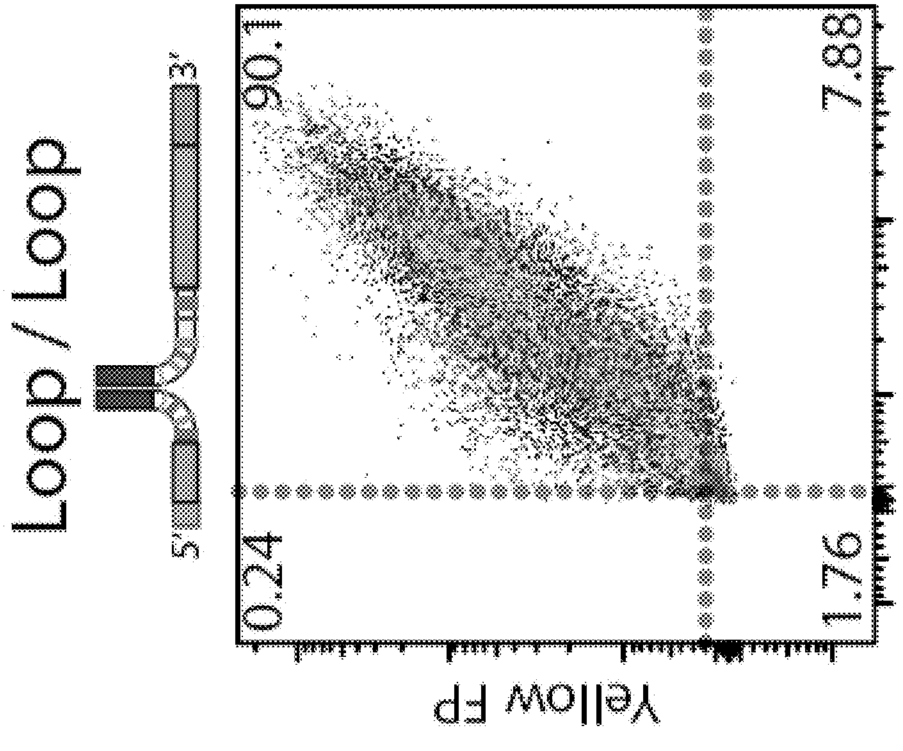
FIG. 1I depicts matching binding domains on both N- and C-terminal half shows strong YFP induction in 90% of the cells.
Figure 1J:
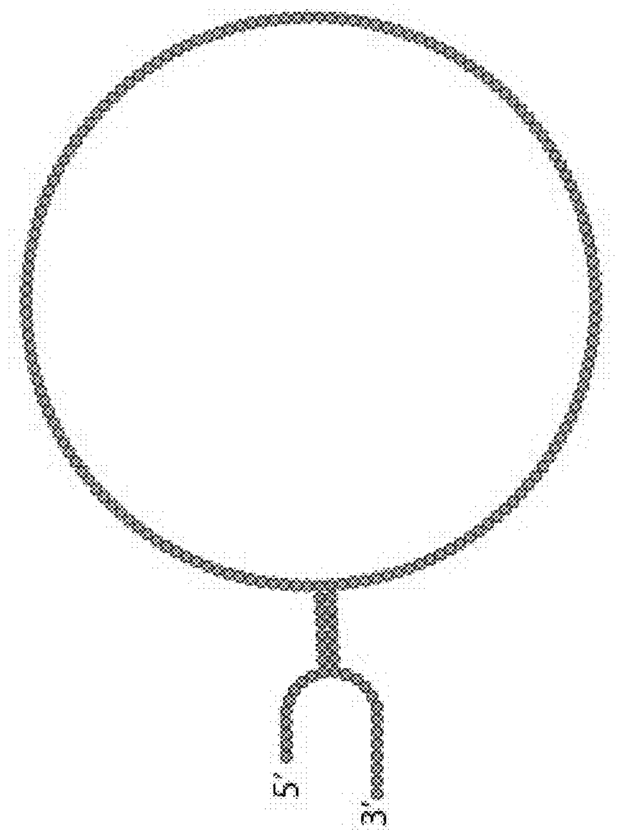
FIGS. 1J-1N depict data equivalent to that in FIGS. 1E-1I for a configuration of a binding domain with a stretch of 150 hypodiverse exclusively pyrimidine or exclusively purine containing sequence resulting in a fully open configuration.
Figure 1K:
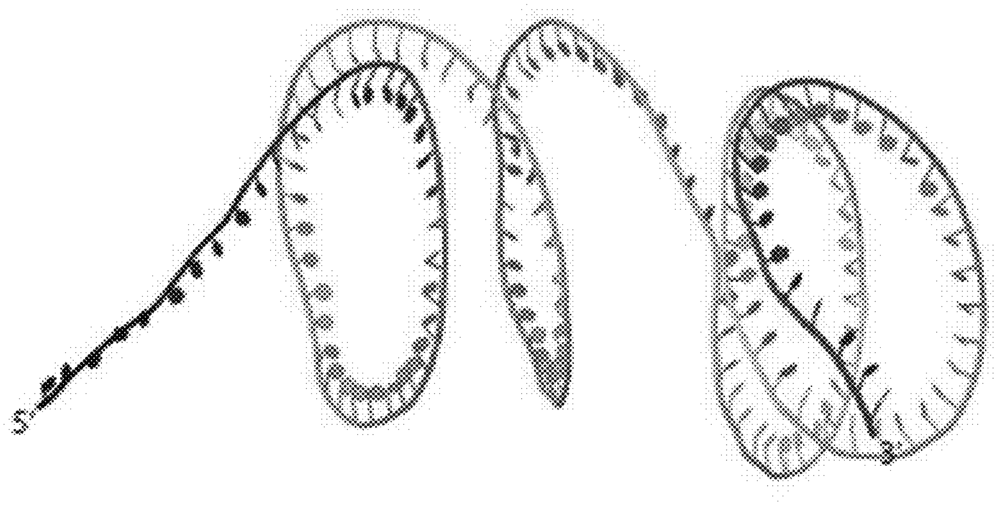

FIG. 1I depicts matching binding domains on both N- and C-terminal half shows strong YFP induction in 90% of the cells. Flow cytometry displaying red and green fluorescence values for 20 k BFP+ cells.

FIGS. 1J-1N depict data equivalent to that in FIGS. 1E-1I for a configuration of a binding domain with a stretch of 150 hypodiverse exclusively pyrimidine or exclusively purine containing sequence resulting in a fully open configuration.

Figure 1L:
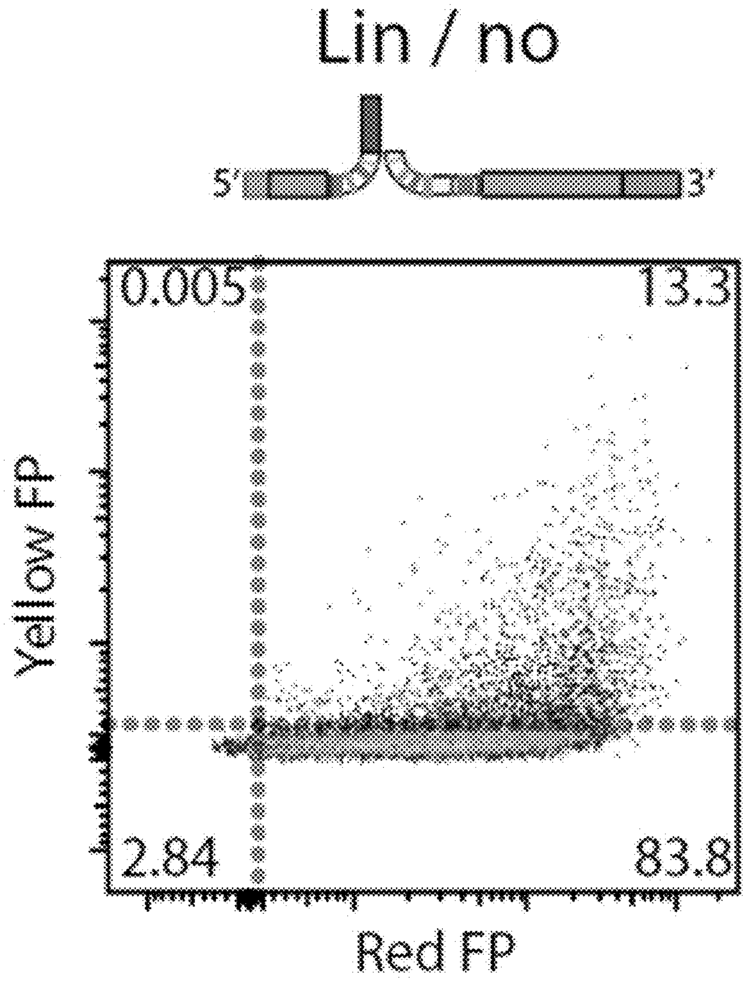
Figure 1N:
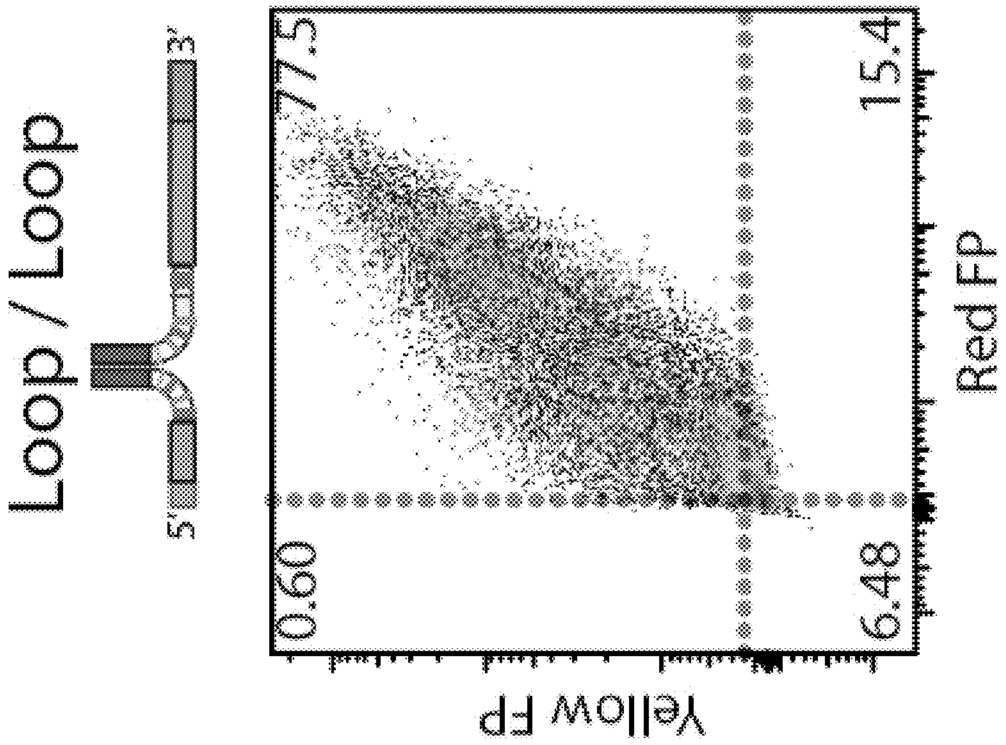
Figure 1M:
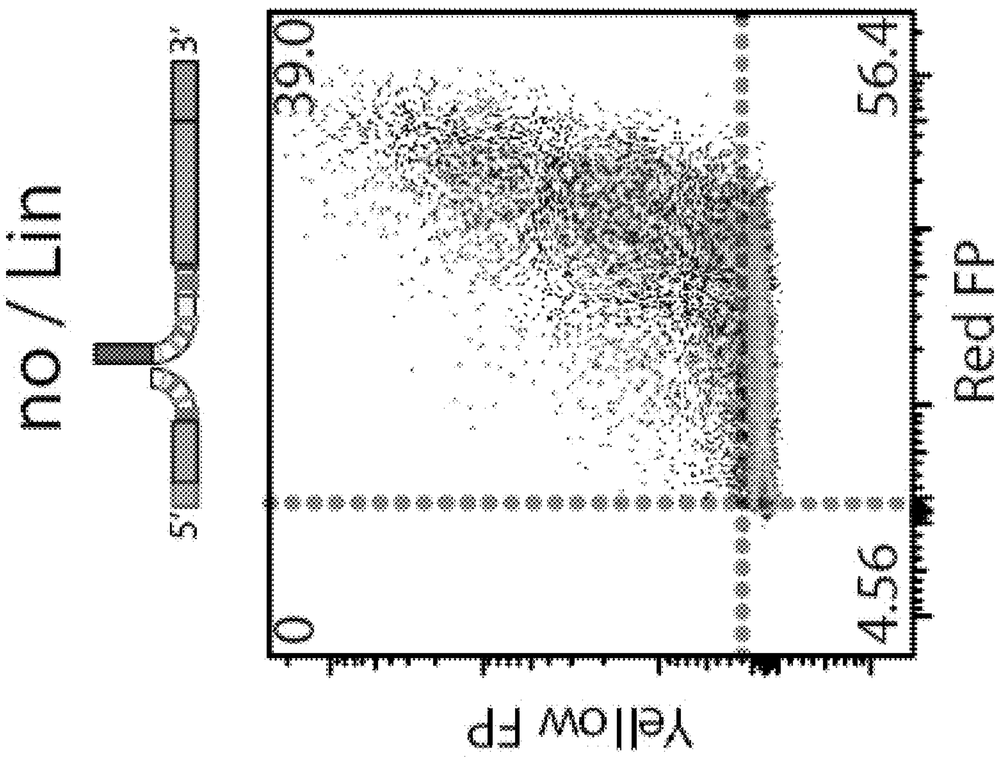
Figure 1P:
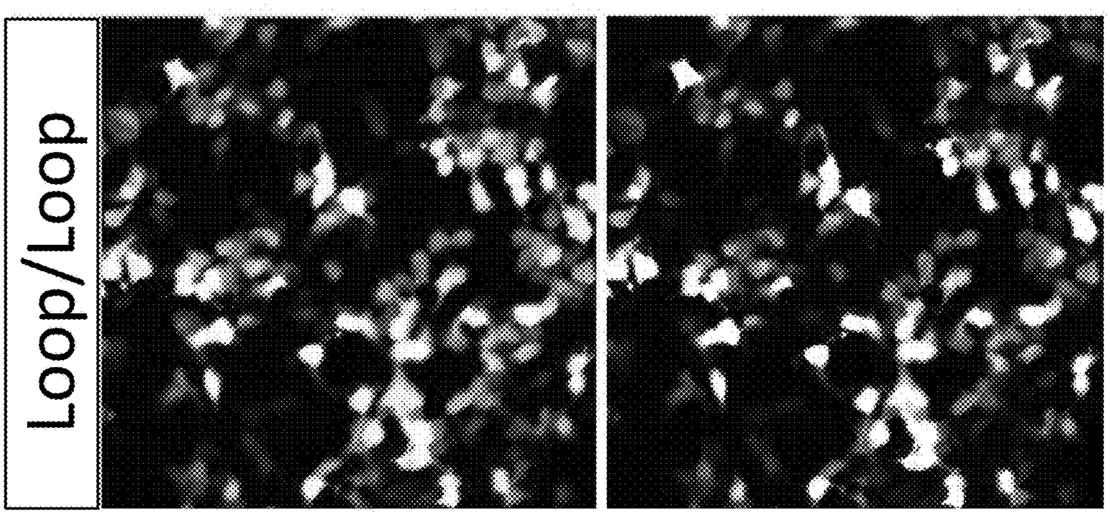
FIG. 1P depicts representative fluorescence images for cells shown in FIG. 1L.
Figure 1O:
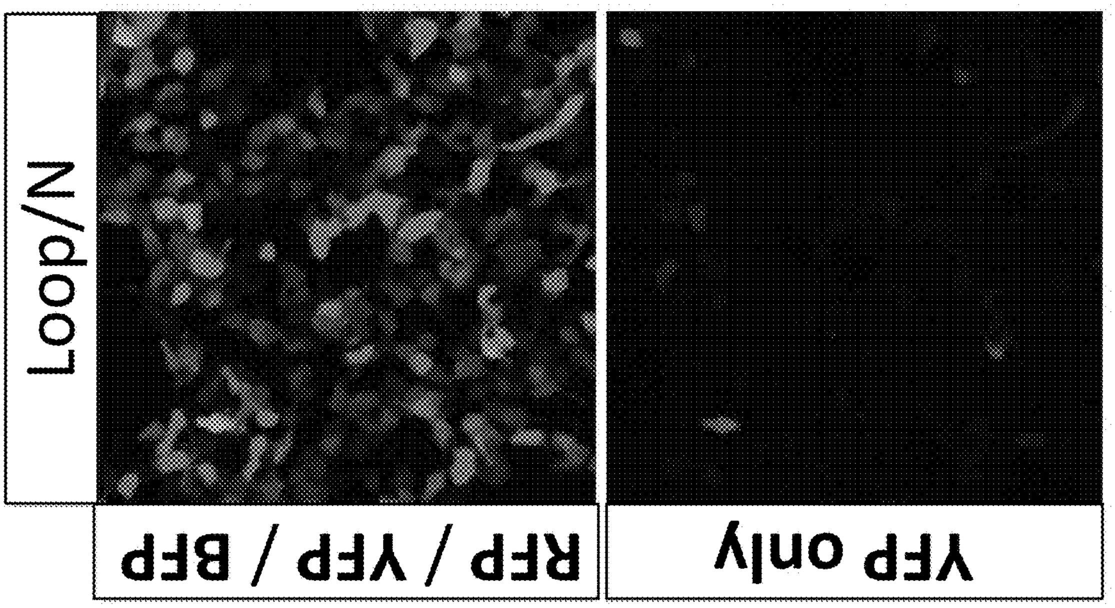
FIG. 1O depicts representative fluorescence images for cells shown in FIG. 1G.

FIG. 1O depicts representative fluorescence images for cells shown in FIG. 1G.

FIG. 1P depicts representative fluorescence images for cells shown in FIG. 1L.

Figure 1Q:
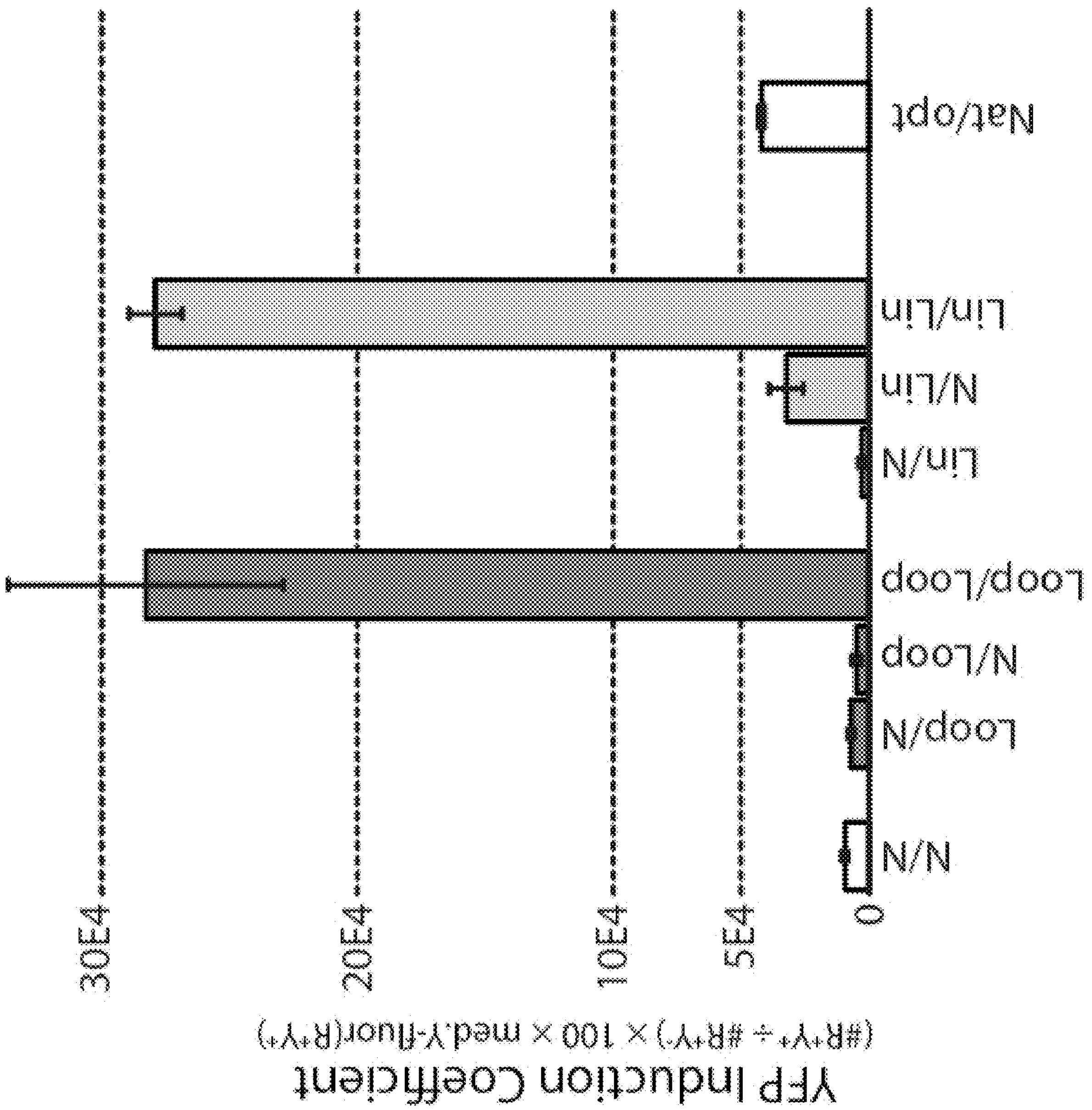
FIG. 1Q depicts a comparison of conditions shown in FIG. 1D, FIGS. 1G-1I, and FIGS. 1L-1N.

FIG. 1Q depicts a comparison of conditions shown in FIG. 1D, FIGS. 1G-1I, and FIGS. 1L-1N. YFP induction coefficient is calculated: (#R+Y+÷#R+Y−)×100×med.Y-fluor(R+Y+). For comparison the recombination efficiency of a native intron (intron I of the mouse parvalbumin gene) on the N-terminus and an optimized binding domain for that intron on the C-terminal fragment are shown (white bar). This illustrates the benefits of the optimized synthetic RNA dimerization and recombination domains.

Example 2

Reconstitution of Protein from Three Synthetic Fragments

Figure 2A:
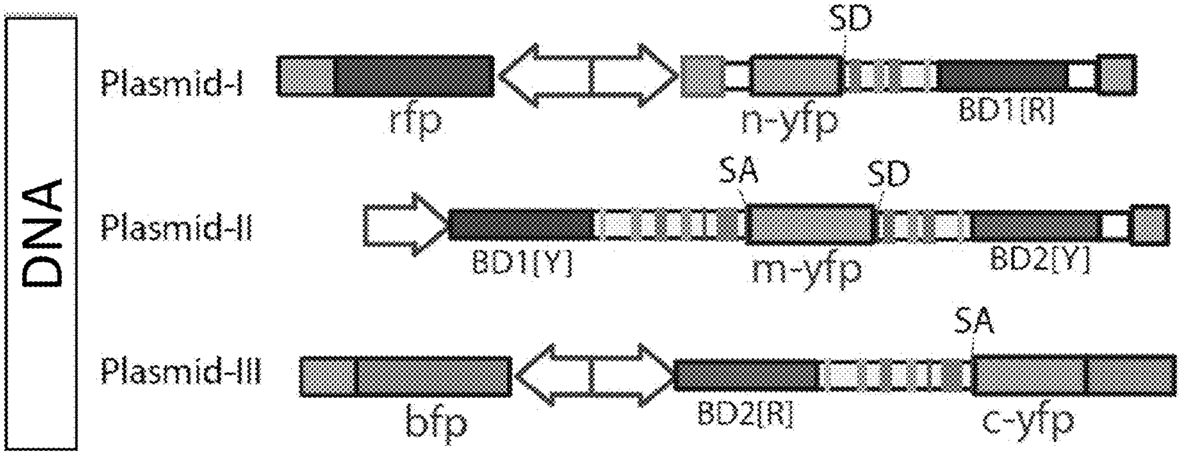
FIG. 2A depicts schematic of vector designs. The protein coding sequence of a yellow fluorescent protein (YFP) is split into an N-terminal, a middle fragment (m-yfp) and a C-terminal fragment. The junction of the n and m fragments is joined by a looped design binding domain (BD1) and the junction between m and c fragments is joined by a looped binding domain (BD2). The pyrimidine (Y) and purine (R) sequences are arranged in such a way as to avoid self-circularization of the m-fragment and avoid direct recombination of the N- and C-fragment. The N-terminal fragment is co-expressed with red fluorescent protein as a transfection control, the C-terminal fragment is coexpressed with blue fluorescent protein as a transfection control.

FIG. 2A depicts an exemplary schematic of vector designs. The protein coding sequence of a YFP is split into an N-terminal fragment, a middle fragment (m-yfp) and a C-terminal fragment. The junction of the n and m fragments is joined by a looped design binding domain (BD1) and the junction between m and c fragments is joined by a looped binding domain (BD2). The pyrimidine (Y) and purine (R) sequences are arranged to avoid self-circularization of the m-fragment and avoid direct recombination of the N- and C-fragment. The N-terminal fragment is co-expressed with red fluorescent protein as a transfection control, the C-terminal fragment is coexpressed with blue fluorescent protein as a transfection control.

Figure 2B:
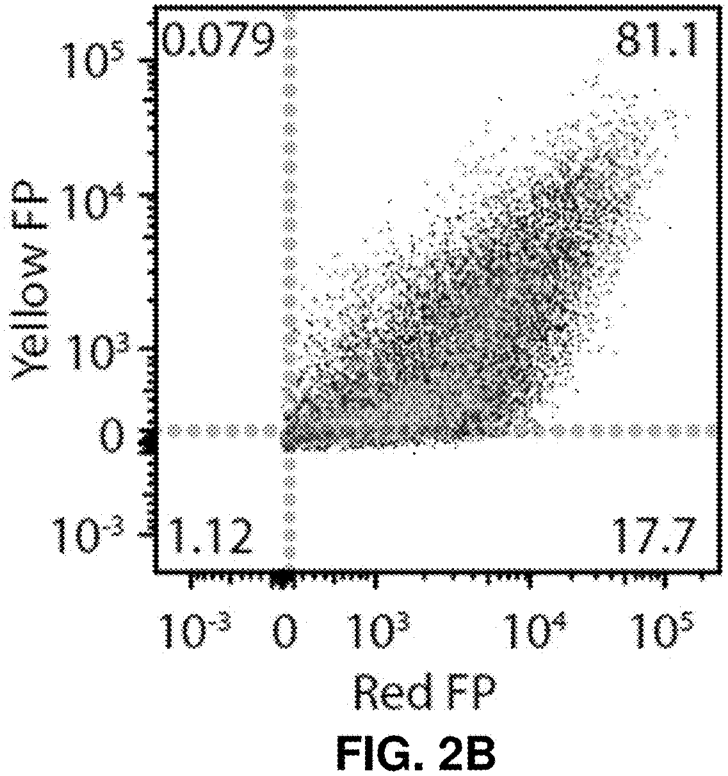
FIG. 2B depicts matching binding domains on all three fragments shows strong YFP induction in 80% of the cells. Flow cytometry displaying red and green fluorescence values for 20 k BFP+ cells.

FIG. 2B depicts matching binding domains on all three fragments shows strong YFP induction in 80% of the cells. Flow cytometry displaying red and green fluorescence values for 20 k BFP+ cells.

Figure 2E:
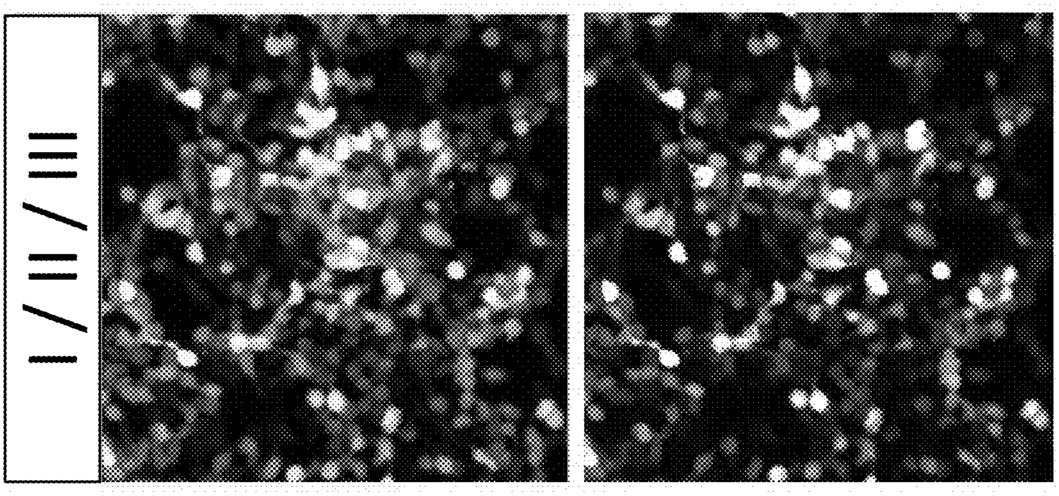
FIG. 2E depicts representative fluorescent image showing that strong YFP fluorescence is induced by co-transfection of all three fragments.
Figure 2D:
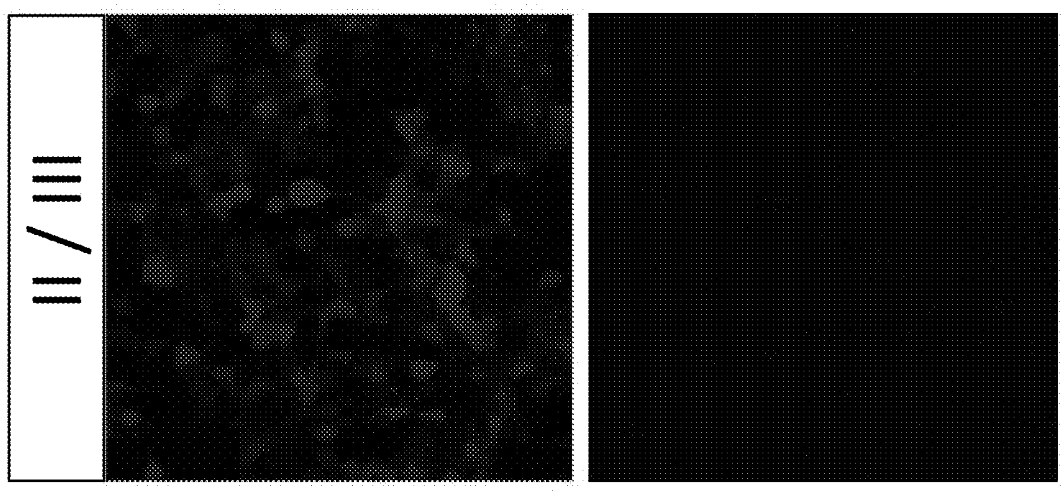
FIG. 2D depicts representative fluorescent image of expression of the m and c fragment only shows no yfp fluorescence (negative control).
Figure 2C:
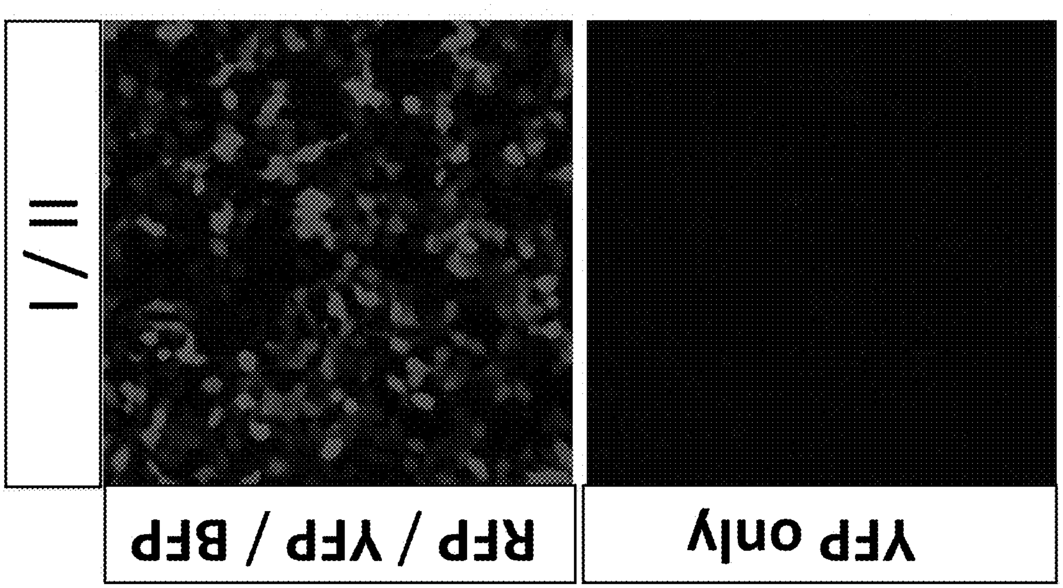
FIG. 2C depicts representative fluorescent image of expression of the n and m fragment only shows no yfp fluorescence (negative control).

FIG. 2C depicts representative fluorescent image of expression of the n and m fragment only shows no YFP fluorescence (negative control).

FIG. 2D depicts representative fluorescent image of expression of the m and c fragment only shows no YFP fluorescence (negative control).

FIG. 2E depicts representative fluorescent image showing that strong YFP fluorescence is induced by co-transfection of all three fragments.

Example 3

In Vivo Delivery of Reconstituted Full-Length YFP Divided into Two Portions

Reconstitution of a YFP coding sequence from two fragments is achieved by using two synthetic RNA sequences, wherein one included the n-terminal coding half fragment of YFP, and one included the c-terminal coding half fragment (FIG. 3A) (SEQ ID NOS 1 and 2). Each fragment was expressed from AAV2/8 after systemic (iv) administration in newborn (P3) mouse pups. A total of 1.88E11 viral genomes for each of the two fragments were administered per mouse. Expression of YFP was detected 3 weeks later in the liver, heart muscle, and skeletal muscle using fluorescence microscopy.

Figure 3A:
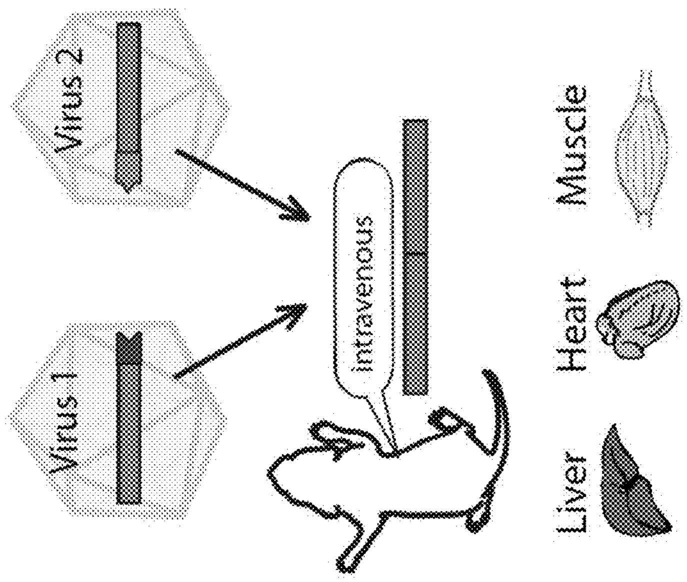
FIGS. 3A-3D depict efficient reconstitution of yellow fluorescent protein (YFP) from two fragments (SEQ ID NOS: 1 and 2) expressed from two AAV2/8s after systemic administration in the newborn (P3) mouse pup. (A) depicts one RNA encoding the n-terminal half fragment of YFP, and one RNA encoding the c-terminal half fragment, which are coexpressed using AAV. (B) depicts native YFP fluorescence in the liver of the juvenile mouse at the time of sacrifice (green). Uninjected liver is shown for comparison. DRAQ5 nuclear stain is shown in magenta for context. (C) depicts strong native YFP fluorescence in the heart muscle at the time of sacrifice (green). Top panels show macroscopic view and red autofluorescence for context (in magenta). Bottom panel shows cross-section with DRAQ5 nuclear stain for context (in magenta). Uninjected mouse heart is shown for control. (D) depicts strong native YFP fluorescence in the skeletal muscles of the leg at the time of sacrifice. Uninjected mouse legs are shown for comparison. Top panels show macroscopic view with red autofluorescence in magenta. Bottom panel shows microscopic image of a cross-section through the leg. Bottom panel shows DRAQ5 nuclear stain in magenta for context.
Figure 3B:
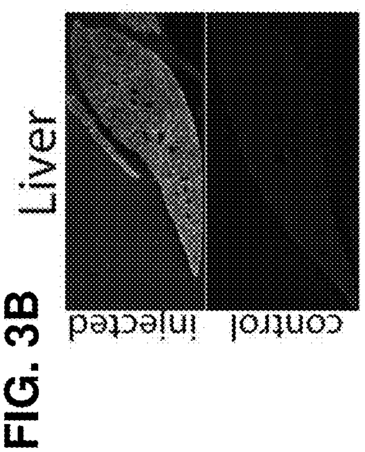

As shown in FIG. 3B, expression of full-length YFP was detected in the liver of the juvenile mouse, while uninjected liver showed no YFP expression.

Figure 3C:
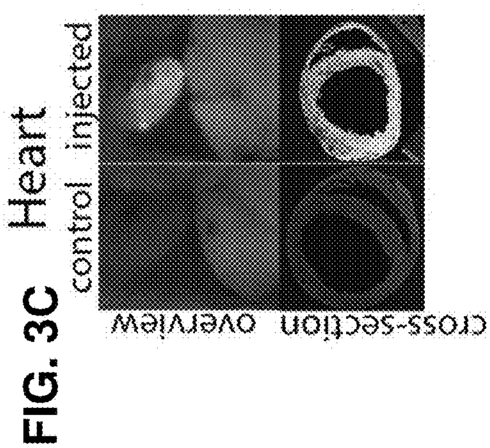

As shown in FIG. 3C, expression of full-length YFP was detected in the heart muscle of the juvenile mouse, while uninjected heart muscle showed no YFP expression.

Figure 3D:
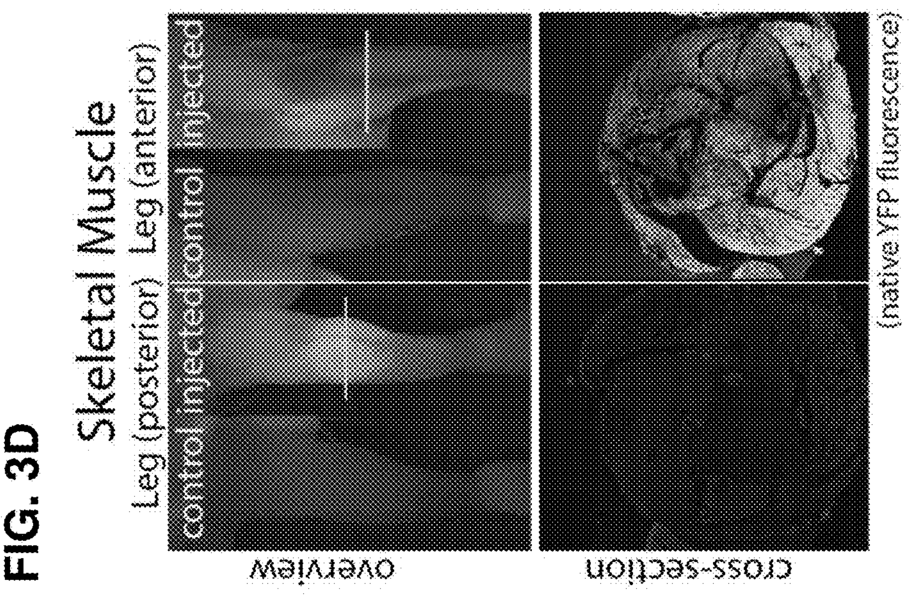

As shown in FIG. 3D, expression of full-length YFP was detected in the skeletal muscles of the leg, while uninjected liver showed no YFP expression.

Thus, the disclosed systems can be used to express full-length proteins in vivo, from two or more separate synthetic RNA molecules.

Example 4

In Vivo Delivery of Reconstituted Full-Length YFP Divided into Three Portions Reconstitution of a YFP coding sequence from three fragments is achieved by using three synthetic RNA sequences, wherein one included the n-terminal fragment of YFP, one included a middle fragment of YFP, and one included the c-terminal fragment (FIG. 4A) (SEQ ID NOS: 145, 146 and 2 respectively).

Each fragment was expressed from AAV2/8 after intramuscular injection into the e tibialis anterior muscle of newborn (P3) mouse pups. A total of 1E11 viral genomes for each of the fragments was administered intramuscularly. Expression of YFP was detected 3 weeks later in the skeletal muscle using fluorescence microscopy.

Figure 4A:
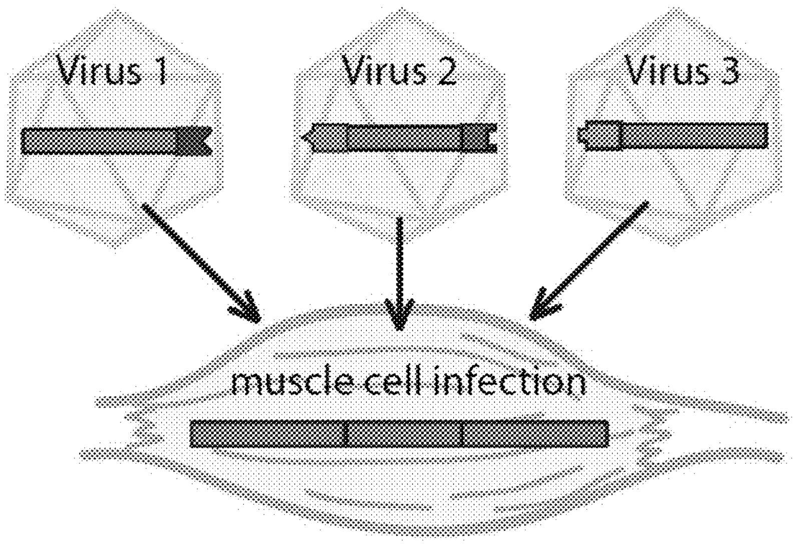
FIGS. 4A-4B depict efficient reconstitution of yellow fluorescent protein (YFP) from three fragments (SEQ ID NOS: 145, 146 and 2, respectively) in the mouse tibialis anterior muscle after intramuscular injection of three AAV2/8 in the newborn (P3) mouse pup. (A) depicts a schematic of three AAV particles encoding a full-length YFP that is split into three fragments. (B) Shows strong native YFP fluorescence in a longitudinal section of the tibialis anterior muscle of a mouse injected with all three viral particles. DRAQ5 nuclear stain is shown in magenta for context.
Figure 4B:
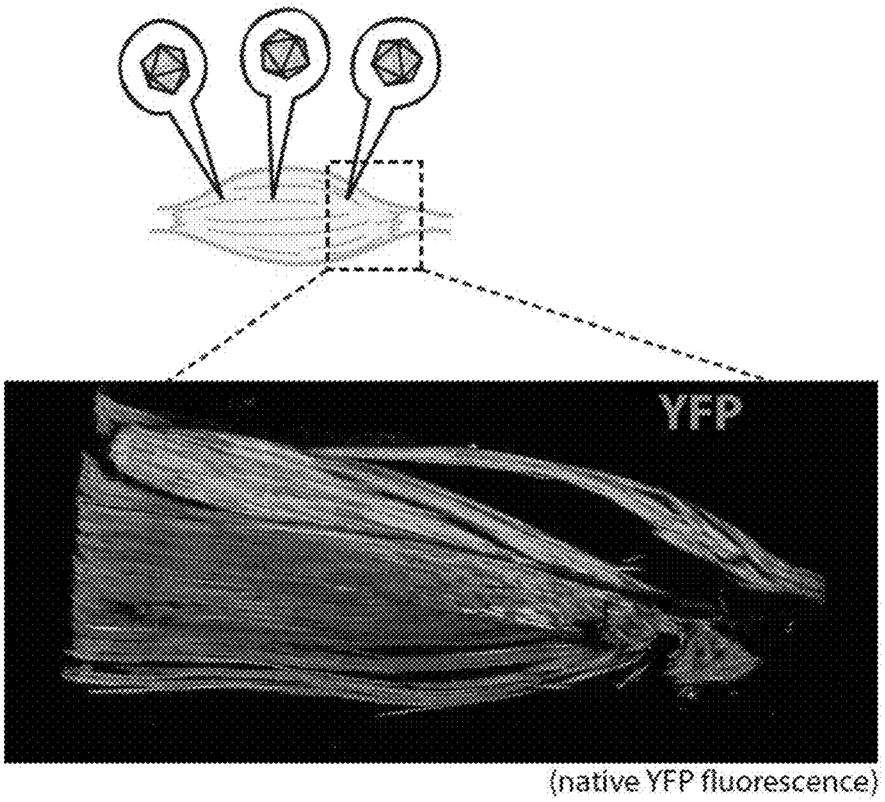

As shown in FIG. 4B, expression of full-length YFP fluorescence was observed in the tibialis anterior muscle.

Thus, the disclosed systems can be used to express full-length proteins in vivo, from three or more separate synthetic RNA molecules.

Example 5

In Vivo Delivery of Reconstituted Full-Length Protein

To demonstrate the feasibility of a three-part sRdR system in vivo, a combination of either two or three AAV-transfer plasmids (the DNA precursor plasmids of AAV) containing fragments of the YFP were transcutaneously electroporated into the tibialis anterior (TA) hindlimb muscle of adult mice. Efficient reconstitution of both the two part split-YFP system as well as the three part split-YFP system was observed five days after intramuscular electroporation (FIGS. 5A-5F).

Figure 5A:
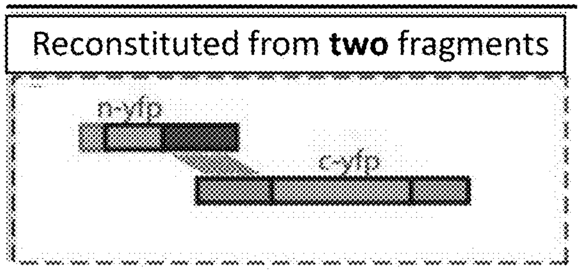
FIGS. 5A-5F depict efficient reconstitution of yellow fluorescent protein (YFP) from two and from three fragments in adult mouse tibialis anterior muscle. (A) depicts N-terminal and C-terminal halves of YFP coding sequence are equipped with synthetic RNA-dimerization and recombination domains. (B) depicts two AAV transfer plasmids expressing these two fragments were electroporated transcutaneously into adult mouse tibialis anterior (TA) muscle and strong fluorescence was detected at 5 days post electroporation. (C) depicts no fluorescence was detectable in contralateral non-injected TA. (D) depicts n-terminal, middle, and c-terminal YFP coding sequence are equipped with synthetic RNA-dimerization and recombination domains linking each fragment to its adjacent fragment(s). (E) depicts transcutaneous electroporation of three AAV transfer plasmids expressing these three fragments. Strong YFP fluorescence is detected indicating efficient reconstitution of YFP from three fragments. (F) depicts fluorescence in contralateral non-injected TA. Fluorescent channel is overlaid onto grey scale photographs for context.
Figure 5B:
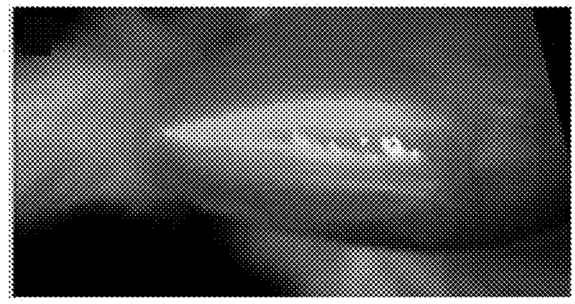
Figure 5C:
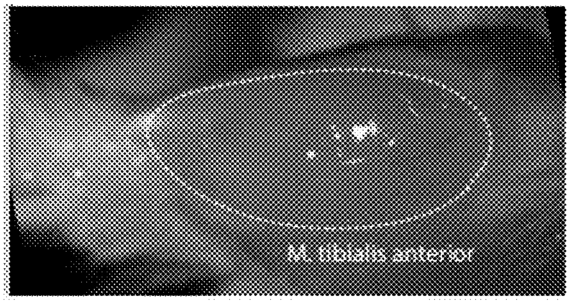
Figure 5D:
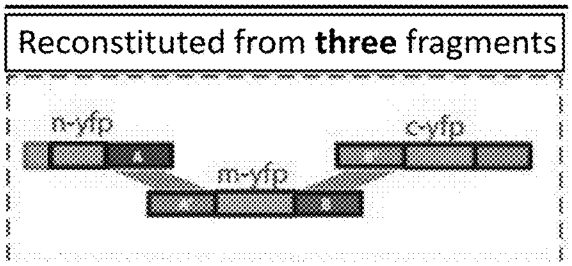
Figure 5E:
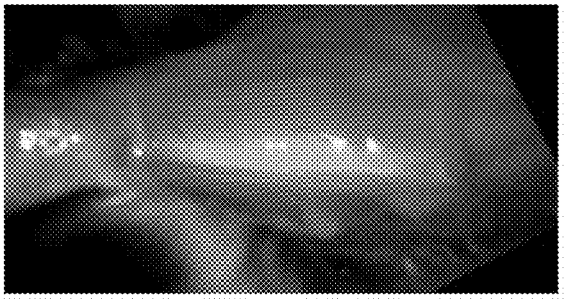
Figure 5F:
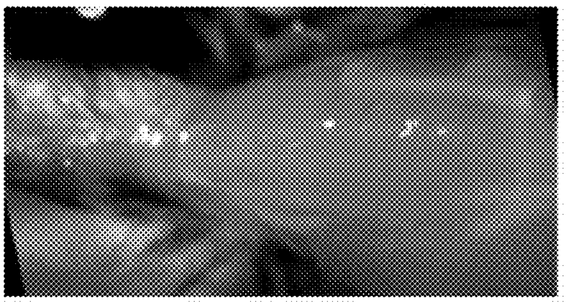

FIGS. 5A-5F depict efficient reconstitution of YFP from two and from three fragments in adult mouse tibialis anterior muscle. FIG. 5A depicts N-terminal and C-terminal halves of YFP coding sequences are equipped with synthetic RNA-dimerization and recombination domains. FIG. 5B depicts two AAV transfer plasmids expressing these two fragments were electroporated transcutaneously into adult mouse tibialis anterior (TA) muscle and strong fluorescence was detected at 5 days post electroporation. FIG. 5C shows no fluorescence was detectable in contralateral non-injected TA. FIG. 5D depicts N-terminal, middle, and C-terminal YFP coding sequence are equipped with synthetic RNA-dimerization and recombination domains linking each fragment to its adjacent fragment(s). FIG. 5E depicts transcutaneous electroporation of three AAV transfer plasmids expressing these three fragments. Strong YFP fluorescence is detected indicating efficient reconstitution of YFP from three fragments. FIG. 5F depicts fluorescence in contralateral non-injected TA. Fluorescent channel is overlaid onto grey scale photographs for context.

Data are also provided on pages 13-14 of Exhibit A, where two or three vectors were used to express YFP in liver, cardiac muscle and skeletal muscle (two AAV vectors), and in skeletal muscle (three AAV vectors).

Hence the synthetic RNA-dimerization and recombination system provided herein can be deployed in the muscle. Based on these results, one can substitute the YFP coding sequence with a dystrophin (or other gene) coding sequence to achieve therapeutic full-length dystrophin (or other gene) expression from AAVs into a desired subject and/or tissue.

Example 6

Delivery of Reconstituted Full-Length Dystrophin to Treat DMD

An effective gene therapy using full-length dystrophin for patients who suffer from Duchenne muscular dystrophy (DMD) has remained challenging, because the coding sequence of this large protein exceeds the capacity of most viral vectors. Adeno-associated viruses (AAVs) are a common and the preferred method of gene delivery in gene replacement therapy. AAVs are non-toxic, well tolerated, and lead to long term expression of the replacement gene without random integration into the genome. However, the dystrophin gene is too large to be delivered by a single virus. If broken down into fragments, full-length dystrophin can only be delivered using a minimum of three viruses. Smaller versions of dystrophin called "micro-Dystrophin" or "mini-Dystrophin" are currently being tested for dystrophin gene replacement therapy, but these truncated versions of dystrophin are not expected to have full functionality as they are missing key domains in the rod and hinge section of the protein. To date, past attempts to overcome this limitation have not yielded the efficiency required for treating DMD.

Provided herein is a novel RNA based technology that can be used to efficiently reconstitute the coding sequence of large genes, including dystrophin, from multiple serial fragments. Using this technology in combination with AAV as a delivery vector, full-length dystrophin will be expressed in a murine model (as well as pig and canine models) for DMD. In one example the subject is a human adult, juvenile, or infant with DMD. For example, the disclosed methods and systems can be used to deliver synthetic RNA-dimerization and recombination domains encoding full-length dystrophin over two or three AAVs (e.g., each AAV delivering a half or a third of the full-length coding sequence). In one example, the AAVs are myotropic AAVs (e.g., those that preferentially infect muscles). This approach can be used to ameliorate or prevent the onset of dystrophy symptoms in a mouse or canine model for DMD, as well as human subjects.

Part 1: Construct efficiently reconstituted three-way split dystrophin expression cassettes. Three expression cassettes are constructed that efficiently reconstitute the full-length dystrophin coding sequence in vitro while each individual expression cassette is within the packaging limit of conventional AAV vectors. To achieve therapeutically effective levels of dystrophin, the expression system can be optimized to achieve roughly physiological levels of dystrophin or moderately supraphysiological levels. Up to 50-fold overexpression of dystrophin is tolerated without adverse effects. The dystrophin coding sequence can be split at a number of different points along its length. Efficiency of reconstitution, however, is affected by the local RNA microenvironment and maximization of reconstitution efficiency is done empirically by comparing efficiency of several possible split points. The natural dystrophin coding sequence can be codon optimized for optimal expression and modified to accommodate maximal reconstitution efficiency. It is expected that the full-length dystrophin coding sequence can be reconstituted from a three-way split precursor using the synthetic RNA-dimerization and recombination approach herein disclosed. In screening different configurations, the set of three expression cassettes that lead to the most efficient reconstitution of dystrophin (e.g., approximately physiological or moderately supraphysiological levels) are selected. Experiments can be performed in HEK293T or Human Skeletal Muscle Cells (HSkMC, either primary or trans-differentiated). Using endogenous vs. exogenous specific quantitative RT-PCR probes, and by epitope tag detection in the exogenous dystrophin protein and Western blot analysis, reconstitution efficiencies will be determined different configurations of the split/reconstituted dystrophin.

Part 2: Maximize full-length dystrophin expression over non-reconstituted fragments. Suppression of fragmented background expression of non-reconstituted dystrophin can be achieved by modification of the synthetic RNA-dimerization and recombination domains. Non-reconstituted fragment expression caused by inefficiencies in RNA-recombination may lead to background expression of dystrophin fragments. Further, suppression of this fragmented background expression may be achieved by modification of the synthetic RNA-dimerization and recombination domains. With the disclosed approach, each fragment of dystrophin is transcribed separately. Reconstitution occurs on the RNA level. Each individual fragment can therefore potentially be translated without being reconstituted. In a western blot, with full-length dystrophin running at roughly 430 kDa, these fragments would run at sizes of about ⅔ (~290 kDa) and ⅓ (~140 kDa) of that. The synthetic RNA-dimerization and recombination domains can be optimized to avoid non-reconstituted fragment expression and favor full length expression of dystrophin. This can for example be achieved by strategically placing degron sequences, disrupting RNA nuclear export of non-recombined fragments, and introducing decoy translation initiation points. Experiments are carried out in HEK293T and HSkMC. The dystrophin coding sequence can be bookended with epitope tags that allow for identification and quantification of not fully reconstituted fragments of dystrophin using western blot analysis. Cellular distribution of these dystrophin fragments will be assessed using immunohistochemistry in skeletal human muscle cells. Additionally, quantitative assessment of fragment suppression will be done using conventional molecular biology techniques, including quantitative RT PCR across the recombination junctions will be used to determine how efficient the reconstitution on an RNA level occurs. It is expected that low levels of fragmented dystrophin expression will be observed. By modifying the synthetic RNA-dimerization and recombination domains, these fragments can be suppressed.

Part 3. Create high-titer AAV stocks of full-length dystrophin modules for in vitro and in vivo expression. Dystrophin expressing AAVs will be produced with high purity and viral genome counts higher than 3E13 GC/ml. Three myotropic AAV serotypes will be produced: AAV2/8, AAV2/9, and AAV2/rh10. A tripartite split fluorescent protein, a tripartite split of a full-length dystrophin bookended with epitope tags (see Part 2 above), and a non-tagged tripartite split of full-length dystrophin will be produced, resulting in 27 high-titer AAV preparations. Systemic delivery of therapeutic AAV particles requires high concentration large virus preparations. To achieve reconstituted expression of dystrophin form three separate viruses, repeated administration of the virus may be performed. AAV production in HEK293T cells. Iodixanol or CsCl purification. All batches will be tested in vitro in HEK293T and human skeletal muscle cells. As outlined in Part 1 and 2, reconstitution efficiency and unwanted fragment expression will be assessed.

Part 4. Measure expression/reconstitution levels of FLD-AAV modules in vivo and tissue distribution in vivo of full-length dystrophin expressing AAV modules. The same are assessed for a tripartite split fluorescent protein, as surrogate indicator. For in vivo delivery, direct intramuscular (cardiac and skeletal muscles) and systemic intravenous delivery in newborn and juvenile mice will be compared. Direct muscle injection of FLD-AAV may result in efficient expression of full-length dystrophin as indicated in the Examples above. Systemic delivery of FLD-AAV will be examined using immunohistochemistry and western blot analysis. Different routes of administration, including direct intramuscular and systemic intravenous delivery, in newborn and juvenile mice will be compared. The analysis will focus on: (1) skeletal muscles (major forelimb, hindlimb, shoulder, abdominal and, face muscles) and differential infectivity of fast vs. slow twitch muscles, will be assessed by comparing tibialis anterior and soleus muscles, (2) cardiac muscle expression, and (3) liver expression. This cohort of animals will be monitored for possible adverse effects of the high-titer AAV injections.

Although direct muscular injection of AAVs represents an approach to delivering the FLD-AAV modules (which in light of the results in FIGS. 5A-5F is likely to be successful), it is nonetheless desirable from a clinical perspective to achieve full-length dystrophin expression using systemic i.v. delivery of the virus. In vitro FLD-AAV testing will be used to determine how AAV copy number and reconstituted dystrophin levels correlate. Tissue distribution and efficiency of reconstitution will be assessed in vivo, and different delivery paradigms (e.g., serotype, viral titer, route of application, number of repeat applications) will be examined to achieve optimal tissue distribution. Tissue coverage and expression levels will be assessed. Beneficial outcomes can be achieved even if only a portion of muscle fibers express dystrophin (e.g., normal heart function with only about 50% of cardiomyocytes being dystrophin deficient under non-stress conditions). Both, physiological and supraphysiological levels of dystrophin are of therapeutic value. Quantitative assessment will be performed as outlined in Part 1 & 2. In vivo intramuscular and systemic virus application will be performed in neonatal or juvenile mice under aseptic condition.

Part 5. Treat DMD mouse model (mdx) with FLD-AAV and assess disease onset/progression. FLD-AAV delivery in neonatal mdx mice may prevent the onset and progression of myopathy and cardiomyopathy. After optimization of the viral delivery of reconstituted full-length dystrophin (Parts 1-4) FLD-AAV treatment will be administered to a mouse model of DMD. These mice, depending on the genetic background they are bred, present with myopathy that is notably less pronounced than human DMD. Mice with the genetic background that presents with a more severe phenotype (D2.B10-Dmdmdx) show increased hind-limb weakness, lower muscle weight, fewer myofibers, and increased fat and fibrosis. These parameters can be compared between wild-type controls, treated mdx, and untreated mdx mice. The desired outcome is an amelioration or prevention of disease onset/progression.

Two mouse lines, C57BL/10ScSn-Dmdmdx/J, and D2.B10-Dmdmdx/J, which carry a mutation in the dystrophin gene are used. FLD-AAV is delivered according to parameters established as described under Part 4. Animals are injected in the first postnatal week, in a time window before onset of myonecrosis in mdx mice. Wild-type, treated-mdx and vehicle/sham-treated-mdx mice are e assessed for behavioral and anatomical signs of skeletal and cardiac myopathy. Using kinematic and electromyographic testing equipment, performance of these mice in a variety of motor tasks is assessed, such as balance beam, grip strength, horizontal ladder, treadmill speed challenge, over ground locomotor kinematic assessment, and swimming kinematic assessment (ambient temperature and cold water challenge). It will be determined whether FLD-AAV therapy can prevent the presentation of cardiomyopathy in mdx mice following chemical challenge.

The desired outcome of these experiments would be an amelioration or prevention of disease onset/progression.

Example 7

Delivery of Reconstituted Full-Length MYO7A Treat Usher Syndrome

A first half of the MYO7A coding sequence is appended with a synthetic RNA dimerization and recombination domain and expressed from a first vector/plasmid. The second half of MYO7A is appended to the complementary RNA dimerization and recombination domain and expressed from a second vector/plasmid. If expressed together in the same cell the two halves of MYO7A are recombined to form the full-length MYO7A transcript which is then translated into protein.

Example 8

Transcriptional/Expressional Logic Gate

Breaking a target gene into two nonfunctional halves that get expressed from either two different promoters or using two different delivery vehicles can result in an intersectional expression pattern.

For example, promoter 1 of a first synthetic nucleic acid molecule provided herein can drive expression of the N-terminal half of the coding sequence in for example cell types A, B, and C, while promoter 2 of a second synthetic nucleic acid molecule provided herein drives expression of the C-terminal half in a subset of cells A, D, E, and F. In such an example, the effector gene encoding the target protein is only expressed in the overlapping area (in this example in cell population A).

A similar intersectionality can be used by making the two halves conditionally expressed, for example, under the condition of the presence of a recombinase. Another level at which intersectionality can be achieved is by delivering the two halves with two viruses that have different tropisms.

Example 9

Complementation

The disclosed methods and systems can be used to make any gene (and corresponding target protein) into complementation parts (similar to the principle of alpha complementation of LacZ), by encoding two non-functional halves on separate plasmids that only become active when both plasmids are present.

Example 10

Trigger RNA

The disclosed systems and methods can be configured such that reconstitution of the two or more portions of the RNA coding sequences of the target protein depends on the presence of a specific "trigger" RNA molecule. As shown in FIG. 7B, in this example, the dimerization domains of each synthetic nucleic acid molecule are not reverse complements of one another, but instead specifically hybridize to adjacent regions of a third RNA molecule, a "trigger RNA", which serves as a bridge to bring two synthetic nucleic acid molecules together. In this example, the system can "report" the presence of a specific RNA molecule which allows for "cell type specific triggering" of a reporter/effector protein.

Example 11

Inclusion of Stabilizing Element in 3'-UTR

This example describes methods used to evaluate recombination of split coding sequences in the presence of a sequence in the 3'-UTR that stabilizes RNA. Woodchuck hepatitis posttranscriptional regulatory element 3 (WPRE3) was used as an exemplary stabilizing sequence. One skilled in the art will appreciate that other RNA sequence stabilizers can be used in place of WPRE3.

Median YFP fluorescence was measured by flow-cytometry for a two-way split YFP that is reconstituted using the disclosed synthetic RNA dimerization and recombination approach. The C-terminal YFP coding fragment is followed by a poly adenylation signal only (w/o WPRE3) or by a truncated version of the woodchuck hepatitis posttranscriptional regulatory element, WPRE3 followed by a poly adenylation signal (labelled w/WPRE3). The N-terminal YFP coding fragment is coexpressed with a red fluorescent protein from a bidirectional promoter for transfection control. The C-terminal fragment is co-expressed with a blue fluorescent protein from a bidirectional promoter as transfection control. Cells with equal red and blue fluorescent control values between conditions are compared.

Figure 8:
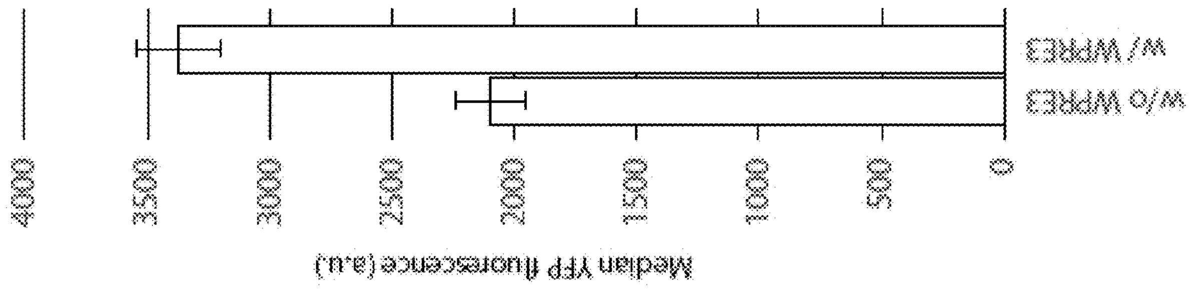
FIG. 8 is a bar graph comparing reconstitution of YFP protein expression in the presence (w/) or absence (w/o) of a WPRE3 sequence in the 3' untranslated region. N=3 replicates per sample are shown.

As shown in FIG. 8, inclusion of a stabilizing element in the 3'-UTR increased expression efficiency of the recombined full-length YFP by about 50-60%. This enhancement is observed even though WPRE sequences stimulate nuclear export of the RNA molecule they are contained in, which may have negatively impacted the RNA joining reaction (and thus gene expression) by shuttling molecule 150 of FIG. 6A outside the nucleus before the spliceosome mediated RNA joining can occur and thus rendering it non-functional.

Thus, the disclosed synthetic RNA molecules (such as any of SEQ ID NOS: 1, 2, 3, 4, 5, 6, 7, 8, 9, 10, 11, 12, 13, 14, 15, 16, 17, 18, 19, 20, 21, 22, 23, 24, 25, 145, 146, 17, and 148) can be modified to further include a RNA sequence stabilizer.

Example 12

Effect of Binding Domain Length on Reconstitution Efficiency

Binding domain length was assessed as follows. YFP was split into two non-fluorescent halves (SEQ ID NOS: 1 and 2, but with different length binding domains). Reconstitution efficiency for different length binding domains (ranging from 50 to 500 nucleotides) was assessed in cultured HEK 293t cells. N-terminal YFP is expressed from a bidirectional CMV promoter with a Red Fluorescent Protein (RFP) as a transfection control. C-terminal YFP is expressed from a bidirectional CMV promoter with a Blue Fluorescent Protein (BFP) as a transfection control. For the different binding domain lengths, YFP median fluorescence intensity was compared. Cells with matching RFP and BFP transfection levels are compared between conditions.

Figure 11:
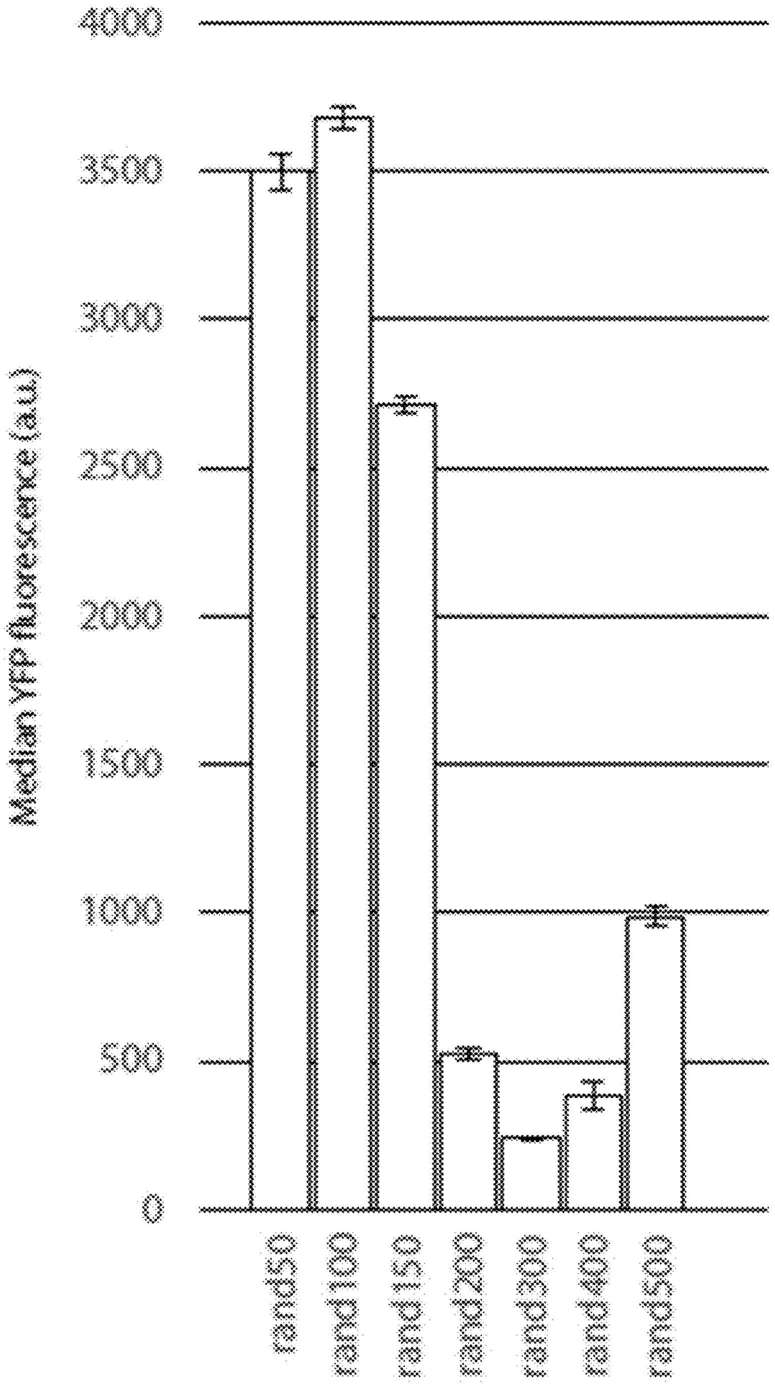
FIG. 11 is a bar graph showing the reconstitution efficiency of different length random complimentary binding domains (50 bp, 100 bp, 150 bp, 200 bp, 300 bp, 400 bp, and 500 bp). YFP median fluorescence intensity is compared between cells with matching RFP and BFP transfection levels. n=3 samples per condition. n=3 samples per condition.

As shown in FIG. 11, all of the molecules achieved some level of expression of the full-length YFP, with varying degrees of reconstitution efficiency. Although maximal performance was observed with binding domain lengths of 150 bp and below (e.g. 50-150 bp), binding domain lengths of up to 500 bp were still able to recombine and express full-length YFP.

Example 13

Effect of Splicing Enhancer Sequences

This example describes methods used to assess the effect of including one or more intronic splicing enhancer sequences (e.g., 118, 120, 156 in FIG. 6A) in the disclosed synthetic introns.

Figure 12B:
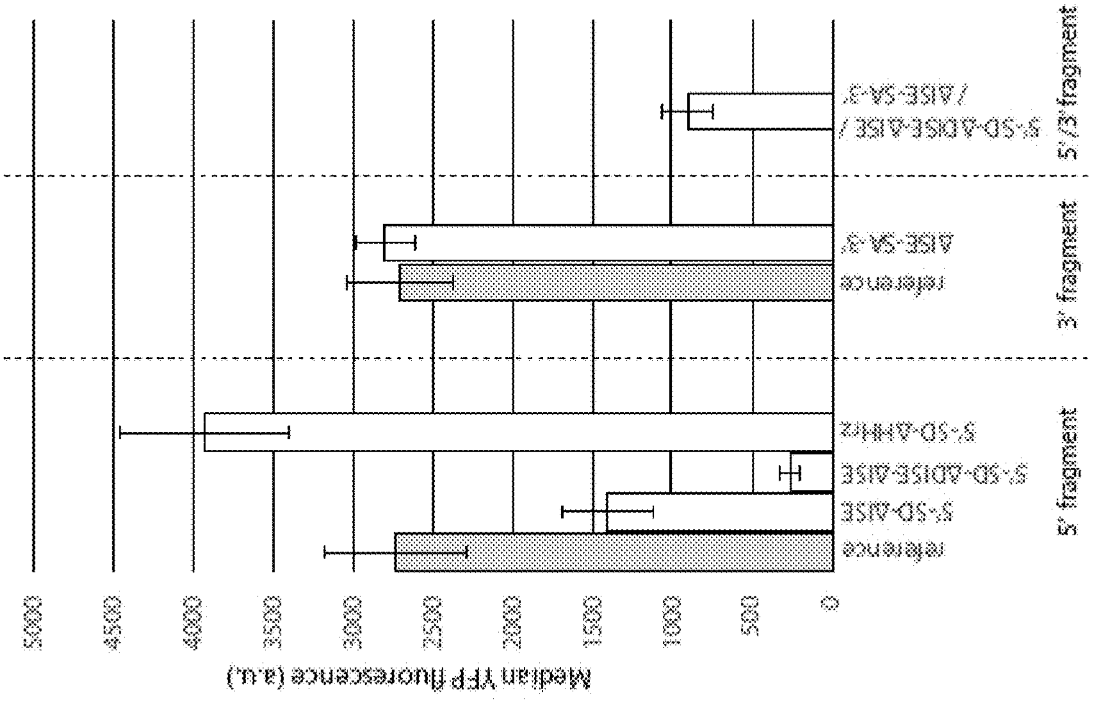
FIGS. 12A-12B show that inclusion of a splice enhancer into the synthetic intron increases the reconstitution efficiency.
Figure 12A:
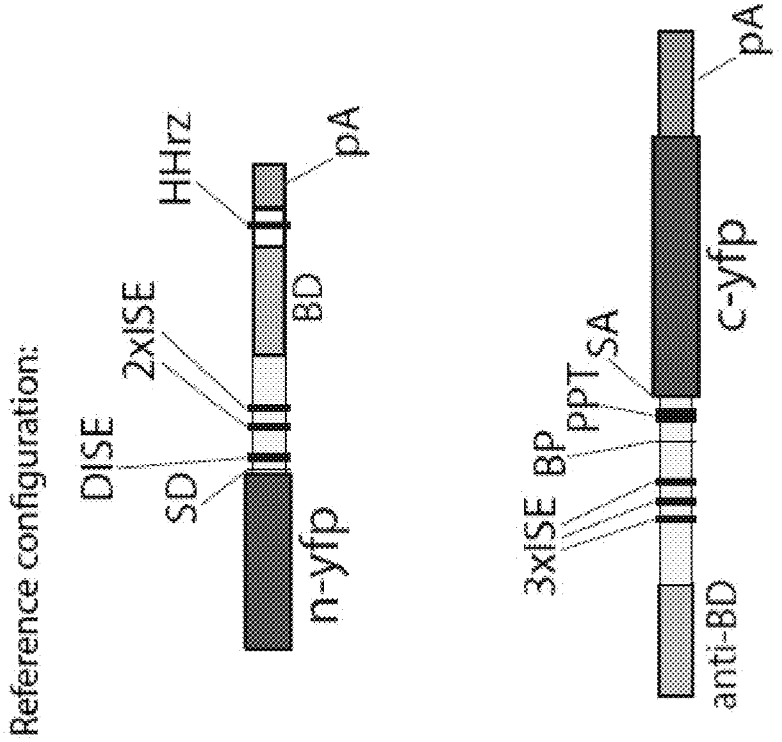

YFP was split into two non-fluorescent halves (FIG. 12A). Reconstitution efficiency for different intron configurations was assessed in cultured HEK 293t cells. N-terminal YFP was expressed from a bidirectional CMV promoter with a Red Fluorescent Protein (RFP) as a transfection control. C-terminal YFP was expressed from a bidirectional CMV promoter with a Blue Fluorescent Protein (BFP) as a transfection control. For the different intron configurations, YFP median fluorescence intensity is compared. Cells with matching RFP and BFP transfection levels are compared between conditions.

As shown in FIG. 12A, the 5' molecule (SEQ ID NO: 1) includes the coding region of the N-terminal portion of YFP (n-yfp), followed by a splice donor sequence (SD), a downstream intronic splicing enhancer (DISE), and two intronic splicing enhancers (2xISE), a binding domain (BD), a self-cleaving hammerhead ribozyme (HHrz), ending with a poly adenylation signal (pA). The 3' molecule (SEQ ID NO: 2) includes the complementary binding domain (anti-BD), followed by three intronic splicing enhancer sequences (3xISE), a branch point (BP), a polypyrimidine tract (PPT), a splice acceptor sequence (SA), the c-terminal proton of the YFP coding sequence, ending with a poly adenylation signal (pA).

As shown in FIG. 12B, inclusion of splice enhancers to both the 5' and the 3' molecules increases reconstitution efficiency of the full-length YFP. Removal of the splice enhancers reduces the reconstitution efficiency of the two coding sequences by about 50-90%. In the first column, YFP is reconstituted using the reference configuration (SEQ ID NOS: 1 and 2), the second column shows the reconstitution efficiency with deletion of the ISE elements in the 5' fragment, the third column shows reconstitution efficiency after deletion of the ISE and the DISE in the 5' fragment. The fourth column shows the reconstitution efficiency after deletion of the HHrz in the 5' fragment. The fifth column shows reconstitution efficiency using the reference configuration. The sixth column shows reconstitution efficiency after deletion of the ISE elements in the 3' fragment. The seventh shows reconstitution efficiency after deletion of the ISE in both 5' and 3' fragment and the DISE in the 5' fragment.

Example 14

Dual Projection Tracing

This example describes methods used to perform dual projection tracing by reconstitution of full-length flp recombinase (Flpo) from two fragments (SEQ ID NOS: 147 and 148). As shown in FIG. 13A, Flp recombinase is split into two non-functional haves. The N-terminal half of Flpo is appended with a synthetic intron and dimerization domain (RNA end joining module, REJ). The C-terminal half of Flpo is prepended with a synthetic intron and a binding domain (REJ-module). Upon infection of a cell of both constructs, the full length Flpo recombinase mRNA and subsequently the functional recombinase protein are produced by reconstitution of the two fragments. FIG. 13B shows a schematic of an flp activity reporter mouse carrying a flpo dependent red fluorescent protein (tdTomato) (Rosa-CAG-frt-STOP-frt-tdTomato). The two halves of flpo are packaged into separate adeno-associated viruses (retrogradely transported serotype AAV2/retro). The AAV2/retro-n-flpo is injected in the left primary motor cortex of the mouse, the AAV2/retro-c-flpo is injected in the right primary motor cortex of the mouse.

As shown in FIGS. 13C-13D, cells with dual projections to both primary motor cortices are labelled in red. Hoechst staining (nuclei) is shown for context.

Example 15

Expression of Long Protein In Vivo

This example describes methods used to achieve efficient expression of oversized cargo in cell culture and in vivo in the mouse primary motor cortex.

Figure 14C:
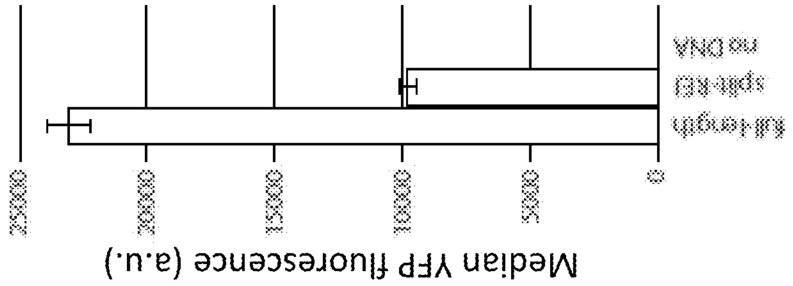
FIGS. 14A-14D show expression of oversized cargo in cell culture and in vivo in the mouse primary motor cortex. (A) Schematic representation of the 5'- and 3'-sequences used to reconstitute YFP, which include long stuffer sequences (uninterrupted open reading frames; SEQ ID NOS: 22 and 23, respectively). (B) Quantitative real-time PCR analysis of reconstitution efficiency of the oversize YFP constructs in HEK 293t cells. N=3 per condition. (C) Reconstituted YFP protein expression from full-length oversized YFP expression and split-REJ expression assessed by flow cytometry of transiently transfected HEK 293t cells. Median yellow fluorescence intensity is compared between cell populations with equal transfection control (blue and red) fluorescence for the different conditions. Y-axis shows median yellow fluorescence intensity [a.u.]. N=3 per condition. (D) Schematic of injections into mouse primary motor cortex, and images of brain tissue 10 days following injection, showing successful reconstitution of a long (2401 aa) YFP protein in vivo.
Figure 14B:
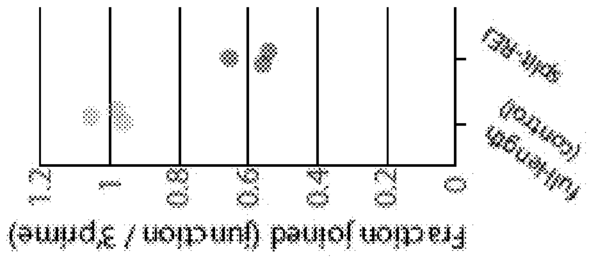
Figure 14A:
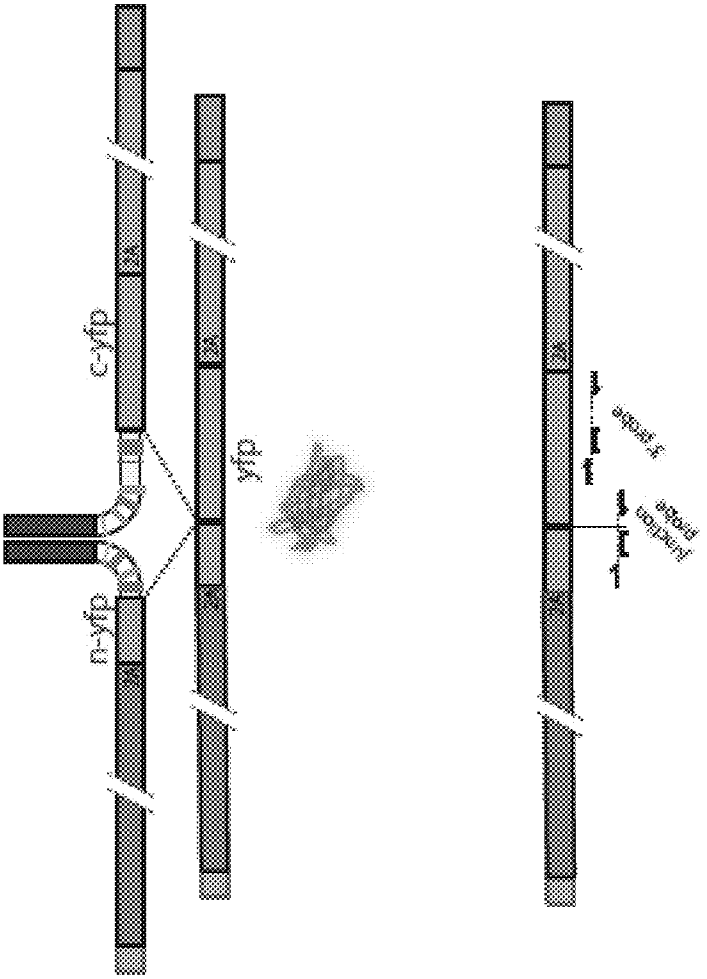

To simulate a large disease-causing gene that fills up the adeno-associated virus (AAV) cargo capacity of two viruses (i.e., it exceeds single AAV packaging capacity), a split YFP was embedded inside a large uninterrupted open reading frame. N-terminally (i.e. on the 5' side) the YFP is flanked with long stuffer sequences (i.e. an uninterrupted open reading frame) followed by a 2A self-cleaving peptide sequence. On the C-terminus (i.e., 3' side) the YFP coding sequence is followed by a 2A self-cleaving peptide sequence and then followed by a long stuffer sequence (i.e., and uninterrupted open reading frame) (FIG. 14A). The resulting RNA molecules expressed are each about 4000nt between the transcriptional start site and the poly adenylation site. The N-terminal (5' fragment; SEQ ID NO: 22) contains a stuffer open reading frame which is followed by a self-cleaving 2A sequence, followed by the N-terminal portion of YFP, followed by a synthetic intron and a dimerization domain (kissing loop architecture). The C-terminal (3' fragment; SEQ ID NO: 23) is composed of a complementary binding domain, a synthetic intron sequence, followed by the C-terminal portion of YFP, followed by a self-cleaving 2A sequence, followed by a stuffer open reading frame, followed by a poly adenylation signal. During translation, the 2A sequences flanking the YFP result in the cleaving off of the N and C-terminal stuffer sequences and the production of functional YFP protein.

To determine reconstitution efficiency on an RNA level, two probe based (5'-hydrolysis) quantitative real-time PCR assays are used. The first assay spans a sequence fully contained in the 3' exonic YFP sequence (labelled 3' probe). The second assay spans the junction between the 5' and the 3' exonic YFP sequence (labelled junction probe). Reconstitution efficiency is calculated as the ratio of (junction probe count)/(3' probe count).

Quantitative real-time PCR analysis of reconstitution efficiency of the oversize YFP constructs in HEK 293t cells was performed. Full-length oversized YFP is used as reference. The full-length oversized YFP ratio is set to 1 (FIG. 14B). Ratio of reconstituted is expressed as fraction of full-length (labelled split-REJ (split RNA end joining)). Reconstitution efficiency is calculated as follows: junction/3'prime. As shown in FIG. 14B about 60% of the RNAs joined in the split-REJ system.

Figure 14D:
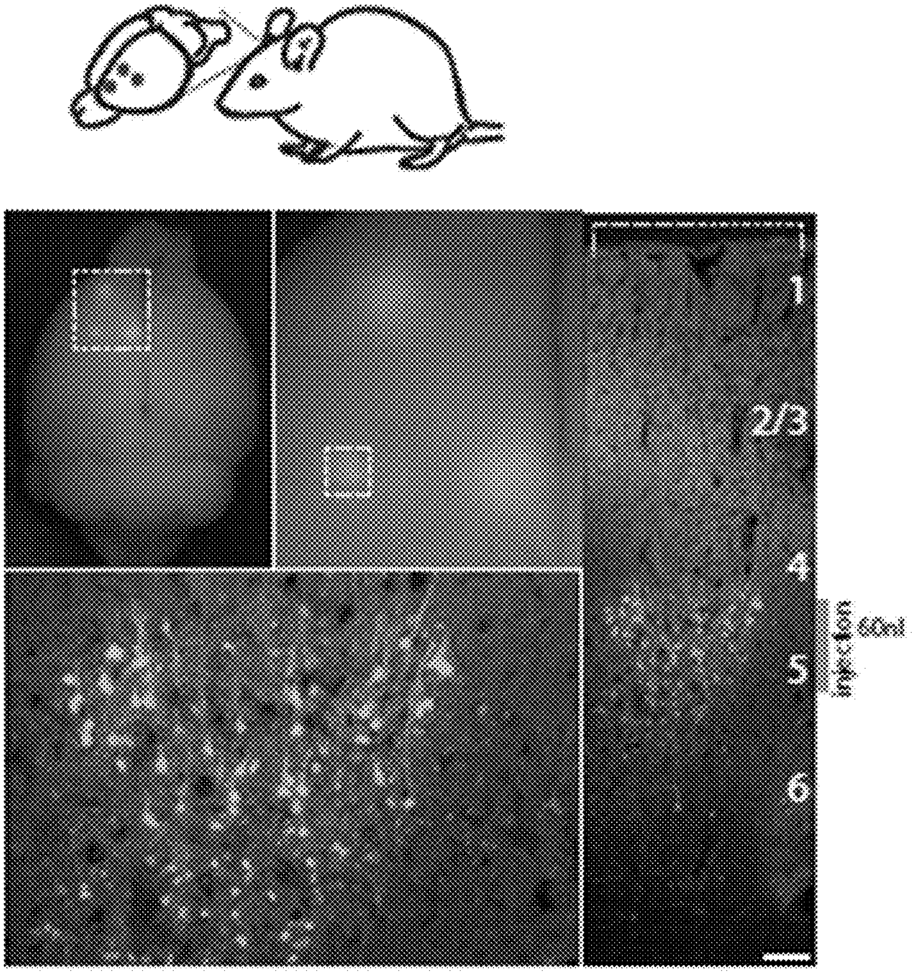

Reconstituted YFP protein expression from full-length oversized YFP expression and split-REJ expression is assessed by flow cytometry of transiently transfected HEK 293t cells. As shown in FIG. 14C, the split REJ system achieved about a 45% joining efficiency, even with the large cargo.

in vivo analysis of reconstitution of the large YFP protein was performed as follows. 60 nl of adeno-associated virus 2/8, containing 3E9 vg/injection/fragment, was injected into the primary motor cortex of the mouse. Tissue was harvested 10 days post injection. As shown in FIG. 14D, YFP fluorescence is readily detectable in the bulk tissue (top left, top middle panel, macroscopic top view of the mouse brain, YFP fluorescence plus auto-fluorescence for context are shown). Strong YFP signal is detected at and around the virus injection site in layer 5 of the motor cortex (right panel, cortical layers are numbered 1 to 6, approximate injection depth is indicated by gray bar, scale bar=100 micrometers). Thus, the disclosed system can be used to express large proteins in vivo.

Example 16

Expression of Factor VIII

This example describes methods used to achieve efficient reconstitution of full-length human coagulation factor VIII (FVIII).

Figure 15B:
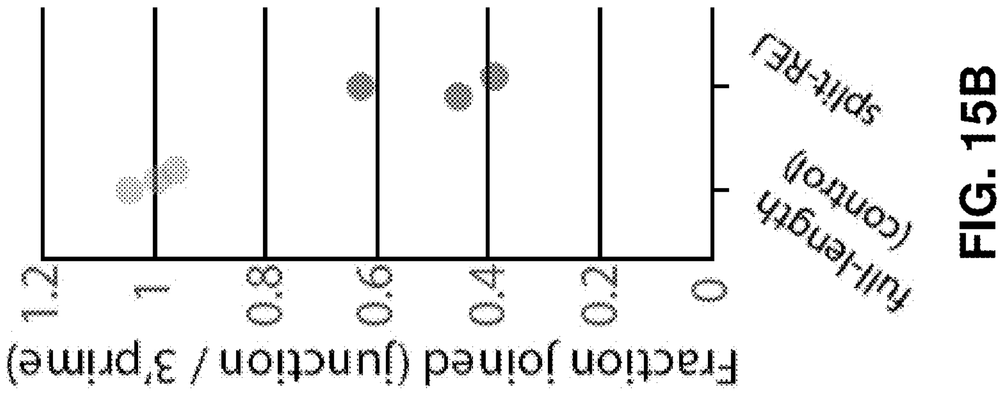
FIGS. 15A-15C show efficient reconstitution of full-length human coagulation factor VIII (FVIII) with N-terminal HA tag (substituting the N-terminal signal peptide) (2317 aa). (A) Schematic representation of the 5'- and 3'-sequences used to reconstitute FVIII (SEQ ID NOS: 24 and 25, respectively). (B) PCR amplification of the junction. (C) Western blot showing expression of FVIII. Lanes 1-3: expression of full-length FVIII (290 kDa band shows full length, unprocessed FVIII). Lanes 4-6: expression of reconstituted FVIII (band at 290 kDa shows successfully reconstituted FVIII). Lanes 7 and 8: expression of the N-terminus only shows absence of full-length FVIII band at 290 kDa. For all lanes: Expected proteolytic processing products are observed ranging from ~75 kDa to ~210 kDa. FVIII is probed for using a mouse anti-HA primary antibody. All lanes were loaded with 5 micrograms of cleared cell protein extract. GAPDH (rabbit anti-GAPDH) is probed for as loading control.
Figure 15A:
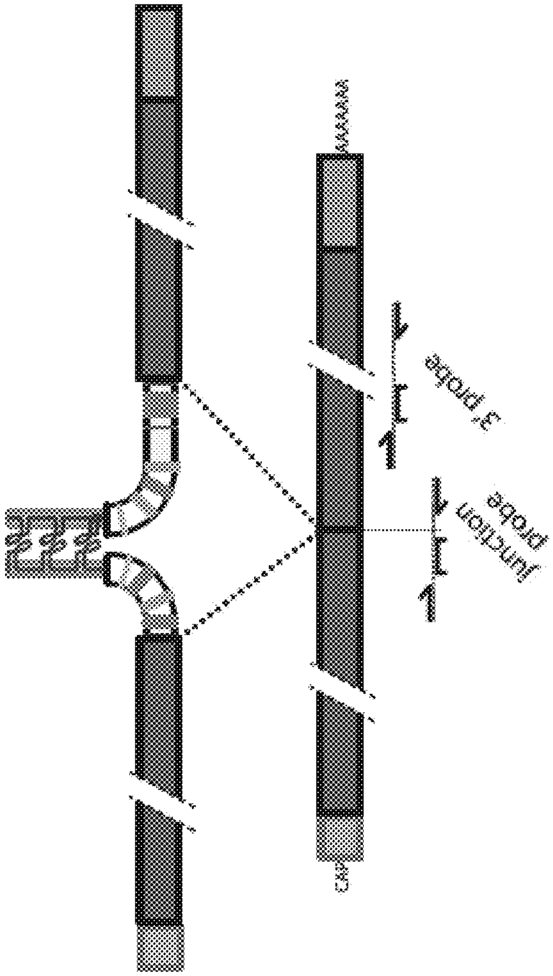

A schematic of the 5' and 3' molecules used are shown in FIG. 15A (SEQ ID NOS: 24 and 25, respectively). Each half includes about 3.8 kb of FVIII coding sequence. The 5'-sequence containing the N-terminal half (e.g., 110 of FIG. 6A) of FVIII is followed by an efficient synthetic intron and a binding domain. The 3'-sequence containing the C-terminal half (e.g., 150 of FIG. 6A) is preceded by the complementary binding domain and an efficient synthetic intron sequence. To determine reconstitution efficiency on an RNA level, two probe based (5'-hydrolysis) quantitative real-time PCR assays are used. The first assay spans a sequence fully contained in the 3' exonic FVIII sequence (labelled 3' probe). The second assay spans the junction between the 5' and the 3' exonic FVIII sequence (labelled junction probe). Reconstitution efficiency is calculated as the ratio of (junction probe count)/(3' probe count).

PCR quantification of reconstitution efficiency after two days of expression in HEK 293t cells was performed. Full-length FVIII is used as reference. Full-length FVIII ratio is set to one. Reconstituted FVIII assay ratios are expressed as fraction of full-length (labelled split-REJ). As shown in FIG. 15B, a reconstitution efficiency of about 40-60% was achieved (that is about 40-60% of the two RNAs joined in the split-REJ system).

Figure 15C:
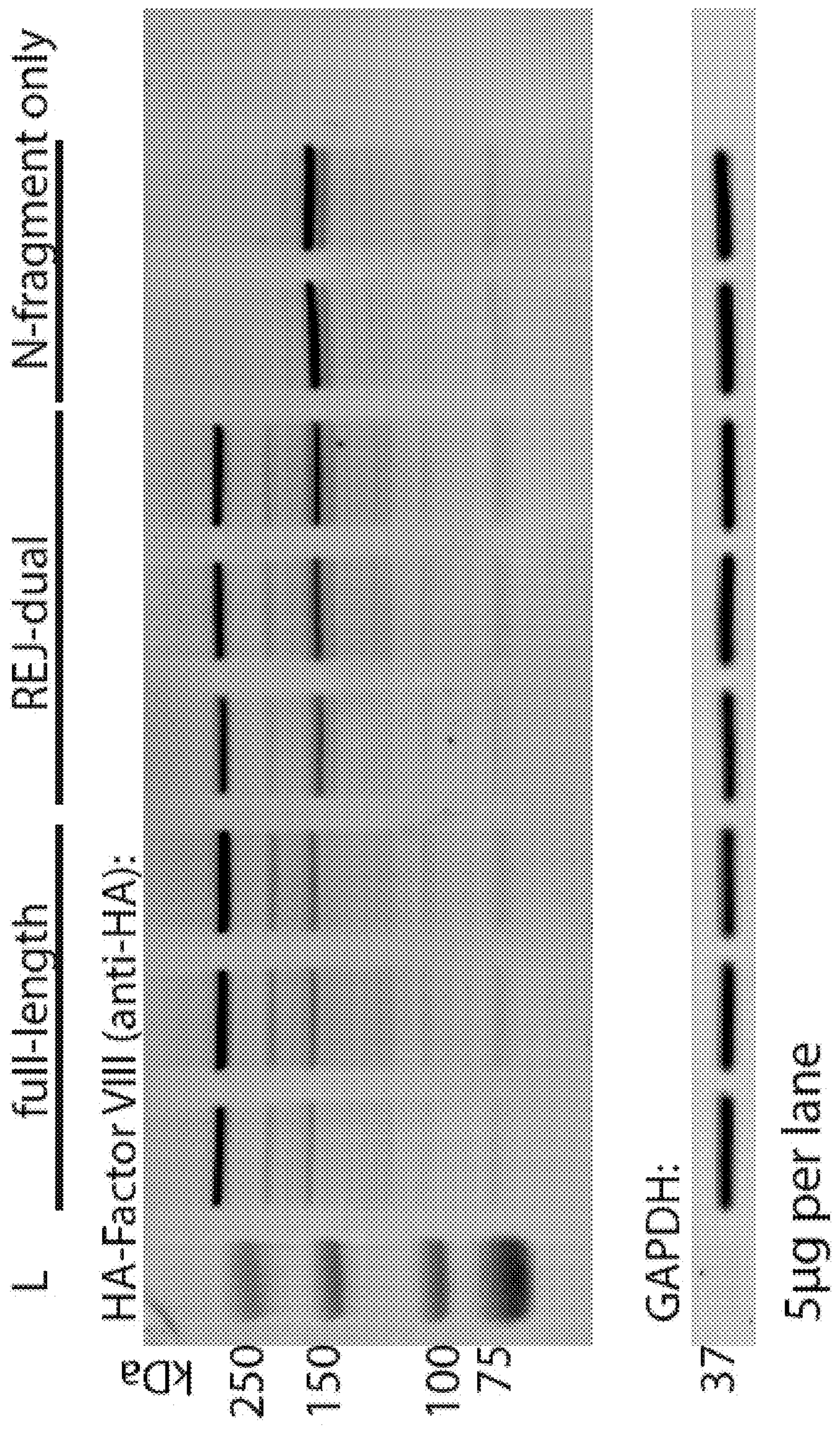

To demonstrate expression of FVIII in vitro, Western blotting was used. FVIII was tagged with an HA-tag at the N-terminus. Constructs are expressed in HEK 293t cells for 2 days. As shown in FIG. 15C, the disclosed split-REJ system successfully expressed full-length FVIII in vitro.

Based on these observations, expression of a full-length FVIII protein in vivo can be achieved, for example to treat hemophilia A. For example, a first half of a FVIII coding sequence is appended with a synthetic RNA dimerization and recombination domain and expressed from a first vector/plasmid. The second half of FVIII is appended to the complementary RNA dimerization and recombination domain and expressed from a second vector/plasmid. If expressed together in the same cell the two halves of FVIII are recombined to form the full-length FVIII transcript which is then translated into protein. For example, a sequence having at least 80%, at least 90%, at least 95%, at least 96%, at least 97%, at least 98%, at least 99% or 100% sequence identity to SEQ ID NO: 24, which includes an N-terminal FVIII coding sequence, and SEQ ID NO: 25 which includes a C-terminal FVIII coding sequence, can be utilized for in vivo expression.

Example 17

Expression of Abca4

This example describes methods used to achieve efficient reconstitution of full-length human ATP binding cassette subfamily A member 4 (Abca4).

Figure 16B:
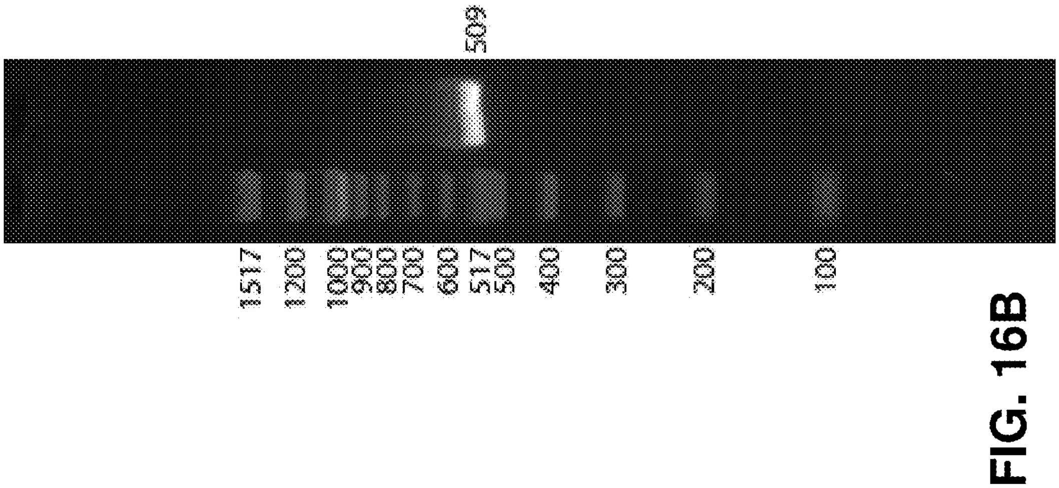
FIGS. 16A-16F show efficient reconstitution of full-length human Abca4 with C-terminal FLAG-tag (2300 aa). (A) Schematic representation of the 5'- and 3'-sequences used to reconstitute Abca4 (SEQ ID NOS: 20 and 21, respectively), and a Sanger sequencing trace across the junction. (B) PCR amplification of the junction. (C) Schematic representation of the probes used to assay recombination of the 5'- and 3'-fragments. (D) PCR quantification of reconstitution efficiency after two days of expression in HEK 293t cells. N=2 per condition. (E) Western blot showing expression of Abca4. Lanes 1-3: expression of full-length Abca4 (~260 kDa band shows full length Abca4). Lanes 4-6: expression of reconstituted Abca4 (band at 260 kDa shows successfully reconstituted Abca4). Lanes 7 and 8: no transfection control (i.e., HEK 293t lysate only) shows absence of any signal. Abca4 is probed for using a mouse anti-HA primary antibody. All lanes were loaded with 5 micrograms of cleared cell protein extract. GAPDH (rabbit anti-GAPDH) is probed for as loading control. (F) Quantification of the western blot in (E) normalized for differential BFP concentration. Data is shown as normalized to the average of full-length expression control.
Figure 16A:
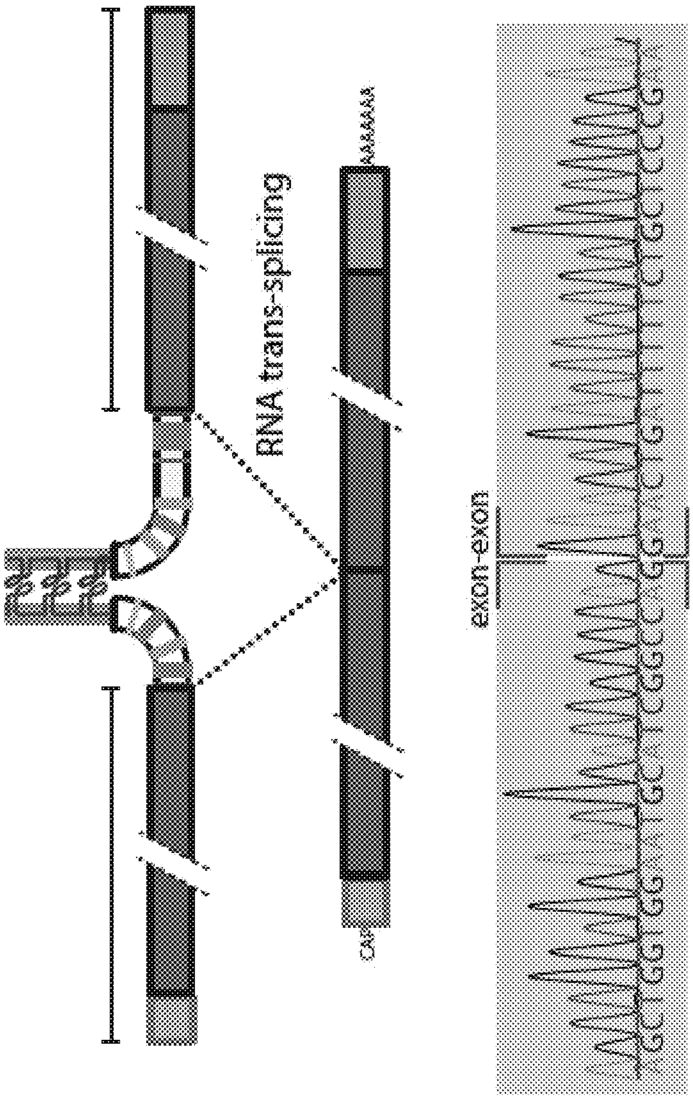

A schematic of the 5' and 3' molecules used are shown in FIG. 16A (SEQ ID NOS: 19 and 21, respectively). The 5' half includes about 3.6 kb of Abca4 coding sequence, the 3' half about 3.2 kb of the Abca4 coding region plus a C-terminal 3xFLAG tag. The 3'-sequence containing the C-terminal half (e.g., 150 of FIG. 6A) is preceded by the complementary binding domain and an efficient synthetic intron sequence. A Sanger sequencing trace across the junction is shown.

Figure 16C:
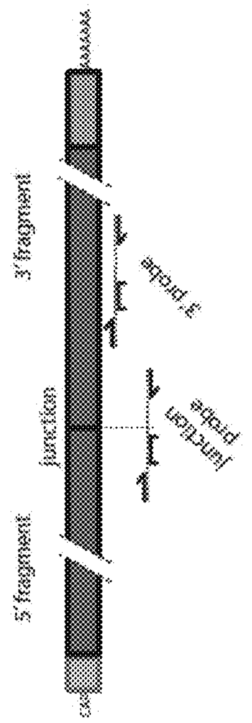
Figure 16D:
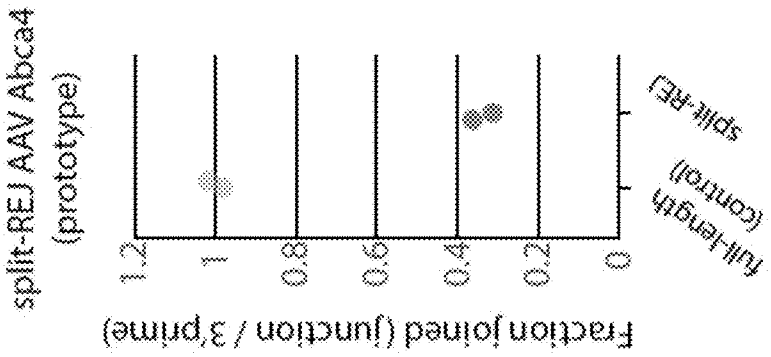

As shown in FIG. 16B, PCR amplification of the junction demonstrates faithful joining of the two coding sequences. To determine reconstitution efficiency on an RNA level, two probe based (5'-hydrolysis) quantitative real-time PCR assays are used (FIG. 16C). The first assay spans a sequence fully contained in the 3' exonic Abca4 sequence (labelled 3' probe). The second assay spans the junction between the 5' and the 3' exonic Abca4 sequence (labelled junction probe). Reconstitution efficiency is calculated as the ratio of (junction probe count)/(3' probe count). PCR quantification of reconstitution efficiency after two days of expression in HEK 293t cells is shown in FIG. 16D. Full-length Abca4 is used as reference. Average full-length Abca4 ratio is set to one. Reconstituted Abca4 assay ratios are expressed as fraction of full-length (labelled split-REJ). As shown in FIG. 16D, a reconstitution efficiency of about 35% was achieved (that is about 30-40% of the two RNAs joined in the split-REJ system).

Figure 16E:
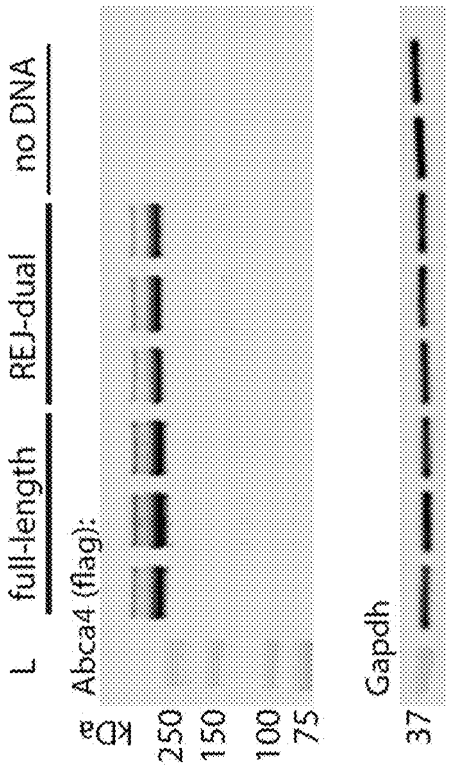

To demonstrate expression of Abca4 in vitro, Western blotting was used. Abca4 is tagged with a 3xFLAG-tag at the C-terminus. Constructs are expressed in HEK 293t cells for 2 days. As shown in FIG. 16E, the disclosed split-REJ system successfully expressed full-length Abca4 in vitro.

Figure 16F:
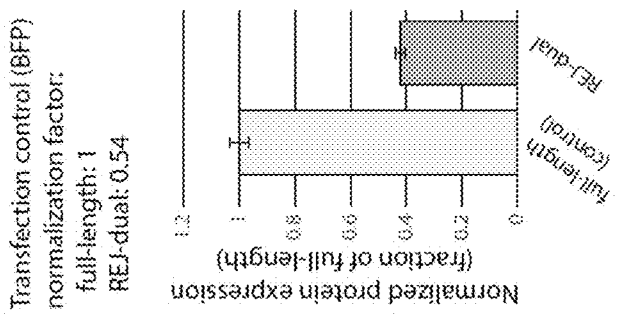

Quantification of the western blot is shown in FIG. 16F. To normalize for differential transfection efficiency between conditions, the full-length plasmid and the C-terminal plasmid co-express a Blue Fluorescent Protein for transfection control. BFP concentration in each sample was determined by dot blot and used to normalize between conditions. As shown in FIG. 16F reconstituted Abca4 is expressed at approximately 40% of the levels when compared with direct full-length expression. Hence, the protein levels as determined by western blot, track well with the RNA reconstitution efficiency determined by qPCR.

Based on these observations, expression of a full-length ABCA4 protein in vivo can be achieved, for example to treat Stargardt's Disease. For example, a first half of the ABCA4 coding sequence is appended with a synthetic RNA dimerization and recombination domain and expressed from a first vector/plasmid. The second half of ABCA4 is appended to the complementary RNA dimerization and recombination domain and expressed from a second vector/plasmid. If expressed together in the same cell the two halves of ABCA4 are recombined to form the full-length ABCA4 transcript which is then translated into protein. For example, a sequence having at least 80%, at least 90%, at least 95%, at least 96%, at least 97%, at least 98%, at least 99% or 100% sequence identity to SEQ ID NO: 20 (FIGS. 10R-10U), which includes an N-terminal Abca4 coding sequence, and SEQ ID NO: 21 (FIGS. 10V-10Z) which includes a C-terminal Abca4 coding sequence, can be utilized for in vivo expression.

In view of the many possible embodiments to which the principles of the disclosure may be applied, it should be recognized that the illustrated embodiments are only examples of the invention and should not be taken as limiting the scope of the invention. Rather, the scope of the invention is defined by the following claims. We therefore claim as our invention all that comes within the scope and spirit of these claims.

We claim:

1. A system for expressing a target protein, comprising:

(a) a first synthetic nucleic acid molecule comprising, from 5' to 3', a sequence encoding:

an RNA molecule encoding an N-terminal portion of the target protein, comprising a splice junction at a 3'-end of the RNA molecule encoding the N-terminal portion of the target protein;

a splice donor; and a first dimerization domain comprising a first RNA hairpin, wherein the first RNA hairpin comprises RNA complementary sequences separated by a region of a non-complementary RNA sequence, wherein base pairing between the complementary sequences forms a first stem and the region of the non-complementary RNA sequence forms a first loop; and (b) a second synthetic nucleic acid molecule comprising, from 5' to 3', a sequence encoding:

a second dimerization domain comprising a second RNA hairpin, wherein the second RNA hairpin comprises RNA complementary sequences separated by a region of a non-complementary RNA sequence, wherein base pairing between the complementary sequences forms a second stem and the region of the non-complementary RNA sequence of the second RNA hairpin forms a second loop;

a branch point sequence;

a polypyrimidine tract;

a splice acceptor; and an RNA molecule encoding a C-terminal portion of the target protein, comprising a splice junction at a 5'-end of the RNA molecule encoding the C-terminal portion of the target protein, wherein the first loop hybridizes with the second loop, and wherein the first and second loops avoid intramolecular annealing.

2. A system for expressing a target protein, comprising:

(a) a first synthetic nucleic acid molecule comprising, from 5' to 3', a sequence encoding:

an RNA molecule encoding an N-terminal portion of the target protein, comprising a splice junction at a 3'-end of the RNA molecule encoding the N-terminal portion of the target protein;

a first splice donor; and a first dimerization domain comprising a first RNA hairpin, wherein the first RNA hairpin comprises RNA complementary sequences separated by a region of a non-complementary RNA sequence, wherein base pairing between the complementary sequences forms a first stem and the region of the non-complementary RNA sequence forms a first loop;

(b) a second synthetic nucleic acid molecule comprising, from 5' to 3', a sequence encoding:

a second dimerization domain comprising a second RNA hairpin, wherein the second RNA hairpin comprises RNA complementary sequences separated by a region of a non-complementary RNA sequence, wherein base pairing between the complementary sequences forms a second stem and the region of the non-complementary RNA sequence of the second RNA hairpin forms a second loop;

a first branch point sequence;

a first polypyrimidine tract;

a first splice acceptor;

an RNA molecule encoding a middle portion of the target protein, comprising a splice junction at a 5'-end of the RNA molecule encoding the middle portion of the target protein and a splice junction at a 3'-end of the RNA molecule encoding the middle portion of the target protein;

a second splice donor; and a third dimerization domain comprising a third RNA hairpin, wherein the third RNA hairpin comprises RNA complementary sequences separated by a region of a non-complementary RNA sequence, wherein base pairing between the complementary sequences forms a third stem and the region of the non-complementary RNA sequence of the third RNA hairpin forms a third loop; and (c) a third synthetic nucleic acid molecule comprising, from 5' to 3', a sequence encoding:

a fourth dimerization domain comprising a fourth RNA hairpin, wherein the fourth RNA hairpin comprises RNA complementary sequences separated by a region of a non-complementary RNA sequence, wherein base pairing between the complementary sequences forms a fourth stem and the region of the non-complementary RNA sequence of the fourth RNA hairpin forms a fourth loop;
a second branch point sequence;
a second polypyrimidine tract;
a second splice acceptor; and
an RNA molecule encoding a C-terminal portion of the target protein, comprising a splice junction at a 5'-end of the RNA molecule encoding the C-terminal portion of the target protein,
wherein the first loop hybridizes with the second loop, wherein the third loop hybridizes with the fourth loop, and wherein the first, second, third, and fourth loops avoid intramolecular annealing.

3. The system of claim 2, further comprising:
(d) a fourth synthetic nucleic acid molecule comprising, from 5' to 3', a sequence encoding:
a fifth dimerization domain comprising a fifth RNA hairpin, wherein the fifth RNA hairpin comprises RNA complementary sequences separated by a region of a non-complementary RNA sequence, wherein base pairing between the complementary sequences forms a fifth stem and the region of the non-complementary RNA sequence of the fifth RNA hairpin forms a fifth loop;
a third branch point sequence;
a third polypyrimidine tract;
a third splice acceptor;
an RNA molecule encoding a second middle portion of the target protein, comprising a splice junction at a 5'-end of the RNA molecule encoding the second middle portion of the target protein and a splice junction at a 3'-end of the RNA molecule encoding the second middle portion of the target protein;
a third splice donor; and
a sixth dimerization domain comprising a sixth RNA hairpin, wherein the sixth RNA hairpin comprises RNA complementary sequences separated by a region of a non-complementary RNA sequence, wherein base pairing between the complementary sequences forms a sixth stem and the region of the non-complementary RNA sequence of the sixth RNA hairpin forms a sixth loop,
wherein the sixth loop hybridizes with the fourth loop, wherein the fourth loop does not hybridize to the third loop,
wherein the fifth loop hybridizes with the third loop, and wherein the fifth and sixth loops avoid intramolecular annealing.

4. The system of claim 1, wherein the first and second loops comprise hypodiverse sequences.

5. The system of claim 1, wherein the first, second, or both dimerization domains do not comprise a cryptic splice acceptor.

6. The system of claim 1, wherein the target protein is a protein associated with disease, or a therapeutic protein.

7. The system of claim 6, wherein the disease is a monogenic disease, a recessive genetic disease, a disease caused by a mutation in a gene greater than 4500 nt, or a combination thereof.

8. The system of claim 6, wherein the therapeutic protein is a toxin.

9. The system of claim 6, wherein the disease is a retinal disorder, a blood cell disorder, a primary immunodeficiency disease or disorder, a monogenetic disorder, a mucopolysaccaridosis disorder, a cancer, or a neurological disorder.

10. The system of claim 1, wherein the target protein is encoded by a coding sequence of at least 4500 nucleotides.

11. The system of claim 6, wherein the disease is selected from: Duchenne muscular dystrophy; Becker muscular dystrophy; Dysferlinopathy; Cystic fibrosis; Usher's Syndrome 1B; Stargardt disease 1; Von Willebrand disease; Marfan Syndrome; Von Recklinghausen disease; sickle cell anemia; hemophilia; hemophilia A; hemophilia B; Alpha-Thalassemia; Beta-Thalassemia; Delta-Thalassemia; von Willebrand Disease; pernicious anemia; Fanconi anemia; Thrombocytopenia purpura; thrombophilia; T-B+SCID; T-B-SCID; WHIM syndrome; IL-7 receptor severe combined immune deficiency (SCID); Adenosine deaminase deficiency SCID; Purine nucleoside phosphorylase deficiency; Wiskott-Aldrich syndrome; Chronic granulomatous disease; Leukocyte adhesion deficiency; HIV disease; Glycogen storage disease type IA; Retinal Dystrophy; X-linked immunodeficiency with magnesium defect, Epstein-Barr virus infection, and neoplasia (XMEN); Metachromatic leukodystrophy (MLD); Adrenoleukodystrophy (ALD); Hunter syndrome; Hurler syndrome; Scheie syndrome; Sanfilippo syndrome A, B, C, and D; Morquio syndrome A; Morquio syndrome B; Maroteaux-Lamy syndrome; Sly syndrome; Natowicz syndrome; Alpha mannosidosis; Nieman Pick disease types A, B, and C; Polycystic kidney disease; Tay Sachs Disease; Gaucher disease; Huntington's disease; Neurofibromatosis types 1 and 2; Familial hypercholesterolemia; Chronic myeloid leukemia; Acute myeloid leukemia; Osteosarcoma; Colorectal cancer; Gastric cancer; Melanoma; Prostate cancer; Cervical cancer; Glioblastoma; Alzheimer's disease; Multiple sclerosis; X-linked adrenoleukodystrophy; AACD deficiency; Batten disease; Canavan disease; Giant axonal neuropathy; Leber's hereditary optic neuropathy; MPS IIIA; Parkinson's disease; Pompe disease; and Spinal muscular atrophy type 1.

12. The system of claim 1, wherein:
the first synthetic nucleic acid molecule further comprises a downstream intronic splice enhancer (DISE) 3' to the splice donor and 5' to the first dimerization domain, an intronic splice enhancer (ISE) 3' to the splice donor and 5' to the first dimerization domain, or both a DISE and ISE;
the second synthetic nucleic acid molecule further comprises an ISE 3' to the second dimerization domain and 5' to the branch point sequence; or
any combination thereof.

13. The system of claim 1, wherein:
the synthetic first and second nucleic acid molecules, when introduced into a cell, recombine such that the RNA molecule encoding the N-terminal portion of the target protein and the RNA molecule encoding the C-terminal portion of the target protein combine into a full-length coding sequence of the target protein.

14. The system of claim 1, wherein the synthetic first nucleic acid molecule is part of a first viral vector, and
wherein the second nucleic acid molecule is part of a second viral vector.

15. The system of claim 14, wherein the first and second viral vectors are AAVs.

16. The system of claim 1, wherein:
the first dimerization domain and the second dimerization domain are each no more than 1000 nt, and
the system has a recombination efficiency of at least 20%, at least 30% at least 40%, at least 50%, at least 60%, at least 70%, at least 75%, at least 80%, or at least 90%.

17. The system of claim 1, wherein the target protein is selected from: Dystrophin; Dysferlin; Myosin VIIA; Fibrillin 1; Neurofibromatosis-1; ß-globin chain of hemoglobin; Clotting factor I; Clotting factor II; Clotting factor III;

Clotting factor IV; Clotting factor V; Clotting factor VI; Clotting factor VII; Clotting factor VIII; Clotting factor IX; Clotting factor X; Clotting factor XI; Clotting factor XII; Clotting factor XIII; HBA1; HBA2; HBB; HBD; von Willebrand factor; MTHFR; FANCA; FANCC; FANCD2; FANCG; FANCJ; ADAMTS13; Factor V Leiden Prothrombin; IL-2RG; JAK3; IL-2 receptor gamma chain; IL-4 receptor gamma chain; IL-7 receptor gamma chain; IL-9 receptor gamma chain; IL-15receptor gamma chain; IL-21 receptor gamma chain; RAG1; RAG2; CXCR4; IL7 receptor; ADA; PNP; WAS; CYBA; CYBB; NCF1; NCF2; NCF4; Beta-2 integrin; C-C chemokine receptor type 5 (CCR5); MSRB1; CSCR4; P17; PSIP1; CCR5; DMD; G6Pase; CEP290; ABCA4; MAGT1; arylsulfatase A (ARSA); ABCD1; IDS; IDUA; SGSH; NAGLU; HGSNAT; GNS; GALNS; GLB1; ARSB; GUSB; HYAL1; MAN2B1; SMPD1; NPC1; NPC2; CFTR; PKD-1; PDK-2; PDK-3; HEXA; GBA; HTT; NF-1; NF2; APOB; LDLR; LDLRAP1; PCSK9; BCR-ABL; ASXL1; RUNX2; EPHA1; PD-1; Androgen receptor; E6; E7; CD; NGF; MBP; WASP; AADC; CLN2; ASPA; GAN; MT-ND4; SUMF1; GAD; NTRN; TH; CH1; GDNF; GAA; SMN; and thymidine kinase.

18. A method of expressing a protein in a cell, comprising:
introducing the system of claim 1 into a cell; and
expressing system in the cell.

19. The method of claim 18, wherein the cell is in a subject, and introducing comprises administering a therapeutically effective amount of the system to the subject.

20. The method of claim 18, wherein the method treats a genetic disease caused by a mutation in a gene encoding the target protein in the subject, wherein the method results in expression of functional target protein in the subject.

21. The method of claim 20, wherein:
the genetic disease is Duchenne muscular dystrophy and the target protein is dystrophin;
the genetic disease is hemophilia A and the target protein is Coagulation Factor VIII;
the genetic disease is Stargardt disease and the target protein is ABCA4;
the genetic disease is Retinal Dystrophy and the target protein is CEP290;
the genetic disease is Dysferlinopathy and the target protein is Dysferlin; or the genetic disease is Usher syndrome and the target protein is MYO7A.

22. The system of claim 1, wherein the first synthetic nucleic acid molecule further comprises a first promoter 5' to the sequence encoding the RNA molecule encoding the N-terminal portion of the target protein; and
wherein the second synthetic nucleic acid molecule further comprises a second promoter 5' to the sequence encoding the second dimerization domain.

23. The system of claim 2, wherein the first nucleic synthetic molecule further comprises a first promoter 5' to the sequence encoding the RNA molecule encoding the N-terminal portion of the target protein molecule,
wherein the second synthetic nucleic acid molecule further comprises a second promoter 5' to the sequence encoding the second dimerization domain, and
wherein the third synthetic nucleic acid molecule further comprises a third promoter 5' to the sequence encoding the fourth dimerization domain.

24. The system of claim 3, wherein the first nucleic synthetic molecule further comprises a first promoter 5' to the sequence encoding the RNA molecule encoding the N-terminal portion of the target protein molecule,
wherein the second synthetic nucleic acid molecule further comprises a second promoter 5' to the sequence encoding the second dimerization domain,
wherein the third synthetic nucleic acid molecule further comprises a third promoter 5' to the sequence encoding the fourth dimerization domain, and
wherein the fourth synthetic nucleic acid molecule further comprises a fourth promoter 5' to the sequence encoding the fifth dimerization domain.

25. The method of claim 18, wherein the first synthetic nucleic acid molecule in a) further comprises a first promoter 5' to the sequence encoding the RNA molecule encoding the N-terminal portion of the target protein, and wherein the second synthetic nucleic acid molecule in b) further comprises a second promoter 5' to the sequence encoding the second dimerization domain.

26. The system of claim 1, wherein the first RNA hairpin is a plurality of the first RNA hairpins, and
wherein the second RNA hairpin is a plurality of the second RNA hairpins.

27. A system for expressing a target protein, comprising:
(a) a first synthetic nucleic acid molecule comprising, from 5' to 3', a sequence encoding:
a first RNA molecule encoding an N-terminal portion of the target protein, the first RNA molecule comprising, at a 3' end, a splice junction;
a splice donor; and
a first dimerization domain comprising an aptamer that binds to an aptamer target; and
(b) a second synthetic nucleic acid molecule comprising, from 5' to 3', a sequence encoding:
a second dimerization domain comprising an aptamer that binds to the aptamer target bound by the first dimerization domain;
a branch point sequence;
a polypyrimidine tract;
a splice acceptor; and
a second RNA molecule encoding a C-terminal portion of the target protein, the second RNA molecule comprising, at a 5' end, a splice junction,
wherein the aptamers of the first and second dimerization domains bind the aptamer target in single-stranded regions that avoid intramolecular annealing.

* * * * *

SEQUENCE LISTING

```
<160> NUMBER OF SEQ ID NOS: 154

<210> SEQ ID NO 1
<211> LENGTH: 1491
<212> TYPE: DNA
<213> ORGANISM: Artificial Sequence
<220> FEATURE:
<223> OTHER INFORMATION: Synthetic nucleic acid sequence

<400> SEQUENCE: 1

cgttacataa cttacggtaa atggcccgcc tggctgaccg cccaacgacc cccgcccatt      60

gacgtcaata atgacgtatg ttcccatagt aacgccaata gggactttcc attgacgtca     120
```

atgggtggag tatttacggt aaactgccca cttggcagta catcaagtgt atcatatgcc 180
aagtacgccc cctattgacg tcaatgacgg taaatggccc gcctggcatt atgcccagta 240
catgacctta tgggactttc ctacttggca gtacatctac gtattagtca tcgctattac 300
catggtgatg cggttttggc agtacatcaa tgggcgtgga tagcggtttg actcacgggg 360
atttccaagt ctccacccca ttgacgtcaa tgggagtttg ttttggcacc aaaatcaacg 420
ggactttcca aaatgtcgta acaactccgc cccattgacg caaatgggcg gtaggcgtgt 480
acggtgggag gtctatataa gcagagcttg gatgttgcct ttacttctag gcgcgccgcc 540
accatggtga gcaagggcga ggagctgttc accggggtgg tgcccatcct ggtcgagctg 600
gacggcgacg taaacggcca caagttcagc gtgtccggcg agggcgaggg cgatgccacc 660
tacggcaagc tgaccctgaa gttcatctgc accaccggca agctgcccgt gccctggccc 720
accctcgtga ccaccttcgg ctacggcctg atgtgcttcg cccgctaccc cgaccacatg 780
aagcagcacg acttcttcaa gtccgccatg cccgaaggct acgtccagga gcgcaccatc 840
ttcttcaagg acgacggcaa ctacaagacc cgcgccgagg tgaagttcga gggcgacacc 900
ctggtgaacc gcatcgagct gaagggcatc gacttcaagg aggacggcaa catcctgggg 960
cacaagctgg agtacaacta caacagccac aacgtctata tcatggccga caagcagaag 1020
aacggcatca aggtaagtat tagctctttc tttccatggg ttggcctcgc cgcgtgggct 1080
gagggaagga ctgtcctggg actggacagg cgggttatgg gacctgaaaa gcggccctga 1140
aaaagggccg cgatgaaaac gaagcgagct aaagcctcct ctctcttctt cagaactcct 1200
ctcttttctc tcctccagga gttcttcctc tctcccttct tctcaaatgc tttctccctc 1260
tctcctgcat ttgagctcct tctttcctct ctcgacaatc ccttttctc cctcttgatt 1320 gtcgactagc tcgcaatcat cgcggtatca aaaagcggtc aggcagctaa accaaaaggt 1380
ttagcaattg cctctgatga gtcgctgaaa tgcgacgaaa accgcttttt ggtaccaata 1440
aaatatcttt attttcatta catctgtgtg ttggtttttt gtgtgactag t 1491

<210> SEQ ID NO 2
<211> LENGTH: 1302
<212> TYPE: DNA
<213> ORGANISM: Artificial Sequence
<220> FEATURE:
<223> OTHER INFORMATION: Synthetic nucleic acid sequence

<400> SEQUENCE: 2
cgttacataa cttacggtaa atggcccgcc tggctgaccg cccaacgacc cccgcccatt 60
gacgtcaata atgacgtatg ttcccatagt aacgccaata gggactttcc attgacgtca 120
atgggtggag tatttacggt aaactgccca cttggcagta catcaagtgt atcatatgcc 180
aagtacgccc cctattgacg tcaatgacgg taaatggccc gcctggcatt atgcccagta 240
catgacctta tgggactttc ctacttggca gtacatctac gtattagtca tcgctattac 300
catggtgatg cggttttggc agtacatcaa tgggcgtgga tagcggtttg actcacgggg 360
atttccaagt ctccacccca ttgacgtcaa tgggagtttg ttttggcacc aaaatcaacg 420
ggactttcca aaatgtcgta acaactccgc cccattgacg caaatgggcg gtaggcgtgt 480
acggtgggag gtctatataa gcagagcttg gatgttgcct ttacttctag gcgcgccgcg 540
gaaaaccgcg ggataccgcg atgattgcga gctagtcgac aatcaagagg gagaaaaggg 600
gattgtcgag agaggaaaga aggagctcaa atgcaggaga gagggagaaa gcatttgaga 660
agaagggaga gaggaacaac tcgtggagga gagaaaagag acgagttgtg aagaagagag 720
aggaggcttt agctcgcttc gttttcatca ttattgcggc cctgaaaaag ggccgcttat 780
aacgttgctc gaattcgggt tatgggacca gtgaaggctg agggaaggac tgtcctggga 840
ctggacaggc gggttatggg acctgaaaat actaacaatc gatttttttt cccttttttt 900
ccaggtgaac ttcaagatcc gccacaacat cgaggacggc agcgtgcagc tcgccgacca 960
ctaccagcag aacaccccca tcggcgacgg ccccgtgctg ctgcccgaca accactacct 1020
gagctaccag tccgccctga gcaaagaccc caacgagaag cgcgatcaca tggtcctgct 1080
ggagttcgtg accgccgccg ggatcactct cggcatggac gagctgtaca aggacctttg 1140
agaattcctc acctgcgatc tcgatgcttt atttgtgaaa tttgtgatgc tattgcttta 1200
tttgtaacca ttataagctg caataaacaa gttaacaaca acaattgcat tcattttatg 1260
tttcaggttc agggggaggt gtgggaggtt ttttaaacta gt 1302

<210> SEQ ID NO 3
<211> LENGTH: 404
<212> TYPE: DNA
<213> ORGANISM: Artificial Sequence
<220> FEATURE:
<223> OTHER INFORMATION: Synthetic nucleic acid sequence

<400> SEQUENCE: 3
gtaagtatta gctctttctt tccatgggtt ggcctcgccg cgtgggctga gggaaggact 60
gtcctgggac tggacaggcg ggttatggga cctgaaaagc ggccctgaaa aagggccgcg 120
atgaaaacga agcgagctaa agcctcctct ctcttcttca gaactcctct cttttctctc 180
ctccaggagt tcttcctctc tcccttcttc tcaaatgctt tctccctctc tcctgcattt 240
gagctccttc tttcctctct cgacaatccc cttttctccc tcttgattgt cgactagctc 300
gcaatcatcg cggtatcaaa aagcggtcag gcagctaaac caaaaggttt agcaattgcc 360
tctgatgagt cgctgaaatg cgacgaaaac cgctttttgg tacc 404

<210> SEQ ID NO 4
<211> LENGTH: 382
<212> TYPE: DNA
<213> ORGANISM: Artificial Sequence
<220> FEATURE:
<223> OTHER INFORMATION: Synthetic nucleic acid sequence

<400> SEQUENCE: 4
acttctaggc gcgccgcgga aaaccgcggg ataccgcgat gattgcgagc tagtcgacaa 60
tcaagaggga gaaaagggga ttgtcgagag aggaaagaag gagctcaaat gcaggagaga 120
gggagaaagc atttgagaag aagggagaga ggaacaactc gtggaggaga gaaaagagac 180
gagttgtgaa gaagagagag gaggctttag ctcgcttcgt tttcatcatt attgcggccc 240
tgaaaaaggg ccgcttataa cgttgctcga attcgggtta tgggaccagt gaaggctgag 300
ggaaggactg tcctgggact ggacaggcgg gttatgggac ctgaaaatac taacaatcga 360 tttttttcc cttttttcc ag 382

<210> SEQ ID NO 5
<211> LENGTH: 489
<212> TYPE: DNA
<213> ORGANISM: Artificial Sequence
<220> FEATURE:
<223> OTHER INFORMATION: Synthetic nucleic acid sequence

<400> SEQUENCE: 5
atggtgagca agggcgagga gctgttcacc ggggtggtgc ccatcctggt cgagctggac 60
ggcgacgtaa acggccacaa gttcagcgtg tccggcgagg gcgagggcga tgccacctac 120
ggcaagctga ccctgaagtt catctgcacc accggcaagc tgcccgtgcc ctggcccacc 180
ctcgtgacca ccttcggcta cggcctgatg tgcttcgccc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaac gtctatatca tggccgacaa gcagaagaac 480
ggcatcaag 489

<210> SEQ ID NO 6
<211> LENGTH: 237
<212> TYPE: DNA
<213> ORGANISM: Artificial Sequence
<220> FEATURE:
<223> OTHER INFORMATION: Synthetic nucleic acid sequence

<400> SEQUENCE: 6
gtgaacttca agatccgcca caacatcgag gacggcagcg tgcagctcgc cgaccactac 60
cagcagaaca cccccatcgg cgacggcccc gtgctgctgc ccgacaacca ctacctgagc 120
taccagtccg ccctgagcaa agaccccaac gagaagcgcg atcacatggt cctgctggag 180
ttcgtgaccg ccgccgggat cactctcggc atggacgagc tgtacaagga cctttga 237

<210> SEQ ID NO 7
<211> LENGTH: 382
<212> TYPE: DNA
<213> ORGANISM: Artificial Sequence
<220> FEATURE:
<223> OTHER INFORMATION: Synthetic nucleic acid sequence

<400> SEQUENCE: 7
acttctaggc gcgccgcgga aaaccgcggg ataccgcgat gattgcgagc tagggagaga 60
gaggggaaag aaaagagaaa gaggaggagg aaagagggga gagaggggag ggaaaggaga 120
gaagggagga agggaagaaa gaaagaagag gaaaagaggg gaggaggagg agaaaggaga 180
aaaaaagaag ggaagggaga aaggctttag ctcgcttcgt tttcatcatt attgcggccc 240
tgaaaaaggg ccgcttataa cgttgctcga attcgggtta tgggaccagt gaaggctgag 300
ggaaggactg tcctgggact ggacaggcgg gttatgggac ctgaaaatac taacaatcga 360
ttttttttcc cttttttttcc ag 382

<210> SEQ ID NO 8
<211> LENGTH: 301
<212> TYPE: DNA
<213> ORGANISM: Artificial Sequence
<220> FEATURE:
<223> OTHER INFORMATION: Synthetic nucleic acid sequence

<400> SEQUENCE: 8
gtaagtgtcc cgcggaacat tattataacg ttgctcgaag atatcagatg gtgcgctcct 60
ggacgtagcc ttcgggcatg gcggacttga agaagtcgtg ctgcttcatg tggtcggggt 120
agcggctgaa gcactgcacg ccgtaggtca gggtggtcac gagggtgggc cagggcacgg 180
gcagcttgcc ggtggtgcag atgaacttca gggtcagctt gccgtaggtg gcatcgccct 240
cgccctcgcc ggacacgctg aacttgtggc cgtttacgtc gccgtccagc tcgactctag 300
a 301

<210> SEQ ID NO 9
<211> LENGTH: 326
<212> TYPE: DNA
<213> ORGANISM: Artificial Sequence
<220> FEATURE:
<223> OTHER INFORMATION: Synthetic nucleic acid sequence

<400> SEQUENCE: 9
gctagcgtcg agctggacgg cgacgtaaac ggccacaagt tcagcgtgtc cggcgagggc 60
gagggcgatg ccacctacgg caagctgacc ctgaagttca tctgcaccac cggcaagctg 120
cccgtgccct ggcccaccct cgtgaccacc ctgacctacg gcgtgcagtg cttcagccgc 180
taccccgacc acatgaagca gcacgacttc ttcaagtccg ccatgcccga aggctacgtc 240
caggagcgca ccatctccgc ggaacattat tataacgttg ctcgaatact aactggtacc 300
tcttcttttt tttttgatat ctgcag 326

<210> SEQ ID NO 10
<211> LENGTH: 278
<212> TYPE: DNA
<213> ORGANISM: Artificial Sequence
<220> FEATURE:
<223> OTHER INFORMATION: Synthetic nucleic acid sequence

<400> SEQUENCE: 10
gttgccttta cttctggcgc gccaaaaggc gtgccagaag taccgggcta ataatgtttc 60
gcggtcctct taaatctgcc taaatacgta taaatttgat cgccctgaaa aagggcgatc 120
aaagccctga aaaagggcat acgtagccct gaaaaagggc aggcagagcc ctgaaaaagg 180
gcaagaggac cgcggaacat tattagccgc caccatggac aggcgggtta tgggacctga 240
aaatactaac aatcgatttt ttttcccttt ttttccag 278

<210> SEQ ID NO 11
<211> LENGTH: 190
<212> TYPE: DNA
<213> ORGANISM: Artificial Sequence
<220> FEATURE:
<223> OTHER INFORMATION: Synthetic nucleic acid sequence

<400> SEQUENCE: 11
acttctaggc gcgccgcgga aaaccgcggg atatcattat tgcggccctg aaaaagggcc 60
gcttataacg ttgctcgaat tcgggttatg ggaccagtga aggctgaggg aaggactgtc 120
ctgggactgg acaggcgggt tatgggacct gaaaatacta acaatcgatt ttttttccct 180
ttttttccag 190

<210> SEQ ID NO 12
<211> LENGTH: 459
<212> TYPE: DNA
<213> ORGANISM: Artificial Sequence
<220> FEATURE:
<223> OTHER INFORMATION: Synthetic nucleic acid sequence

<400> SEQUENCE: 12
gtaagtatta gctctttctt tccatgggtt ggcctcgccg cgtgggctga gggaaggact 60
gtcctgggac tggacaggcg ggttatggga cctgaaaagc ggccctgaaa aagggccgcg 120
atgaaaacga agcgagctaa agcctcctct ctcttcttca gaactcctct cttttctctc 180

```
ctccaggagt tcttcctctc tcccttcttc tcaaatgctt tctccctctc tcctgcattt    240

gagctccttc tttcctctct cgacaatccc cttttctccc tcttgattgt cgactagctc    300

gcaatcatcg cggtatcaaa aagcggtcag gcagctaaac caaaaggttt agcaattgcc    360

tctgatgagt cgctgaaatg cgacgaaaac cgctttttgg taccaataaa atatctttat    420

tttcattaca tctgtgtgtt ggtttttgt gtgactagt                            459


<210> SEQ ID NO 13
<211> LENGTH: 382
<212> TYPE: DNA
<213> ORGANISM: Artificial Sequence
<220> FEATURE:
<223> OTHER INFORMATION: Synthetic nucleic acid sequence

<400> SEQUENCE: 13

acttctaggc gcgccgcgga aaaccgcggg ataccgcgat gattgcgagc tagtcgacaa     60

tcaagaggga gaaaagggga ttgtcgagag aggaaagaag gagctcaaat gcaggagaga    120

gggagaaagc atttgagaag aagggagaga ggaagaactc ctggaggaga gaaaagagag    180

gagttctgaa gaagagagag gaggctttag ctcgcttcgt tttcatcatt attgcggccc    240

tgaaaaaggg ccgcttataa cgttgctcga attcgggtta tgggaccagt gaaggctgag    300

ggaaggactg tcctgggact ggacaggcgg gttatgggac ctgaaaatac taacaatcga    360

tttttttcc cttttttcc ag                                               382


<210> SEQ ID NO 14
<211> LENGTH: 372
<212> TYPE: DNA
<213> ORGANISM: Artificial Sequence
<220> FEATURE:
<223> OTHER INFORMATION: Synthetic nucleic acid sequence

<400> SEQUENCE: 14

gtaagtatta agcggccctg aaaaagggcc gcgatgaaaa cgaagcgagc taaagcctcc     60

tctctcttct tcagaactcc tctcttttct ctcctccagg agttcttcct ctctcccttc    120

ttctcaaatg ctttctccct ctctcctgca tttgagctcc ttctttcctc tctcgacaat    180

ccccttttct ccctcttgat tgtcgactag ctcgcaatca tcgcggtatc aaaaagcggt    240

caggcagcta aaccaaaagg tttagcaatt gcctctgatg agtcgctgaa atgcgacgaa    300

aaccgctttt tggtaccaat aaaatatctt tattttcatt acatctgtgt gttggttttt    360

tgtgtgacta gt                                                        372


<210> SEQ ID NO 15
<211> LENGTH: 407
<212> TYPE: DNA
<213> ORGANISM: Artificial Sequence
<220> FEATURE:
<223> OTHER INFORMATION: Synthetic nucleic acid sequence

<400> SEQUENCE: 15

gtaagtatta gctctttctt tccatgggtt ggcctcgccg cgtgaagcgg ccctgaaaaa     60

gggccgcgat gaaaacgaag cgagctaaag cctcctctct cttcttcaga actcctctct    120

tttctctcct ccaggagttc ttcctctctc ccttcttctc aaatgctttc tccctctctc    180

ctgcatttga gctccttctt tcctctctcg acaatcccct tttctccctc ttgattgtcg    240

actagctcgc aatcatcgcg gtatcaaaaa gcggtcaggc agctaaacca aaaggtttag    300

caattgcctc tgatgagtcg ctgaaatgcg acgaaaaccg ctttttggta ccaataaaat    360
```

atctttattt tcattacatc tgtgtgttgg ttttttgtgt gactagt 407

<210> SEQ ID NO 16
<211> LENGTH: 378
<212> TYPE: DNA
<213> ORGANISM: Artificial Sequence
<220> FEATURE:
<223> OTHER INFORMATION: Synthetic nucleic acid sequence

<400> SEQUENCE: 16
gtaagtatta gctctttctt tccatgggtt ggcctcgccg cgtgggctga gggaaggact 60
gtcctgggac tggacaggcg ggttatggga cctgaaaagc ggccctgaaa aagggccgcg 120
atgaaaacga agcgagctaa agcctcctct ctcttcttca gaactcctct cttttctctc 180
ctccaggagt tcttcctctc tcccttcttc tcaaatgctt tctccctctc tcctgcattt 240
gagctccttc tttcctctct cgacaatccc cttttctccc tcttgattgt cgactagctc 300
gcaatcatcg cggtatcggt accaataaaa tatctttatt ttcattacat ctgtgtgttg 360 gtttttgtg tgactagt 378

<210> SEQ ID NO 17
<211> LENGTH: 309
<212> TYPE: DNA
<213> ORGANISM: Artificial Sequence
<220> FEATURE:
<223> OTHER INFORMATION: Synthetic nucleic acid sequence

<400> SEQUENCE: 17
acttctaggc gcgccgcgga aaaccgcggg ataccgcgat gattgcgagc tagtcgacaa 60
tcaagaggga gaaaagggga ttgtcgagag aggaaagaag gagctcaaat gcaggagaga 120
gggagaaagc atttgagaag aagggagaga ggaagaactc ctggaggaga gaaaagagag 180
gagttctgaa gaagagagag gaggctttag ctcgcttcgt tttcatcatt attgcggccc 240
tgaaaaaggg ccgcttataa cgttgctcga attctactaa caatcgattt tttttccctt 300
tttttccag 309

<210> SEQ ID NO 18
<211> LENGTH: 419
<212> TYPE: DNA
<213> ORGANISM: Artificial Sequence
<220> FEATURE:
<223> OTHER INFORMATION: Synthetic nucleic acid sequence

<400> SEQUENCE: 18
atatcctttt agggcagagt gaagagttag gaggaaggtg gttgggagag ggatttccag 60
gccttaggac atcatgacag atgaaaacga agcgagctaa agcctcctct ctcttcttca 120
gaactcctct cttttctctc ctccaggagt tcttcctctc tcccttcttc tcaaatgctt 180
tctccctctc tcctgcattt gagctccttc tttcctctct cgacaatccc cttttctccc 240
tcttgattgt cgactagctc gcaatcatcg cggtatcaaa aagcggtcag gcagctaaac 300
caaaaggttt agcaattgcc tctgatgagt cgctgaaatg cgacgaaaac cgctttttgg 360
taccaataaa atatctttat tttcattaca tctgtgtgtt ggtttttgt gtgactagt 419

<210> SEQ ID NO 19
<211> LENGTH: 275
<212> TYPE: DNA
<213> ORGANISM: Artificial Sequence
<220> FEATURE:

<223> OTHER INFORMATION: Synthetic nucleic acid sequence

<400> SEQUENCE: 19
acttctaggc gcgccgcgga aaaccgcggg ataccgcgat gattgcgagc tagtcgacaa 60
tcaagaggga gaaaagggga ttgtcgagag aggaaagaag gagctcaaat gcaggagaga 120
gggagaaagc atttgagaag aagggagaga ggaacaactc gtggaggaga gaaaagagac 180
gagttgtgaa gaagagagag gaggctttag ctcgcttcgt tttcatcatt tccaggcctt 240
aggacatcat gacatttttc cttaactttg ctcac 275

<210> SEQ ID NO 20
<211> LENGTH: 3975
<212> TYPE: DNA
<213> ORGANISM: Artificial Sequence
<220> FEATURE:
<223> OTHER INFORMATION: Synthetic nucleic acid sequence

<400> SEQUENCE: 20
acttctaggc gcgccgccac catgggattc gtgcggcaga ttcagctgct gctgtggaag 60
aactggaccc tgcggaagcg gcagaaaatc agattcgtgg tggaactcgt gtggcccctg 120
agcctgtttc tggtgctgat ctggctgcgg aacgccaatc ctctgtacag ccaccacgag 180
tgtcacttcc ccaacaaggc catgccttct gccggaatgc tgccttggct gcagggcatc 240
ttctgcaacg tgaacaaccc ctgctttcaa agccccacac ctggcgaaag ccctggcatc 300
gtgtccaact acaacaacag catcctggcc agagtgtacc gggacttcca agagctgctg 360
atgaacgccc ctgagtctca gcacctgggc agaatctgga ccgagctgca catcctgagc 420
cagttcatgg acaccctgag aacacacccc gagagaatcg ccggcagggg catcagaatc 480
cgggacatcc tgaaggacga ggaaaccctg acactgttcc tcatcaagaa catcggcctg 540
agcgacagcg tggtgtacct gctgatcaac agccaagtgc ggcccgagca gtttgctcat 600
ggcgtgccag atctcgccct gaaggatatc gcctgttctg aggccctgct ggaacggttc 660
atcatcttca gccagcggag aggcgccaag accgtcagat atgccctgtg cagtctgagc 720
cagggaaccc tgcagtggat cgaggatacc ctgtacgcca acgtggactt cttcaagctg 780
ttccgggtgc tgcccacact gctggattct cggtcccaag gcatcaacct gagaagctgg 840
ggcggcatcc tgtccgacat gagcccaaga atccaagagt tcatccaccg gcctagcatg 900
caggacctgc tgtgggttac cagacctctg atgcagaacg gcggacccga gacattcacc 960
aagctgatgg gcattctgag cgatctgctg tgcggctacc ctgaaggcgg aggatctaga 1020
gtgctgagct tcaattggta cgaggacaac aactacaagg ccttcctggg catcgactcc 1080
accagaaagg accccatcta cagctacgac cggcggacaa ccagcttctg caatgccctg 1140
atccagagcc tggaaagcaa ccctctgacc aagatcgctt ggagggccgc caaacctctg 1200
ctgatgggaa agatcctgta cacccctgac agccctgccg ccagaagaat cctgaagaac 1260
gccaacagca ccttcgagga actggaacac gtgcgcaagc tggtcaaggc ctgggaagaa 1320
gtgggacctc agatctggta cttcttcgac aatagcaccc agatgaacat gatcagagac 1380
accctgggca accctaccgt gaaggacttc ctgaacagac agctgggcga agagggcatt 1440
accgccgagg ccatcctgaa ctttctgtac aagggcccca gagagtccca ggccgacgac 1500
atggccaact tcgattggcg ggacatcttc aacatcaccg acagaaccct gcggctggtc 1560
aaccagtacc tggaatgcct ggtgctggac aagttcgaga gctacaacga cgagacacag 1620
ctgacccaga gagccctgtc tctgctggaa gagaatatgt tctgggctgg cgtggtgttc 1680

-continued

```
cccgacatgt acccttggac aagcagcctg cctcctcacg tgaagtacaa gatccggatg   1740
gacatcgacg tggtcgaaaa gaccaacaag atcaaggacc ggtactggga cagcggccct   1800
agagctgatc ccgtggaaga ttttcgctac atctggggcg gattcgcata cctgcaggac   1860
atggtggaac agggaatcac acggtcccag gtgcaggctg aagctcctgt gggaatctac   1920
ctgcagcaga tgccttatcc ttgcttcgtg gacgacagct tcatgatcat cctgaatcgg   1980
tgcttcccca tcttcatggt gctggcctgg atctactccg tgtctatgac cgtgaagtcc   2040
atcgtgctgg aaaaagagct gcggctgaaa gagacactga agaaccaggg cgtgtccaat   2100
gccgtgatct ggtgcacctg gtttctggac agcttctcca ttatgagcat gagcatcttt   2160
ctgctgacga tcttcatcat gcacggccgg atcctgcact acagcgaccc ctttatcctc   2220
ttcctgttcc tgctggcctt ctccaccgct acaatcatgc tgtgttttct gctgtccacc   2280
ttcttctcca aagcctctct ggccgctgct tgtagcggcg tgatctactt caccctgtac   2340
ctgcctcaca tcctgtgctt cgcatggcag gacagaatga ccgccgagct gaagaaagct   2400
gtgtccctgc tgagccctgt ggcctttggc tttggcaccg agtacctcgt cagatttgag   2460
gaacaaggac tgggactgca gtggtccaac atcggcaata gccctacaga gggcgacgag   2520
ttcagcttcc tgctgtctat gcaaatgatg ctgctggacg ccgccgtgta tggactgctg   2580
gcttggtatc tggaccaggt gttccctgcc gattacggca ctcctctgcc ttggtatttc   2640
ctgctgcaag agagctactg gctcggcggc gagggatgta gcaccagaga agaaagagcc   2700
ctggaaaaga ccgagcctct gaccgaggaa acagaggacc ctgaacaccc agagggcatc   2760
cacgatagct tttcgagag agaacacccc ggctgggtgc caggcgtgtg tgtgaagaat   2820
ctggtcaaga tcttcgagcc ctgcggcaga cctgccgtgg acagactgaa catcaccttc   2880
tacgagaacc agattaccgc ctttctgggc cacaacggcg ctggcaagac aaccacactg   2940
agcatcctca ccggcctgct gcctccaaca agcggcacag ttctcgttgg cggcagagac   3000
atcgagacaa gcctggatgc cgtcagacag tccctgggca tgtgccctca gcacaacatc   3060
ctgtttcacc acctgaccgt ggccgagcac atgctgtttt atgcccagct gaagggcaag   3120
agccaagaag aggctcagct ggaaatggaa gccatgctcg aggacaccgg cctgcaccac   3180
aagagaaatg aggaagccca ggatctgagc ggcggcatgc agagaaaact gagcgtggcc   3240
attgccttcg tgggcgacgc caaggttgtg atcctggatg agcctacaag cggcgtggac   3300
ccttacagca gaagatccat ctgggatctg ctgctgaagt acagaagcgg ccggaccatc   3360
atcatgagca cccaccacat ggacgaggcc gatctgctcg gagacagaat cgccatcatt   3420
gctcagggca gactgtactg cagcggcacc ccactgtttc tgaagaactg tttcggcacc   3480
ggactgtatc tgaccctcgt gcggaagatg aagaacatcc agtctcagcg gaagggcagc   3540
gagggcacct gtagctgttc tagcaagggc tttagcacca cctgtccagc tcacgtggac   3600
gatctgaccc ctgaacaggt gctggatggc gacgtgaacg agctgatgga cgtggtgctg   3660
caccatgtgc ctgaggccaa gctggtggaa tgcatcggcc aggtaagtat tagctctttc   3720
tttccatggg ttggcctcgc cgcgtgggct gagggaagga ctgtcctggg actggacagg   3780
cgggttatgg gacctgaagc gataaaaggc atgcacgttt gcggctacgt gcatgccaaa   3840
aggagtcggg cttgcctccg tgcccgactc caaaagacct gctcgaggag gtggacgagc   3900
aggtcaaaaa tccgggtacc aataaaatat ctttattttc attacatctg tgtgttggtt   3960
ttttgtgtga ctagt                                                    3975
```

<210> SEQ ID NO 21
<211> LENGTH: 3611
<212> TYPE: DNA
<213> ORGANISM: Artificial Sequence
<220> FEATURE:
<223> OTHER INFORMATION: Synthetic nucleic acid sequence

<400> SEQUENCE: 21
aggatttttg acctgctcga ttgtccactg cgagcaggtc ttttggagtc gggcgaggcg 60
gaagcccgac tccttttggc atgcacgcta gccgcgtcgt gcatgccttt tatcgaattc 120
gggttatggg accagtgaag gctgagggaa ggactgtcct gggactggac aggcgggtta 180
tgggacctga aaatactaac aatcgatttt ttttcccttt ttttccagga actgattttt 240
ctgctcccga acaagaactt caagcaccgg gcctacgcca gcctgttcag agagctggaa 300
gaaaccctgg ccgacctggg cctgtctagc tttggcatca gcgacacccc tctcgaagag 360
atcttcctga aagtgacaga ggacagcgat agcggccctc tgtttgctgg cggagcacag 420
caaaagcgcg agaacgtgaa ccctagacac ccctgtctgg gcccaagaga gaaagccgga 480
cagacccctc aggacagcaa tgtgtgctct cctggtgctc ctgccgctca tcctgaggga 540
caacctccac ctgaacctga gtgtcctgga cctcagctga acaccggaac acagctggtt 600
ctgcagcacg tgcaggctct gctcgtgaag agattccagc acaccatcag aagccacaag 660
gactttctgg cccagatcgt gctgcccgcc acctttgttt ttctggctct gatgctgagc 720
atcgtgatcc ctccattcgg cgagtacccc gctctgacac tgcacccttg gatctacggc 780
cagcagtaca ccttttctc catggacgaa cccggcagcg agcagttcac agtgctggct 840
gatgtcctgc tgaacaagcc cggcttcggc aaccggtgtc tgaaagaagg atggctgcct 900
gagtaccctt gcggcaacag cacaccttgg aaaaccccta gcgtgtcccc taacatcacc 960
cagctgttcc aaaagcagaa atggacccaa gtgaacccct ctccatcctg ccggtgctcc 1020
acaagggaaa agctgaccat gctgcccgag tgtccagaag gcgctggcgg acttcctcca 1080
cctcagagaa cacagagatc caccgagatt ctccaggacc tgaccgaccg gaatatcagc 1140
gacttcctgg ttaagacata ccccgcactg atccggtcca gcctgaagtc caagttctgg 1200
gtcaacgaac agagatacgg cggcatcagc atcggcggaa aactgcctgt ggtgcctatc 1260
acaggcgagg cccttgtggg ctttctgtcc gatctgggga gaatcatgaa cgtgtccggc 1320
ggacctatca ccagggaagc cagcaaagag atccccgatt tcctgaagca cctggaaacc 1380
gaggacaata tcaaagtgtg gttcaacaac aaaggatggc acgccctcgt gtcttttctg 1440
aacgtggccc acaatgccat cctgcgggct agcctgccta aggacagaag ccctgaggaa 1500
tacggcatca ccgtgatctc ccagcctctg aatctgacca aagagcagct gagcgagatc 1560
accgtgctga ccacctctgt ggatgctgtg gtggccatct gcgtgatctt cagcatgagc 1620
ttcgtgcccg cctccttcgt gctgtacctg attcaagaga gagtgaacaa gagcaagcac 1680
ctccagttca tctccggggt gtccccaacc acctactggg tcaccaattt tctgtgggac 1740
atcatgaact acagcgtgtc agccggcctg gtcgtgggca tctttatcgg ctttcaaaag 1800
aaggcctaca cgagccccga gaacctgcct gctttggttg ctctgctgct cctgtatggc 1860
tgggccgtga ttcccatgat gtaccccgcc agctttctgt ttgacgtgcc cagcacagcc 1920
tacgtggccc tgtcttgcgc caatctgttc atcggcatca acagcagcgc catcacattc 1980
atcctggaac tgttcgagaa caacaggacc ctgctgcggt tcaacgccgt gctgcggaaa 2040
ctgctgatcg tgttccctca cttctgtctc ggccggggcc tgatcgacct ggctctgtct 2100

```
caagccgtga ccgatgtgta cgccagattt ggcgaggaac actccgccaa tccattccac   2160
tgggacctga tcggcaagaa cctgttcgcc atggtggtgg aaggcgtcgt gtacttcctg   2220
ctcactctgc tggtgcagag acactttttt ctgtcccaat ggatcgccga gcctaccaaa   2280
gaacccattg tggacgagga cgacgatgtg gccgaggaaa gacagagaat catcaccggc   2340
ggcaacaaga ccgatatcct gagactgcac gagctgacaa agatctaccc cggcacaagc   2400
tccccagccg tggataggct ttgtgtggga gttagacccg gcgagtgctt tggcctgctg   2460
ggagttaatg gcgccggaaa gaccaccacc ttcaagatgc tgaccggcga caccacagtg   2520
acaagcggag atgctacagt ggccggcaag agcatcctga ccaacatcag cgaagtgcat   2580
cagaacatgg gctactgccc tcagttcgac gccatcgacg aactgctgac aggccgcgaa   2640
cacctgtatc tgtatgccag actgagaggc gtgcccgctg aagagatcga gaaggtggcc   2700
aactggtcca tcaagtctct gggcctgaca gtgtacgccg actgtctggc cggaacatac   2760
agcggaggaa acaagcggaa gctgagcacc gccattgctc tgatcggatg cccacctctg   2820
gtcctgctgg atgaacccac caccggaatg gatccccagg ctagaagaat gctctggaac   2880
gtgatcgtgt ctatcatccg cgagggcaga gctgtggtgc tgacctctca ctccatggaa   2940
gagtgcgagg ctctgtgtac ccggctggcc attatggtca agggcgcctt cagatgcatg   3000
ggcaccattc agcatctgaa aagcaagttc ggcgacggct acatcgtgac aatgaagatc   3060
aagagcccca aggacgacct cctgcctgat ctgaaccccg tggaacagtt ttttcagggc   3120
aacttccccg gctccgtgca gcgggaaaga cactataaca tgctgcagtt tcaggtgtcc   3180
tcctccagcc tggctcggat ctttcaactg ctgctctctc acaaggacag cctgctgatt   3240
gaagagtaca gcgtgacaca gaccacactc gaccaggttt tcgtgaactt cgccaagcag   3300
cagaccgaga gccacgacct gcctctgcat cctcgggccg ctggtgcctc tagacaagct   3360
caggacggcg ctcgggctga ctacaaagac catgacggtg attataaaga tcatgacatc   3420
gactataagg atgacgatga caaatgaggt accaattcct cacctgcgat ctcgagcttt   3480
atttgtgaaa tttgtgatgc tattgcttta tttgtaacca ttataagctg caataaacaa   3540
gttaacaaca acaattgcat tcattttatg tttcaggttc agggggaggt gtgggaggtt   3600
ttttaaacta g                                                        3611
```

<210> SEQ ID NO 22
<211> LENGTH: 3975
<212> TYPE: DNA
<213> ORGANISM: Artificial Sequence
<220> FEATURE:
<223> OTHER INFORMATION: Synthetic nucleic acid sequence

<400> SEQUENCE: 22

```
acttctaggc gcgccgccac catggcccca aagaagaagc ggaaggtcgg tatccacgga     60
gtcccagcag ccaagcggaa ctacatcctg ggcctggaca tcggcatcac cagcgtgggc    120
tacggcatca tcgactacga gacacgggac gtgatcgatg ccggcgtgcg gctgttcaaa    180
gaggccaacg tggaaaacaa cgagggcagg cggagcaaga gaggcgccag aaggctgaag    240
cggcggaggc ggcatagaat ccagagagtg aagaagctgc tgttcgacta caacctgctg    300
accgaccaca gcgagctgag cggcatcaac ccctacgagg ccagagtgaa gggcctgagc    360
cagaagctga gcgaggaaga gttctctgcc gccctgctgc acctggccaa gagaagaggc    420
gtgcacaacg tgaacgaggt ggaagaggac accggcaacg agctgtccac caaagagcag    480
```

atcagccgga acagcaaggc cctggaagag aaatacgtgg ccgaactgca gctggaacgg 540
ctgaagaaag acggcgaagt gcggggcagc atcaacagat tcaagaccag cgactacgtg 600
aaagaagcca aacagctgct gaaggtgcag aaggcctacc accagctgga ccagagcttc 660
atcgacacct acatcgacct gctggaaacc cggcggacct actatgaggg acctggcgag 720
ggcagcccct tcggctggaa ggacatcaaa gaatggtacg agatgctgat gggccactgc 780
acctacttcc ccgaggaact gcggagcgtg aagtacgcct acaacgccga cctgtacaac 840
gccctgaacg acctgaacaa tctcgtgatc accagggacg agaacgagaa gctggaatat 900
tacgagaagt tccagatcat cgagaacgtg ttcaagcaga agaagaagcc caccctgaag 960
cagatcgcca aagaaatcct cgtgaacgaa gaggatatta agggctacag agtgaccagc 1020
accggcaagc ccgagttcac caacctgaag gtgtaccacg acatcaagga cattaccgcc 1080
cggaaagaga ttattgagaa cgccgagctg ctggatcaga ttgccaagat cctgaccatc 1140
taccagagca gcgaggacat ccaggaagaa ctgaccaatc tgaactccga gctgacccag 1200
gaagagatcg agcagatctc taatctgaag ggctataccg gcacccacaa cctgagcctg 1260
aaggccatca acctgatcct ggacgagctg tggcacacca acgacaacca gatcgctatc 1320
ttcaaccggc tgaagctggt gcccaagaag gtggacctgt cccagcagaa agagatcccc 1380
accaccctgg tggacgactt catcctgagc cccgtcgtga agagaagctt catccagagc 1440
atcaaagtga tcaacgccat catcaagaag tacggcctgc ccaacgacat cattatcgag 1500
ctggcccgcg agaagaactc caaggacgcc cagaaaatga tcaacgagat gcagaagcgg 1560
aaccggcaga ccaacgagcg gatcgaggaa atcatccgga ccaccggcaa agagaacgcc 1620
aagtacctga tcgagaagat caagctgcac gacatgcagg aaggcaagtg cctgtacagc 1680
ctggaagcca tccctctgga agatctgctg aacaacccct tcaactatga ggtggaccac 1740
atcatcccca gaagcgtgtc cttcgacaac agcttcaaca acaaggtgct cgtgaagcag 1800
gaagaaaaca gcaagaaggg caaccggacc ccattccagt acctgagcag cagcgacagc 1860
aagatcagct acgaaacctt caagaagcac atcctgaatc tggccaaggg caagggcaga 1920
atcagcaaga ccaagaaaga gtatctgctg gaagaacggg acatcaacag gttctccgtg 1980
cagaaagact tcatcaaccg gaacctggtg gataccagat acgccaccag aggcctgatg 2040
aacctgctgc ggagctactt cagagtgaac aacctggacg tgaaagtgaa gtccatcaat 2100
ggcggcttca ccagctttct gcggcggaag tggaagttta agaaagagcg gaacaagggg 2160
tacaagcacc acgccgagga cgccctgatc attgccaacg ccgatttcat cttcaaagag 2220
tggaagaaac tggacaaggc caaaaaagtg atggaaaacc agatgttcga ggaaaagcag 2280
gccgagagca tgcccgagat cgaaaccgag caggagtaca aagagatctt catcaccccc 2340
caccagatca agcacattaa ggacttcaag gactacaagt acagccaccg ggtggacaag 2400
aagcctaata gagagctgat taacgacacc ctgtactcca cccggaagga cgacaagggc 2460
aacaccctga tcgtgaacaa tctgaacggc ctgtacgaca aggacaatga caagctgaaa 2520
aagctgatca acaagagccc cgaaaagctg ctgatgtacc accacgaccc ccagacctac 2580
cagaaactga agctgattat ggaacagtac ggcgacgaga agaatcccct gtacaagtac 2640
tacgaggaaa ccgggaacta cctgaccaag tactccaaaa aggacaacgg ccccgtgatc 2700
aagaagatta agtattacgg caacaaactg aacgcccatc tggacatcac cgacgactac 2760
cccaacagca gaaacaaggt cgtgaagctg tccctgaagc cctacagatt cgacgtgtac 2820
ctggacaatg gcgtgtacaa gttcgtgacc gtgaagaatc tggatgtgat caaaaaagaa 2880
aactactacg aagtgaatag caagtgctat gaggaagcta agaagctgaa gaagatcagc 2940
aaccaggccg agtttatcgc ctccttctac aacaacgatc tgatcaagat caacggcgag 3000
ctgtatagag tgatcggcgt gaacaacgac ctgctgaacc ggatcgaagt gaacatgatc 3060
gacatcacct accgcgagta cctggaaaac atgaacgaca agaggccccc caggatcatt 3120
aagacaatcg ccggaagcgg agctactaac ttcagcctgc tgaagcaggc tggagacgtg 3180
gaggagaacc ctggacctag gcgcgccgcc accatggtga gcaagggcga ggagctgttc 3240
accggggtgg tgcccatcct ggtcgagctg gacggcgacg taaacggcca caagttcagc 3300
gtgtccggcg agggcgaggg cgatgccacc tacggcaagc tgaccctgaa gttcatctgc 3360
accaccggca agctgcccgt gccctggccc accctcgtga ccaccttcgg ctacggcctg 3420
atgtgcttcg cccgctaccc cgaccacatg aagcagcacg acttcttcaa gtccgccatg 3480
cccgaaggct acgtccagga gcgcaccatc ttcttcaagg acgacggcaa ctacaagacc 3540
cgcgccgagg tgaagttcga gggcgacacc ctggtgaacc gcatcgagct gaagggcatc 3600
gacttcaagg aggacggcaa catcctgggg cacaagctgg agtacaacta caacagccac 3660
aacgtctata tcatggccga caagcagaag aacggcatca aggtaagtat tagctctttc 3720
tttccatggg ttggcctcgc cgcgtgggct gagggaagga ctgtcctggg actggacagg 3780
cgggttatgg gacctgaagc gataaaaggc atgcacgttt gcggctacgt gcatgccaaa 3840
aggagtcggg cttgcctccg tgcccgactc caaaagacct gctcgaggag gtggacgagc 3900
aggtcaaaaa tccgggtacc aataaaatat ctttattttc attacatctg tgtgttggtt 3960
ttttgtgtga ctagt 3975

<210> SEQ ID NO 23
<211> LENGTH: 3912
<212> TYPE: DNA
<213> ORGANISM: Artificial Sequence
<220> FEATURE:
<223> OTHER INFORMATION: Synthetic nucleic acid sequence

<400> SEQUENCE: 23
aggatttttg acctgctcga ttgtccactg cgagcaggtc ttttggagtc gggcgaggcg 60
gaagcccgac tccttttggc atgcacgcta gccgcgtcgt gcatgccttt tatcttcggg 120
ttatgggacc agtgaaggct gagggaagga ctgtcctggg actggacagg cgggttatgg 180
gacctgaaaa tactaacaat cgattttttt tcccttttt tccaggtgaa cttcaagatc 240
cgccacaaca tcgaggacgg cagcgtgcag ctcgccgacc actaccagca gaacaccccc 300
atcggcgacg gccccgtgct gctgcccgac aaccactacc tgagctacca gtccgccctg 360
agcaaagacc ccaacgagaa gcgcgatcac atggtcctgc tggagttcgt gaccgccgcc 420
gggatcactc tcggcatgga cgagctgtac aaggaccttg gaagcggagc tactaacttc 480
agcctgctga agcaggctgg agacgtggag gagaaccctg gacctatcac aaagaagcac 540
acagcccact tctccaagaa gggcgaagag gaaaacctgg aaggcctggg caatcagacc 600
aagcagatcg tcgagaagta cgcctgcacc accagaatca gccccaacac aagccagcag 660
aacttcgtga cccagcggag caaaagagcc ctgaagcagt ttcggctgcc cctggaagaa 720
accgagctgg aaaagcggat catcgtggac gacaccagca cacagtggtc caagaacatg 780
aagcacttga cccctagcac actgacccag atcgactaca acgagaaaga gaagggcgct 840
atcacacaga gcccactgag cgactgtctg accagaagcc acagcatccc tcaggccaac 900
agatcccctc tgccaatcgc caaagtgtct agcttcccca gcatcagacc catctacctg 960
accagagtgc tgttccagga caacagcagc catctgccag ccgccagcta ccggaagaaa 1020
gatagcggcg tgcaagagtc cagccacttt ctgcaaggcg ctaagaagaa caatctgagc 1080
ctggctattc tgaccctgga aatgaccggc gatcagagag aagtcggctc tctgggcacc 1140
agcgccacaa atagcgtgac ctacaaaaag gtggaaaaca ccgtgctgcc taagcctgac 1200
ctgccaaaga caagcggcaa ggtggaactg ctgccaaagg tgcacatcta ccagaaggac 1260
ctgtttccta ccgagacaag caacggctct cccggccatc tggatctggt ggaaggatct 1320
ctgctgcagg gaaccgaggg cgccatcaag tggaacgagg ccaatagacc tggcaaggtg 1380
cccttcctga gagtggccac agagtctagc gccaagacac cctccaaact gctggatccc 1440
ctggcctggg ataaccacta cggcactcag atccccaaag aggaatggaa gtcccaagag 1500
aagtcccctg aaaagaccgc cttcaagaag aaggacacca ttctgtccct gaatgcctgc 1560
gagagcaacc acgccattgc cgccatcaat gagggccaga acaagcccga gatcgaagtg 1620
acctgggcca agcagggaag aaccgagaga ctgtgctccc agaatcctcc tgtgctgaag 1680
cggcaccaga gagaaatcac ccggaccaca ctgcagagcg accaagaaga gatcgattac 1740
gacgatacca tcagcgtcga gatgaagaaa gaagatttcg acatctacga cgaggacgag 1800
aatcagagcc ctcggagctt ccagaagaaa accaggcact actttattgc cgccgtcgag 1860
cggctgtggg actacggaat gtctagctct cctcacgtgc tgcggaatag agcccagtct 1920
ggtagcgtgc cccagttcaa aaaggtcgtg ttccaagagt tcaccgacgg cagcttcacc 1980
cagccactgt atagaggcga gctgaacgag catctgggcc tgctgggccc ttatatcaga 2040
gccgaagtgg aagataacat catggtcacc ttccggaatc aggcctctcg gccctacagc 2100
ttctacagct ccctgatctc ctacgaagag gaccagagac agggcgcaga gccccggaag 2160
aatttcgtga agcccaacga gactaagacc tacttttgga aggtgcagca ccatatggcc 2220
cctacaaagg acgagttcga ctgcaaagcc tgggcctact tctccgatgt ggacctcgag 2280
aaggatgtgc acagcggact catcggccca ctgcttgtgt gccacaccaa cacactgaac 2340
cccgctcacg gcagacaagt gacagtgcaa gaattcgccc tgtttttcac catcttcgac 2400
gaaacgaagt cctggtactt caccgaaaac atggaaagaa actgcagggc cccttgcaac 2460
attcagatgg aagatcccac cttcaaagag aactaccggt tccacgccat caacggctac 2520
atcatggaca cactgcccgg cctggttatg gctcaggatc agagaatccg gtggtatctg 2580
ctgtccatgg gctccaacga gaatatccac tccatccact tctccggcca cgtgttcacc 2640
gtgcggaaaa aagaagagta caaaatggcc ctgtacaatc tgtaccctgg ggtgttcgaa 2700
accgttgaga tgctgcctag caaggccgga atttggagag tggaatgtct gattggagag 2760
cacctccacg ccgggatgag caccctgttt ctggtgtact ccaacaagtg tcagacccct 2820
ctcggcatgg cctctggcca cattagagac ttccagatca ccgccagcgg acagtatgga 2880
cagtgggccc ctaaactggc cagactgcac tactccggca gcatcaatgc ctggtccacc 2940
aaagagcctt tcagctggat caaagtggac ctgctggctc ccatgatcat ccacggaatc 3000
aagacccagg gcgccagaca aaagttcagc agcctgtaca tcagccagtt catcatcatg 3060
tacagcctgg acggaaagaa gtggcagacc taccggggca atagcaccgg cacactgatg 3120
gtgttcttcg gcaacgtgga ctccagcggc attaagcaca acatcttcaa ccctccaatc 3180
attgcccgat acatccggct gcaccccaca cactacagca tcaggtctac cctgagaatg 3240
gaactgatgg gctgcgacct gaacagctgc agcatgcccc tcggaatgga aagcaaggcc 3300
atcagcgacg cccagatcac agcctctagc tacttcacca acatgttcgc cacttggagc 3360
ccctctaagg cccggcttca tctgcaaggc agaagcaacg cttggaggcc ccaagtgaac 3420
aaccccaaag aatggctgca ggtcgacttt cagaaaacca tgaaagtgac aggcgtgacc 3480
acacagggcg tcaagtccct gctgacctct atgtacgtga aagagtttct gatcagctcc 3540
agccaggacg gccaccagtg gaccctgttc ttccaaaacg gcaaagtgaa agtgttccag 3600
ggaaatcagg acagcttcac acccgtggtc aactccctgg atcctccact gctgacaaga 3660
tacctgcgga ttcaccctca gtcttgggtg caccagattg ccctgcggat ggaagtgctg 3720
ggctgtgaag ctcaggacct ctactgaggt accaattcct cacctgcgat ctcgatgctt 3780
tatttgtgaa atttgtgatg ctattgcttt atttgtaacc attataagct gcaataaaca 3840
agttaacaac aacaattgca ttcattttat gtttcaggtt cagggggagg tgtgggaggt 3900
tttttaaact ag 3912

<210> SEQ ID NO 24
<211> LENGTH: 3828
<212> TYPE: DNA
<213> ORGANISM: Artificial Sequence
<220> FEATURE:
<223> OTHER INFORMATION: Synthetic nucleic acid sequence

<400> SEQUENCE: 24
acttctaggc gcgccgccac catgtaccca tacgatgttc cagattacgc ttatccttat 60
gacgtgcctg actacgccta tccctacgac gtccccgact atgcagtgta caagaaaacc 120
ctgttcgtgg aattcaccga ccacctgttc aatatcgcca agcctcggcc tccttggatg 180
ggactgctgg gacctacaat tcaggccgag gtgtacgaca ccgtggtcat caccctgaag 240
aacatggcca gccatcctgt gtctctgcac gccgtgggag tgtcttactg gaaggcttct 300
gagggcgccg agtacgacga tcagacaagc cagagagaga aagaggacga caaggttttc 360
cctggcggca gccacaccta tgtctggcaa gtcctgaaag aaaacggccc tatggcctcc 420
gatcctctgt gcctgacata cagctacctg agccacgtgg acctggtcaa ggacctgaat 480
tctggcctga tcggagccct gctcgtgtgt agagaaggca gcctggccaa agagaaaacc 540
cagacactgc acaagttcat cctgctgttc gccgtgttcg acgagggcaa gagctggcac 600
agcgagacaa agaacagcct gatgcaggac agggatgccg cctctgctcg ggcttggcct 660
aagatgcaca ccgtgaacgg ctacgtgaac agaagcctgc ctggactgat cggctgccac 720
agaaagtccg tgtactggca cgtgatcggc atgggcacaa cacctgaggt gcacagcatc 780
tttctggaag gacacacctt cctcgtgcgg aaccatagac aggccagcct ggaaatcagc 840
cctatcacct tcctgaccgc tcagaccctg ctgatggatc tgggccagtt tctgctgttc 900
tgccacatca gctcccacca gcacgatggc atggaagcct acgtgaaggt ggacagctgc 960
cccgaagaac cccagctgcg gatgaagaac aacgaggaag ccgaggacta cgacgacgac 1020
ctgaccgact ctgagatgga cgtcgtcaga ttcgacgacg ataacagccc cagcttcatc 1080
caaatcagaa gcgtggccaa gaagcacccc aagacctggg tgcactatat cgccgccgag 1140
gaagaggact gggattacgc tcctctggtg ctggcccctg acgacagaag ctacaagagc 1200
cagtacctga acaacggccc tcagcggatc ggccggaagt ataagaaagt gcggttcatg 1260
gcctacaccg acgagacatt caagaccaga gaggccatcc agcacgagag cggaattctg 1320
ggccctctgc tgtatggcga agtgggcgat acactgctga tcatcttcaa gaaccaggcc 1380

-continued

```
agcagaccct acaacatcta ccctcacggc atcaccgatg tgcggcccct gtattctaga   1440
aggctgccca agggcgtgaa gcacctgaag gacttcccta tcctgcctgg cgagatcttc   1500
aagtacaagt ggaccgtgac cgtggaagat ggccccacca agagcgaccc tagatgtctg   1560
acacggtact acagcagctt cgtgaacatg gaacgcgacc tggccagcgg cctgattgga   1620
cctctgctga tctgctacaa agaaagcgtg gaccagcggg gcaaccagat catgagcgac   1680
aagcggaacg tgatcctgtt tagcgtgttc gatgagaacc ggtcctggta tctgaccgag   1740
aacatccagc ggtttctgcc caatcctgct ggcgtgcagc tggaagatcc tgagttccag   1800
gcctccaaca tcatgcactc catcaatggc tatgtgttcg acagcctgca gctgagcgtg   1860
tgcctgcacg aagtggccta ctggtacatc ctgagcattg gcgcccagac cgacttcctg   1920
tccgtgttct tttccggcta caccttcaag cacaagatgg tgtacgagga taccctgaca   1980
ctgttcccat tctccggcga gacagtgttc atgagcatgg aaaaccccgg cctgtggatc   2040
ctgggctgtc acaacagcga cttccggaac agaggcatga cagccctgct gaaggtgtcc   2100
agctgcgaca agaacaccgg cgactactac gaggacagct atgaggacat cagcgcctac   2160
ctgctgagca agaacaatgc catcgagccc agaagcttca gccagaatag cagacacccc   2220
tccaccagac agaagcagtt caacgccaca acaatccccg agaacgacat cgagaaaacc   2280
gatccttggt ttgcccaccg gacccctatg cctaagatcc agaacgtgtc ctccagcgat   2340
ctgctgatgc tcctgagaca gagccctaca cctcacggac tgagcctgtc cgatctgcaa   2400
gaggccaaat acgaaacctt cagcgacgac ccttctcctg gcgccatcga cagcaacaat   2460
agcctgagcg agatgaccca cttcagacca cagctgcacc acagcggcga catggtgttt   2520
acacctgaga gcggcctcca gctgagactg aatgagaagc tgggaaccac cgccgccacc   2580
gagctgaaga aactggactt caaggtgtcc tctaccagca acaacctgat cagcacaatc   2640
ccctccgaca acctggctgc cggcaccgac aacacatctt ctctgggccc acctagcatg   2700
cccgtgcact acgatagcca gctggatacc acactgttcg gcaagaagtc tagccctctg   2760
acagagtctg gcggccctct gtctctgagc gaggaaaaca acgacagcaa gctgctggaa   2820
tccggcctga tgaacagcca agagtcctcc tggggcaaga atgtgtccag caccgagtcc   2880
ggcagactgt tcaagggaaa gagagcccac ggacctgctc tgctgaccaa ggataacgcc   2940
ctgttcaaag tgtccatcag cctgctcaag accaacaaga cctccaacaa ctccgccacc   3000
aacagaaaga cccacatcga cggccctagc ctgctgatcg agaatagccc tagcgtctgg   3060
cagaatatcc tggaaagcga caccgagttc aagaaagtga cccctctgat ccacgaccgg   3120
atgctcatgg acaagaacgc caccgctctg cggctgaacc acatgagcaa caagacaacc   3180
agcagcaaga atatggaaat ggtgcagcag aagaaagagg gccccattcc tccagacgct   3240
cagaaccccg atatgagctt cttcaagatg ctctttctgc ccgagagcgc ccggtggatc   3300
cagagaacac acggcaagaa ctccctgaac tccggccagg gaccttctcc aaagcagctg   3360
gtttccctgg gacctgagaa gtccgtggaa ggccagaact tcctgagcga aaagaacaaa   3420
gtggtcgtcg gcaagggcga gttcaccaag gatgtgggcc tgaaagagat ggtctttccc   3480
agcagccgga acctgttcct gaccaacctg gacaacctgc acgagaacaa cacccacaat   3540
caagagaaga agatccaaga ggtaagtatt agctctttct ttccatgggt tggcctcgcc   3600
gcgtgggctg agggaaggac tgtcctggga ctggacaggc gggttatggg acctgaagcg   3660
ataaaaggca tgcacgtttg cggctacgtg catgccaaaa ggagtcgggc ttgcctccgt   3720
gcccgactcc aaaagacctg ctcgaggagg tggacgagca ggtcaaaaat ccgggtacca   3780
```

ataaaatatc tttattttca ttacatctgt gtgttggttt tttgtgtg 3828

<210> SEQ ID NO 25
<211> LENGTH: 3802
<212> TYPE: DNA
<213> ORGANISM: Artificial Sequence
<220> FEATURE:
<223> OTHER INFORMATION: Synthetic nucleic acid sequence

<400> SEQUENCE: 25
aggatttttg acctgctcga ttgtccactg cgagcaggtc ttttggagtc gggcgaggcg 60
gaagcccgac tccttttggc atgcacgcta gccgcgtcgt gcatgccttt tatcttcggg 120
ttatgggacc agtgaaggct gagggaagga ctgtcctggg actggacagg cgggttatgg 180
gacctgaaaa tactaacaat cgattttttt tccctttttt tccaggaaat cgaaaagaaa 240
gagacactca tccaagagaa cgtggtgctg cctcagatcc acacagtgac cggcaccaag 300
aactttatga agaatctgtt cctgctgagt acccggcaga atgtggaagg cagctacgac 360
ggcgcttatg cccctgtgct gcaagacttc agatccctga acgactccac caatcggaca 420
aagaagcaca cagcccactt ctccaagaag ggcgaagagg aaaacctgga aggcctgggc 480
aatcagacca agcagatcgt cgagaagtac gcctgcacca ccagaatcag ccccaacaca 540
agccagcaga acttcgtgac ccagcggagc aaaagagccc tgaagcagtt tcggctgccc 600
ctggaagaaa ccgagctgga aaagcggatc atcgtggacg acaccagcac acagtggtcc 660
aagaacatga agcacttgac ccctagcaca ctgacccaga tcgactacaa cgagaaagag 720
aagggcgcta tcacacagag cccactgagc gactgtctga ccagaagcca cagcatccct 780
caggccaaca gatcccctct gccaatcgcc aaagtgtcta gcttccccag catcagaccc 840
atctacctga ccagagtgct gttccaggac aacagcagcc atctgccagc cgccagctac 900
cggaagaaag atagcggcgt gcaagagtcc agccactttc tgcaaggcgc taagaagaac 960
aatctgagcc tggctattct gaccctggaa atgaccggcg atcagagaga agtcggctct 1020
ctgggcacca gcgccacaaa tagcgtgacc tacaaaaagg tggaaaacac cgtgctgcct 1080
aagcctgacc tgccaaagac aagcggcaag gtggaactgc tgccaaaggt gcacatctac 1140
cagaaggacc tgtttcctac cgagacaagc aacggctctc ccggccatct ggatctggtg 1200
gaaggatctc tgctgcaggg aaccgagggc gccatcaagt ggaacgaggc caatagacct 1260
ggcaaggtgc ccttcctgag agtggccaca gagtctagcg ccaagacacc ctccaaactg 1320
ctggatcccc tggcctggga taaccactac ggcactcaga tccccaaaga ggaatggaag 1380
tcccaagaga agtcccctga aaagaccgcc ttcaagaaga aggacaccat tctgtccctg 1440
aatgcctgcg agagcaacca cgccattgcc gccatcaatg agggccagaa caagcccgag 1500
atcgaagtga cctgggccaa gcagggaaga accgagagac tgtgctccca gaatcctcct 1560
gtgctgaagc ggcaccagag agaaatcacc cggaccacac tgcagagcga ccaagaagag 1620
atcgattacg acgataccat cagcgtcgag atgaagaaag aagatttcga catctacgac 1680
gaggacgaga atcagagccc tcggagcttc cagaagaaaa ccaggcacta ctttattgcc 1740
gccgtcgagc ggctgtggga ctacggaatg tctagctctc ctcacgtgct gcggaataga 1800
gcccagtctg gtagcgtgcc ccagttcaaa aaggtcgtgt tccaagagtt caccgacggc 1860
agcttcaccc agccactgta tagaggcgag ctgaacgagc atctgggcct gctgggccct 1920
tatatcagag ccgaagtgga agataacatc atggtcacct tccggaatca ggcctctcgg 1980

```
ccctacagct tctacagctc cctgatctcc tacgaagagg accagagaca gggcgcagag   2040

ccccggaaga atttcgtgaa gcccaacgag actaagacct acttttggaa ggtgcagcac   2100

catatggccc ctacaaagga cgagttcgac tgcaaagcct gggcctactt ctccgatgtg   2160

gacctcgaga aggatgtgca cagcggactc atcggcccac tgcttgtgtg ccacaccaac   2220

acactgaacc ccgctcacgg cagacaagtg acagtgcaag aattcgccct gtttttcacc   2280

atcttcgacg aaacgaagtc ctggtacttc accgaaaaca tggaaagaaa ctgcagggcc   2340

ccttgcaaca ttcagatgga agatcccacc ttcaaagaga actaccggtt ccacgccatc   2400

aacggctaca tcatggacac actgcccggc ctggttatgg ctcaggatca gagaatccgg   2460

tggtatctgc tgtccatggg ctccaacgag aatatccact ccatccactt ctccggccac   2520

gtgttcaccg tgcggaaaaa agaagagtac aaaatggccc tgtacaatct gtaccctggg   2580

gtgttcgaaa ccgttgagat gctgcctagc aaggccggaa tttggagagt ggaatgtctg   2640

attggagagc acctccacgc cgggatgagc accctgtttc tggtgtactc caacaagtgt   2700

cagacccctc tcggcatggc ctctggccac attagagact tccagatcac cgccagcgga   2760

cagtatggac agtgggcccc taaactggcc agactgcact actccggcag catcaatgcc   2820

tggtccacca aagagccttt cagctggatc aaagtggacc tgctggctcc catgatcatc   2880

cacggaatca agacccaggg cgccagacaa aagttcagca gcctgtacat cagccagttc   2940

atcatcatgt acagcctgga cggaaagaag tggcagacct accggggcaa tagcaccggc   3000

acactgatgg tgttcttcgg caacgtggac tccagcggca ttaagcacaa catcttcaac   3060

cctccaatca ttgcccgata catccggctg caccccacac actacagcat caggtctacc   3120

ctgagaatgg aactgatggg ctgcgacctg aacagctgca gcatgcccct cggaatggaa   3180

agcaaggcca tcagcgacgc ccagatcaca gcctctagct acttcaccaa catgttcgcc   3240

acttggagcc cctctaaggc ccggcttcat ctgcaaggca gaagcaacgc ttggaggccc   3300

caagtgaaca accccaaaga atggctgcag gtcgactttc agaaaaccat gaaagtgaca   3360

ggcgtgacca cacagggcgt caagtccctg ctgacctcta tgtacgtgaa agagtttctg   3420

atcagctcca gccaggacgg ccaccagtgg accctgttct tccaaaacgg caaagtgaaa   3480

gtgttccagg gaaatcagga cagcttcaca cccgtggtca actccctgga tcctccactg   3540

ctgacaagat acctgcggat tcaccctcag tcttgggtgc accagattgc cctgcggatg   3600

gaagtgctgg gctgtgaagc tcaggacctc tactgaggta ccaattcctc acctgcgatc   3660

tcgatgcttt atttgtgaaa tttgtgatgc tattgcttta tttgtaacca ttataagctg   3720

caataaacaa gttaacaaca acaattgcat tcattttatg tttcaggttc agggggaggt   3780

gtgggaggtt ttttaaacta gt                                            3802
```

<210> SEQ ID NO 26
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 26

```
tggggggagg                                                            10
```

<210> SEQ ID NO 27
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 27
gtagtgaggg 10

<210> SEQ ID NO 28
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 28
gttggtggtt 10

<210> SEQ ID NO 29
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 29
agttgtggtt 10

<210> SEQ ID NO 30
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 30
gtattgggtc 10

<210> SEQ ID NO 31
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 31
agtgtgaggg 10

<210> SEQ ID NO 32
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 32
gggtaatggg 10

<210> SEQ ID NO 33
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 33
tcattggggt 10

<210> SEQ ID NO 34
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 34
ggtgggggtc 10

<210> SEQ ID NO 35
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 35
ggttttgttg 10

<210> SEQ ID NO 36
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 36
tatactcccg 10

<210> SEQ ID NO 37
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 37
gtattcgatc 10

<210> SEQ ID NO 38
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 38
gtagttccct 10

<210> SEQ ID NO 39
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 39
gttaatagta 10

<210> SEQ ID NO 40
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 40
tgctggttag 10

<210> SEQ ID NO 41
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 41
ataggtaacg 10

<210> SEQ ID NO 42
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 42
tctgaattgc 10

<210> SEQ ID NO 43
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 43
tctgggtttg 10

<210> SEQ ID NO 44
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 44
cattctcttt 10

<210> SEQ ID NO 45
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 45
gtattggtgt 10

<210> SEQ ID NO 46
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 46
tttagatttg 10

<210> SEQ ID NO 47

<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 47
ataagtactg 10

<210> SEQ ID NO 48
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 48
tagtctatta 10

<210> SEQ ID NO 49
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 49
aggtattgca 10

<210> SEQ ID NO 50
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 50
gtagattacg 10

<210> SEQ ID NO 51
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 51
gggcgggtgc 10

<210> SEQ ID NO 52
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 52
cgtttacaat 10

<210> SEQ ID NO 53
<211> LENGTH: 11
<212> TYPE: DNA
<213> ORGANISM: Artificial Sequence
<220> FEATURE:
<223> OTHER INFORMATION: Synthetic nucleic acid sequence

<400> SEQUENCE: 53
gtacagggat g 11

<210> SEQ ID NO 54
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 54
aatcagggga 10

<210> SEQ ID NO 55
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 55
ggaggttttg 10

<210> SEQ ID NO 56
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 56
gtattccctg 10

<210> SEQ ID NO 57
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 57
tggtaagatc 10

<210> SEQ ID NO 58
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 58
gtagttaagt 10

<210> SEQ ID NO 59
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 59
gttggtttgg 10

<210> SEQ ID NO 60
<211> LENGTH: 10
<212> TYPE: DNA

<213> ORGANISM: Artificial Sequence
<220> FEATURE:
<223> OTHER INFORMATION: Synthetic nucleic acid sequence

<400> SEQUENCE: 60
gtatttactt 10

<210> SEQ ID NO 61
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 61
gtaacggggt 10

<210> SEQ ID NO 62
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 62
tttttttctg 10

<210> SEQ ID NO 63
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 63
ggggaaggga 10

<210> SEQ ID NO 64
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 64
ttaccccggt 10

<210> SEQ ID NO 65
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 65
gtattctatg 10

<210> SEQ ID NO 66
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 66
aggtattgtg 10

<210> SEQ ID NO 67
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 67
tttggggggg 10

<210> SEQ ID NO 68
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 68
gttgttagcg 10

<210> SEQ ID NO 69
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 69
ggtagttggg 10

<210> SEQ ID NO 70
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 70
ctaagtactg 10

<210> SEQ ID NO 71
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 71
aaccatcttc 10

<210> SEQ ID NO 72
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 72
gtacctgggt 10

<210> SEQ ID NO 73
<211> LENGTH: 10
<212> TYPE: DNA
<213> ORGANISM: Artificial Sequence
<220> FEATURE:

<223> OTHER INFORMATION: Synthetic nucleic acid sequence

<400> SEQUENCE: 73
gtatctcatt 10

<210> SEQ ID NO 74
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 74
aaataaaatt 10

<210> SEQ ID NO 75
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 75
ggtgggttat 10

<210> SEQ ID NO 76
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 76
taagggaggg 10

<210> SEQ ID NO 77
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 77
tatgggaggg 10

<210> SEQ ID NO 78
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 78
gatgggaggg 10

<210> SEQ ID NO 79
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 79
tgggggggt 10

<210> SEQ ID NO 80
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 80
ggggaagggg 10

<210> SEQ ID NO 81
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 81
tggtaagagg 10

<210> SEQ ID NO 82
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 82
gggttagggt 10

<210> SEQ ID NO 83
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 83
gtatcggggg 10

<210> SEQ ID NO 84
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 84
ggttttgctg 10

<210> SEQ ID NO 85
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 85
tgggggtgga 10

<210> SEQ ID NO 86
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 86
acttttagag 10

<210> SEQ ID NO 87
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 87
gtaacgggtt 10

<210> SEQ ID NO 88
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 88
gtttggggga 10

<210> SEQ ID NO 89
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 89
atttttagag 10

<210> SEQ ID NO 90
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 90
ttaaagtagg 10

<210> SEQ ID NO 91
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 91
gtattaatat 10

<210> SEQ ID NO 92
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 92
ggtttgggtg 10

<210> SEQ ID NO 93
<211> LENGTH: 10

<212> TYPE: DNA
<213> ORGANISM: Artificial Sequence
<220> FEATURE:
<223> OTHER INFORMATION: Synthetic nucleic acid sequence

<400> SEQUENCE: 93
tatgggaaag 10

<210> SEQ ID NO 94
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 94
ggttgggagg 10

<210> SEQ ID NO 95
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 95
gtatttagtg 10

<210> SEQ ID NO 96
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 96
gagttaaatg 10

<210> SEQ ID NO 97
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 97
ttgtaagttg 10

<210> SEQ ID NO 98
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 98
tgggggtagg 10

<210> SEQ ID NO 99
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 99
gttcttaggg 10

<210> SEQ ID NO 100
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 100
gtattctaag 10

<210> SEQ ID NO 101
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 101
ggaggttttg 10

<210> SEQ ID NO 102
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 102
agaatatgta 10

<210> SEQ ID NO 103
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 103
atctttcggg 10

<210> SEQ ID NO 104
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 104
ttgcattgaa 10

<210> SEQ ID NO 105
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 105
ggtgggattt 10

<210> SEQ ID NO 106
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 106
tttatctaat 10

<210> SEQ ID NO 107
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 107
gcgggtggtg 10

<210> SEQ ID NO 108
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 108
ggtttagata 10

<210> SEQ ID NO 109
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 109
tttatgcgtt 10

<210> SEQ ID NO 110
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 110
tgggtaaggc 10

<210> SEQ ID NO 111
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 111
gggggtggtc 10

<210> SEQ ID NO 112
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 112
gtagtatatt 10

<210> SEQ ID NO 113
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 113
ggaggtattt 10

<210> SEQ ID NO 114
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 114
gtattgtaag 10

<210> SEQ ID NO 115
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 115
tttacgggag 10

<210> SEQ ID NO 116
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 116
tagttctggg 10

<210> SEQ ID NO 117
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 117
ccacgtctat 10

<210> SEQ ID NO 118
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 118
agtgggtagg 10

<210> SEQ ID NO 119
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 119
caatttttac 10

<210> SEQ ID NO 120
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 120
ggtctggggg 10

<210> SEQ ID NO 121
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 121
atcaagattg 10

<210> SEQ ID NO 122
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 122
gttagctaaa 10

<210> SEQ ID NO 123
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 123
agtgtggggt 10

<210> SEQ ID NO 124
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 124
ggtatgtggg 10

<210> SEQ ID NO 125
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 125
gtagtgtggg 10

<210> SEQ ID NO 126

<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 126
aggaggtgtt 10

<210> SEQ ID NO 127
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 127
gttggtaggt 10

<210> SEQ ID NO 128
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 128
gtaggtggtt 10

<210> SEQ ID NO 129
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 129
aggtgttggt 10

<210> SEQ ID NO 130
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 130
tatggttgtg 10

<210> SEQ ID NO 131
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 131
ttaggttagt 10

<210> SEQ ID NO 132
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 132
gattggagtt 10

<210> SEQ ID NO 133
<211> LENGTH: 10
<212> TYPE: DNA
<213> ORGANISM: Artificial Sequence
<220> FEATURE:
<223> OTHER INFORMATION: Synthetic nucleic acid sequence

<400> SEQUENCE: 133
gtagagtgga 10

<210> SEQ ID NO 134
<211> LENGTH: 24
<212> TYPE: RNA
<213> ORGANISM: Artificial Sequence
<220> FEATURE:
<223> OTHER INFORMATION: Synthetic nucleic acid sequence

<400> SEQUENCE: 134
cucuuucuuu uccaugggu ggcu 24

<210> SEQ ID NO 135
<211> LENGTH: 24
<212> TYPE: RNA
<213> ORGANISM: Artificial Sequence
<220> FEATURE:
<223> OTHER INFORMATION: Synthetic nucleic acid sequence

<400> SEQUENCE: 135
ggcugaggga aggacugucc uggg 24

<210> SEQ ID NO 136
<211> LENGTH: 13
<212> TYPE: RNA
<213> ORGANISM: Artificial Sequence
<220> FEATURE:
<223> OTHER INFORMATION: Synthetic nucleic acid sequence

<400> SEQUENCE: 136
ggguuauggg acc 13

<210> SEQ ID NO 137
<211> LENGTH: 12
<212> TYPE: RNA
<213> ORGANISM: Artificial Sequence
<220> FEATURE:
<223> OTHER INFORMATION: Synthetic nucleic acid sequence

<400> SEQUENCE: 137
auauccuuuu ua 12

<210> SEQ ID NO 138
<211> LENGTH: 12
<212> TYPE: RNA
<213> ORGANISM: Artificial Sequence
<220> FEATURE:
<223> OTHER INFORMATION: Synthetic nucleic acid sequence

<400> SEQUENCE: 138
guauccuuuu ua 12

<210> SEQ ID NO 139
<211> LENGTH: 33
<212> TYPE: RNA

<213> ORGANISM: Artificial Sequence
<220> FEATURE:
<223> OTHER INFORMATION: Synthetic nucleic acid sequence

<400> SEQUENCE: 139
aggcuucgga gcaaggaggc agcuccgaag ccu 33

<210> SEQ ID NO 140
<211> LENGTH: 33
<212> TYPE: RNA
<213> ORGANISM: Artificial Sequence
<220> FEATURE:
<223> OTHER INFORMATION: Synthetic nucleic acid sequence

<400> SEQUENCE: 140
aggcuucgga gcaagccucc agcuccgaag ccu 33

<210> SEQ ID NO 141
<211> LENGTH: 29
<212> TYPE: RNA
<213> ORGANISM: Artificial Sequence
<220> FEATURE:
<223> OTHER INFORMATION: Synthetic nucleic acid sequence

<400> SEQUENCE: 141
gucgaggccg agcgggcaaa ggccucgac 29

<210> SEQ ID NO 142
<211> LENGTH: 29
<212> TYPE: RNA
<213> ORGANISM: Artificial Sequence
<220> FEATURE:
<223> OTHER INFORMATION: Synthetic nucleic acid sequence

<400> SEQUENCE: 142
gucgaggccg agcccgcaaa ggccucgac 29

<210> SEQ ID NO 143
<211> LENGTH: 10
<212> TYPE: RNA
<213> ORGANISM: Artificial Sequence
<220> FEATURE:
<223> OTHER INFORMATION: Synthetic nucleic acid sequence
<220> FEATURE:
<221> NAME/KEY: misc_feature
<222> LOCATION: (1)..(3)
<223> OTHER INFORMATION: n is a, c, g, or u
<220> FEATURE:
<221> NAME/KEY: misc_feature
<222> LOCATION: (8)..(10)
<223> OTHER INFORMATION: n is a, c, g, or u

<400> SEQUENCE: 143 nnnaggunnn 10

<210> SEQ ID NO 144
<211> LENGTH: 12
<212> TYPE: RNA
<213> ORGANISM: Artificial Sequence
<220> FEATURE:
<223> OTHER INFORMATION: Synthetic nucleic acid sequence

<400> SEQUENCE: 144
uuuuccuuaa cu 12

<210> SEQ ID NO 145
<211> LENGTH: 1305

<212> TYPE: DNA
<213> ORGANISM: Artificial Sequence
<220> FEATURE:
<223> OTHER INFORMATION: Synthetic nucleic acid sequence

<400> SEQUENCE: 145
cgttacataa cttacggtaa atggcccgcc tggctgaccg cccaacgacc cccgcccatt 60
gacgtcaata atgacgtatg ttcccatagt aacgccaata gggactttcc attgacgtca 120
atgggtggag tatttacggt aaactgccca cttggcagta catcaagtgt atcatatgcc 180
aagtacgccc cctattgacg tcaatgacgg taaatggccc gcctggcatt atgcccagta 240
catgacctta tgggactttc ctacttggca gtacatctac gtattagtca tcgctattac 300
catggtgatg cggttttggc agtacatcaa tgggcgtgga tagcggtttg actcacgggg 360
atttccaagt ctccacccca ttgacgtcaa tgggagtttg ttttggcacc aaaatcaacg 420
ggactttcca aaatgtcgta acaactccgc cccattgacg caaatgggcg gtaggcgtgt 480
acggtgggag gtctatataa gcagagcttg gatgttgcct ttacttctag gcgcgccgcc 540
accatggtga gcaagggcga ggagctgttc accggggtgg tgcccatcct ggtcgagctg 600
gacggcgacg taaacggcca caagttcagc gtgtccggcg agggcgaggg cgatgccacc 660
tacggcaagc tgaccctgaa gttcatctgc accaccggca agctgcccgt gccctggccc 720
accctcgtga ccaccttcgg ctacggcctg atgtgcttcg cccgctaccc cgaccacatg 780
aagcagcacg acttcttcaa gtccgccatg cccgaaggct acgtccagga gcgcaccatc 840
ttcttcaagg taagtattag ctctttcttt ccatgggttg gcctcgccgc gtgggctgag 900
ggaaggactg tcctgggact ggacaggcgg gttatgggac ctgaaaagcg gccctgaaaa 960
agggccgcga tctgtagaaa gcgagctagt gccggacagt tagaggaaaa ggggaagaac 1020
tgtccgaaaa aaggggggga agacagtgac tagaaaggga agggagaagt cactgtagag 1080
gggaaggaaa aggctagcta gaggagaagg aaagaggcta gctagcagag gagaaggaaa 1140
ggcgccagca gttcggtgct atcaaaaagc ggtcaggcag ctaaaccaaa aggtttagca 1200
attgcctctg atgagtcgct gaaatgcgac gaaaaccgct ttttggtacc aataaaatat 1260
ctttattttc attacatctg tgtgttggtt ttttgtgtga ctagt 1305

<210> SEQ ID NO 146
<211> LENGTH: 1543
<212> TYPE: DNA
<213> ORGANISM: Artificial Sequence
<220> FEATURE:
<223> OTHER INFORMATION: Synthetic nucleic acid sequence

<400> SEQUENCE: 146
cgttacataa cttacggtaa atggcccgcc tggctgaccg cccaacgacc cccgcccatt 60
gacgtcaata atgacgtatg ttcccatagt aacgccaata gggactttcc attgacgtca 120
atgggtggag tatttacggt aaactgccca cttggcagta catcaagtgt atcatatgcc 180
aagtacgccc cctattgacg tcaatgacgg taaatggccc gcctggcatt atgcccagta 240
catgacctta tgggactttc ctacttggca gtacatctac gtattagtca tcgctattac 300
catggtgatg cggttttggc agtacatcaa tgggcgtgga tagcggtttg actcacgggg 360
atttccaagt ctccacccca ttgacgtcaa tgggagtttg ttttggcacc aaaatcaacg 420
ggactttcca aaatgtcgta acaactccgc cccattgacg caaatgggcg gtaggcgtgt 480
acggtgggag gtctatataa gcagagcttg gatgttgcct ttacttctag gcgcgccgcg 540

```
gaaaaccgcg ggatagcacc gaactgctgg cgcctttcct tctcctctgc tagctagcct    600

ctttccttct cctctagcta gccttttcct tcccctctac agtgacttct cccttccctt    660

tctagtcact gtcttccccc ccttttttcg gacagttctt ccccttttcc tctaactgtc    720

cggcactagc tcgctttcta cagatcatta ttgcggccct gaaaaagggc cgcttataac    780

gttgctcgaa ttcgggttat gggaccagtg aaggctgagg gaaggactgt cctgggactg    840

gacaggcggg ttatgggacc tgaaaatact aacaatcgat ttttttttccc tttttttcca    900

ggacgacggc aactacaaga cccgcgccga ggtgaagttc gagggcgaca ccctggtgaa    960

ccgcatcgag ctgaagggca tcgacttcaa ggaggacggc aacatcctgg ggcacaagct   1020

ggagtacaac tacaacagcc acaacgtcta tatcatggcc gacaagcaga agaacggcat   1080

caaggtaagt attagctctt tctttccatg ggttggcctc gccgcgtggg ctgagggaag   1140

gactgtcctg ggactggaca ggcgggttat gggacctgaa aagcggccct gaaaaagggc   1200

cgcagcgaaa acgaagcgag ctaaagcctc ctctctcttc ttcagaactc ctctcttttc   1260

tctcctccag gagttcttcc tctctccctt cttctcaaat gctttctccc tctctcctgc   1320

atttgagctc cttctttcct ctctcgacaa tccccttttc tccctcttga ttgtcgacta   1380

gctcgcaatc atcgcggtgc taaaaagcgg tcaggcagct aaaccaaaag gtttagcaat   1440

tgcctctgat gagtcgctga aatgcgacga aaaccgcttt ttggtaccaa taaaatatct   1500

ttattttcat tacatctgtg tgttggtttt ttgtgtgact agt                      1543
```

```
<210> SEQ ID NO 147
<211> LENGTH: 1571
<212> TYPE: DNA
<213> ORGANISM: Artificial Sequence
<220> FEATURE:
<223> OTHER INFORMATION: Synthetic nucleic acid sequence

<400> SEQUENCE: 147
```

```
cgttacataa cttacggtaa atggcccgcc tggctgaccg cccaacgacc cccgcccatt     60

gacgtcaata atgacgtatg ttcccatagt aacgccaata gggactttcc attgacgtca    120

atgggtggag tatttacggt aaactgccca cttggcagta catcaagtgt atcatatgcc    180

aagtacgccc cctattgacg tcaatgacgg taaatggccc gcctggcatt atgcccagta    240

catgacctta tgggactttc ctacttggca gtacatctac gtattagtca tcgctattac    300

catggtgatg cggttttggc agtacatcaa tgggcgtgga tagcggtttg actcacgggg    360

atttccaagt ctccacccca ttgacgtcaa tgggagtttg ttttggcacc aaaatcaacg    420

ggactttcca aaatgtcgta acaactccgc cccattgacg caaatgggcg gtaggcgtgt    480

acggtgggag gtctatataa gcagagcttg gatgttgcct ttacttctag gcgcgccacc    540

atgagccagt tcgacatcct gtgcaagacc ccccccaagg tgctggtgcg gcagttcgtg    600

gagagattcg agaggcccag cggcgagaag atcgccagct gtgccgccga gctgacctac    660

ctgtgctgga tgatcaccca caacggcacc gccatcaaga gggccacctt catgagctac    720

aacaccatca tcagcaacag cctgagcttc gacatcgtga acaagagcct gcagttcaag    780

tacaagaccc agaaggccac catcctggag gccagcctga agaagctgat ccccgcctgg    840

gagttcacca tcatccctta caacggccag aagcaccaga gcgacatcac cgacatcgtg    900

tccagcctgc agctgcagtt cgagagcagc gaggaggccg acaagggcaa cagccacagc    960

aagaagatgc tgaaggccct gctgtccgag ggcgagagca tctgggagat caccgagaag   1020

atcctgaaca gcttcgagta caccagcagg ttcaccaaga ccaagaccct gtaccagttc   1080
```

ctgttcctgg ccacattcat caactgcggc aggtaagtat tagctctttc tttccatggg 1140
ttggcctcgc cgcgtgggct gagggaagga ctgtcctggg actggacagg cgggttatgg 1200
gacctgaaaa gcggccctga aaaagggccg cgatgaaaac gaagcgagct aaagcctcct 1260
ctctcttctt cagaactcct ctcttttctc tcctccagga gttcttcctc tctcccttct 1320
tctcaaatgc tttctccctc tctcctgcat ttgagctcct tctttcctct ctcgacaatc 1380
cccttttctc cctcttgatt gtcgactagc tcgcaatcat cgcggtatca aaaagcggtc 1440
aggcagctaa accaaaaggt ttagcaattg cctctgatga gtcgctgaaa tgcgacgaaa 1500
accgcttttt ggtaccaata aaatatcttt attttcatta catctgtgtg ttggtttttt 1560
gtgtgactag t 1571

<210> SEQ ID NO 148
<211> LENGTH: 1765
<212> TYPE: DNA
<213> ORGANISM: Artificial Sequence
<220> FEATURE:
<223> OTHER INFORMATION: Synthetic nucleic acid sequence

<400> SEQUENCE: 148
cgttacataa cttacggtaa atggcccgcc tggctgaccg cccaacgacc cccgcccatt 60
gacgtcaata atgacgtatg ttcccatagt aacgccaata gggactttcc attgacgtca 120
atgggtggag tatttacggt aaactgccca cttggcagta catcaagtgt atcatatgcc 180
aagtacgccc cctattgacg tcaatgacgg taaatggccc gcctggcatt atgcccagta 240
catgacctta tgggactttc ctacttggca gtacatctac gtattagtca tcgctattac 300
catggtgatg cggttttggc agtacatcaa tgggcgtgga tagcggtttg actcacgggg 360
atttccaagt ctccacccca ttgacgtcaa tgggagtttg ttttggcacc aaaatcaacg 420
ggactttcca aaatgtcgta acaactccgc cccattgacg caaatgggcg gtaggcgtgt 480
acggtgggag gtctatataa gcagagcttg gatgttgcct ttacttctag gcgcgccgcg 540
gaaaaccgcg ggataccgcg atgattgcga gctagtcgac aatcaagagg gagaaaaggg 600
gattgtcgag agaggaaaga aggagctcaa atgcaggaga gagggagaaa gcatttgaga 660
agaagggaga gaggaagaac tcctggagga gagaaaagag aggagttctg aagaagagag 720
aggaggcttt agctcgcttc gttttcatca ttattgcggc cctgaaaaag ggccgcttat 780
aacgttgctc gaattcgggt tatgggacca gtgaaggctg agggaaggac tgtcctggga 840
ctggacaggc gggttatggg acctgaaaat actaacaatc gatttttttt cccttttttt 900
ccaggttcag cgacatcaag aacgtggacc ccaagagctt caagctggtg cagaacaagt 960
acctgggcgt gatcattcag tgcctggtga ccgagaccaa gacaagcgtg tccaggcaca 1020
tctacttttt cagcgccaga ggcaggatcg accccctggt gtacctggac gagttcctga 1080
ggaacagcga gcccgtgctg aagagagtga acaggaccgg caacagcagc agcaacaagc 1140
aggagtacca gctgctgaag gacaacctgg tgcgcagcta caacaaggcc ctgaagaaga 1200
acgcccccta ccccatcttc gctatcaaga acggccctaa gagccacatc ggcaggcacc 1260
tgatgaccag ctttctgagc atgaagggcc tgaccgagct gacaaacgtg gtgggcaact 1320
ggagcgacaa gagggcctcc gccgtggcca ggaccaccta cacccaccag atcaccgcca 1380
tccccgacca ctacttcgcc ctggtgtcca ggtactacgc ctacgacccc atcagcaagg 1440
agatgatcgc cctgaaggac gagaccaacc ccatcgagga gtggcagcac atcgagcagc 1500
tgaagggcag cgccgagggc agcatcagat accccgcctg gaacggcatc atcagccagg 1560
aggtgctgga ctacctgagc agctacatca acaggcggat ctgagaattc ctcacctgcg 1620
atctcgatgc tttatttgtg aaatttgtga tgctattgct ttatttgtaa ccattataag 1680
ctgcaataaa caagttaaca acaacaattg cattcatttt atgtttcagg ttcaggggga 1740
ggtgtgggag gtttttttaaa ctagt 1765

<210> SEQ ID NO 149
<211> LENGTH: 10
<212> TYPE: RNA
<213> ORGANISM: Artificial Sequence
<220> FEATURE:
<223> OTHER INFORMATION: Synthetic nucleic acid sequence

<400> SEQUENCE: 149
aaagaaggaa 10

<210> SEQ ID NO 150
<211> LENGTH: 12
<212> TYPE: RNA
<213> ORGANISM: Artificial Sequence
<220> FEATURE:
<223> OTHER INFORMATION: Synthetic nucleic acid sequence

<400> SEQUENCE: 150
cuuucuuuuc uu 12

<210> SEQ ID NO 151
<211> LENGTH: 11
<212> TYPE: RNA
<213> ORGANISM: Artificial Sequence
<220> FEATURE:
<223> OTHER INFORMATION: Synthetic nucleic acid sequence
<220> FEATURE:
<221> NAME/KEY: misc_feature
<222> LOCATION: (1)..(3)
<223> OTHER INFORMATION: n is a, c, g, or u
<220> FEATURE:
<221> NAME/KEY: misc_feature
<222> LOCATION: (8)..(11)
<223> OTHER INFORMATION: n is a, c, g, or u

<400> SEQUENCE: 151
nnnaggunnn n 11

<210> SEQ ID NO 152
<211> LENGTH: 11
<212> TYPE: RNA
<213> ORGANISM: Artificial Sequence
<220> FEATURE:
<223> OTHER INFORMATION: Synthetic nucleic acid sequence
<220> FEATURE:
<221> NAME/KEY: misc_feature
<222> LOCATION: (1)..(3)
<223> OTHER INFORMATION: n is a, c, g, or u
<220> FEATURE:
<221> NAME/KEY: misc_feature
<222> LOCATION: (8)..(11)
<223> OTHER INFORMATION: n is a, c, g, or u

<400> SEQUENCE: 152
nnnuggunnn n 11

<210> SEQ ID NO 153
<211> LENGTH: 11
<212> TYPE: RNA
<213> ORGANISM: Artificial Sequence -continued

```
<220> FEATURE:
<223> OTHER INFORMATION: Synthetic nucleic acid sequence
<220> FEATURE:
<221> NAME/KEY: misc_feature
<222> LOCATION: (3)..(8)
<223> OTHER INFORMATION: n is a, c, g, or u

<400> SEQUENCE: 153

gannnnnnaa a                                                            11


<210> SEQ ID NO 154
<211> LENGTH: 12
<212> TYPE: DNA
<213> ORGANISM: Artificial Sequence
<220> FEATURE:
<223> OTHER INFORMATION: Synthetic nucleic acid sequence

<400> SEQUENCE: 154

gccgccacca tg                                                           12
```